United States Patent
Aicher et al.

(10) Patent No.: US 10,377,768 B2
(45) Date of Patent: Aug. 13, 2019

(54) TETRAHYDRONAPHTHYRIDINE AND RELATED BICYCLIC COMPOUNDS FOR INHIBITION OF RORGAMMA ACTIVITY AND THE TREATMENT OF DISEASE

(71) Applicants: Merck Sharp & Dohme Corp., Rahway, NJ (US); Lycera Corporation, Ann Arbor, MI (US)

(72) Inventors: Thomas D. Aicher, Ann Arbor, MI (US); Kenneth J. Barr, Boston, MA (US); Blair T. Lapointe, Brookline, MA (US); Vladimir Simov, Boston, MA (US); Karin A. Stein, Mountain View, CA (US); William D. Thomas, San Jose, CA (US); Peter L. Toogood, Ann Arbor, MI (US); Chad A. Van Huis, Hartland, MI (US); Catherine M. White, Boston, MA (US)

(73) Assignees: Lycera Corporation, Ann Arbor, MI (US); Merck Sharp & Dohme Corp., Rahway, NJ (US)

( * ) Notice: Subject to any disclaimer, the term of this patent is extended or adjusted under 35 U.S.C. 154(b) by 0 days.

(21) Appl. No.: 15/587,934

(22) Filed: May 5, 2017

(65) Prior Publication Data

US 2017/0313722 A1 Nov. 2, 2017

Related U.S. Application Data

(62) Division of application No. 14/398,061, filed as application No. PCT/US2013/039839 on May 7, 2013, now Pat. No. 9,657,033.

(60) Provisional application No. 61/644,158, filed on May 8, 2012.

(51) Int. Cl.
*C07D 498/04* (2006.01)
*C07D 413/06* (2006.01)
*C07D 471/04* (2006.01)

(52) U.S. Cl.
CPC ......... *C07D 498/04* (2013.01); *C07D 413/06* (2013.01); *C07D 471/04* (2013.01)

(58) Field of Classification Search
CPC ... C07D 498/04; C07D 413/06; C07D 471/04
See application file for complete search history.

(56) References Cited

U.S. PATENT DOCUMENTS

| | | |
|---|---|---|
| 5,583,152 A | 12/1996 | Bernstein et al. |
| 5,985,903 A | 11/1999 | Assmann et al. |
| 6,020,354 A | 2/2000 | Assmann et al. |
| 6,037,367 A | 3/2000 | Christensen, IV et al. |
| 6,160,001 A | 12/2000 | Assmann et al. |
| 6,172,092 B1 | 1/2001 | Assmann et al. |
| 6,180,643 B1 | 1/2001 | Zablocki et al. |
| 6,348,032 B1 | 2/2002 | Sperl et al. |
| 6,352,985 B1 | 3/2002 | Yamasaki et al. |
| 6,387,939 B1 | 5/2002 | Assmann et al. |
| 6,440,973 B1 | 8/2002 | Zablocki et al. |
| 6,534,535 B1 | 3/2003 | Zhu et al. |
| 6,605,634 B2 | 8/2003 | Zablocki et al. |
| 6,638,960 B2 | 10/2003 | Assmann et al. |
| 6,683,091 B2 | 1/2004 | Asberom et al. |
| 6,828,344 B1 | 12/2004 | Seehra et al. |
| 7,084,176 B2 | 8/2006 | Morie et al. |
| 7,115,750 B1 | 10/2006 | Kato et al. |
| 7,138,401 B2 | 11/2006 | Kasibhatla et al. |
| 7,329,675 B2 | 2/2008 | Cox et al. |
| 7,420,059 B2 | 9/2008 | O'Connor et al. |
| 7,482,342 B2 | 1/2009 | D'Orchymont et al. |
| 7,569,571 B2 | 8/2009 | Dong et al. |
| 7,696,200 B2 | 4/2010 | Ackermann et al. |
| 7,713,996 B2 | 5/2010 | Ackermann et al. |
| 7,741,495 B2 | 6/2010 | Liou et al. |
| 7,799,933 B2 | 9/2010 | Ceccarelli et al. |
| 9,266,827 B2 | 2/2016 | Aicher et al. |
| 9,512,111 B2 | 12/2016 | Glick et al. |
| 9,657,033 B2 | 5/2017 | Aicher et al. |
| 2006/0004000 A1 | 1/2006 | D'Orchymont et al. |
| 2006/0100230 A1 | 5/2006 | Bischoff et al. |
| 2007/0010537 A1 | 1/2007 | Hamamura et al. |
| 2007/0010670 A1 | 1/2007 | Hirata et al. |
| 2007/0049556 A1 | 3/2007 | Zhang et al. |
| 2007/0060567 A1 | 3/2007 | Ackermann et al. |
| 2007/0154487 A1 | 7/2007 | Littman et al. |
| 2007/0191603 A1 | 8/2007 | Ackermann et al. |
| 2007/0197782 A1 | 8/2007 | Clough et al. |

(Continued)

FOREIGN PATENT DOCUMENTS

| | | |
|---|---|---|
| EP | 0882718 A1 | 12/1998 |
| EP | 1820515 A1 | 8/2007 |

(Continued)

OTHER PUBLICATIONS

Pullagurla (Year: 2005).*
Annunziato et al., "Type 17 T helper cells-origins, features and possible roles in rheumatic disease," 5 Nat. Rev. Rheumatol. 325-31 (2009).
Boaventura et al., "Human mucosal leishmaniasis: Neutrophils infiltrate areas of tissue damage that express high levels of Th17-related cytokines," 40 Eur. J. Immunol. 2830-36 (2010).
Buonocore et al., "Innate lymphoid cells drive interleukin-23-dependent innate intestinal pathology," 464 Nature 1371-75 (2010).
Eberl et al., "An essential function for the nuclear receptor RORγt in the generation of fetal lymphoid tissue inducer cells," 5(1) Nat. Immunol. 64-73 (2004).

(Continued)

*Primary Examiner* — Rachael E Bredefeld
*Assistant Examiner* — Ibrahim D Bori
(74) *Attorney, Agent, or Firm* — Dechert LLP

(57) ABSTRACT

The invention provides tetrahydronaphthyridine and related compounds, pharmaceutical compositions, methods of inhibiting RORγ activity, reducing the amount of IL-17 in a subject, and treating immune disorders and inflammatory disorders using such tetrahydronaphthyridine and related compounds.

28 Claims, No Drawings

(56) References Cited

U.S. PATENT DOCUMENTS

| | | |
|---|---|---|
| 2007/0281922 A1 | 12/2007 | Liu et al. |
| 2008/0027100 A1 | 1/2008 | McCormick et al. |
| 2008/0058386 A1 | 3/2008 | Liou et al. |
| 2008/0153805 A1 | 6/2008 | Ceccarelli et al. |
| 2008/0305169 A1 | 12/2008 | Miki et al. |
| 2009/0005410 A1 | 1/2009 | Charvat et al. |
| 2009/0075973 A1 | 3/2009 | Newcom et al. |
| 2009/0247502 A1 | 10/2009 | Newcom et al. |
| 2009/0275586 A1 | 11/2009 | Govek et al. |
| 2010/0022515 A1 | 1/2010 | Alper et al. |
| 2010/0130484 A1 | 5/2010 | Ackermann et al. |
| 2010/0234340 A1 | 9/2010 | Schunk et al. |
| 2011/0053915 A1 | 3/2011 | Ivaschenko et al. |
| 2011/0112070 A1 | 5/2011 | Baldwin et al. |
| 2011/0118246 A1 | 5/2011 | Baldwin et al. |
| 2011/0130384 A1 | 6/2011 | Setoh et al. |
| 2011/0178063 A1 | 7/2011 | Baldwin et al. |
| 2014/0088094 A1 | 3/2014 | Glick et al. |
| 2015/0111877 A1 | 4/2015 | Aicher et al. |
| 2015/0126493 A1 | 5/2015 | Aicher et al. |
| 2016/0304476 A1 | 10/2016 | Aicher et al. |
| 2016/0304505 A1 | 10/2016 | Aicher et al. |
| 2016/0311787 A1 | 10/2016 | Aicher et al. |

FOREIGN PATENT DOCUMENTS

| | | |
|---|---|---|
| EP | 2181710 A1 | 5/2010 |
| JP | 6-250441 A | 9/1994 |
| JP | 2004307487 A | 11/2004 |
| WO | WO-92/13856 A1 | 8/1992 |
| WO | WO-97/01561 A1 | 1/1997 |
| WO | WO-97/48697 A1 | 12/1997 |
| WO | WO-98/22457 A1 | 5/1998 |
| WO | WO-00/17202 A1 | 3/2000 |
| WO | WO-01/012600 A1 | 2/2001 |
| WO | WO-02/100819 A1 | 12/2002 |
| WO | WO-03/014075 A2 | 2/2003 |
| WO | WO-2004/056830 A1 | 7/2004 |
| WO | WO-05/028434 A2 | 3/2005 |
| WO | WO-2005/037834 A1 | 4/2005 |
| WO | WO-2006/007486 A2 | 1/2006 |
| WO | WO-2006/057460 A1 | 6/2006 |
| WO | WO-2007/024944 A1 | 3/2007 |
| WO | WO-2007/031429 A1 | 3/2007 |
| WO | WO-2007/093507 A1 | 8/2007 |
| WO | WO-2007/125405 A2 | 11/2007 |
| WO | WO-2007/138998 A1 | 12/2007 |
| WO | WO-2008/003703 A1 | 1/2008 |
| WO | WO-2008/045664 A2 | 4/2008 |
| WO | WO-2008/062740 A1 | 5/2008 |
| WO | WO-2008/074692 A1 | 6/2008 |
| WO | WO-2008/097428 A2 | 8/2008 |
| WO | WO-2008/150827 A1 | 12/2008 |
| WO | WO-2009/032667 A1 | 3/2009 |
| WO | WO-2009/035997 A2 | 3/2009 |
| WO | WO-2009/077956 A1 | 6/2009 |
| WO | WO-2009/147187 A1 | 12/2009 |
| WO | WO-2009/149819 A1 | 12/2009 |
| WO | WO-2009/149820 A1 | 12/2009 |
| WO | WO-2009/157196 A1 | 12/2009 |
| WO | WO-2010/017827 A1 | 2/2010 |
| WO | WO-2010/038901 A1 | 4/2010 |
| WO | WO-2010/057101 A2 | 5/2010 |
| WO | WO-2010/059602 A2 | 5/2010 |
| WO | WO-2010/071853 A1 | 6/2010 |
| WO | WO-2010/102958 A1 | 9/2010 |
| WO | WO-2010/117425 A1 | 10/2010 |
| WO | WO-2010/123139 A1 | 10/2010 |
| WO | WO-2010/125082 A1 | 11/2010 |
| WO | WO-2011/019634 A2 | 2/2011 |
| WO | WO-2011/059839 A1 | 5/2011 |
| WO | WO-2011/067364 A1 | 6/2011 |
| WO | WO-2011/067365 A1 | 6/2011 |
| WO | WO-2011/067366 A1 | 6/2011 |
| WO | WO-2011/109059 A1 | 9/2011 |
| WO | WO-2012/032065 A1 | 3/2012 |
| WO | WO-2012/032067 A1 | 3/2012 |
| WO | WO-2012/037108 A1 | 3/2012 |
| WO | WO-2012/064744 A2 | 5/2012 |
| WO | WO-2012/139775 A1 | 10/2012 |
| WO | WO-2013/169704 A2 | 11/2013 |

OTHER PUBLICATIONS

Figueroa-Vega et al., "Increased Circulating Pro-Inflammatory Cytokines and Th17 Lymphocytes in Hashimoto's Thyroiditis," 95(2) J. Clin. Endocrinol. Metab. 953-62 (2010).

Gennaro (ed.), Remington: The Science and Practice of Pharmacy, 20th edition (2000).

He et al., "RORγt, a Novel Isoform of an Orphan Receptor, Negatively Regulates Fas Ligand Expression and IL-2 Production in T Cells," 9 Immunity 797-806 (1998).

Hirose et al., "RORγ: the third member of ROR/RZR orphan receptor subfamily that is highly expressed in skeletal muscle," 205 Biochem. Biophys. Res. Comm. 1976-83 (1994).

Hueber et al., "Cutting Edge: Mast Cells Express IL-17A in Rheumatoid Arthritis Synovium," 184 J. Immunol. 3336-40 (2010).

Ivanov et al., "The Orphan Nuclear Receptor RORγt Directs the Differentiation Program of Proinflammatory IL-17+ T Helper Cells," 126 *Cell* 1121-33 (2006).

Jia et al., "The T helper type 17/regulatory T cell imbalance in patients with acute Kawasaki disease," 162 Clin. Exp. Immunol. 131-37 (2010).

Jin et al.,"Structural Basis for Hydroxycholesterols as Natural Ligands of Orphan Nuclear Receptor RORγ," *Mol. Endocrinol.* (2010) vol. 24, No. 5, pp. 923-929.

Kastelein et al., "Discovery and Biology of IL-23 and IL-27: Related but Functionally Distinct Regulators of Inflammation," 25 Annu. Rev. Immunol. 221-42 (2007).

Kurebayashi et al., "Selective LXXLL peptides antagonize transcriptional activation by the retinoid-related orphan receptor RORγ," 315 Biochem. Biophys. Res. Comm. 919-27 (2004).

Louten et al., "Development and function of TH17 cells in health and disease," 123(5) J. Allergy Clin. Immunol. 1004-11 (2009).

Miossec et al., "Interleukin-17 and Type 17 Helper T Cells," 361(9) New Eng. J. Med. 888-98 (2009).

Sun et al., "Requirement for RORγ in Thymocyte Survival and Lymphoid Organ Development," 288 Science 2369-72 (2000).

Sutton et al., "Interleukin-1 and IL-23 Induce Innate IL-17 Production from γδ T Cells, Amplifying Th17 Responses and Autoimmunity," 31 Immunity 331-41 (2009).

Wang et al., "Identification of SR1078, a Synthetic Agonist for the Orphan Nuclear Receptors RORα and RORγ," 5(11) ACS Chem. Biol. 1029-34 (2010).

Wang et al., "Modulation of Retinoic Acid Receptor-related Orphan Receptor α and γ Activity by 7-Oxygenated Sterol Ligands," *J. Biol. Chem.* (2010) vol. 285, No. 7, pp. 5013-5025.

Xie et al., "RORγt Recruits Steroid Receptor Coactivators to Ensure Thymocyte Survival," 175(6) J. Immunol. 3800-09 (2005).

Yang et al., "T Helper 17 Lineage Differentiation is programmed by Orphan Nuclear Receptors RORα and RORγ," 28 Immunity 29-39 (2008).

André et al., "Disruption of retinoid-related orphan receptor β changes circadian behaviour, causes retinal degeneration and leads to vacillans phenotype in mice," 17(14) The EMBO J. 3867-77 (1998).

Becker-André et al., "Identification of nuclear receptor mRNAs by RT-PCR amplification of conserved zinc-finger motif sequences," 194(3) Biochem. Biophys. Res. Comm. 1371-79 (1993).

Burris et al., "Targeting Orphan Nuclear Receptors for Treatment of Metabolic Diseases and Autoimmunity," 19(1) Chem. Biol. 51-59 (2012).

Cai et al., "Pivotal Role of Dermal IL-17-Producing γδT Cells in Skin Inflammation", Immunity (2011) vol. 35, pp. 596-610.

Carlberg et al., "RZRs, a new family of retinoid-related orphan receptors that function as both monomers and homodimers," 8 Mol. Endocrinol. 757-70 (1994).

(56) References Cited

OTHER PUBLICATIONS

D. van der Heijde, et al., "Secukinumab Provides Significant and Sustained Inhibition of Joint Structural Damage in a Phase III Study of Active Psoriatic Arthritis" Arthritis & Rheumatology Brief Report, Accepted Article DOI: 10.1002/art.39685, American College of Rheumatology, (2016) pp. 1-27.
Baeten, et al., "Secukinumab, an Interleukin-17A Inhibitor, in Ankylosing Spondylitis", The New England Journal of Medicine, (2015) vol. 373, pp. 2534-2548.
Dussault et al., "Orphan nuclear receptor RORα-deficient mice display the cerebellar defects of staggerer," 70 Mech. Develop. 147-53 (1998).
Giguere et al., "Isoform-specific amino-terminal domains dictate DNA-binding properties of RORα, a novel family of orphan hormone nuclear receptors," 8 Genes & Develop. 538-53 (1994).
Huh et al., "Small molecule inhibitors of RORγt: Targeting Th17 cells and other applications," 42 Eur. J. Immunol. 2232-2237 (2012).
Krueger, "A welcome surprise in psoriasis", Nature Medicine, (2012) vol. 18, No. 12, pp. 1750-1751.
Leonardi, et al., "Anti-Interleukin-17 Monoclonal Antibody Ixekizumab in Chronic Plaque Psoriasis", The New England Journal of Medicine, (2012) vol. 366, Iss. 13, pp. 1-10.
Martinez, "Th17-biased RORγt transgenic mice become susceptible to a viral model for multiple sclerosis", Brain, Behavior, and Immunity, (2014) vol. 43, pp. 86-97.
Medvedev et al., "Cloning of a cDNA encoding the murine orphan receptor RZR/RORγ and characterization of its response element," 181 Gene 199-206 (1996).
Nakajima, et al., "IL-17A as an Inducer for Th2 Immune Responses in Murine Atopic Dermatitis Models", Journal of Investigative Dermatology, (2014) vol. 134, pp. 2122-2130.
Ortiz et al., "TOR: a new orphan receptor expressed in the thymus that can modulate retinoid and thyroid hormone signals," 9 Mol. Endocrinol. 1679-91 (1995).
Papp, et al. "Brodalumab, an Anti-Interleukin-17-Receptor Antibody for Psoriasis", The New England Journal of Medicine, (2012) vol. 366, Iss. 13, 9 pgs.
Skepner, J. et al. "Pharmacologic Inhibition of RORγt Regulates Th17 Signature Gene Expression and Suppresses Cutaneous Inflammation In Vivo," downloaded from the Internet at http://www.jimmunol.org/cgi/doi/10.4049/jimmunol.1302190 on Feb. 17, 2014, published in final edited form in *J. Immunol.* (2014) vol. 192, No. 6, pp. 2564-2575.
Smith, "The Bench-to-Bedside Story of IL-17 and the Therapeutic Efficacy of its Targeting in Spondyloarthritis", Curr Rheumatol Rep. (2016) vol. 18, pp. 1-10.
Solt et al., "Action of RORs and their ligands in (patho)physiology," 23(12) Trends in Endocrinology and Metabolism. 619-627 (2012).
Tlustochowicz, et al. "Efficacy and Safety of Subcutaneous and Intravenous Loading Dose Regimens of Secukinumab in Patients with Active Rheumatoid Arthritis: Results from a Randomized Phase II Study" The Journal of Rheumatology, (2016) vol. 43, No. 3, pp. 495-503.
Villey et al., "RORγT, a thymus-specific isoform of the orphan nuclear receptor RORγ/TOR, is up-regulated by signaling through the pre-T cell receptor and binds to the TEA promoter," 29 Eur. J. Immunol. 4072-80 (1999).
Wiesenberg et al., "Transcriptional activation of the nuclear receptor RZRα by the pineal gland hormone melatonin and identification of CGP 52608 as a synthetic ligand," 23(3) Nucl. Acids Res. 327-33 (1995).
Xiao, et al., "Small-Molecule RORγt Antagonists Inhibit T Helper 17 Cell Transcriptional Network by Divergent Mechanisms", Immunity (2014) vol. 40, pp. 477-489.
Arisawa et al., "Development of Isomerization and Cycloisomerization with Use of a Ruthenium Hydride with N-Heterocyclic Carbene and Its Application to the Synthesis of Heterocycles," 71 J. Org. Chem. 4255-61 (2006).
Berge et al., "Pharmaceutical salts," 66(1) J. Pharm. Sci. 1-19 (1977).
Bhagawanth et al., "Room-Temperature PD-Catalyzed Amidation of Aryl Bromides Using tert-Butyl Carbamate," 74 J. Org. Chem. 4634-37 (2009).
Boger et al., "Regiocontrolled Nucleophilic Addition to Selectively Activated p-Quinone Diimines: Alternative Preparation of a Key Intermediate Employed in the Preparation of the CC-1065 Left-Hand Subunit," 55 J. Org. Chem. 1379-90 (1990).
Carroll et al., "Synthesis, Nicotinic Acetylcholine Receptor Binding, and Antinociceptive Properties of 2-exo-2-(2',3'-Disubstituted 5'-pyridinyl)-y-azabicyclo[2.2.1]heptanes: Epibatidine Analogues," 45 J. Med. Chem. 4755-61 (2002).
Chang et al., "7-Aroyl-aminoindoline-1-sulfonamides as a Novel Class of Potent Antitubulin Agents," 49 J. Med. Chem. 6656-59 (2006).
Colbon et al., "Double Arylation of Allyl Alcohol via a One-Pot Heck Arylation—Isomerization—Acylation Cascade," 13 Org. Lett. 5456-59 (2011).
De et al., Methods in Molecular Biology 1184, second edition, Human Press (2014).
Gould, "Salt selection for basic drugs," 33 Int'l J. Pharmaceutics 201-217 (1986).
Grasa et al., "Amination Reactions of Aryl Halides with Nitrogen-Containing Reagents Mediated by Palladium/Imidazolium Salt Systems," 66 J. Org. Chem. 7729-37 (2001).
Greene & Wuts, Protective Groups in Organic Synthesis, 2d Edition (1991).
Guimond et al., "Rhodium(III)-Catalyzed Isoquinolone Synthesis: The N-O Bond as a Handle for C-N Bond Formation and Catalyst Turnover," 132(20) J. Am. Chem. Soc. 6908-09 (2010).
Hanessian et al., "A versatile protocol for the stereocontrolled elaboration of vicinal secondary and tertiary centers of relevance to natural product synthesis," 52(6) J. Org. Chem. 1170-72 (1987).
Hauser et al., "Relative Ease of Cyclization of 2-, 3-, and 4-Aminopyridine Derivatives. Synthesis of Naphthyridines," 15 J. Org. Chem. 1224-32 (1950).
International Search Report and Written Opinion for PCT/US2011/059788 dated May 23, 2012 (23 pages).
International Search Report and Written Opinion for PCT/US2013/039422 dated Oct. 11, 2013 (9 pages).
International Search Report and Written Opinion for PCT/US2013/039839 dated Oct. 18, 2013 (8 pages).
International Search Report and Written Opinion for PCT/US2013/040085 dated Oct. 23, 2013 (9 pages).
Ishikura et al., "An Efficient Synthesis of 3-Heteroarylpyridines via Diethyl-(3-pyridyl)-borane," Synthesis 936-38 (1984).
Jayashree et al., "Design and synthesis of 2-quinolones as antioxidants and antimicrobials: a rational approach," 19 Med. Chem. Res. 193-209 (2010).
Jiang et al., "Synthesis and Cytotoxicity Evaluation of Novel Indolylpyrimidines and Indolylpyrazines as Potential Antitumor Agents," 9 Bioorg. Med. Chem. 1149-54 (2001).
Li et al., "Chemical Libraries via Sequential C-H Functionalization of Phenols," 10 J. Comb. Chem. 170-74 (2008).
Li et al., "Synthesis and Resolution of a Novel Chiral Diamine Ligand and Application to Asymmetric Lithiation-Substitution," 2 Org. Lett. 875-78 (2000).
Liu et al., "1-Sulfonylindazoles as potent and selective 5-HT6 ligands," 19 Bioorg. Med. Chem. Lett. 2413-15 (2009).
Murase et al., "A New Concise Synthesis of Arcyriacyanin A and Its Unique Inhibitory Activity against a Panel of Human Cancer Cell Line," 48(1) Chem. Pharm. Bull. 81-84 (2000).
Ninomiya et al., "Phosphorous in Organic Synthesis—VII: Diphenyl Phosphorazidate (DPPA). A New Convenient Reagent for a Modified Curtius Reaction," 30 Tetrahedron 2151-57 (1975).
Nyrkova et al., "Synthesis of a New Heterocyclic System—3,4-Diazaphenoxazine," 1(9) J. Org. Chem. USSR, 1711-14, translating 1(9) Zh. Org. Khimii, 1688-91 (1965).
Santilli et al., "Synthesis of 5,6,7,8-Tetrahydro-5-oxopyrido[2,3-d]pyrimidine-6-carbonitriles and—6-carboxylic Acid Esters," 12 J. Het. Chem. 311-16 (1975).

(56) References Cited

OTHER PUBLICATIONS

Skraup, "Eine Synthese des Chinolins," 13 Berichte 2086-87 (1880).
Stefko et al., "General and Modular Synthesis of Isomeric 5-Substituted Pyridin-2-yl and 6-Substituted Pyridin-3-yl C-Ribonucleosides Bearing Diverse Alkyl, Aryl, Hetaryl, Amino, Carbamoyl, and Hydroxy Groups," 76 J. Org. Chem. 6619-35 (2011).
STN Columbus, pp. 1-40 (2011).
Takano et al., "A new synthesis of a steroid side chain via stereocontrolled protonation: synthesis of (-)-desmosterol," 14 J. Chem. Soc., Chem. Commun. 760-61 (1983).
van Heerden et al., "Dibutylboron triflate promoted conjugate addition of benzylic and allylic organocopper reagents to chiral α,β-unsaturated N-acyl imidazolidinones" 38(10) Tet. Lett. 182-124 (1997).
Wang et al., "Synthesis of new carbon-11-labeled 7-aroyl-aminoindoline-1-sulfonamides as potential PET agents for imaging of tubulin polymerization in cancers," 51(1) J. Label. Compd. Radiopharm. 6-11 (2008).
Yeh et al., "Practical Cu-catalyzed amination of functionalized heteroaryl halides," 47(34) Tetrahedron Lett. 6011-16 (2006).
Zhu et al., "The Direct Formulation of Functionalized Alkyl(aryl)zinc halides by Oxidative Addition of Highly Reactive Zinc with Organic Halides and Their Reactions with Acid Chlorides, α,β-Unsaturated Ketones, and Allylic, Aryl, and Vinyl Halides," 56 J. Org. Chem. 1445-53 (1991).
International Search Report and Written Opinion for PCT/US2014/071671 dated Apr. 28, 2015 (10 pages).
International Search Report and Written Opinion for PCT/US2014/071663 dated Apr. 17, 2015 (6 pages).
International Search Report and Written Opinion for PCT/US2014/071656 dated Mar. 12, 2015 (8 pages).

* cited by examiner

TETRAHYDRONAPHTHYRIDINE AND RELATED BICYCLIC COMPOUNDS FOR INHIBITION OF RORGAMMA ACTIVITY AND THE TREATMENT OF DISEASE

CROSS REFERENCE TO RELATED APPLICATIONS

This application is a divisional of U.S. patent application Ser. No. 14/398,061, filed Oct. 30, 2014, which is the national stage of International (PCT) Patent Application Serial No. PCT/US2013/039839, filed May 7, 2013, which claims the benefit of and priority to U.S. Provisional Patent Application Ser. No. 61/644,158, filed May 8, 2012; the contents of each of which are hereby incorporated by reference.

FIELD OF THE INVENTION

The invention provides tetrahydronaphthyridine and related compounds, methods of inhibiting RORγ activity and/or reducing the amount of IL-17 in a subject, and therapeutic uses of the tetrahydronaphthyridine and related compounds. In particular, the invention provides 1-sulfonyl-tetrahydronaphthyridine and related compounds, methods of using such compounds to inhibit RORγ activity and/or reduce the amount of IL-17 in a subject, and treat immune disorders and inflammatory disorders.

BACKGROUND OF THE INVENTION

Retinoid-related orphan receptors (ROR) are reported to have an important role in numerous biological processes. See, for example, Dussault et al. in *Mech. Dev.* (1998) vol. 70, 147-153; and Andre et al. in *EMBO J.* (1998) vol. 17, 3867-3877. Scientific investigations relating to each of retinoid-related orphan receptors RORα, RORβ, and RORγ have been described in the literature. See, for example, Hirose et al. in *Biochem. Biophys. Res. Commun.* (1994) vol. 205, 1976-1983; Giguere et al. in *Genes. Dev.* (1994) vol. 8, 538-553; Medvedev et al. in *Gene* (1996) vol. 181, 199-206; Ortiz et al. in *Mol. Endocrinol.* (1995) vol. 9, 1679-1691; Wiesenberg et al. in *Nucleic Acids Res.* (1995) vol. 23, 327-333; Carlberg et al. in *Mol. Endocrinol.* (1994) vol. 8, 757-770; and Becker-Andre et al. in *Biochem. Biophys. Res. Commun.* (1993) vol. 194, 1371-1379. Continuing research in this field is spurred by the promise of developing new therapeutic agents to treat medical disorders associated with retinoid-related orphan receptor activity.

RORγ has been reported to be expressed in high concentration in various tissues, such as thymus, kidney, liver, muscle, and certain fat tissue. See, for example, Hirose et al. in *Biochem. Biophys. Res. Commun.* (1994) vol. 205, 1976-1983; Medvedev et al. in *Gene* (1996) vol. 181, 199-206; Ortiz et al. in *Mol. Endocrinol.* (1995) vol. 9, 1679-1691; and He et al. in *Immunity* (1998) vol. 9, 797-806. Two isoforms of RORγ have been identified and are referred to as γ1 1 and γ2 (also referred to as RORγt). See, for example, He et al. in *Immunity* (1998) vol. 9, 797-806. Expression of the γ2 isoform has been reported to appear in, for example, double-positive thymocytes. See, for example, He et al. in *Immunity* (1998) vol. 9, 797-806; and Villey et al. in *Eur. J. Immunol.* (1999) vol. 29, 4072-4080. RORγt plays a critical role in regulating differentiation of Th17 cells, a subset of T helper lymphocytes. A number of inflammatory cytokines, such as IL-17, IL-22, and IL-23, are synthesized in Th17 cells. These cytokines are important pathogenic factors for many immune and inflammatory diseases. Compounds capable of modulating RORγt activity are contemplated to provide a therapeutic benefit in the treatment of multiple medical disorders, including immune and inflammatory disorders.

Numerous immune and inflammatory disorders continue to afflict millions of patients worldwide. Significant advances have been made in treating these disorders. However, current therapies do not provide satisfactory results for all patients due to, for example, detrimental side effects or insufficient efficacy. Treatments for immune and inflammatory disorders vary depending on the particular medical disorder, and often involve use of immunosuppressive drugs. Surgery (e.g., splenectomy), plasmapheresis, or radiation can be used in certain instances.

One exemplary immune disorder in need of better therapy is psoriasis. Psoriasis is a T cell-mediated inflammatory disease that affects approximately 2% to 3% of adults and has a substantial adverse impact on the quality of life for patients suffering from this disorder. Plaques resulting from psoriasis can be painful and are visually unappealing. Various therapeutics have been developed in an attempt to treat psoriasis. However, the traditional therapies for psoriasis often have toxic adverse effects.

An exemplary inflammatory disorder in need of better treatment is rheumatoid arthritis. This form of arthritis is characterized by inflammation in the synovial membrane and results in destruction of bone. Numerous therapeutics have been developed in an attempt to treat this disorder. Exemplary therapeutics for treating rheumatoid arthritis include glucocorticoids, methotrexate, hydroxychloroquine, sulfasalazine, and leflunomide. However, current therapies are not effective for all patients. Moreover, some patients develop resistance to current therapies.

Accordingly, a need exists for improved treatments for immune disorders and inflammatory disorders. The present invention addresses this need and provides other related advantages.

SUMMARY

The invention provides tetrahydronaphthyridine and related compounds, pharmaceutical compositions, methods of inhibiting RORγ activity and/or reducing the amount of IL-17 in a subject, and methods of treating various medical disorders using such compounds. In particular, one aspect of the invention provides a collection of tetrahydronaphthyridine and related compounds, such as a compound represented by Formula I:

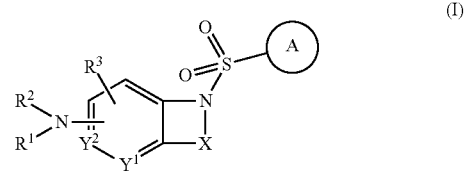

or a pharmaceutically acceptable salt or solvate thereof; wherein the variables are as defined in the detailed description. Further description of additional collections of tetrahydronaphthyridine and related compounds, such as Formulae II-VI, I-A, II-A, and III-A, are described in the detailed description.

Another aspect of the invention provides a method of treating a subject suffering from a medical disorder. The method comprises administering to the subject a therapeutically effective amount of one or more tetrahydronaphthyridine or related compounds described herein, e.g., a compound of Formula I, II, III, IV, V, VI, I-A, II-A, or III-A, wherein Formulae I-VI, I-A, II-A, and III-A, are as described in the detailed description. A large number of disorders can be treated using the tetrahydronaphthyridine and related compounds described herein. For example, the compounds described herein can be used to treat an immune disorder or inflammatory disorder, such as rheumatoid arthritis, psoriasis, chronic graft-versus-host disease, acute graft-versus-host disease, Crohn's disease, inflammatory bowel disease, multiple sclerosis, systemic lupus erythematosus, Celiac Sprue, idiopathic thrombocytopenic thrombotic purpura, myasthenia gravis, Sjogren's syndrome, scleroderma, ulcerative colitis, asthma, epidermal hyperplasia, and other medical disorders described herein. In certain other embodiments, the disorder is rheumatoid arthritis.

Another aspect of the invention provides a method of inhibiting the activity of RORγ. The method comprises exposing a RORγ to an effective amount of one or more tetrahydronaphthyridine or related compounds described herein, e.g., a compound of Formula I, II, III, IV, V, VI, I-A, II-A, or III-A, or a pharmaceutical composition described herein.

Another aspect of the invention provides a method of reducing the amount of IL-17 in a subject. The method comprises administering to a subject an effective amount of one or more tetrahydronaphthyridine or related compounds described herein, e.g., a compound of Formula I, II, III, IV, V, VI, I-A, II-A, or III-A, or a pharmaceutical composition described herein, to reduce the amount of IL-17 in the subject.

DETAILED DESCRIPTION OF THE INVENTION

The invention provides tetrahydronaphthyridine and related compounds, pharmaceutical compositions, methods of inhibiting RORγ activity and/or reducing the amount of IL-17 in a subject, and therapeutic uses of the tetrahydronaphthyridine and related compounds. The practice of the present invention employs, unless otherwise indicated, conventional techniques of organic chemistry, pharmacology, molecular biology (including recombinant techniques), cell biology, biochemistry, and immunology. Such techniques are explained in the literature, such as in "Comprehensive Organic Synthesis" (B. M. Trost & I. Fleming, eds., 1991-1992); "Handbook of experimental immunology" (D. M. Weir & C. C. Blackwell, eds.); "Current protocols in molecular biology" (F. M. Ausubel et al., eds., 1987, and periodic updates); and "Current protocols in immunology" (J. E. Coligan et al., eds., 1991), each of which is herein incorporated by reference in its entirety.

Various aspects of the invention are set forth below in sections; however, aspects of the invention described in one particular section are not to be limited to any particular section. Further, when a variable is not accompanied by a definition, the previous definition of the variable controls.

Definitions

The terms used herein have their ordinary meaning and the meaning of such terms is independent at each occurrence thereof. That notwithstanding and except where stated otherwise, the following definitions apply throughout the specification and claims. Chemical names, common names, and chemical structures may be used interchangeably to describe the same structure. If a chemical compound is referred to using both a chemical structure and a chemical name, and an ambiguity exists between the structure and the name, the structure predominates. These definitions apply regardless of whether a term is used by itself or in combination with other terms, unless otherwise indicated. Hence, the definition of "alkyl" applies to "alkyl" as well as the "alkyl" portions of "hydroxyalkyl," "fluoroalkyl," "—O-alkyl," etc.

The term "alkyl" is art-recognized, and includes saturated aliphatic groups, including straight-chain alkyl groups, branched-chain alkyl groups, cycloalkyl (alicyclic) groups, alkyl substituted cycloalkyl groups, and cycloalkyl substituted alkyl groups. In certain embodiments, a straight chain or branched chain alkyl has about 30 or fewer carbon atoms in its backbone (e.g., $C_1$-$C_{30}$ for straight chain, $C_3$-$C_{30}$ for branched chain), and alternatively, about 20 or fewer. Likewise, cycloalkyls have from about 3 to about 10 carbon atoms in their ring structure, and includes bicycloalkyls such as where two saturated carbocyclic rings are fused together. In certain embodiments, the cycloalkyls have about 5, 6 or 7 carbons in the ring structure. Exemplary alkyl groups include methyl, ethyl, n-propyl, isopropyl, n-butyl, sec-butyl, isobutyl, tert-butyl, cyclopropyl, and cyclobutyl.

The term "alkylene" refers to a diradical of an alkyl group. Exemplary alkylene groups include —$CH_2CH_2$—,

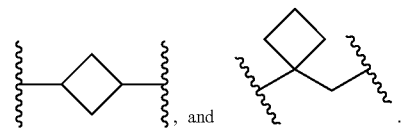

, and

The term "cycloalkylene" refers to a diradical of a cycloalkyl group. Exemplary cycloalkylene groups include

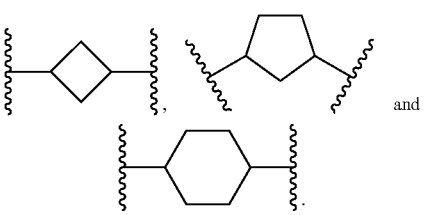

, and

.

The term "haloalkyl" refers to an alkyl group that is substituted with at least one halogen. Exemplary haloalkyl groups include —$CH_2F$, —$CHF_2$, —$CF_3$, —$CH_2CF_3$, —$CF_2CF_3$, and the like.

The term "hydroxyalkyl" refers to an alkyl group that is substituted with at least one hydroxyl group. Exemplary hydroxyl alkyl groups include —$CH_2OH$, —$CH_2CH_2OH$, —$C(H)(OH)C(OH)H_2$, and the like.

The term "aralkyl" refers to an alkyl group substituted with an aryl group. Exemplary aralkyl groups include

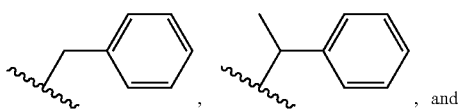

, , and

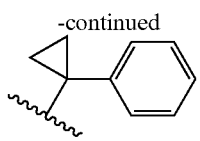

The term "heteroaralkyl" refers to an alkyl group substituted with a heteroaryl group.

The terms "alkenyl" and "alkynyl" are art-recognized and refer to unsaturated aliphatic groups analogous in length and possible substitution to the alkyls described above, but that contain at least one double or triple bond respectively.

The term "aryl" is art-recognized and refers to a carbocyclic aromatic group. Representative aryl groups include phenyl, naphthyl, anthracenyl, and the like. Unless specified otherwise, the aromatic ring may be substituted at one or more ring positions with, for example, halogen, azide, alkyl, aralkyl, alkenyl, alkynyl, cycloalkyl, hydroxyl, alkoxyl, amino, nitro, sulfhydryl, imino, amido, carboxylic acid, —C(O)alkyl, —CO$_2$alkyl, carbonyl, carboxyl, alkylthio, sulfonyl, sulfonamido, sulfonamide, ketone, aldehyde, ester, heterocyclyl, aryl or heteroaryl moieties, —CF$_3$, —CN, or the like. The term "aryl" also includes polycyclic aromatic ring systems having two or more carbocyclic rings in which two or more carbons are common to two adjoining rings (the rings are "fused rings") wherein all of the fused rings are aromatic rings, e.g., in a naphthyl group.

The term "heteroaryl" is art-recognized and refers to aromatic groups that include at least one ring heteroatom. In certain instances, a heteroaryl group contains 1, 2, 3, or 4 ring heteroatoms. Representative examples of heteroaryl groups include pyrrolyl, furanyl, thiophenyl, imidazolyl, oxazolyl, thiazolyl, triazolyl, pyrazolyl, pyridinyl, pyrazinyl, pyridazinyl and pyrimidinyl, and the like. Unless specified otherwise, the heteroaryl ring may be substituted at one or more ring positions with, for example, halogen, azide, alkyl, aralkyl, alkenyl, alkynyl, cycloalkyl, hydroxyl, alkoxyl, amino, nitro, sulfhydryl, imino, amido, carboxylic acid, —C(O)alkyl, —CO$_2$alkyl, carbonyl, carboxyl, alkylthio, sulfonyl, sulfonamido, sulfonamide, ketone, aldehyde, ester, heterocyclyl, aryl or heteroaryl moieties, —CF$_3$, —CN, or the like. The term "heteroaryl" also includes polycyclic aromatic ring systems having two or more rings in which two or more carbons are common to two adjoining rings (the rings are "fused rings") wherein all of the fused rings are heteroaromatic, e.g., in a naphthyridinyl group.

The terms ortho, meta and para are art-recognized and refer to 1,2-, 1,3- and 1,4-disubstituted benzenes, respectively. For example, the names 1,2-dimethylbenzene and ortho-dimethylbenzene are synonymous.

As used herein, the terms "heterocyclic" and "heterocyclyl" represent, for example, an aromatic or nonaromatic ring (e.g., a monocyclic or bicyclic ring) containing one or more heteroatoms. The heteroatoms can be the same or different from each other. Examples of heteroatoms include, but are not limited to nitrogen, oxygen and sulfur. Aromatic and nonaromatic heterocyclic rings are well-known in the art. Some nonlimiting examples of aromatic heterocyclic rings include, but are not limited to, pyridine, pyrimidine, indole, purine, quinoline and isoquinoline. Nonlimiting examples of nonaromatic heterocyclic compounds include, but are not limited to, piperidine, piperazine, morpholine, pyrrolidine and pyrazolidine. Examples of oxygen containing heterocyclic rings include, but are not limited to, furan, oxirane, 2H-pyran, 4H-pyran, 2H-chromene, benzofuran, and 2,3-dihydrobenzo[b][1,4]dioxine. Examples of sulfur-containing heterocyclic rings include, but are not limited to, thiophene, benzothiophene, and parathiazine. Examples of nitrogen containing rings include, but are not limited to, pyrrole, pyrrolidine, pyrazole, pyrazolidine, imidazole, imidazoline, imidazolidine, pyridine, piperidine, pyrazine, piperazine, pyrimidine, indole, purine, benzimidazole, quinoline, isoquinoline, triazole, and triazine. Examples of heterocyclic rings containing two different heteroatoms include, but are not limited to, phenothiazine, morpholine, parathiazine, oxazine, oxazole, thiazine, and thiazole. The heterocyclic ring is optionally further substituted at one or more ring positions with, for example, halogen, azide, alkyl, aralkyl, alkenyl, alkynyl, cycloalkyl, hydroxyl, alkoxyl, amino, nitro, sulfhydryl, imino, amido, carboxylic acid, —C(O)alkyl, —CO$_2$alkyl, carbonyl, carboxyl, alkylthio, sulfonyl, sulfonamido, sulfonamide, ketone, aldehyde, ester, heterocyclyl, aryl or heteroaryl moieties, —CF$_3$, —CN, or the like. In certain embodiments, the heterocyclyl group is a 3-7 membered ring that, unless specified otherwise, is substituted or unsubstituted.

The term "heterocycloalkyl" refers to a saturated heterocyclyl group having, for example, 3-7 ring atoms.

The terms "amine" and "amino" are art-recognized and refer to both unsubstituted and substituted amines, e.g., a moiety that may be represented by the general formulas:

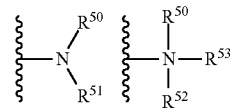

wherein $R^{50}$, $R^{51}$, $R^{52}$ and $R^{53}$ each independently represent a hydrogen, an alkyl, an alkenyl, —(CH$_2$)$_m$—$R^{61}$, or $R^{50}$ and $R^{51}$, taken together with the N atom to which they are attached complete a heterocycle having from 4 to 8 atoms in the ring structure; $R^{61}$ represents an aryl, a cycloalkyl, a cycloalkenyl, a heterocycle or a polycycle; and m is zero or an integer in the range of 1 to 8. In certain embodiments, only one of $R^{50}$ or $R^{51}$ may be a carbonyl, e.g., $R^{50}$, $R^{51}$ and the nitrogen together do not form an imide. In other embodiments, $R^{50}$ and $R^{51}$ (and optionally $R^{52}$) each independently represent a hydrogen, an alkyl, an alkenyl, or —(CH$_2$)$_m$—$R^{61}$.

The terms "alkoxyl" or "alkoxy" are art-recognized and refer to an alkyl group, as defined above, having an oxygen radical attached thereto. Representative alkoxyl groups include methoxy, ethoxy, propyloxy, tert-butoxy and the like. An "ether" is two hydrocarbons covalently linked by an oxygen. Accordingly, the substituent of an alkyl that renders that alkyl an ether is or resembles an alkoxyl, such as may be represented by one of —O-alkyl, —O-alkenyl, —O-alkynyl, and —O—(CH$_2$)$_m$—$R^{61}$, where m and $R^{61}$ are described above.

The term "oxo" is art-recognized and refers to a "=O" substituent. For example, a cyclopentane substituted with an oxo group is cyclopentanone.

The symbol "⌇" indicates a point of attachment.

The term "substituted" means that one or more hydrogens on the atoms of the designated group are replaced with a selection from the indicated group, provided that the atoms' normal valencies under the existing circumstances are not exceeded, and that the substitution results in a stable compound. Combinations of substituents and/or variables are permissible only if such combinations result in stable compounds. The terms "stable compound" or "stable structure"

refer to a compound that is sufficiently robust to survive isolation to a useful degree of purity from a reaction mixture, and formulation into an efficacious therapeutic agent.

When any substituent or variable occurs more than one time in any constituent or the compound of the invention, its definition on each occurrence is independent of its definition at every other occurrence, unless otherwise indicated.

It should also be noted that any carbon as well as heteroatom with unsatisfied valences in the text, schemes, examples and tables herein is assumed to have the sufficient number of hydrogen atom(s) to satisfy the valences.

One or more compounds of the invention may exist in unsolvated as well as solvated forms with pharmaceutically acceptable solvents such as water, ethanol, and the like, and it is intended that the invention embrace both solvated and unsolvated forms. "Solvate" means a physical association of a compound of this invention with one or more solvent molecules. This physical association involves varying degrees of ionic and covalent bonding, including hydrogen bonding. In certain instances the solvate will be capable of isolation, for example when one or more solvent molecules are incorporated in the crystal lattice of the crystalline solid. "Solvate" encompasses both solution-phase and isolatable solvates. Non-limiting examples of suitable solvates include ethanolates, methanolates, and the like. "Hydrate" is a solvate wherein the solvent molecule is $H_2O$.

Certain compounds contained in compositions of the present invention may exist in particular geometric or stereoisomeric forms. Further, certain compounds described herein may be optically active. The present invention contemplates all such compounds, including cis- and trans-isomers, R- and S-enantiomers, diastereomers, (D)-isomers, (L)-isomers, the racemic mixtures thereof, and other mixtures thereof, as falling within the scope of the invention. The compounds may contain one or more stereogenic centers. For example, asymmetric carbon atoms may be present in a substituent such as an alkyl group. All such isomers, as well as mixtures thereof, are intended to be included in this invention, such as, for example, racemic mixtures, single enantiomers, diastereomeric mixtures and individual diastereomers. Additional asymmetric centers may be present depending upon the nature of the various substituents on the molecule. Each such asymmetric center will independently produce two optical isomers, and it is intended that all of the possible optical isomers, diastereomers in mixtures, and pure or partially purified compounds are included within the ambit of this invention.

Diastereomeric mixtures can be separated into their individual diastereomers on the basis of their physical chemical differences by methods known to those skilled in the art, such as, for example, by chromatography and/or fractional crystallization. Enantiomers can be separated by converting the enantiomeric mixture into a diastereomeric mixture by reaction with an appropriate optically active compound (e.g., chiral auxiliary such as a chiral alcohol or Mosher's acid chloride), separating the diastereomers and converting (e.g., hydrolyzing) the individual diastereomers to the corresponding pure enantiomers. Alternatively, a particular enantiomer of a compound of the present invention may be prepared by asymmetric synthesis. Still further, where the molecule contains a basic functional group (such as amino) or an acidic functional group (such as carboxylic acid) diastereomeric salts are formed with an appropriate optically-active acid or base, followed by resolution of the diastereomers thus formed by fractional crystallization or chromatographic means known in the art, and subsequent recovery of the pure enantiomers.

Individual stereoisomers of the compounds of the invention may, for example, be substantially free of other isomers, or may be admixed, for example, as racemates or with all other, or other selected, stereoisomers. Chiral center(s) in a compound of the present invention can have the S or R configuration as defined by the *IUPAC* 1974 Recommendations. Further, to the extent a compound described herein may exist as a atropisomer (e.g., substituted biaryls), all forms of such atropisomer are considered part of this invention.

As used herein, the terms "subject" and "patient" are used interchangeable and refer to organisms to be treated by the methods of the present invention. Such organisms preferably include, but are not limited to, mammals (e.g., murines, simians, equines, bovines, porcines, canines, felines, and the like), and most preferably includes humans.

The term "$EC_{50}$" is art-recognized and refers to the concentration of a compound that is required for 50% maximal effect.

As used herein, the term "effective amount" refers to the amount of a compound sufficient to effect beneficial or desired results (e.g., a therapeutic, ameliorative, inhibitory or preventative result). An effective amount can be administered in one or more administrations, applications or dosages and is not intended to be limited to a particular formulation or administration route. As used herein, the term "treating" includes any effect, e.g., lessening, reducing, modulating, ameliorating or eliminating, that results in the improvement of the condition, disease, disorder, and the like, or ameliorating a symptom thereof.

As used herein, the term "pharmaceutical composition" refers to the combination of an active agent with a carrier, inert or active, making the composition especially suitable for diagnostic or therapeutic use in vivo or ex vivo.

As used herein, the term "pharmaceutically acceptable carrier" refers to any of the standard pharmaceutical carriers, such as a phosphate buffered saline solution, water, emulsions (e.g., such as an oil/water or water/oil emulsions), and various types of wetting agents. The compositions also can include stabilizers and preservatives. For examples of carriers, stabilizers and adjuvants. (See, e.g., Martin, Remington's Pharmaceutical Sciences, 15th Ed., Mack Publ. Co., Easton, Pa. [1975]).

As used herein, the term "pharmaceutically acceptable salt" refers to any pharmaceutically acceptable salt (e.g., acid or base) of a compound of the present invention which, upon administration to a subject, is capable of providing a compound of this invention or an active metabolite or residue thereof. As is known to those of skill in the art, "salts" of the compounds of the present invention may be derived from inorganic or organic acids and bases. Examples of acids include, but are not limited to, hydrochloric, hydrobromic, sulfuric, nitric, perchloric, fumaric, maleic, phosphoric, glycolic, lactic, salicylic, succinic, toluene-p-sulfonic, tartaric, acetic, citric, methanesulfonic, ethanesulfonic, formic, benzoic, malonic, naphthalene-2-sulfonic, benzenesulfonic acid, and the like. Other acids, such as oxalic, while not in themselves pharmaceutically acceptable, may be employed in the preparation of salts useful as intermediates in obtaining the compounds of the invention and their pharmaceutically acceptable acid addition salts.

Examples of bases include, but are not limited to, alkali metals (e.g., sodium) hydroxides, alkaline earth metals (e.g., magnesium), hydroxides, ammonia, and compounds of formula $NW_4^+$, wherein W is $C_{1-4}$ alkyl, and the like.

Examples of salts include, but are not limited to: acetate, adipate, alginate, aspartate, benzoate, benzenesulfonate, bisulfate, butyrate, citrate, camphorate, camphorsulfonate, cyclopentanepropionate, digluconate, dodecylsulfate, ethanesulfonate, fumarate, flucoheptanoate, glycerophosphate, hemisulfate, heptanoate, hexanoate, hydrochloride, hydrobromide, hydroiodide, 2-hydroxyethanesulfonate, lactate, maleate, methanesulfonate, 2-naphthalenesulfonate, nicotinate, oxalate, palmoate, pectinate, persulfate, phenylpropionate, picrate, pivalate, propionate, succinate, tartrate, thiocyanate, tosylate (also known as toluenesulfonate), undecanoate, and the like. Other examples of salts include anions of the compounds of the present invention compounded with a suitable cation such as $Na^+$, $NH_{4+}$, and $NW_{4-}$ (wherein W is a $C_{1-4}$ alkyl group), and the like. Further examples of salts include, but are not limited to: ascorbate, borate, nitrate, phosphate, salicylate, and sulfate. Further, acids which are generally considered suitable for the formation of pharmaceutically useful salts from basic pharmaceutical compounds are discussed, for example, by P. Stahl et al., Camille G. (eds.) *Handbook of Pharmaceutical Salts. Properties, Selection and Use*. (2002) Zurich: Wiley-VCH; S. Berge et al., *Journal of Pharmaceutical Sciences* (1977) 66(1) 1-19; P. Gould, *International J. of Pharmaceutics* (1986) 33 201-217; Anderson et al., *The Practice of Medicinal Chemistry* (1996), Academic Press, New York; and in *The Orange Book* (Food & Drug Administration, Washington, D.C. on their website). These disclosures are incorporated herein by reference.

Additional exemplary basic salts include, but are not limited to: ammonium salts, alkali metal salts such as sodium, lithium, and potassium salts, alkaline earth metal salts such as calcium and magnesium salts, salts with organic bases (for example, organic amines) such as dicyclohexylamines, t-butyl amines, and salts with amino acids such as arginine, lysine and the like. Basic nitrogen-containing groups may be quarternized with agents such as lower alkyl halides (e.g., methyl, ethyl, and butyl chlorides, bromides and iodides), dialkyl sulfates (e.g., dimethyl, diethyl, and dibutyl sulfates), long chain halides (e.g., decyl, lauryl, and stearyl chlorides, bromides and iodides), aralkyl halides (e.g., benzyl and phenethyl bromides), and others.

For therapeutic use, salts of the compounds of the present invention are contemplated as being pharmaceutically acceptable. However, salts of acids and bases that are non-pharmaceutically acceptable may also find use, for example, in the preparation or purification of a pharmaceutically acceptable compound.

In addition, when a compound of the invention contains both a basic moiety (such as, but not limited to, a pyridine or imidazole) and an acidic moiety (such as, but not limited to, a carboxylic acid) zwitterions ("inner salts") may be formed. Such acidic and basic salts used within the scope of the invention are pharmaceutically acceptable (i.e., non-toxic, physiologically acceptable) salts. Such salts of the compounds of the invention may be formed, for example, by reacting a compound of the invention with an amount of acid or base, such as an equivalent amount, in a medium such as one in which the salt precipitates or in an aqueous medium followed by lyophilization.

The present invention includes the compounds of the invention in all their isolated forms (such as any solvates, hydrates, stereoisomers, and tautomers thereof). Further, the invention includes compounds in which one or more of the atoms may be artificially enriched in a particular isotope having the same atomic number, but an atomic mass or mass number different from the atomic mass or mass number predominantly found in nature. The present invention is meant to include all suitable isotopic variations of the compounds of the invention. For example, different isotopic forms of hydrogen (H) include protium ($^1H$) and deuterium ($^2H$). Protium is the predominant hydrogen isotope found in nature. Enriching for deuterium may afford certain therapeutic advantages, such as increasing in vivo half-life or reducing dosage requirements, or may provide a compound useful as a standard for characterization of biological samples. Isotopically-enriched compounds can be prepared without undue experimentation by conventional techniques known to those skilled in the art or by processes analogous to those described in the Schemes and Examples herein using appropriate isotopically-enriched reagents and/or intermediates.

The term "SEA Syndrome" refers to Seronegativity, Enthesopathy, Arthropathy Syndrome.

Throughout the description, where compositions are described as having, including, or comprising specific components, or where processes and methods are described as having, including, or comprising specific steps, it is contemplated that, additionally, there are compositions of the present invention that consist essentially of, or consist of, the recited components, and that there are processes and methods according to the present invention that consist essentially of, or consist of, the recited processing steps.

The terms "a" and "an" as used herein mean "one or more" and include the plural unless the context is inappropriate.

The abbreviation "THF" is art-recognized and refers to tetrahydrofuran. The abbreviation "DCM" is art-recognized and refers to dichloromethane. The abbreviation "DMF" is art-recognized and refers to dimethylformamide. The abbreviation "DMA" is art-recognized and refers to dimethylacetamide. The abbreviation "DTT" is art-recognized and refers to dithiothreitol. The abbreviation "EDTA" is art-recognized and refers to ethylenediaminetetraacetic acid. The abbreviation "TFA" is art-recognized and refers to trifluoroacetic acid.

As a general matter, compositions specifying a percentage are by weight unless otherwise specified.

I. Tetrahydronaphthyridine and Related Compounds

One aspect of the invention provides a compound represented by Formula I:

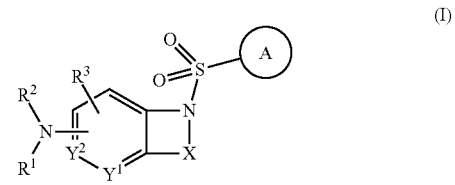

or a pharmaceutically acceptable salt or solvate thereof; wherein:

A is aryl, aralkyl, heteroaryl, cycloalkyl, or heterocloalkyl; each of which is optionally substituted with 1, 2, or 3 substituents independently selected from the group consisting of halogen, hydroxyl, $C_{1-8}$alkyl, $C_{1-6}$haloalkyl, $C_{1-6}$hydroxyalkyl, $C_{1-6}$alkoxy, $C_{1-6}$haloalkoxy, —N($R^4$)($R^5$), —CO$_2$R$^6$, —C(O)R$^6$, —CN, —C$_{1-4}$alkylene-C$_{1-4}$alkoxy, —C$_{1-4}$alkylene-N($R^4$)($R^5$), —C$_{1-4}$alkylene-CO$_2$R$^6$, —O—C$_{1-6}$alkylene-N($R^4$)($R^5$), —N($R^4$)C(O)—C$_{1-6}$alkylene-N($R^4$)($R^5$), —S(O)$_p$C$_{1-6}$alkyl, —SO$_2$N($R^4$)($R^5$), —N($R^4$)SO$_2$(C$_{1-6}$alkyl), —C(O)N($R^4$)($R^5$), and —N($R^4$)C(O)N($R^4$)($R^5$);

X is —O—[C(R⁶)(R⁷)]—[C(R⁶)₂]ₘ-ψ, —O—C(R⁶)₂—C(R⁶)(R⁷)—C(R⁶)₂-ψ, —O—C(R⁶)₂—C(R⁶)(R⁷)-ψ, —C(R⁶)₂—[C(R⁶)(R⁷)]—[C(R⁶)₂]ₘ-ψ, —C(O)—[C(R⁶)(R⁷)]—[C(R⁶)₂]ₘ-ψ, —C(R⁶)₂—N(R⁸)—[C(R⁶)(R⁷)]—[C(R⁶)₂]ₘ-ψ, —C(R⁶)=N-ψ, —C(R⁶)₂C(R⁶)=N-ψ, —N=C(R⁶)-ψ, or —N=C(R⁶)C(R⁶)₂-ψ; wherein ψ is a bond to the sulfonamide ring nitrogen atom in Formula I;

Y¹ and Y² are each independently C(R³) or N, provided that at least one of Y¹ and Y² is N;

R¹ is hydrogen or C₁₋₆alkyl;

R² is hydrogen, —C(O)-aryl, —C(O)-aralkyl, —C(O)—[C(R⁶)₂]ₘ-cycloalkyl, —C(O)—[C(R⁶)₂]ₘ-heterocyclyl, —C(O)—C₁₋₈alkyl, —C(O)—C₁₋₆alkylene-C₁₋₆alkoxyl, —C(O)—C₁₋₆alkylene-cycloalkyl, or —C(O)—C₁₋₆alkylene-heterocycloalkyl; each of which is optionally substituted with 1, 2, or 3 substituents independently selected from the group consisting of halogen, hydroxyl, C₁₋₆alkoxy, C₁₋₆haloalkoxy, C₁₋₆alkyl, C₁₋₆haloalkyl, —N(R⁴)(R⁵), —CN, —CO₂—C₁₋₆alkyl, —C(O)—C₁₋₆alkyl, —C(O)N(R⁴)(R⁵), —S(O)ₚC₁₋₆alkyl, —SO₂N(R⁴)(R⁵), and —N(R⁴)SO₂(C₁₋₆alkyl);

R³ represents independently for each occurrence hydrogen, halogen, or C₁₋₆alkyl;

R⁴ and R⁵ each represent independently for each occurrence hydrogen or C₁₋₆alkyl; or R⁴ and R⁵ taken together with the nitrogen atom to which they are attached form a 3-7 membered heterocyclic ring;

R⁶ represents independently for each occurrence hydrogen or C₁₋₆alkyl;

R⁷ is hydrogen, hydroxyl, C₁₋₆hydroxyalkyl, C₁₋₆alkyl, C₁₋₆haloalkyl, —CO₂R⁶, C₁₋₆alkylene-CO₂R⁶, C₁₋₄hydroxyalkylene-CO₂R⁶, —N(R⁴)(R⁵), C₁₋₆alkylene-N(R⁴)(R⁵), C₁₋₆hydroxyalkylene-N(R⁴)(R⁵), —N(R⁴)C(O)R⁹, C₁₋₆alkylene-N(R⁴)C(O)R⁹, C₁₋₆alkylene-C(O)N(R⁴)(R⁵), —N(R⁴)CO₂—C₁₋₆alkyl, or C₁₋₆alkylene-N(R⁴)(C(O)N(R⁴)(R⁵); or R⁷ is heterocycloalkyl or C₁₋₄alkylene-heterocycloalkyl, wherein the heterocycloalkyl is optionally substituted with 1, 2, or 3 substituents independently selected from the group consisting of oxo, halogen, hydroxyl, C₁₋₆alkyl, C₁₋₆haloalkyl, C₁₋₆hydroxyalkyl, C₁₋₆alkoxy, and C₁₋₆haloalkoxy;

R⁸ is hydrogen, C₁₋₆alkyl, or —C(O)—C₁₋₆alkyl;

R⁹ is hydrogen, C₁₋₆alkyl, C₁₋₆hydroxyalkyl, N(R⁴)(R⁵), C₁₋₆alkylene N(R⁴)(R⁵), or C₁₋₆alkylene N(R⁴)C(O)—C₁₋₆alkyl; each of which is optionally substituted with 1, 2, or 3 halogen, hydroxyl or amino; and m and p each represent independently for each occurrence 0, 1, or 2.

Another aspect of the invention provides a compound represented by Formula I:

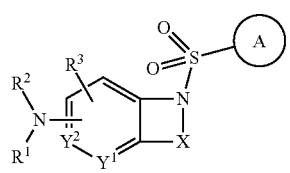

(I)

or a pharmaceutically acceptable salt or solvate thereof; wherein:

A is aryl, aralkyl, heteroaryl, cycloalkyl, or heterocycloalkyl; each of which is optionally substituted with 1, 2, or 3 substituents independently selected from the group consisting of halogen, hydroxyl, C₁₋₈alkyl, C₁₋₆haloalkyl, C₁₋₆hydroxyalkyl, C₁₋₆alkoxy, C₁₋₆haloalkoxy, —N(R⁴)(R⁵), —CO₂R⁶, —C(O)R⁶, —CN, —C₁₋₄alkylene-C₁₋₄alkoxy, —C₁₋₄alkylene-N(R⁴)(R⁵), —C₁₋₄alkylene-CO₂R⁶, —O—C₁₋₆alkylene-N(R⁴)(R⁵), —N(R⁴)C(O)—C₁₋₆alkylene-N(R⁴)(R⁵), —S(O)ₚC₁₋₆alkyl, —SO₂N(R⁴)(R⁵), —N(R⁴)SO₂(C₁₋₆alkyl), —C(O)N(R⁴)(R⁵), and —N(R⁴)C(O)N(R⁴)(R⁵);

X is —O—[C(R⁶)(R⁷)]—[C(R⁶)₂]ₘ-ψ, —O—C(R⁶)₂—C(R⁶)(R⁷)—C(R⁶)₂-ψ, —O—C(R⁶)₂—C(R⁶)(R⁷)-ψ, —C(R⁶)₂—[C(R⁶)(R⁷)]—[C(R⁶)₂]ₘ-ψ, —C(O)—[C(R⁶)(R⁷)]—[C(R⁶)₂]ₘ-ψ, —C(R⁶)₂—N(R⁸)—[C(R⁶)(R⁷)]—[C(R⁶)₂]ₘ-ψ, —C(R⁶)=N-ψ, —C(R⁶)₂C(R⁶)=N-ψ, —N=C(R⁶)-ψ, or —N=C(R⁶)C(R⁶)₂-ψ; wherein ψ is a bond to the sulfonamide ring nitrogen atom in Formula I;

Y¹ and Y² are each independently C(R³) or N, provided that at least one of Y¹ and Y² is N;

R¹ is hydrogen or C₁₋₆alkyl;

R² is —C(O)-aryl, —C(O)-aralkyl, —C(O)—[C(R⁶)₂]ₘ-cycloalkyl, —C(O)—[C(R⁶)₂]ₘ-heterocyclyl, —C(O)—C₁₋₈alkyl, —C(O)—C₁₋₆alkylene-C₁₋₆alkoxyl, —C(O)—C₁₋₆alkylene-cycloalkyl, or —C(O)—C₁₋₆alkylene-heterocycloalkyl; each of which is optionally substituted with 1, 2, or 3 substituents independently selected from the group consisting of halogen, hydroxyl, C₁₋₆alkoxy, C₁₋₆haloalkoxy, C₁₋₆alkyl, C₁₋₆haloalkyl, —N(R⁴)(R⁵), —CN, —CO₂—C₁₋₆alkyl, —C(O)—C₁₋₆alkyl, —C(O)N(R⁴)(R⁵), —S(O)ₚC₁₋₆alkyl, —SO₂N(R⁴)(R⁵), and —N(R⁴)SO₂(C₁₋₆alkyl);

R³ represents independently for each occurrence hydrogen, halogen, or C₁₋₆alkyl;

R⁴ and R⁵ each represent independently for each occurrence hydrogen or C₁₋₆alkyl; or R⁴ and R⁵ taken together with the nitrogen atom to which they are attached form a 3-7 membered heterocyclic ring;

R⁶ represents independently for each occurrence hydrogen or C₁₋₆alkyl;

R⁷ is hydrogen, hydroxyl, C₁₋₆hydroxyalkyl, C₁₋₆alkyl, C₁₋₆haloalkyl, —CO₂R⁶, C₁₋₆alkylene-CO₂R⁶, C₁₋₄hydroxyalkylene-CO₂R⁶, —N(R⁴)(R⁵), C₁₋₆alkylene-N(R⁴)(R⁵), C₁₋₆hydroxyalkylene-N(R⁴)(R⁵), —N(R⁴)C(O)R⁹, C₁₋₆alkylene-N(R⁴)C(O)R⁹, C₁₋₆alkylene-C(O)N(R⁴)(R⁵), —N(R⁴)CO₂—C₁₋₆alkyl, or C₁₋₆alkylene-N(R⁴)(C(O)N(R⁴)(R⁵); or R⁷ is heterocycloalkyl or C₁₋₄alkylene-heterocycloalkyl, wherein the heterocycloalkyl is optionally substituted with 1, 2, or 3 substituents independently selected from the group consisting of oxo, halogen, hydroxyl, C₁₋₆alkyl, C₁₋₆haloalkyl, C₁₋₆hydroxyalkyl, C₁₋₆alkoxy, and C₁₋₆haloalkoxy;

R⁸ is hydrogen, C₁₋₆alkyl, or —C(O)—C₁₋₆alkyl;

R⁹ is hydrogen, C₁₋₆alkyl, C₁₋₆hydroxyalkyl, C₁₋₆alkylene N(R⁴)(R⁵), or C₁₋₆alkylene N(R⁴)C(O)—C₁₋₆alkyl; and m and p each represent independently for each occurrence 0, 1, or 2.

In certain embodiments, A is aryl or heteroaryl; each of which is optionally substituted with 1, 2, or 3 substituents independently selected from the group consisting of halogen, C₁₋₆alkyl, C₁₋₆haloalkyl, C₁₋₆alkoxy, and C₁₋₆haloalkoxy. In certain other embodiments, A is aryl optionally substituted with 1, 2, or 3 substituents independently selected from the group consisting of halogen, C₁₋₆alkyl, C₁₋₆haloalkyl, C₁₋₆alkoxy, and C₁₋₆haloalkoxy. In certain other embodiments, A is phenyl optionally substituted with 1, 2, or 3 substituents independently selected from the group consisting of halogen, C₁₋₆alkyl, C₁₋₆haloalkyl, C₁₋₆alkoxy, and C₁₋₆haloalkoxy. In certain other embodiments, A is phenyl optionally substituted with 1, 2, or 3 substituents independently selected from the group consisting of halogen and $C_{1-6}$haloalkyl. In certain embodiments, at least one substituent is attached at the meta-position of the phenyl ring.

In certain other embodiments, A is heteroaryl optionally substituted with 1, 2, or 3 substituents independently selected from the group consisting of halogen, $C_{1-6}$alkyl, $C_{1-6}$haloalkyl, $C_{1-6}$alkoxy, and $C_{1-6}$haloalkoxy.

In certain embodiments, A is heterocycloalkyl optionally substituted with 1, 2, or 3 substituents independently selected from the group consisting of halogen, $C_{1-6}$alkyl, $C_{1-6}$haloalkyl, $C_{1-6}$alkoxy, and $C_{1-6}$haloalkoxy. In certain embodiments, A is piperidine or pyrrolidine, each of which is optionally substituted with 1, 2, or 3 substituents independently selected from the group consisting of halogen, $C_{1-6}$alkyl, $C_{1-6}$haloalkyl, $C_{1-6}$alkoxy, and $C_{1-6}$haloalkoxy.

In certain embodiments, X is —O—[C(R$^6$)(R$^7$)]—[C(R$^6$)$_2$]$_m$-ψ. In certain other embodiments, X is —C(R$^6$)$_2$—[C(R$^6$)(R$^7$)]—[C(R$^6$)$_2$]$_m$-ψ. In certain other embodiments, X is —C(O)—[C(R$^6$)(R$^7$)]—[C(R$^6$)$_2$]$_m$-ψ. In certain other embodiments, X is —C(R$^6$)$_2$—N(R$^8$)—[C(R$^6$)(R$^7$)]—[C(R$^6$)$_2$]$_m$-ψ. In certain other embodiments, X is —C(R$^6$)═N-ψ.

In certain embodiments, Y$^1$ is N, and Y$^2$ is C(R$^3$). In certain other embodiments, Y$^1$ is C(R$^3$), and Y$^2$ is N. In certain other embodiments, Y$^1$ is N, and Y$^2$ is CH. In certain other embodiments, Y$^1$ is CH, and Y$^2$ is N.

In certain embodiments, R$^1$ is hydrogen.

In certain embodiments, R$^2$ is hydrogen, —C(O)-aryl or —C(O)-aralkyl; each of which is optionally substituted with 1, 2, or 3 substituents independently selected from the group consisting of halogen, hydroxyl, $C_{1-6}$alkoxy, $C_{1-6}$haloalkoxy, $C_{1-6}$alkyl, and $C_{1-6}$haloalkyl. In certain other embodiments, R$^2$ is —C(O)-aryl or —C(O)-aralkyl; each of which is substituted with 2 substituents independently selected from the group consisting of halogen, hydroxyl, $C_{1-6}$alkoxy, $C_{1-6}$haloalkoxy, $C_{1-6}$alkyl, and $C_{1-6}$haloalkyl, and said substituents are located at the ortho-positions of the aromatic ring. In certain other embodiments, R$^2$ is —C(O)-phenyl or —C(O)-benzyl; each of which is optionally substituted with 1, 2, or 3 substituents independently selected from the group consisting of halogen, hydroxyl, $C_{1-6}$alkoxy, $C_{1-6}$haloalkoxy, $C_{1-6}$alkyl, and $C_{1-6}$haloalkyl. In certain other embodiments, R$^2$ is —C(O)-phenyl or —C(O)-benzyl; each of which is optionally substituted with 1, 2, or 3 substituents independently selected from the group consisting of halogen, $C_{1-6}$alkyl, and $C_{1-6}$haloalkyl. In certain other embodiments, R$^2$ is represented by:

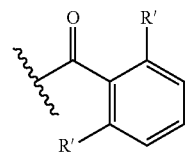

wherein each R' is independently halogen, hydroxyl, $C_{1-6}$alkoxy, $C_{1-6}$haloalkoxy, $C_{1-6}$alkyl, or $C_{1-6}$haloalkyl. In certain other embodiments, R$^2$ is represented by:

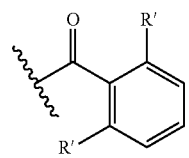

wherein each R' is independently halogen, $C_{1-6}$alkyl, or $C_{1-6}$haloalkyl.

In certain embodiments, R$^2$ is —C(O)-aryl or —C(O)-aralkyl; each of which is optionally substituted with 1, 2, or 3 substituents independently selected from the group consisting of halogen, hydroxyl, $C_{1-6}$alkoxy, $C_{1-6}$haloalkoxy, $C_{1-6}$alkyl, and $C_{1-6}$haloalkyl. In certain other embodiments, R$^2$ is —C(O)-aryl or —C(O)-aralkyl; each of which is substituted with 2 substituents independently selected from the group consisting of halogen, hydroxyl, $C_{1-6}$alkoxy, $C_{1-6}$haloalkoxy, $C_{1-6}$alkyl, and $C_{1-6}$haloalkyl, and said substituents are located at the ortho-positions of the aromatic ring. In certain other embodiments, R$^2$ is —C(O)-phenyl or —C(O)-benzyl; each of which is optionally substituted with 1, 2, or 3 substituents independently selected from the group consisting of halogen, hydroxyl, $C_{1-6}$alkoxy, $C_{1-6}$haloalkoxy, $C_{1-6}$alkyl, and $C_{1-6}$haloalkyl. In certain other embodiments, R$^2$ is —C(O)-phenyl or —C(O)-benzyl; each of which is optionally substituted with 1, 2, or 3 substituents independently selected from the group consisting of halogen, $C_{1-6}$alkyl, and $C_{1-6}$haloalkyl. In certain other embodiments, R$^2$ is represented by:

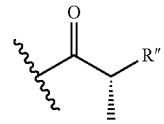

wherein R" is $C_{1-6}$alkyl, aryl, or heterocyclyl, each of which is optionally substituted with 1, 2, or 3 substituents independently selected from the group consisting of halogen, hydroxyl, $C_{1-6}$alkoxy, $C_{1-6}$haloalkoxy, $C_{1-6}$alkyl, $C_{1-6}$haloalkyl, —N(R$^4$)(R$^5$), —CN, —CO$_2$—C$_{1-6}$alkyl, —C(O)—C$_{1-6}$alkyl, —C(O)N(R$^4$)(R$^5$), —S(O)$_p$C$_{1-6}$alkyl, —SO$_2$N(R$^4$)(R$^5$), and —N(R$^4$)SO$_2$(C$_{1-6}$alkyl). In certain embodiments, R" is phenyl optionally substituted with 1, 2, or 3 substituents independently selected from the group consisting of halogen, $C_{1-6}$alkyl, and $C_{1-6}$haloalkyl.

In certain embodiments, R$^3$ is hydrogen.

In certain embodiments, R$^7$ is hydrogen. In certain other embodiments, R$^7$ is hydroxyl, $C_{1-6}$hydroxyalkyl, $C_{1-6}$alkyl, $C_{1-6}$haloalkyl, —CO$_2$R$^6$, $C_{1-6}$alkylene-CO$_2$R$^6$, $C_{1-4}$hydroxyalkylene-CO$_2$R$^6$, —N(R$^4$)(R$^5$), $C_{1-6}$alkylene-N(R$^4$)(R$^5$), $C_{1-6}$hydroxyalkylene-N(R$^4$)(R$^5$), —N(R$^4$)C(O)R$^9$, $C_{1-6}$alkylene-N(R$^4$)C(O)R$^9$, $C_{1-6}$alkylene-C(O)N(R$^4$)(R$^5$), —N(R$^4$)CO$_2$—C$_{1-6}$alkyl, or —N(R$^4$)C(O)R$^9$. In certain other embodiments, R$^7$ is $C_{1-6}$hydroxyalkyl, $C_{1-6}$alkyl, $C_{1-6}$alkylene-CO$_2$R$^6$, —N(R$^4$)(R$^5$), $C_{1-6}$alkylene-N(R$^4$)(R$^5$), or $C_{1-6}$alkylene-N(R$^4$)C(O)R$^9$. In certain other embodiments, R$^7$ is $C_{1-3}$hydroxyalkyl, methyl, ethyl, or $C_{1-3}$alkylene-N(H)C(O)—C$_{1-4}$alkyl.

In certain other embodiments, R$^7$ is heterocycloalkyl or $C_{1-4}$alkylene-heterocycloalkyl, wherein the heterocycloalkyl is optionally substituted with 1, 2, or 3 substituents independently selected from the group consisting of oxo, halogen, hydroxyl, $C_{1-6}$alkyl, $C_{1-6}$haloalkyl, $C_{1-6}$hydroxyalkyl, $C_{1-6}$alkoxy, and $C_{1-6}$haloalkoxy.

Another aspect of the invention provides a compound represented by Formula I-A:

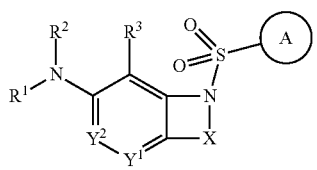

(I-A)

or a pharmaceutically acceptable salt or solvate thereof; wherein:

A is aryl, aralkyl, heteroaryl, cycloalkyl, or heterocycloalkyl; each of which is optionally substituted with 1, 2, or 3 substituents independently selected from the group consisting of halogen, hydroxyl, $C_{1-6}$alkyl, $C_{1-6}$haloalkyl, $C_{1-6}$hydroxyalkyl, $C_{1-6}$alkoxy, $C_{1-6}$haloalkoxy, —N($R^4$)($R^5$), —$CO_2R^6$, —C(O)$R^6$, —CN, —$C_{1-4}$alkylene-$C_{1-4}$alkoxy, —$C_{1-4}$alkylene-N($R^4$)($R^5$), —$C_{1-4}$alkylene-$CO_2R^6$, —O—$C_{1-6}$alkylene-N($R^4$)($R^5$), —N($R^4$)C(O)—$C_{1-6}$alkylene-N($R^4$)($R^5$), —S(O)$_p$$C_{1-6}$alkyl, —$SO_2$N($R^4$)($R^5$), —N($R^4$)$SO_2$($C_{1-6}$alkyl), —C(O)N($R^4$)($R^5$), and —N($R^4$)C(O)N($R^4$)($R^5$);

X is —O—[C($R^6$)($R^7$)]—[C($R^6$)$_2$]$_m$-ψ, —O—C($R^6$)$_2$—C($R^6$)($R^7$)—C($R^6$)$_2$-ψ, —O—C($R^6$)$_2$—C($R^6$)($R^7$)-ψ, —C($R^6$)$_2$—[C($R^6$)($R^7$)]—[C($R^6$)$_2$]$_m$-ψ, —C(O)—[C($R^6$)($R^7$)]—[C($R^6$)$_2$]$_m$-ψ, —C($R^6$)$_2$—N($R^8$)—[C($R^6$)($R^7$)]—[C($R^6$)$_2$]$_m$-ψ, —C($R^6$)=N-ψ, —C($R^6$)$_2$C($R^6$)=N-ψ, —N=C($R^6$)-ψ, or —N=C($R^6$)C($R^6$)$_2$-ψ; wherein ψ is a bond to the sulfonamide ring nitrogen atom in Formula I-A;

$Y^1$ and $Y^2$ are each independently C($R^3$) or N, provided that at least one of $Y^1$ and $Y^2$ is N;

$R^1$ is hydrogen or $C_{1-6}$alkyl;

$R^2$ is hydrogen, —C(O)-aryl, —C(O)-aralkyl, —C(O)—[C($R^6$)$_2$]$_m$-cycloalkyl, —C(O)—[C($R^6$)$_2$]$_m$-heterocyclyl, —C(O)—$C_{1-8}$alkyl, —C(O)—$C_{1-6}$alkylene-$C_{1-6}$alkoxyl, —C(O)—$C_{1-6}$alkylene-cycloalkyl, or —C(O)—$C_{1-6}$alkylene-heterocycloalkyl; each of which is optionally substituted with 1, 2, or 3 substituents independently selected from the group consisting of halogen, hydroxyl, $C_{1-6}$alkoxy, $C_{1-6}$haloalkoxy, $C_{1-6}$alkyl, $C_{1-6}$haloalkyl, —N($R^4$)($R^5$), —CN, —$CO_2$—$C_{1-6}$alkyl, —C(O)—$C_{1-6}$alkyl, —C(O)N($R^4$)($R^5$), —S(O)$_p$$C_{1-6}$alkyl, —$SO_2$N($R^4$)($R^5$), and —N($R^4$)$SO_2$($C_{1-6}$alkyl);

$R^3$ represents independently for each occurrence hydrogen, halogen, or $C_{1-6}$alkyl;

$R^4$ and $R^5$ each represent independently for each occurrence hydrogen or $C_{1-6}$alkyl; or $R^4$ and $R^5$ taken together with the nitrogen atom to which they are attached form a 3-7 membered heterocyclic ring;

$R^6$ represents independently for each occurrence hydrogen or $C_{1-6}$alkyl;

$R^7$ is hydrogen, hydroxyl, $C_{1-6}$hydroxyalkyl, $C_{1-6}$alkyl, $C_{1-6}$haloalkyl, —$CO_2R^6$, $C_{1-6}$alkylene-$CO_2R^6$, $C_{1-4}$hydroxyalkylene-$CO_2R^6$, —N($R^4$)($R^5$), $C_{1-6}$alkylene-N($R^4$)($R^5$), $C_{1-6}$hydroxyalkylene-N($R^4$)($R^5$), —N($R^4$)C(O)$R^9$, $C_{1-6}$alkylene-N($R^4$)C(O)$R^9$, $C_{1-6}$alkylene-C(O)N($R^4$)($R^5$), —N($R^4$)$CO_2$—$C_{1-6}$alkyl, or $C_{1-6}$alkylene-N($R^4$)(C(O)N($R^4$)($R^5$); or $R^7$ is heterocycloalkyl or $C_{1-4}$alkylene-heterocycloalkyl, wherein the heterocycloalkyl is optionally substituted with 1, 2, or 3 substituents independently selected from the group consisting of oxo, halogen, hydroxyl, $C_{1-6}$alkyl, $C_{1-6}$haloalkyl, $C_{1-6}$hydroxyalkyl, $C_{1-6}$alkoxy, and $C_{1-6}$haloalkoxy;

$R^8$ is hydrogen, $C_{1-6}$alkyl, or —C(O)—$C_{1-6}$alkyl;

$R^9$ is hydrogen, $C_{1-6}$alkyl, $C_{1-6}$hydroxyalkyl, N($R^4$)($R^5$), $C_{1-6}$alkylene N($R^4$)($R^5$), or $C_{1-6}$alkylene N($R^4$)C(O)—$C_{1-6}$alkyl; each of which is optionally substituted with 1, 2, or 3 halogen, hydroxyl or amino; and m and p each represent independently for each occurrence 0, 1, or 2.

The definitions of variables in Formulae I-A above encompass multiple chemical groups. The application contemplates embodiments where, for example, i) the definition of a variable is a single chemical group selected from those chemical groups set forth above, ii) the definition of a variable is a collection of two or more of the chemical groups selected from those set forth above, and iii) the compound is defined by a combination of variables in which the variables are defined by (i) or (ii), e.g., such as where A is aryl, and $R^2$ is —C(O)-aryl. Further, the definitions of variables A, X, $Y^1$, $Y^2$, $R^1$ to $R^9$, m, and p described in the preceding paragraphs in connection with Formula I are reiterated here for use in association with Formula I-A.

Another aspect of the invention provides a compound represented by Formula II:

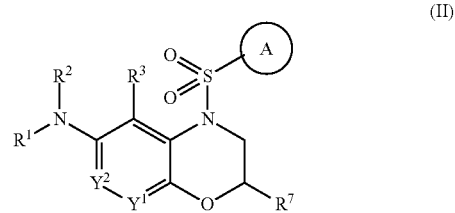

(II)

or a pharmaceutically acceptable salt or solvate thereof; wherein:

A is aryl, aralkyl, heteroaryl, cycloalkyl, or heterocycloalkyl; each of which is optionally substituted with 1, 2, or 3 substituents independently selected from the group consisting of halogen, hydroxyl, $C_{1-6}$alkyl, $C_{1-6}$haloalkyl, $C_{1-6}$hydroxyalkyl, $C_{1-6}$alkoxy, $C_{1-6}$haloalkoxy, —N($R^4$)($R^5$), —$CO_2R^6$, —C(O)$R^6$, —CN, —$C_{1-4}$alkylene-$C_{1-4}$alkoxy, and —$C_{1-4}$alkylene-N($R^4$)($R^5$);

$Y^1$ and $Y^2$ are each independently C($R^3$) or N, provided that at least one of $Y^1$ and $Y^2$ is N;

$R^1$ is hydrogen or $C_{1-6}$alkyl;

$R^2$ is hydrogen, —C(O)-aryl, —C(O)-aralkyl, —C(O)—[C($R^6$)$_2$]$_m$-cycloalkyl, —C(O)—[C($R^6$)$_2$]$_m$-heterocyclyl, —C(O)—$C_{1-8}$alkyl, —C(O)—$C_{1-6}$alkylene-$C_{1-6}$alkoxyl, —C(O)—$C_{1-6}$alkylene-cycloalkyl, or —C(O)—$C_{1-6}$alkylene-heterocycloalkyl; each of which is optionally substituted with 1, 2, or 3 substituents independently selected from the group consisting of halogen, hydroxyl, $C_{1-6}$alkoxy, $C_{1-6}$haloalkoxy, $C_{1-6}$alkyl, $C_{1-6}$haloalkyl, —N($R^4$)($R^5$), —CN, —$CO_2$—$C_{1-6}$alkyl, —C(O)—$C_{1-6}$alkyl, —C(O)N($R^4$)($R^5$), —S(O)$_p$$C_{1-6}$alkyl, —$SO_2$N($R^4$)($R^5$), and —N($R^4$)$SO_2$($C_{1-6}$alkyl);

$R^3$ represents independently for each occurrence hydrogen, halogen, or $C_{1-6}$alkyl;

$R^4$ and $R^5$ each represent independently for each occurrence hydrogen or $C_{1-6}$alkyl; or $R^4$ and $R^5$ taken together with the nitrogen atom to which they are attached form a 3-7 membered heterocyclic ring;

$R^6$ represents independently for each occurrence hydrogen or $C_{1-6}$alkyl;

$R^7$ is hydrogen, hydroxyl, $C_{1-6}$hydroxyalkyl, $C_{1-6}$alkyl, $C_{1-6}$haloalkyl, —$CO_2R^6$, $C_{1-6}$alkylene-$CO_2R^6$, $C_{1-4}$hydroxyalkylene-$CO_2R^6$, —N($R^4$)($R^5$), $C_{1-6}$alkylene-N($R^4$)($R^5$), $C_{1-6}$hydroxyalkylene-N($R^4$)($R^5$), —N($R^4$)C(O)$R^9$, $C_{1-6}$alkylene-N($R^4$)C(O)$R^9$, $C_{1-6}$alkylene-C(O)N($R^4$)($R^5$), —N(R⁴)CO₂—C₁₋₆alkyl, or C₁₋₆alkylene-N(R⁴)(C(O)N(R⁴)(R⁵); or R⁷ is heterocycloalkyl or C₁₋₄alkylene-heterocycloalkyl, wherein the heterocycloalkyl is optionally substituted with 1, 2, or 3 substituents independently selected from the group consisting of oxo, halogen, hydroxyl, C₁₋₆alkyl, C₁₋₆haloalkyl, C₁₋₆hydroxyalkyl, C₁₋₆alkoxy, and C₁₋₆haloalkoxy;

R⁹ is hydrogen, C₁₋₆alkyl, C₁₋₆hydroxyalkyl, N(R⁴)(R⁵), C₁₋₆alkylene N(R⁴)(R⁵), or C₁₋₆alkylene N(R⁴)C(O)—C₁₋₆alkyl; each of which is optionally substituted with 1, 2, or 3 halogen, hydroxyl or amino; and m and p each represent independently for each occurrence 0, 1, or 2.

In certain embodiments, A is aryl or heteroaryl; each of which is optionally substituted with 1, 2, or 3 substituents independently selected from the group consisting of halogen, C₁₋₆alkyl, C₁₋₆haloalkyl, C₁₋₆alkoxy, and C₁₋₆haloalkoxy. In certain other embodiments, A is aryl optionally substituted with 1, 2, or 3 substituents independently selected from the group consisting of halogen, C₁₋₆alkyl, C₁₋₆haloalkyl, C₁₋₆alkoxy, and C₁₋₆haloalkoxy. In certain other embodiments, A is phenyl optionally substituted with 1, 2, or 3 substituents independently selected from the group consisting of halogen, C₁₋₆alkyl, C₁₋₆haloalkyl, C₁₋₆alkoxy, and C₁₋₆haloalkoxy. In certain other embodiments, A is phenyl optionally substituted with 1, 2, or 3 substituents independently selected from the group consisting of halogen and C₁₋₆haloalkyl. In certain embodiments, at least one substituent is attached at the meta-position of the phenyl ring.

In certain other embodiments, A is heterocycloalkyl optionally substituted with 1, 2, or 3 substituents independently selected from the group consisting of halogen, C₁₋₆alkyl, C₁₋₆haloalkyl, C₁₋₆alkoxy, and C₁₋₆haloalkoxy. In certain embodiments, A is piperidine or pyrrolidine, each of which is optionally substituted with 1, 2, or 3 substituents independently selected from the group consisting of halogen, C₁₋₆alkyl, C₁₋₆haloalkyl, C₁₋₆alkoxy, and C₁₋₆haloalkoxy.

In certain embodiments, $Y^1$ is N, and $Y^2$ is C(R³). In certain other embodiments, $Y^1$ is C(R³), and $Y^2$ is N. In certain other embodiments, $Y^1$ is N, and $Y^2$ is CH. In certain other embodiments, $Y^1$ is CH, and $Y^2$ is N.

In certain embodiments, R¹ is hydrogen.

In certain embodiments, R² is hydrogen, —C(O)-aryl or —C(O)-aralkyl; each of which is optionally substituted with 1, 2, or 3 substituents independently selected from the group consisting of halogen, hydroxyl, C₁₋₆alkoxy, C₁₋₆haloalkoxy, C₁₋₆alkyl, and C₁₋₆haloalkyl. In certain other embodiments, R² is —C(O)-aryl or —C(O)-aralkyl; each of which is substituted with 2 substituents independently selected from the group consisting of halogen, hydroxyl, C₁₋₆alkoxy, C₁₋₆haloalkoxy, C₁₋₆alkyl, and C₁₋₆haloalkyl, and said substituents are located at the ortho-positions of the aromatic ring. In certain other embodiments, R² is —C(O)-phenyl or —C(O)-benzyl; each of which is optionally substituted with 1, 2, or 3 substituents independently selected from the group consisting of halogen, hydroxyl, C₁₋₆alkoxy, C₁₋₆haloalkoxy, C₁₋₆alkyl, and C₁₋₆haloalkyl. In certain other embodiments, R² is —C(O)-phenyl or —C(O)-benzyl; each of which is optionally substituted with 1, 2, or 3 substituents independently selected from the group consisting of halogen, C₁₋₆alkyl, and C₁₋₆haloalkyl. In certain other embodiments, R² is represented by:

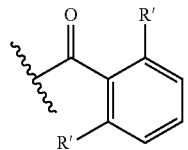

wherein each R' is independently halogen, hydroxyl, C₁₋₆alkoxy, C₁₋₆haloalkoxy, C₁₋₆alkyl, or C₁₋₆haloalkyl. In certain other embodiments, R² is represented by:

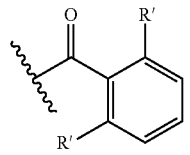

wherein each R' is independently halogen, C₁₋₆alkyl, or C₁₋₆haloalkyl.

In certain embodiments, R² is represented by:

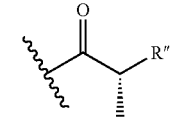

wherein R" is C₁₋₆alkyl, aryl, or heterocyclyl, each of which is optionally substituted with 1, 2, or 3 substituents independently selected from the group consisting of halogen, hydroxyl, C₁₋₆alkoxy, C₁₋₆haloalkoxy, C₁₋₆alkyl, C₁₋₆haloalkyl, —N(R⁴)(R⁵), —CN, —CO₂—C₁₋₆alkyl, —C(O)—C₁₋₆alkyl, —C(O)N(R⁴)(R⁵), —S(O)ₚC₁₋₆alkyl, —SO₂N(R⁴)(R⁵), and —N(R⁴)SO₂(C₁₋₆alkyl). In certain embodiments, R" is phenyl optionally substituted with 1, 2, or 3 substituents independently selected from the group consisting of halogen, C₁₋₆alkyl, and C₁₋₆haloalkyl.

In certain embodiments, R³ is hydrogen.

In certain embodiments, R⁷ is hydrogen. In certain other embodiments, R⁷ is hydroxyl, C₁₋₆hydroxyalkyl, C₁₋₆alkyl, C₁₋₆haloalkyl, —CO₂R⁶, C₁₋₆alkylene-CO₂R⁶, C₁₋₄hydroxyalkylene-CO₂R⁶, —N(R⁴)(R⁵), C₁₋₆alkylene-N(R⁴)(R⁵), C₁₋₆hydroxyalkylene-N(R⁴)(R⁵), —N(R⁴)C(O)R⁹, C₁₋₆alkylene-N(R⁴)C(O)R⁹, C₁₋₆alkylene-C(O)N(R⁴)(R⁵), —N(R⁴)CO₂—C₁₋₆alkyl, or —N(R⁴)C(O)R⁹. In certain other embodiments, R⁷ is C₁₋₆hydroxyalkyl, C₁₋₆alkyl, C₁₋₆alkylene-CO₂R⁶, C₁₋₆alkylene-N(R⁴)(R⁵), or C₁₋₆alkylene-N(R⁴)C(O)R⁹. In certain other embodiments, R⁷ is C₁₋₃hydroxyalkyl, methyl, ethyl, or C₁₋₃alkylene-N(H)C(O)—C₁₋₄alkyl.

Another aspect of the invention provides a compound represented by Formula II-A:

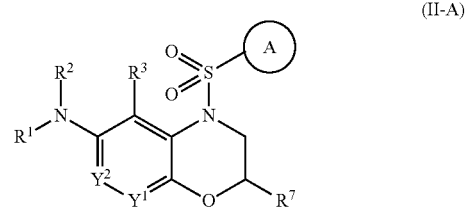

(II-A)

or a pharmaceutically acceptable salt or solvate thereof; wherein:

A is aryl, heteroaryl, or heterocycloalkyl; each of which is optionally substituted with 1, 2, or 3 substituents independently selected from the group consisting of halogen, hydroxyl, $C_{1-6}$alkyl, $C_{1-6}$haloalkyl, $C_{1-6}$alkoxy, and $C_{1-6}$haloalkoxy;

$Y^1$ and $Y^2$ are each independently C(H) or N, provided that at least one of $Y^1$ and $Y^2$ is N;

$R^1$ is hydrogen;

$R^2$ is —C(O)-phenyl substituted with 2 substituents independently selected from the group consisting of halogen, $C_{1-6}$alkyl, and $C_{1-6}$haloalkyl, wherein the substituents are located at the ortho positions of the phenyl ring;

$R^3$ is hydrogen;

$R^4$ and $R^5$ each represent independently for each occurrence hydrogen or $C_{1-6}$alkyl; or $R^4$ and $R^5$ taken together with the nitrogen atom to which they are attached form a 3-7 membered heterocyclic ring;

$R^6$ represents independently for each occurrence hydrogen or $C_{1-6}$alkyl;

$R^7$ is hydrogen, hydroxyl, $C_{1-6}$hydroxyalkyl, $C_{1-6}$alkyl, $C_{1-6}$haloalkyl, —$CO_2R^6$, $C_{1-6}$alkylene-$CO_2R^6$, $C_{1-4}$hydroxyalkylene-$CO_2R^6$, —$N(R^4)(R^5)$, $C_{1-6}$alkylene-$N(R^4)$ $(R^5)$, $C_{1-6}$hydroxyalkylene-$N(R^4)(R^5)$, —$N(R^4)C(O)R^9$, $C_{1-6}$alkylene-$N(R^4)C(O)R^9$, $C_{1-6}$alkylene-$C(O)N(R^4)(R^5)$, —$N(R^4)CO_2$—$C_{1-6}$alkyl, or $C_{1-6}$alkylene-$N(R^4)(C(O)N(R^4)(R^5)$; or $R^7$ is heterocycloalkyl or $C_{1-4}$alkylene-heterocycloalkyl, wherein the heterocycloalkyl is optionally substituted with 1, 2, or 3 substituents independently selected from the group consisting of oxo, halogen, hydroxyl, $C_{1-6}$alkyl, $C_{1-6}$haloalkyl, $C_{1-6}$hydroxyalkyl, $C_{1-6}$alkoxy, and $C_{1-6}$haloalkoxy;

$R^9$ is hydrogen, $C_{1-6}$alkyl, $C_{1-6}$hydroxyalkyl, $N(R^4)(R^5)$, $C_{1-6}$alkylene $N(R^4)(R^5)$, or $C_{1-6}$alkylene $N(R^4)C(O)$—$C_{1-6}$alkyl; each of which is optionally substituted with 1, 2, or 3 halogen, hydroxyl or amino; and m and p each represent independently for each occurrence 0, 1, or 2.

In certain embodiments, A is aryl or heteroaryl; each of which is optionally substituted with 1, 2, or 3 substituents independently selected from the group consisting of halogen, hydroxyl, $C_{1-6}$alkyl, $C_{1-6}$haloalkyl, $C_{1-6}$alkoxy, and $C_{1-6}$haloalkoxy. In certain other embodiments, A is aryl optionally substituted with 1, 2, or 3 substituents independently selected from the group consisting of halogen, $C_{1-6}$alkyl, $C_{1-6}$haloalkyl, $C_{1-6}$alkoxy, and $C_{1-6}$haloalkoxy. In certain other embodiments, A is phenyl optionally substituted with 1, 2, or 3 substituents independently selected from the group consisting of halogen, $C_{1-6}$alkyl, $C_{1-6}$haloalkyl, $C_{1-6}$alkoxy, and $C_{1-6}$haloalkoxy. In certain other embodiments, A is phenyl optionally substituted with 1, 2, or 3 substituents independently selected from the group consisting of halogen and $C_{1-6}$haloalkyl. In certain embodiments, at least one substituent is attached at the meta-position of the phenyl ring.

In certain other embodiments, A is heterocycloalkyl optionally substituted with 1, 2, or 3 substituents independently selected from the group consisting of halogen, $C_{1-6}$alkyl, $C_{1-6}$haloalkyl, $C_{1-6}$alkoxy, and $C_{1-6}$haloalkoxy. In certain embodiments, A is piperidine or pyrrolidine, each of which is optionally substituted with 1, 2, or 3 substituents independently selected from the group consisting of halogen, $C_{1-6}$alkyl, $C_{1-6}$haloalkyl, $C_{1-6}$alkoxy, and $C_{1-6}$haloalkoxy.

In certain embodiments, $Y^1$ is N, and $Y^2$ is C(H). In certain other embodiments, $Y^1$ is C(H), and $Y^2$ is N.

In certain embodiments, $R^2$ is represented by:

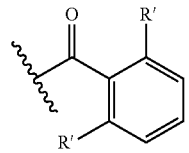

wherein each R' is independently fluoro, chlorooo, or $C_{1-6}$haloalkyl.

In certain embodiments, $R^7$ is hydrogen. In certain other embodiments, $R^7$ is $C_{1-6}$hydroxyalkyl, $C_{1-6}$alkyl, $C_{1-6}$haloalkyl, —$CO_2R^6$, $C_{1-6}$alkylene-$CO_2R^6$, $C_{1-4}$hydroxyalkylene-$CO_2R^6$, —$N(R^4)(R^5)$, $C_{1-6}$alkylene-$N(R^4)(R^5)$, $C_{1-6}$hydroxyalkylene-$N(R^4)(R^5)$, —$N(R^4)C(O)R^9$, $C_{1-6}$alkylene-$N(R^4)C(O)R^9$, $C_{1-6}$alkylene-$C(O)N(R^4)(R^5)$, —$N(R^4)CO_2$—$C_{1-6}$alkyl, or —$N(R^4)C(O)R^9$. In certain other embodiments, $R^7$ is $C_{1-6}$hydroxyalkyl, $C_{1-6}$alkyl, $C_{1-6}$alkylene-$CO_2R^6$, $C_{1-6}$alkylene-$N(R^4)(R^5)$, or $C_{1-6}$alkylene-$N(R^4)C(O)R^9$. In certain other embodiments, $R^7$ is $C_{1-3}$hydroxyalkyl, methyl, ethyl, or $C_{1-3}$alkylene-N(H)C(O)—$C_{1-4}$alkyl.

Another aspect of the invention provides a compound represented by Formula III:

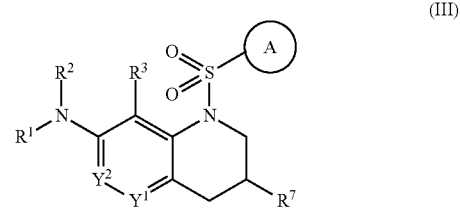

(III)

or a pharmaceutically acceptable salt or solvate thereof; wherein:

A is aryl, aralkyl, heteroaryl, cycloalkyl, or heterocycloalkyl; each of which is optionally substituted with 1, 2, or 3 substituents independently selected from the group consisting of halogen, hydroxyl, $C_{1-6}$alkyl, $C_{1-6}$haloalkyl, $C_{1-6}$hydroxyalkyl, $C_{1-6}$alkoxy, $C_{1-6}$haloalkoxy, —$N(R^4)$ $(R^5)$, —$CO_2R^6$, —$C(O)R^6$, —CN, —$C_{1-4}$alkylene-$C_{1-4}$alkoxy, and —$C_{1-4}$alkylene-$N(R^4)(R^5)$;

$Y^1$ and $Y^2$ are each independently $C(R^3)$ or N, provided that at least one of $Y^1$ and $Y^2$ is N;

$R^1$ is hydrogen or $C_{1-6}$alkyl;

$R^2$ is hydrogen, —C(O)-aryl, —C(O)-aralkyl, —C(O)—$[C(R^6)_2]_m$-cycloalkyl, —C(O)—$[C(R^6)_2]_m$-heterocyclyl, —C(O)—$C_{1-8}$alkyl, —C(O)—$C_{1-6}$alkylene-$C_{1-6}$alkoxyl, —C(O)—$C_{1-6}$alkylene-cycloalkyl, or —C(O)—$C_{1-6}$alkylene-heterocycloalkyl; each of which is optionally substituted with 1, 2, or 3 substituents independently selected from the group consisting of halogen, hydroxyl, $C_{1-6}$alkoxy, $C_{1-6}$haloalkoxy, $C_{1-6}$alkyl, $C_{1-6}$haloalkyl, —$N(R^4)(R^5)$, —CN, —$CO_2$—$C_{1-6}$alkyl, —C(O)—$C_{1-6}$alkyl, —C(O)N$(R^4)(R^5)$, —$S(O)_pC_{1-6}$alkyl, —$SO_2N(R^4)(R^5)$, and —$N(R^4)SO_2(C_{1-6}$alkyl);

$R^3$ represents independently for each occurrence hydrogen, halogen, or $C_{1-6}$alkyl;

$R^4$ and $R^5$ each represent independently for each occurrence hydrogen or $C_{1-6}$alkyl; or $R^4$ and $R^5$ taken together with the nitrogen atom to which they are attached form a 3-7 membered heterocyclic ring;

$R^6$ represents independently for each occurrence hydrogen or $C_{1-6}$alkyl;

$R^7$ is hydrogen, hydroxyl, $C_{1-6}$hydroxyalkyl, $C_{1-6}$alkyl, $C_{1-6}$haloalkyl, —$CO_2R^6$, $C_{1-6}$alkylene-$CO_2R^6$, $C_{1-4}$hydroxyalkylene-$CO_2R^6$, —$N(R^4)(R^5)$, $C_{1-6}$alkylene-$N(R^4)(R^5)$, $C_{1-6}$hydroxyalkylene-$N(R^4)(R^5)$, —$N(R^4)C(O)R^9$, $C_{1-6}$alkylene-$N(R^4)C(O)R^9$, $C_{1-6}$alkylene-$C(O)N(R^4)(R^5)$, —$N(R^4)CO_2$—$C_{1-6}$alkyl, or $C_{1-6}$alkylene-$N(R^4)(C(O)N(R^4)(R^5)$; or $R^7$ is heterocycloalkyl or $C_{1-4}$alkylene-heterocycloalkyl, wherein the heterocycloalkyl is optionally substituted with 1, 2, or 3 substituents independently selected from the group consisting of oxo, halogen, hydroxyl, $C_{1-6}$alkyl, $C_{1-6}$haloalkyl, $C_{1-6}$hydroxyalkyl, $C_{1-6}$alkoxy, and $C_{1-6}$haloalkoxy;

$R^9$ is hydrogen, $C_{1-6}$alkyl, $C_{1-6}$hydroxyalkyl, $N(R^4)(R^5)$, $C_{1-6}$alkylene $N(R^4)(R^5)$, or $C_{1-6}$alkylene $N(R^4)C(O)$—$C_{1-6}$alkyl; each of which is optionally substituted with 1, 2, or 3 halogen, hydroxyl or amino; and m and p each represent independently for each occurrence 0, 1, or 2.

In certain embodiments, A is aryl or heteroaryl; each of which is optionally substituted with 1, 2, or 3 substituents independently selected from the group consisting of halogen, $C_{1-6}$alkyl, $C_{1-6}$haloalkyl, $C_{1-6}$alkoxy, and $C_{1-6}$haloalkoxy. In certain other embodiments, A is aryl optionally substituted with 1, 2, or 3 substituents independently selected from the group consisting of halogen, $C_{1-6}$alkyl, $C_{1-6}$haloalkyl, $C_{1-6}$alkoxy, and $C_{1-6}$haloalkoxy. In certain other embodiments, A is phenyl optionally substituted with 1, 2, or 3 substituents independently selected from the group consisting of halogen, $C_{1-6}$alkyl, $C_{1-6}$haloalkyl, $C_{1-6}$alkoxy, and $C_{1-6}$haloalkoxy. In certain other embodiments, A is phenyl optionally substituted with 1, 2, or 3 substituents independently selected from the group consisting of halogen and $C_{1-6}$haloalkyl. In certain embodiments, at least one substituent is attached at the meta-position of the phenyl ring.

In certain other embodiments, A is heterocycloalkyl optionally substituted with 1, 2, or 3 substituents independently selected from the group consisting of halogen, $C_{1-6}$alkyl, $C_{1-6}$haloalkyl, $C_{1-6}$alkoxy, and $C_{1-6}$haloalkoxy. In certain embodiments, A is piperidine or pyrrolidine, each of which is optionally substituted with 1, 2, or 3 substituents independently selected from the group consisting of halogen, $C_{1-6}$alkyl, $C_{1-6}$haloalkyl, $C_{1-6}$alkoxy, and $C_{1-6}$haloalkoxy.

In certain embodiments, $Y^1$ is N, and $Y^2$ is $C(R^3)$. In certain other embodiments, $Y^1$ is $C(R^3)$, and $Y^2$ is N. In certain other embodiments, $Y^1$ is N, and $Y^2$ is CH. In certain other embodiments, $Y^1$ is CH, and $Y^2$ is N.

In certain embodiments, $R^1$ is hydrogen.

In certain embodiments, $R^2$ is —C(O)-aryl or —C(O)-aralkyl; each of which is optionally substituted with 1, 2, or 3 substituents independently selected from the group consisting of halogen, hydroxyl, $C_{1-6}$alkoxy, $C_{1-6}$haloalkoxy, $C_{1-6}$alkyl, and $C_{1-6}$haloalkyl. In certain other embodiments, $R^2$ is —C(O)-aryl or —C(O)-aralkyl; each of which is substituted with 2 substituents independently selected from the group consisting of halogen, hydroxyl, $C_{1-6}$alkoxy, $C_{1-6}$haloalkoxy, $C_{1-6}$alkyl, and $C_{1-6}$haloalkyl, and said substituents are located at the ortho-positions of the aromatic ring. In certain other embodiments, $R^2$ is —C(O)-phenyl or —C(O)-benzyl; each of which is optionally substituted with 1, 2, or 3 substituents independently selected from the group consisting of halogen, hydroxyl, $C_{1-6}$alkoxy, $C_{1-6}$haloalkoxy, $C_{1-6}$alkyl, and $C_{1-6}$haloalkyl. In certain other embodiments, $R^2$ is —C(O)-phenyl or —C(O)-benzyl; each of which is optionally substituted with 1, 2, or 3 substituents independently selected from the group consisting of halogen, $C_{1-6}$alkyl, and $C_{1-6}$haloalkyl. In certain other embodiments, $R^2$ is represented by:

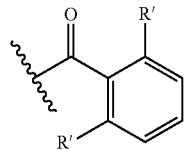

wherein each R' is independently halogen, hydroxyl, $C_{1-6}$alkoxy, $C_{1-6}$haloalkoxy, $C_{1-6}$alkyl, or $C_{1-6}$haloalkyl. In certain other embodiments, $R^2$ is represented by:

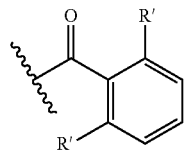

wherein each R' is independently halogen, $C_{1-6}$alkyl, or $C_{1-6}$haloalkyl.

In certain embodiments, $R^2$ is represented by:

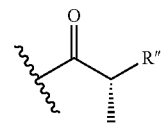

wherein R" is $C_{1-6}$alkyl, aryl, or heterocyclyl, each of which is optionally substituted with 1, 2, or 3 substituents independently selected from the group consisting of halogen, hydroxyl, $C_{1-6}$alkoxy, $C_{1-6}$haloalkoxy, $C_{1-6}$alkyl, $C_{1-6}$haloalkyl, —$N(R^4)(R^5)$, —CN, —$CO_2$—$C_{1-6}$alkyl, —$C(O)$—$C_{1-6}$alkyl, —$C(O)N(R^4)(R^5)$, —$S(O)_pC_{1-6}$alkyl, —$SO_2N(R^4)(R^5)$, and —$N(R^4)SO_2(C_{1-6}$alkyl). In certain embodiments, R" is phenyl optionally substituted with 1, 2, or 3 substituents independently selected from the group consisting of halogen, $C_{1-6}$alkyl, and $C_{1-6}$haloalkyl.

In certain embodiments, $R^3$ is hydrogen.

In certain embodiments, $R^7$ is hydrogen. In certain other embodiments $R^7$ is hydroxyl, $C_{1-6}$hydroxyalkyl, $C_{1-6}$alkyl, $C_{1-6}$haloalkyl, —$CO_2R^6$, $C_{1-6}$alkylene-$CO_2R^6$, $C_{1-4}$hydroxyalkylene-$CO_2R^6$, —$N(R^4)(R^5)$, $C_{1-6}$alkylene-$N(R^4)(R^5)$, $C_{1-6}$hydroxyalkylene-$N(R^4)(R^5)$, —$N(R^4)C(O)R^9$, $C_{1-6}$alkylene-$N(R^4)C(O)R^9$, $C_{1-6}$alkylene-$C(O)N(R^4)(R^5)$, —$N(R^4)CO_2$—$C_{1-6}$alkyl, or —$N(R^4)C(O)R^9$. In certain other embodiments, $R^7$ is $C_{1-6}$hydroxyalkyl, $C_{1-6}$alkyl, $C_{1-6}$alkylene-$CO_2R^6$, —$N(R^4)(R^5)$, $C_{1-6}$alkylene-$N(R^4)(R^5)$, or $C_{1-6}$alkylene-$N(R^4)C(O)R^9$. In certain other embodiments, $R^7$ is $C_{1-3}$hydroxyalkyl, methyl, ethyl, or $C_{1-3}$alkylene-$N(H)C(O)$—$C_{1-4}$alkyl.

Another aspect of the invention provides a compound represented by Formula III-A:

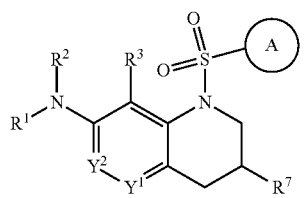

(III-A)

or a pharmaceutically acceptable salt or solvate thereof; wherein:

A is aryl, heteroaryl, or heterocycloalkyl; each of which is optionally substituted with 1, 2, or 3 substituents independently selected from the group consisting of halogen, hydroxyl, $C_{1-6}$alkyl, $C_{1-6}$haloalkyl, $C_{1-6}$alkoxy, and $C_{1-6}$haloalkoxy;

$Y^1$ and $Y^2$ are each independently C(H) or N, provided that at least one of $Y^1$ and $Y^2$ is N;

$R^1$ is hydrogen;

$R^2$ is —C(O)-phenyl substituted with 2 substituents independently selected from the group consisting of halogen, $C_{1-6}$alkyl, and $C_{1-6}$haloalkyl, wherein the substituents are located at the ortho positions of the phenyl ring;

$R^3$ is hydrogen;

$R^4$ and $R^5$ each represent independently for each occurrence hydrogen or $C_{1-6}$alkyl; or $R^4$ and $R^5$ taken together with the nitrogen atom to which they are attached form a 3-7 membered heterocyclic ring;

$R^6$ represents independently for each occurrence hydrogen or $C_{1-6}$alkyl;

$R^7$ is hydrogen, hydroxyl, $C_{1-6}$hydroxyalkyl, $C_{1-6}$alkyl, $C_{1-6}$haloalkyl, —$CO_2R^6$, $C_{1-6}$alkylene-$CO_2R^6$, $C_{1-4}$hydroxyalkylene-$CO_2R^6$, —$N(R^4)(R^5)$, $C_{1-6}$alkylene-$N(R^4)(R^5)$, $C_{1-6}$hydroxyalkylene-$N(R^4)(R^5)$, —$N(R^4)C(O)R^9$, $C_{1-6}$alkylene-$N(R^4)C(O)R^9$, $C_{1-6}$alkylene-$C(O)N(R^4)(R^5)$, —$N(R^4)CO_2$—$C_{1-6}$alkyl, or $C_{1-6}$alkylene-$N(R^4)(C(O)N(R^4)(R^5)$; or $R^7$ is heterocycloalkyl or $C_{1-4}$alkylene-heterocycloalkyl, wherein the heterocycloalkyl is optionally substituted with 1, 2, or 3 substituents independently selected from the group consisting of oxo, halogen, hydroxyl, $C_{1-6}$alkyl, $C_{1-6}$haloalkyl, $C_{1-6}$hydroxyalkyl, $C_{1-6}$alkoxy, and $C_{1-6}$haloalkoxy;

$R^9$ is hydrogen, $C_{1-6}$alkyl, $C_{1-6}$hydroxyalkyl, $N(R^4)(R^5)$, $C_{1-6}$alkylene $N(R^4)(R^5)$, or $C_{1-6}$alkylene $N(R^4)C(O)$—$C_{1-6}$alkyl; each of which is optionally substituted with 1, 2, or 3 halogen, hydroxyl or amino; and m and p each represent independently for each occurrence 0, 1, or 2.

In certain embodiments, A is aryl or heteroaryl; each of which is optionally substituted with 1, 2, or 3 substituents independently selected from the group consisting of halogen, hydroxyl, $C_{1-6}$alkyl, $C_{1-6}$haloalkyl, $C_{1-6}$alkoxy, and $C_{1-6}$haloalkoxy. In certain other embodiments, A is aryl optionally substituted with 1, 2, or 3 substituents independently selected from the group consisting of halogen, $C_{1-6}$alkyl, $C_{1-6}$haloalkyl, $C_{1-6}$alkoxy, and $C_{1-6}$haloalkoxy. In certain other embodiments, A is phenyl optionally substituted with 1, 2, or 3 substituents independently selected from the group consisting of halogen, $C_{1-6}$alkyl, $C_{1-6}$haloalkyl, $C_{1-6}$alkoxy, and $C_{1-6}$haloalkoxy. In certain other embodiments, A is phenyl optionally substituted with 1, 2, or 3 substituents independently selected from the group consisting of halogen and $C_{1-6}$haloalkyl. In certain embodiments, at least one substituent is attached at the meta-position of the phenyl ring.

In certain other embodiments, A is heterocycloalkyl optionally substituted with 1, 2, or 3 substituents independently selected from the group consisting of halogen, $C_{1-6}$alkyl, $C_{1-6}$haloalkyl, $C_{1-6}$alkoxy, and $C_{1-6}$haloalkoxy. In certain embodiments, A is piperidine or pyrrolidine, each of which is optionally substituted with 1, 2, or 3 substituents independently selected from the group consisting of halogen, $C_{1-6}$alkyl, $C_{1-6}$haloalkyl, $C_{1-6}$alkoxy, and $C_{1-6}$haloalkoxy.

In certain embodiments, $Y^1$ is N, and $Y^2$ is C(H). In certain other embodiments, $Y^1$ is C(H), and $Y^2$ is N.

In certain embodiments, $R^2$ is represented by:

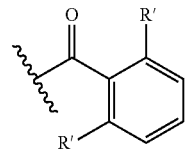

wherein each R' is independently fluoro, chloroo, or $C_{1-6}$haloalkyl.

In certain embodiments, $R^7$ is hydrogen. In certain other embodiments, $R^7$ is $C_{1-6}$hydroxyalkyl, $C_{1-6}$alkyl, $C_{1-6}$haloalkyl, —$CO_2R^6$, $C_{1-6}$alkylene-$CO_2R^6$, $C_{1-4}$hydroxyalkylene-$CO_2R^6$, —$N(R^4)(R^5)$, $C_{1-6}$alkylene-$N(R^4)(R^5)$, $C_{1-6}$hydroxyalkylene-$N(R^4)(R^5)$, —$N(R^4)C(O)R^9$, $C_{1-6}$alkylene-$N(R^4)C(O)R^9$, $C_{1-6}$alkylene-$C(O)N(R^4)(R^5)$, —$N(R^4)CO_2$—$C_{1-6}$alkyl, or —$N(R^4)C(O)R^9$. In certain other embodiments, $R^7$ is $C_{1-6}$hydroxyalkyl, $C_{1-6}$alkyl, $C_{1-6}$alkylene-$CO_2R^6$, $C_{1-6}$alkylene-$N(R^4)(R^5)$, or $C_{1-6}$alkylene-$N(R^4)C(O)R^9$. In certain other embodiments, $R^7$ is $C_{1-3}$hydroxyalkyl, methyl, ethyl, or $C_{1-3}$alkylene-N(H)C(O)—$C_{1-4}$alkyl.

Another aspect of the invention provides a compound represented by Formula IV:

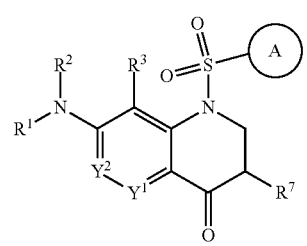

(IV)

or a pharmaceutically acceptable salt or solvate thereof; wherein:

A is aryl, aralkyl, heteroaryl, cycloalkyl, or heterocycloalkyl; each of which is optionally substituted with 1, 2, or 3 substituents independently selected from the group consisting of halogen, hydroxyl, $C_{1-6}$alkyl, $C_{1-6}$haloalkyl, $C_{1-6}$hydroxyalkyl, $C_{1-6}$alkoxy, $C_{1-6}$haloalkoxy, —$N(R^4)(R^5)$, —$CO_2R^6$, —$C(O)R^6$, —CN, —$C_{1-4}$alkylene-$C_{1-4}$alkoxy, and —$C_{1-4}$alkylene-$N(R^4)(R^5)$;

$Y^1$ and $Y^2$ are each independently $C(R^3)$ or N, provided that at least one of $Y^1$ and $Y^2$ is N;

$R^1$ is hydrogen or $C_{1-6}$alkyl;

$R^2$ is hydrogen, —C(O)-aryl, —C(O)-aralkyl, —C(O)—$[C(R^6)_2]_m$-cycloalkyl, —C(O)—$[C(R^6)_2]_m$-heterocyclyl, —C(O)—$C_{1-8}$alkyl, —C(O)—$C_{1-6}$alkylene-$C_{1-6}$alkoxyl, —C(O)—$C_{1-6}$alkylene-cycloalkyl, or —C(O)—$C_{1-6}$alkylene-heterocycloalkyl; each of which is optionally substituted with 1, 2, or 3 substituents independently selected from the group consisting of halogen, hydroxyl, $C_{1-6}$alkoxy, $C_{1-6}$haloalkoxy, $C_{1-6}$alkyl, $C_{1-6}$haloalkyl, —N($R^4$)($R^5$), —CN, —CO$_2$—$C_{1-6}$alkyl, —C(O)—$C_{1-6}$alkyl, —C(O)N($R^4$)($R^5$), —S(O)$_p$$C_{1-6}$alkyl, —SO$_2$N($R^4$)($R^5$), and —N($R^4$)SO$_2$($C_{1-6}$alkyl);

$R^3$ represents independently for each occurrence hydrogen, halogen, or $C_{1-6}$alkyl;

$R^4$ and $R^5$ each represent independently for each occurrence hydrogen or $C_{1-6}$alkyl; or $R^4$ and $R^5$ taken together with the nitrogen atom to which they are attached form a 3-7 membered heterocyclic ring;

$R^6$ represents independently for each occurrence hydrogen or $C_{1-6}$alkyl;

$R^7$ is hydrogen, hydroxyl, $C_{1-6}$hydroxyalkyl, $C_{1-6}$alkyl, $C_{1-6}$haloalkyl, —CO$_2$$R^6$, $C_{1-6}$alkylene-CO$_2$$R^6$, $C_{1-4}$hydroxyalkylene-CO$_2$$R^6$, —N($R^4$)($R^5$), $C_{1-6}$alkylene-N($R^4$)($R^5$), $C_{1-6}$hydroxyalkylene-N($R^4$)($R^5$), —N($R^4$)C(O)$R^9$, $C_{1-6}$alkylene-N($R^4$)C(O)$R^9$, $C_{1-6}$alkylene-C(O)N($R^4$)($R^5$), —N($R^4$)CO$_2$—$C_{1-6}$alkyl, or $C_{1-6}$alkylene-N($R^4$)(C(O)N($R^4$)($R^5$); or $R^7$ is heterocycloalkyl or $C_{1-4}$alkylene-heterocycloalkyl, wherein the heterocycloalkyl is optionally substituted with 1, 2, or 3 substituents independently selected from the group consisting of oxo, halogen, hydroxyl, $C_{1-6}$alkyl, $C_{1-6}$haloalkyl, $C_{1-6}$hydroxyalkyl, $C_{1-6}$alkoxy, and $C_{1-6}$haloalkoxy;

$R^9$ is hydrogen, $C_{1-6}$alkyl, $C_{1-6}$hydroxyalkyl, N($R^4$)($R^5$), $C_{1-6}$alkylene N($R^4$)($R^5$), or $C_{1-6}$alkylene N($R^4$)C(O)—$C_{1-6}$alkyl; each of which is optionally substituted with 1, 2, or 3 halogen, hydroxyl or amino; and m and p each represent independently for each occurrence 0, 1, or 2.

In certain embodiments, A is aryl or heteroaryl; each of which is optionally substituted with 1, 2, or 3 substituents independently selected from the group consisting of halogen, $C_{1-6}$alkyl, $C_{1-6}$haloalkyl, $C_{1-6}$alkoxy, and $C_{1-6}$haloalkoxy. In certain other embodiments, A is aryl optionally substituted with 1, 2, or 3 substituents independently selected from the group consisting of halogen, $C_{1-6}$alkyl, $C_{1-6}$haloalkyl, $C_{1-6}$alkoxy, and $C_{1-6}$haloalkoxy. In certain other embodiments, A is phenyl optionally substituted with 1, 2, or 3 substituents independently selected from the group consisting of halogen, $C_{1-6}$alkyl, $C_{1-6}$haloalkyl, $C_{1-6}$alkoxy, and $C_{1-6}$haloalkoxy. In certain other embodiments, A is phenyl optionally substituted with 1, 2, or 3 substituents independently selected from the group consisting of halogen and $C_{1-6}$haloalkyl. In certain embodiments, at least one substituent is attached at the meta-position of the phenyl ring.

In certain other embodiments, A is heterocycloalkyl optionally substituted with 1, 2, or 3 substituents independently selected from the group consisting of halogen, $C_{1-6}$alkyl, $C_{1-6}$haloalkyl, $C_{1-6}$alkoxy, and $C_{1-6}$haloalkoxy. In certain embodiments, A is piperidine or pyrrolidine, each of which is optionally substituted with 1, 2, or 3 substituents independently selected from the group consisting of halogen, $C_{1-6}$alkyl, $C_{1-6}$haloalkyl, $C_{1-6}$alkoxy, and $C_{1-6}$haloalkoxy.

In certain embodiments, $Y^1$ is N, and $Y^2$ is C($R^3$). In certain other embodiments, $Y^1$ is C($R^3$), and $Y^2$ is N. In certain other embodiments, $Y^1$ is N, and $Y^2$ is CH. In certain other embodiments, $Y^1$ is CH, and $Y^2$ is N.

In certain embodiments, $R^1$ is hydrogen.

In certain embodiments, $R^2$ is —C(O)-aryl or —C(O)-aralkyl; each of which is optionally substituted with 1, 2, or 3 substituents independently selected from the group consisting of halogen, hydroxyl, $C_{1-6}$alkoxy, $C_{1-6}$haloalkoxy, $C_{1-6}$alkyl, and $C_{1-6}$haloalkyl. In certain other embodiments, $R^2$ is —C(O)-aryl or —C(O)-aralkyl; each of which is substituted with 2 substituents independently selected from the group consisting of halogen, hydroxyl, $C_{1-6}$alkoxy, $C_{1-6}$haloalkoxy, $C_{1-6}$alkyl, and $C_{1-6}$haloalkyl, and said substituents are located at the ortho-positions of the aromatic ring. In certain other embodiments, $R^2$ is —C(O)-phenyl or —C(O)-benzyl; each of which is optionally substituted with 1, 2, or 3 substituents independently selected from the group consisting of halogen, hydroxyl, $C_{1-6}$alkoxy, $C_{1-6}$haloalkoxy, $C_{1-6}$alkyl, and $C_{1-6}$haloalkyl. In certain other embodiments, $R^2$ is —C(O)-phenyl or —C(O)-benzyl; each of which is optionally substituted with 1, 2, or 3 substituents independently selected from the group consisting of halogen, $C_{1-6}$alkyl, and $C_{1-6}$haloalkyl. In certain other embodiments, $R^2$ is represented by:

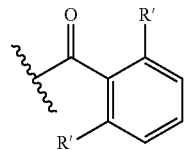

wherein each R' is independently halogen, hydroxyl, $C_{1-6}$alkoxy, $C_{1-6}$haloalkoxy, $C_{1-6}$alkyl, or $C_{1-6}$haloalkyl. In certain other embodiments, $R^2$ is represented by:

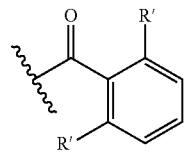

wherein each R' is independently halogen, $C_{1-6}$alkyl, or $C_{1-6}$haloalkyl.

In certain embodiments, $R^2$ is represented by:

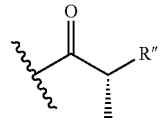

wherein R" is $C_{1-6}$alkyl, aryl, or heterocyclyl, each of which is optionally substituted with 1, 2, or 3 substituents independently selected from the group consisting of halogen, hydroxyl, $C_{1-6}$alkoxy, $C_{1-6}$haloalkoxy, $C_{1-6}$alkyl, $C_{1-6}$haloalkyl, —N($R^4$)($R^5$), —CN, —CO$_2$—$C_{1-6}$alkyl, —C(O)—$C_{1-6}$alkyl, —C(O)N($R^4$)($R^5$), —S(O)$_p$$C_{1-6}$alkyl, —SO$_2$N($R^4$)($R^5$), and —N($R^4$)SO$_2$($C_{1-6}$alkyl). In certain embodiments, R" is phenyl optionally substituted with 1, 2, or 3 substituents independently selected from the group consisting of halogen, $C_{1-6}$alkyl, and $C_{1-6}$haloalkyl.

In certain embodiments, $R^3$ is hydrogen.

In certain embodiments, $R^7$ is hydrogen. In certain other embodiments $R^7$ is hydroxyl, $C_{1-6}$hydroxyalkyl, $C_{1-6}$alkyl, $C_{1-6}$haloalkyl, —CO$_2$$R^6$, $C_{1-6}$alkylene-CO$_2$$R^6$, $C_{1-4}$hydroxyalkylene-CO$_2$$R^6$, —N($R^4$)($R^5$), $C_{1-6}$alkylene-N($R^4$)($R^5$), $C_{1-6}$hydroxyalkylene-N($R^4$)($R^5$), —N($R^4$)C(O)$R^9$, $C_{1-6}$alkylene-N($R^4$)C(O)$R^9$, $C_{1-6}$alkylene-C(O)N($R^4$)($R^5$), —N($R^4$)CO$_2$—$C_{1-6}$alkyl, or —N($R^4$)C(O)$R^9$. In certain other embodiments, $R^7$ is $C_{1-6}$hydroxyalkyl, $C_{1-6}$alkyl, $C_{1-6}$alkylene-$CO_2R^6$, —$N(R^4)(R^5)$, $C_{1-6}$alkylene-$N(R^4)$ $(R^5)$, or $C_{1-6}$alkylene-$N(R^4)C(O)R^9$. In certain other embodiments, $R^7$ is $C_{1-3}$hydroxyalkyl, methyl, ethyl, or $C_{1-3}$alkylene-N(H)C(O)—$C_{1-4}$alkyl.

Another aspect of the invention provides a compound of Formula V:

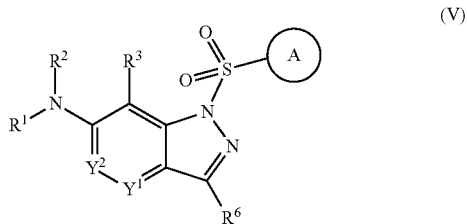

or a pharmaceutically acceptable salt or solvate thereof; wherein:

A is aryl, aralkyl, heteroaryl, cycloalkyl, or heterocycloalkyl; each of which is optionally substituted with 1, 2, or 3 substituents independently selected from the group consisting of halogen, hydroxyl, $C_{1-6}$alkyl, $C_{1-6}$haloalkyl, $C_{1-6}$hydroxyalkyl, $C_{1-6}$alkoxy, $C_{1-6}$haloalkoxy, —$N(R^4)$ $(R^5)$, —$CO_2R^6$, —$C(O)R^6$, —CN, —$C_{1-4}$alkylene-$C_{1-4}$alkoxy, and —$C_{1-4}$alkylene-$N(R^4)(R^5)$;

$Y^1$ and $Y^2$ are each independently $C(R^3)$ or N, provided that at least one of $Y^1$ and $Y^2$ is N;

$R^1$ is hydrogen or $C_{1-6}$alkyl;

$R^2$ is hdyrogen, —C(O)-aryl, —C(O)-aralkyl, —C(O)-[C$(R^6)_2]_m$-cycloalkyl, —C(O)—[C$(R^6)_2]_m$-heterocyclyl, —C(O)—$C_{1-8}$alkyl, —C(O)—$C_{1-6}$alkylene-$C_{1-6}$alkoxyl, —C(O)—$C_{1-6}$alkylene-cycloalkyl, or —C(O)—$C_{1-6}$alkylene-heterocycloalkyl; each of which is optionally substituted with 1, 2, or 3 substituents independently selected from the group consisting of halogen, hydroxyl, $C_{1-6}$alkoxy, $C_{1-6}$haloalkoxy, $C_{1-6}$alkyl, $C_{1-6}$haloalkyl, —$N(R^4)(R^5)$, —CN, —$CO_2$—$C_{1-6}$alkyl, —C(O)—$C_{1-6}$alkyl, —C(O)N$(R^4)(R^5)$, —$S(O)_pC_{1-6}$alkyl, —$SO_2N(R^4)(R^5)$, and —$N(R^4)$ $SO_2(C_{1-6}$alkyl);

$R^3$ represents independently for each occurrence hydrogen, halogen, or $C_{1-6}$alkyl;

$R^4$ and $R^5$ each represent independently for each occurrence hydrogen or $C_{1-6}$alkyl; or $R^4$ and $R^5$ taken together with the nitrogen atom to which they are attached form a 3-7 membered heterocyclic ring;

$R^6$ represents independently for each occurrence hydrogen or $C_{1-6}$alkyl; and m and p each represent independently for each occurrence 0, 1, or 2.

In certain embodiments, A is aryl or heteroaryl; each of which is optionally substituted with 1, 2, or 3 substituents independently selected from the group consisting of halogen, $C_{1-6}$alkyl, $C_{1-6}$haloalkyl, $C_{1-6}$alkoxy, and $C_{1-6}$haloalkoxy. In certain other embodiments, A is aryl optionally substituted with 1, 2, or 3 substituents independently selected from the group consisting of halogen, $C_{1-6}$alkyl, $C_{1-6}$haloalkyl, $C_{1-6}$alkoxy, and $C_{1-6}$haloalkoxy. In certain other embodiments, A is phenyl optionally substituted with 1, 2, or 3 substituents independently selected from the group consisting of halogen, $C_{1-6}$alkyl, $C_{1-6}$haloalkyl, $C_{1-6}$alkoxy, and $C_{1-6}$haloalkoxy. In certain other embodiments, A is phenyl optionally substituted with 1, 2, or 3 substituents independently selected from the group consisting of halogen and $C_{1-6}$haloalkyl. In certain embodiments, at least one substituent is attached at the meta-position of the phenyl ring.

In certain other embodiments, A is heterocycloalkyl optionally substituted with 1, 2, or 3 substituents independently selected from the group consisting of halogen, $C_{1-6}$alkyl, $C_{1-6}$haloalkyl, $C_{1-6}$alkoxy, and $C_{1-6}$haloalkoxy. In certain embodiments, A is piperidine or pyrrolidine, each of which is optionally substituted with 1, 2, or 3 substituents independently selected from the group consisting of halogen, $C_{1-6}$alkyl, $C_{1-6}$haloalkyl, $C_{1-6}$alkoxy, and $C_{1-6}$haloalkoxy.

In certain embodiments, $Y^1$ is N, and $Y^2$ is $C(R^3)$. In certain other embodiments, $Y^1$ is $C(R^3)$, and $Y^2$ is N. In certain other embodiments, $Y^1$ is N, and $Y^2$ is CH. In certain other embodiments, $Y^1$ is CH, and $Y^2$ is N.

In certain embodiments, $R^1$ is hydrogen.

In certain embodiments, $R^2$ is —C(O)-aryl or —C(O)-aralkyl; each of which is optionally substituted with 1, 2, or 3 substituents independently selected from the group consisting of halogen, hydroxyl, $C_{1-6}$alkoxy, $C_{1-6}$haloalkoxy, $C_{1-6}$alkyl, and $C_{1-6}$haloalkyl. In certain other embodiments, $R^2$ is —C(O)-aryl or —C(O)-aralkyl; each of which is substituted with 2 substituents independently selected from the group consisting of halogen, hydroxyl, $C_{1-6}$alkoxy, $C_{1-6}$haloalkoxy, $C_{1-6}$alkyl, and $C_{1-6}$haloalkyl, and said substituents are located at the ortho-positions of the aromatic ring. In certain other embodiments, $R^2$ is —C(O)-phenyl or —C(O)-benzyl; each of which is optionally substituted with 1, 2, or 3 substituents independently selected from the group consisting of halogen, hydroxyl, $C_{1-6}$alkoxy, $C_{1-6}$haloalkoxy, $C_{1-6}$alkyl, and $C_{1-6}$haloalkyl. In certain other embodiments, $R^2$ is —C(O)-phenyl or —C(O)-benzyl; each of which is optionally substituted with 1, 2, or 3 substituents independently selected from the group consisting of halogen, $C_{1-6}$alkyl, and $C_{1-6}$haloalkyl. In certain other embodiments, $R^2$ is represented by:

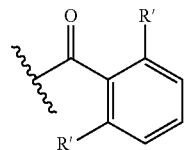

wherein each R' is independently halogen, hydroxyl, $C_{1-6}$alkoxy, $C_{1-6}$haloalkoxy, $C_{1-6}$alkyl, or $C_{1-6}$haloalkyl. In certain other embodiments, $R^2$ is represented by:

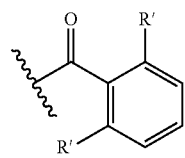

wherein each R' is independently halogen, $C_{1-6}$alkyl, or $C_{1-6}$haloalkyl.

In certain embodiments, $R^2$ is represented by:

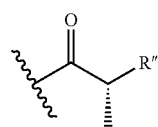

wherein R" is $C_{1-6}$alkyl, aryl, or heterocyclyl, each of which is optionally substituted with 1, 2, or 3 substituents independently selected from the group consisting of halogen, hydroxyl, $C_{1-6}$alkoxy, $C_{1-6}$haloalkoxy, $C_{1-6}$alkyl, $C_{1-6}$haloalkyl, —N($R^4$)($R^5$), —CN, —$CO_2$—$C_{1-6}$alkyl, —C(O)—$C_{1-6}$alkyl, —C(O)N($R^4$)($R^5$), —S(O)$_p C_{1-6}$alkyl, —$SO_2$N($R^4$)($R^5$), and —N($R^4$)$SO_2$($C_{1-6}$alkyl). In certain embodiments, R" is phenyl optionally substituted with 1, 2, or 3 substituents independently selected from the group consisting of halogen, $C_{1-6}$alkyl, and $C_{1-6}$haloalkyl.

In certain embodiments, $R^3$ is hydrogen.

In certain embodiments, $R^7$ is hydrogen. In certain other embodiments $R^7$ is hydroxyl, $C_{1-6}$hydroxyalkyl, $C_{1-6}$alkyl, $C_{1-6}$haloalkyl, —$CO_2R^6$, $C_{1-6}$alkylene-$CO_2R^6$, $C_{1-4}$hydroxyalkylene-$CO_2R^6$, —N($R^4$)($R^5$), $C_{1-6}$alkylene-N($R^4$)($R^5$), $C_{1-6}$hydroxyalkylene-N($R^4$)($R^5$), —N($R^4$)C(O)$R^9$, $C_{1-6}$alkylene-N($R^4$)C(O)$R^9$, $C_{1-6}$alkylene-C(O)N($R^4$)($R^5$), —N($R^4$)$CO_2$—$C_{1-6}$alkyl, or —N($R^4$)C(O)$R^9$. In certain other embodiments, $R^7$ is $C_{1-6}$hydroxyalkyl, $C_{1-6}$alkyl, $C_{1-6}$alkylene-$CO_2R^6$, —N($R^4$)($R^5$), $C_{1-6}$alkylene-N($R^4$)($R^5$), or $C_{1-6}$alkylene-N($R^4$)C(O)$R^9$. In certain other embodiments, $R^7$ is $C_{1-3}$hydroxyalkyl, methyl, ethyl, or $C_{1-3}$alkylene-N(H)C(O)—$C_{1-4}$alkyl.

Another aspect of the invention provides a compound represented by Formula VI:

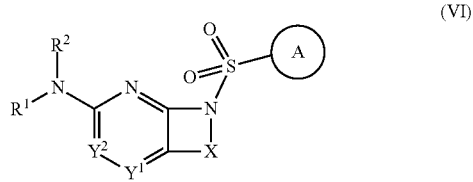

(VI)

or a pharmaceutically acceptable salt or solvate thereof; wherein:

A is aryl, aralkyl, heteroaryl, cycloalkyl, or heterocycloalkyl; each of which is optionally substituted with 1, 2, or 3 substituents independently selected from the group consisting of halogen, hydroxyl, $C_{1-6}$alkyl, $C_{1-6}$haloalkyl, $C_{1-6}$hydroxyalkyl, $C_{1-6}$alkoxy, $C_{1-6}$haloalkoxy, —N($R^4$)($R^5$), —$CO_2R^6$, —C(O)$R^6$, —CN, —$C_{1-4}$alkylene-$C_{1-4}$alkoxy, —$C_{1-4}$alkylene-N($R^4$)($R^5$), —$C_{1-4}$alkylene-$CO_2R^6$, —O—$C_{1-4}$alkylene-N($R^4$)($R^5$), —N($R^4$)C(O)—$C_{1-6}$alkylene-N($R^4$)($R^5$), —S(O)$_p C_{1-6}$alkyl, —$SO_2$N($R^4$)($R^5$), —N($R^4$)$SO_2$($C_{1-6}$alkyl), —C(O)N($R^4$)($R^5$), and —N($R^4$)C(O)N($R^4$)($R^5$);

X is —O—[C($R^6$)($R^7$)]—[C($R^6$)$_2$]$_m$-ψ, —O—C($R^6$)$_2$—C($R^6$)($R^7$)—C($R^6$)$_2$-ψ, —O—C($R^6$)$_2$—C($R^6$)($R^7$)-ψ, —C($R^6$)$_2$—[C($R^6$)($R^7$)]—[C($R^6$)$_2$]$_m$-ψ, —C(O)—[C($R^6$)($R^7$)]—[C($R^6$)$_2$]$_m$-ψ, —C($R^6$)$_2$—N($R^8$)—[C($R^6$)($R^7$)]—[C($R^6$)$_2$]$_m$-ψ, —C($R^6$)=N-ψ, —C($R^6$)$_2$C($R^6$)=N-ψ, —N=C($R^6$)-ψ, or —N=C($R^6$)C($R^6$)$_2$-ψ; wherein ψ is a bond to the sulfonamide ring nitrogen atom in Formula VI;

$Y^1$ and $Y^2$ are each independently C($R^3$) or N, provided that at least one of $Y^1$ and $Y^2$ is N;

$R^1$ is hydrogen or $C_{1-6}$alkyl;

$R^2$ is hydrogen, —C(O)-aryl, —C(O)-aralkyl, —C(O)—[C($R^6$)$_2$]$_m$-cycloalkyl, —C(O)—[C($R^6$)$_2$]$_m$-heterocyclyl, —C(O)—$C_{1-8}$alkyl, —C(O)—$C_{1-6}$alkylene-$C_{1-6}$alkoxyl, —C(O)—$C_{1-6}$alkylene-cycloalkyl, or —C(O)—$C_{1-6}$alkylene-heterocycloalkyl; each of which is optionally substituted with 1, 2, or 3 substituents independently selected from the group consisting of halogen, hydroxyl, $C_{1-6}$alkoxy, $C_{1-6}$haloalkoxy, $C_{1-6}$alkyl, $C_{1-6}$haloalkyl, —N($R^4$)($R^5$), —CN, —$CO_2$—$C_{1-6}$alkyl, —C(O)—$C_{1-6}$alkyl, —C(O)N($R^4$)($R^5$), —S(O)$_p C_{1-6}$alkyl, —$SO_2$N($R^4$)($R^5$), and —N($R^4$)$SO_2$($C_{1-6}$alkyl);

$R^3$ represents independently for each occurrence hydrogen, halogen, or $C_{1-6}$alkyl;

$R^4$ and $R^5$ each represent independently for each occurrence hydrogen or $C_{1-6}$alkyl; or $R^4$ and $R^5$ taken together with the nitrogen atom to which they are attached form a 3-7 membered heterocyclic ring;

$R^6$ represents independently for each occurrence hydrogen or $C_{1-6}$alkyl;

$R^7$ is hydrogen, hydroxyl, $C_{1-6}$hydroxyalkyl, $C_{1-6}$alkyl, $C_{1-6}$haloalkyl, —$CO_2R^6$, $C_{1-6}$alkylene-$CO_2R^6$, $C_{1-4}$hydroxyalkylene-$CO_2R^6$, —N($R^4$)($R^5$), $C_{1-6}$alkylene-N($R^4$)($R^5$), $C_{1-6}$hydroxyalkylene-N($R^4$)($R^5$), —N($R^4$)C(O)$R^9$, $C_{1-6}$alkylene-N($R^4$)C(O)$R^9$, $C_{1-6}$alkylene-C(O)N($R^4$)($R^5$), —N($R^4$)$CO_2$—$C_{1-6}$alkyl, or $C_{1-6}$alkylene-N($R^4$)(C(O)N($R^4$)($R^5$); or $R^7$ is heterocycloalkyl or $C_{1-4}$alkylene-heterocycloalkyl, wherein the heterocycloalkyl is optionally substituted with 1, 2, or 3 substituents independently selected from the group consisting of oxo, halogen, hydroxyl, $C_{1-6}$alkyl, $C_{1-6}$haloalkyl, $C_{1-6}$hydroxyalkyl, $C_{1-6}$alkoxy, and $C_{1-6}$haloalkoxy;

$R^8$ is hydrogen, $C_{1-6}$alkyl, or —C(O)—$C_{1-6}$alkyl;

$R^9$ is hydrogen, $C_{1-6}$alkyl, $C_{1-6}$hydroxyalkyl, N($R^4$)($R^5$), $C_{1-6}$alkylene N($R^4$)($R^5$), or $C_{1-6}$alkylene N($R^4$)C(O)—$C_{1-6}$alkyl; each of which is optionally substituted with 1, 2, or 3 halogen, hydroxyl or amino; and m and p each represent independently for each occurrence 0, 1, or 2.

In certain embodiments, A is aryl or heteroaryl; each of which is optionally substituted with 1, 2, or 3 substituents independently selected from the group consisting of halogen, $C_{1-6}$alkyl, $C_{1-6}$haloalkyl, $C_{1-6}$alkoxy, and $C_{1-6}$haloalkoxy. In certain other embodiments, A is aryl optionally substituted with 1, 2, or 3 substituents independently selected from the group consisting of halogen, $C_{1-6}$alkyl, $C_{1-6}$haloalkyl, $C_{1-6}$alkoxy, and $C_{1-6}$haloalkoxy. In certain other embodiments, A is phenyl optionally substituted with 1, 2, or 3 substituents independently selected from the group consisting of halogen, $C_{1-6}$alkyl, $C_{1-6}$haloalkyl, $C_{1-6}$alkoxy, and $C_{1-6}$haloalkoxy. In certain other embodiments, A is phenyl optionally substituted with 1, 2, or 3 substituents independently selected from the group consisting of halogen and $C_{1-6}$haloalkyl. In certain embodiments, at least one substituent is attached at the meta-position of the phenyl ring.

In certain other embodiments, A is heteroaryl optionally substituted with 1, 2, or 3 substituents independently selected from the group consisting of halogen, $C_{1-6}$alkyl, $C_{1-6}$haloalkyl, $C_{1-6}$alkoxy, and $C_{1-6}$haloalkoxy.

In certain embodiments, A is heterocycloalkyl optionally substituted with 1, 2, or 3 substituents independently selected from the group consisting of halogen, $C_{1-6}$alkyl, $C_{1-6}$haloalkyl, $C_{1-6}$alkoxy, and $C_{1-6}$haloalkoxy. In certain embodiments, A is piperidine or pyrrolidine, each of which is optionally substituted with 1, 2, or 3 substituents independently selected from the group consisting of halogen, $C_{1-6}$alkyl, $C_{1-6}$haloalkyl, $C_{1-6}$alkoxy, and $C_{1-6}$haloalkoxy.

In certain embodiments, X is —O—[C($R^6$)($R^7$)]—[C($R^6$)$_2$]$_m$-ψ. In certain other embodiments, X is —C($R^6$)$_2$—[C($R^6$)($R^7$)]—[C($R^6$)$_2$]$_m$-ψ. In certain other embodiments, X is —C(O)—[C($R^6$)($R^7$)]—[C($R^6$)$_2$]$_m$-ψ. In certain other embodiments, X is —C($R^6$)$_2$—N($R^8$)—[C($R^6$)($R^7$)]—[C($R^6$)$_2$]$_m$-ψ. In certain other embodiments, X is —C($R^6$)=N-ψ.

In certain embodiments, $Y^1$ is N, and $Y^2$ is $C(R^3)$. In certain other embodiments, $Y^1$ is $C(R^3)$, and $Y^2$ is N. In certain other embodiments, $Y^1$ is N, and $Y^2$ is CH. In certain other embodiments, $Y^1$ is CH, and $Y^2$ is N.

In certain embodiments, $R^1$ is hydrogen.

In certain embodiments, $R^2$ is —C(O)-aryl or —C(O)-aralkyl; each of which is optionally substituted with 1, 2, or 3 substituents independently selected from the group consisting of halogen, hydroxyl, $C_{1-6}$alkoxy, $C_{1-6}$haloalkoxy, $C_{1-6}$alkyl, and $C_{1-6}$haloalkyl. In certain other embodiments, $R^2$ is —C(O)-aryl or —C(O)-aralkyl; each of which is substituted with 2 substituents independently selected from the group consisting of halogen, hydroxyl, $C_{1-6}$alkoxy, $C_{1-6}$haloalkoxy, $C_{1-6}$alkyl, and $C_{1-6}$haloalkyl, and said substituents are located at the ortho-positions of the aromatic ring. In certain other embodiments, $R^2$ is —C(O)-phenyl or —C(O)-benzyl; each of which is optionally substituted with 1, 2, or 3 substituents independently selected from the group consisting of halogen, hydroxyl, $C_{1-6}$alkoxy, $C_{1-6}$haloalkoxy, $C_{1-6}$alkyl, and $C_{1-6}$haloalkyl. In certain other embodiments, $R^2$ is —C(O)-phenyl or —C(O)-benzyl; each of which is optionally substituted with 1, 2, or 3 substituents independently selected from the group consisting of halogen, $C_{1-6}$alkyl, and $C_{1-6}$haloalkyl. In certain other embodiments, $R^2$ is represented by:

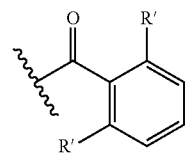

wherein each R' is independently halogen, hydroxyl, $C_{1-6}$alkoxy, $C_{1-6}$haloalkoxy, $C_{1-6}$alkyl, or $C_{1-6}$haloalkyl. In certain other embodiments, $R^2$ is represented by:

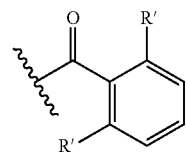

wherein each R' is independently halogen, $C_{1-6}$alkyl, or $C_{1-6}$haloalkyl.

In certain embodiments, $R^2$ is represented by:

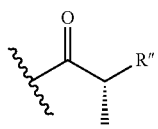

wherein R" is $C_{1-6}$alkyl, aryl, or heterocyclyl, each of which is optionally substituted with 1, 2, or 3 substituents independently selected from the group consisting of halogen, hydroxyl, $C_{1-6}$alkoxy, $C_{1-6}$haloalkoxy, $C_{1-6}$alkyl, $C_{1-6}$haloalkyl, —N($R^4$)($R^5$), —CN, —$CO_2$—$C_{1-6}$alkyl, —C(O)—$C_{1-6}$alkyl, —C(O)N($R^4$)($R^5$), —S(O)$_p$$C_{1-6}$alkyl, —$SO_2$N($R^4$)($R^5$), and —N($R^4$)$SO_2$($C_{1-6}$alkyl). In certain embodiments, R" is phenyl optionally substituted with 1, 2, or 3 substituents independently selected from the group consisting of halogen, $C_{1-6}$alkyl, and $C_{1-6}$haloalkyl.

In certain embodiments, $R^3$ is hydrogen.

In certain embodiments, $R^7$ is hydrogen. In certain other embodiments, $R^7$ is hydroxyl, $C_{1-6}$hydroxyalkyl, $C_{1-6}$alkyl, $C_{1-6}$haloalkyl, —$CO_2R^6$, $C_{1-6}$alkylene-$CO_2R^6$, $C_{1-4}$hydroxyalkylene-$CO_2R^6$, —N($R^4$)($R^5$), $C_{1-6}$alkylene-N($R^4$)($R^5$), $C_{1-6}$hydroxyalkylene-N($R^4$)($R^5$), —N($R^4$)C(O)$R^9$, $C_{1-6}$alkylene-N($R^4$)C(O)$R^9$, $C_{1-6}$alkylene-C(O)N($R^4$)($R^5$), —N($R^4$)$CO_2$—$C_{1-6}$alkyl, or —N($R^4$)C(O)$R^9$. In certain other embodiments, $R^7$ is $C_{1-6}$hydroxyalkyl, $C_{1-6}$alkyl, $C_{1-6}$alkylene-$CO_2R^6$, —N($R^4$)($R^5$), $C_{1-6}$alkylene-N($R^4$)($R^5$), or $C_{1-6}$alkylene-N($R^4$)C(O)$R^9$. In certain other embodiments, $R^7$ is $C_{1-3}$hydroxyalkyl, methyl, ethyl, or $C_{1-3}$alkylene-N(H)C(O)—$C_{1-4}$alkyl.

In certain other embodiments, $R^7$ is heterocycloalkyl or $C_{1-4}$alkylene-heterocycloalkyl, wherein the heterocycloalkyl is optionally substituted with 1, 2, or 3 substituents independently selected from the group consisting of oxo, halogen, hydroxyl, $C_{1-6}$alkyl, $C_{1-6}$haloalkyl, $C_{1-6}$hydroxyalkyl, $C_{1-6}$alkoxy, and $C_{1-6}$haloalkoxy.

The definitions of variables in Formulae I-VI, I-A, II-A, and III-A above encompass multiple chemical groups. The application contemplates embodiments where, for example, i) the definition of a variable is a single chemical group selected from those chemical groups set forth above, ii) the definition is a collection of two or more of the chemical groups selected from those set forth above, and iii) the compound is defined by a combination of variables in which the variables are defined by (i) or (ii).

In certain other embodiments, the compound is one of the compounds listed in Tables 1-3 herein below, Tables 4-9 in the Examples, or a pharmaceutically acceptable salt of any of the foregoing.

TABLE 1

| No. | Y | Z |
|---|---|---|
| I-1 | 2,6-substituted benzamide with Cl and $CF_3$ | 4-fluorophenyl |
| I-2 | 2,6-substituted benzamide with F and $CF_3$ | 3-chlorophenyl |
| I-3 | 2,6-substituted benzamide with $CF_3$ and $CF_3$ | 3-cyclopropylphenyl |

TABLE 1-continued

| No. | Y | Z |
|---|---|---|
| I-4 | 2-chloro-6-fluorobenzamide | 4-fluorophenyl |
| I-5 | 2,6-difluorobenzamide | 3-chlorophenyl |
| I-6 | 2,6-dichlorobenzamide | 3-cyclopropylphenyl |
| I-7 | 2-(4-chlorophenyl)acetamide | 4-fluorophenyl |
| I-8 | pyridine-3-carboxamide | 3-chlorophenyl |
| I-9 | (2R)-2-phenylpropanamide | 3-cyclopropylphenyl |
| I-10 | cyclohexanecarboxamide | 4-fluorophenyl |

TABLE 1-continued

| No. | Y | Z |
|---|---|---|
| I-11 | 2-chloro-6-(trifluoromethyl)benzamide | 3-(trifluoromethyl)phenyl |
| I-12 | 2-fluoro-6-(trifluoromethyl)benzamide | 3,4-difluorophenyl |
| I-13 | 2-chloro-6-(trifluoromethyl)benzamide | 3-(trifluoromethyl)phenyl |
| I-14 | 2-chloro-6-fluorobenzamide | 3,4-difluorophenyl |
| I-15 | 2,6-difluorobenzamide | 3-(trifluoromethyl)phenyl |
| I-16 | 2,6-dichlorobenzamide | 3,4-difluorophenyl |
| I-17 | 2-(4-chlorophenyl)acetamide | 3-(trifluoromethyl)phenyl |

TABLE 1-continued

| No. | Y | Z |
|---|---|---|
| I-18 | nicotinamide | 3,4-difluorophenyl |
| I-19 | (S)-2-phenylpropanamide | 3-(trifluoromethyl)phenyl |
| I-20 | cyclohexanecarboxamide | 3,4-difluorophenyl |
| I-21 | 2-chloro-6-(trifluoromethyl)benzamide | 1-methyl-1H-pyrazol-4-yl |
| I-22 | 2-fluoro-6-(trifluoromethyl)benzamide | 1-methyl-1H-pyrazol-4-yl |
| I-23 | 2-chloro-6-(trifluoromethyl)benzamide | 5-fluoropyridin-2-yl |
| I-24 | 2-chloro-6-fluorobenzamide | piperidin-1-yl |
| I-25 | 2,6-difluorobenzamide | 1-methylpyrrolidin-3-yl |
| I-26 | 2,6-dichlorobenzamide | 1H-pyrazol-1-yl |
| I-27 | 2-(4-chlorophenyl)acetamide | 1H-imidazol-1-yl |
| I-28 | nicotinamide | 5-fluoropyridin-2-yl |
| I-29 | (S)-2-phenylpropanamide | piperidin-1-yl |
| I-30 | cyclohexanecarboxamide | 1-methylpyrrolidin-3-yl |
| I-31 | isobutyramide | 3-methoxyphenyl |
| I-32 | isobutyramide | 4-fluorophenyl |

TABLE 1-continued

| No. | Y | Z |
|---|---|---|
| I-33 | isobutyramide | 3-Cl-phenyl |
| I-34 | (R)-2-methoxypropanamide | 3-OMe-phenyl |
| I-35 | (R)-2-methoxypropanamide | 3-Cl-phenyl |
| I-36 | bicyclopentane propanamide | 3-Cl-phenyl |
| I-37 | bicyclopentane propanamide | 3-OMe-phenyl |
| I-38 | 2-Cl-6-CF3-benzamide | 3-OMe-phenyl |
| I-39 | 2-F-6-CF3-benzamide | octahydrocyclopenta[c]pyrrole |
| I-40 | 2-Cl-6-CF3-benzamide | 5-methyl-2-(hydroxymethyl)piperidine |

TABLE 2

| No. | Y | | Z |
|---|---|---|---|
| II-1 | 2-Cl-6-CF3-benzamide | tetrahydro-1,5-naphthyridine | 4-F-phenyl |

TABLE 2-continued
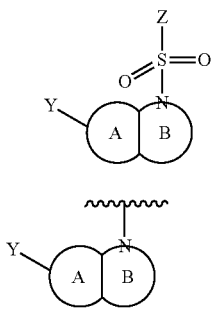
| No. | Y | | Z |
|---|---|---|---|
| II-2 | 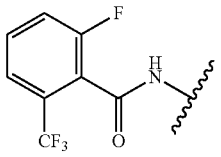 | 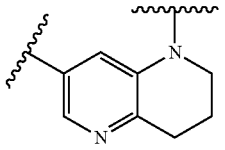 [SMILES: *c1cnc2c(c1)N(*)CCC2] | 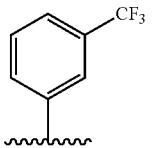 [SMILES: *c1cccc(C(F)(F)F)c1] |
| II-3 | 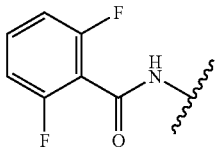 [SMILES: *NC(=O)c1c(F)cccc1F] | 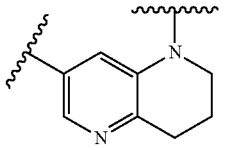 [SMILES: *c1cnc2c(c1)N(*)CCC2] | 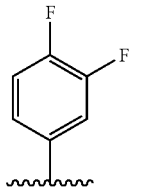 |
| II-4 | 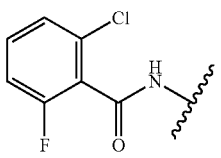 | 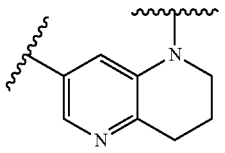 | 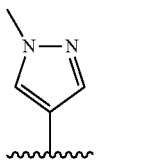 |
| II-5 |  | 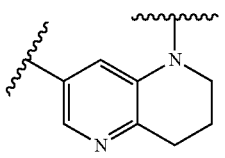 [SMILES: *c1cnc2c(c1)N(*)CCC2] | 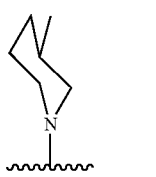 [SMILES: *N1CCCC(C)C1] |
| II-6 | 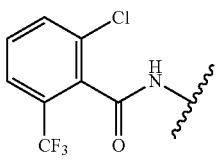 | 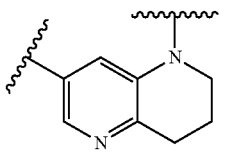 [SMILES: *c1cnc2c(c1)N(*)CCC2] | 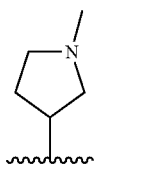 [SMILES: *C1CCN(C)C1] |
| II-7 | 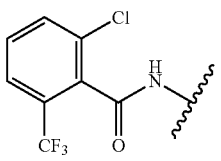 [SMILES: *NC(=O)c1c(Cl)cccc1C(F)(F)F] | 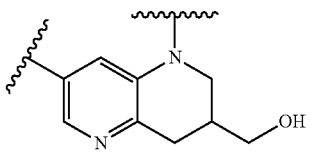 [SMILES: *c1cnc2c(c1)N(*)CC(CO)C2] | 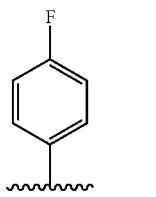 |
| II-8 | 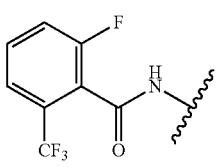 | 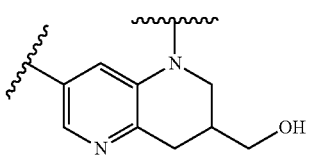 [SMILES: *c1cnc2c(c1)N(*)CC(CO)C2] | 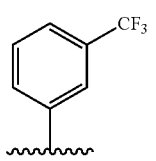 [SMILES: *c1cccc(C(F)(F)F)c1] |

TABLE 2-continued

| No. | Y | | Z |
|---|---|---|---|
| II-9 | 2,6-difluorophenyl-C(O)NH- | 1,2,3,4-tetrahydro-1,5-naphthyridin-7-yl with 3-CH2N(H)C(O)CH3 | 3,4-difluorophenyl |
| II-10 | 2-chloro-6-fluorophenyl-C(O)NH- | 1,2,3,4-tetrahydro-1,5-naphthyridin-7-yl with 3-CH2N(H)C(O)CH3 | 1-methyl-1H-pyrazol-4-yl |
| II-11 | 2-chloro-6-trifluoromethylphenyl-C(O)NH- | 5,6,7,8-tetrahydro-1,6-naphthyridin-3-yl | piperidin-1-yl |
| II-12 | 2-fluoro-6-trifluoromethylphenyl-C(O)NH- | 5,6,7,8-tetrahydro-1,6-naphthyridin-3-yl | 4-fluorophenyl |
| II-13 | 2,6-difluorophenyl-C(O)NH- | 5,6,7,8-tetrahydro-1,6-naphthyridin-3-yl | 3-trifluoromethylphenyl |
| II-14 | 2-chloro-6-fluorophenyl-C(O)NH- | 5,6,7,8-tetrahydro-1,6-naphthyridin-3-yl | 3,4-difluorophenyl |
| II-15 | 2,6-dichlorophenyl-C(O)NH- | 5,6,7,8-tetrahydro-1,6-naphthyridin-3-yl | 1-methyl-1H-pyrazol-4-yl |

TABLE 2-continued

| No. | Y | | Z |
|---|---|---|---|
| II-16 |  |  |  |
| II-17 |  |  |  |
| II-18 |  |  |  |
| II-19 |  |  |  |
| II-20 |  |  |  |
| II-21 |  |  |  |
| II-22 | 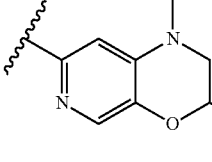 | 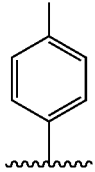 | |

TABLE 2-continued

| No. | Y | | Z |
|---|---|---|---|
| II-23 | 2,6-difluorobenzamide | 7-yl-3-(hydroxymethyl)-3,4-dihydro-2H-pyrido[3,2-b][1,4]oxazin-4-yl | 3-(trifluoromethyl)phenyl |
| II-24 | 2-chloro-6-fluorobenzamide | 7-yl-3-(hydroxymethyl)-3,4-dihydro-2H-pyrido[3,2-b][1,4]oxazin-4-yl | 3,4-difluorophenyl |
| II-25 | 2,6-dichlorobenzamide | 7-yl-3-(N(H)C(O)CH₃-methyl)-3,4-dihydro-2H-pyrido[3,2-b][1,4]oxazin-4-yl | 1-methyl-1H-pyrazol-4-yl |
| II-26 | 2-chloro-6-(trifluoromethyl)benzamide | 7-yl-3-(N(H)C(O)CH₃-methyl)-3,4-dihydro-2H-pyrido[3,2-b][1,4]oxazin-4-yl | piperidin-1-yl |
| II-27 | 2-fluoro-6-(trifluoromethyl)benzamide | 7-yl-3-(N(H)C(O)CH₃-methyl)-3,4-dihydro-2H-pyrido[3,2-b][1,4]oxazin-4-yl | 4-fluorophenyl |
| II-28 | 2,6-difluorobenzamide | 7-yl-3-methyl-3,4-dihydro-2H-pyrido[3,2-b][1,4]oxazin-4-yl | 3-(trifluoromethyl)phenyl |
| II-29 | 2-chloro-6-fluorobenzamide | 7-yl-3-methyl-3,4-dihydro-2H-pyrido[3,2-b][1,4]oxazin-4-yl | 3,4-difluorophenyl |

Note: I was unable to render the exact structural drawings as images; the descriptions above approximate the Y, middle (A/B ring system), and Z substituents shown in the original table.

TABLE 2-continued
| No. | Y | | Z |
|---|---|---|---|
| II-30 | 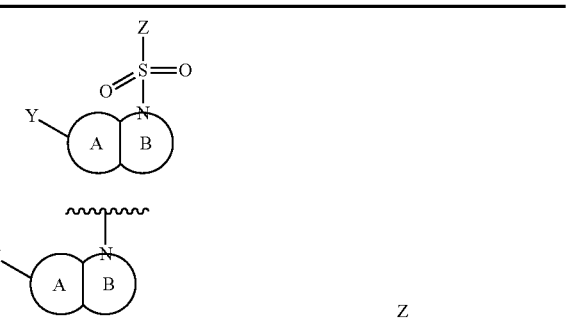 | 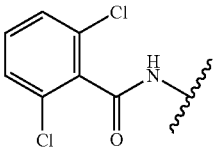 | 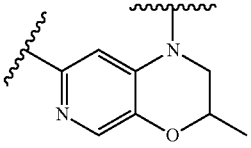 [SMILES: *c1cc2c(cn1)OC(C)CN2*] |
| II-31 | 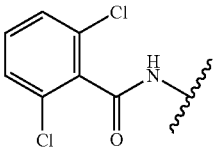 | 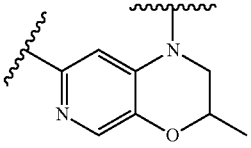 [SMILES: *c1cc2c(cn1)OC(C)CN2*] | 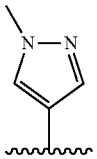 |
| II-32 | 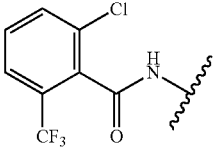 | 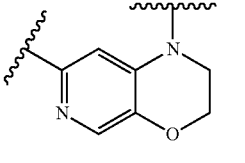 [SMILES: *c1cc2c(cn1)OCCN2*] |  |
| II-33 | 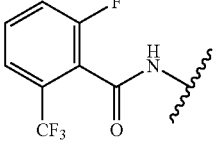 | 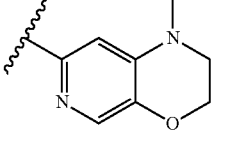 | 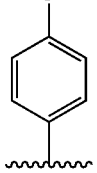 |
| II-34 | 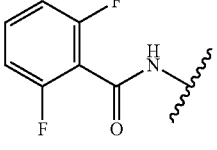 | 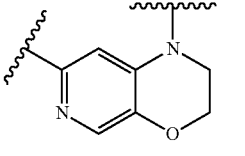 [SMILES: *c1cc2c(cn1)OCCN2*] | 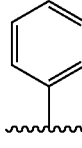 |
| II-35 | 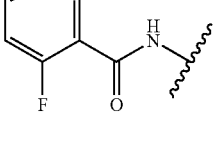 | 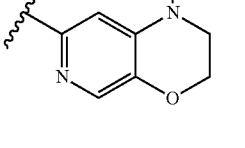 | 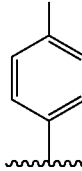 |
| II-36 | 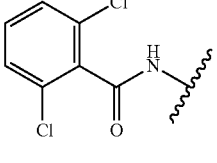 | 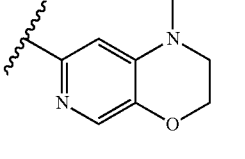 |  |

TABLE 2-continued
| No. | Y | | Z |
|---|---|---|---|
| II-37 | 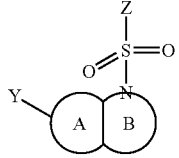 | 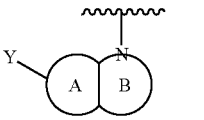 | 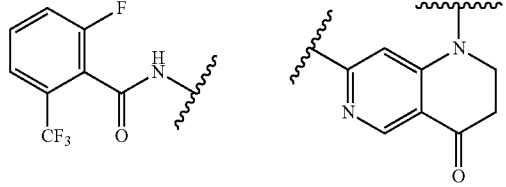 |
| II-38 | 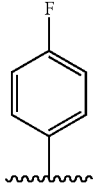 | | 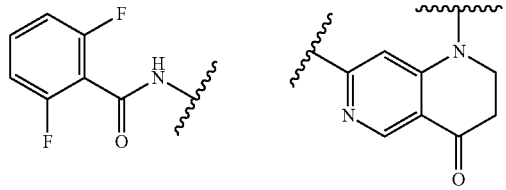 |
| II-39 | 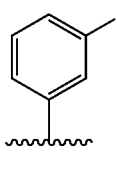 | | 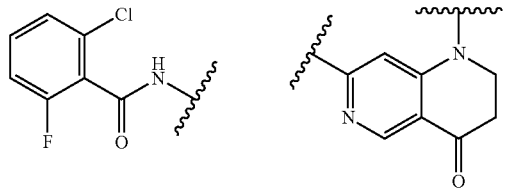 |
| II-40 | 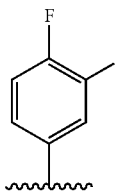 | | 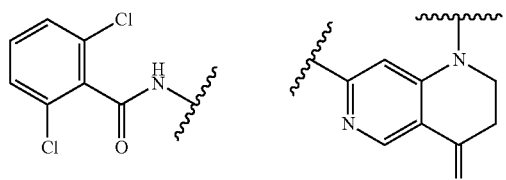 |
| II-41 | 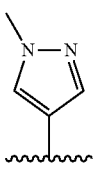 | | 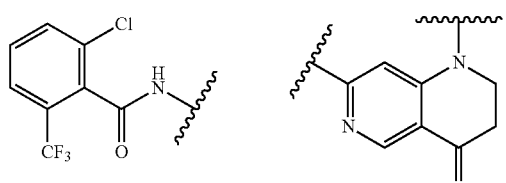 |
| II-42 | 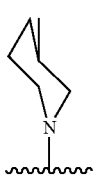 | 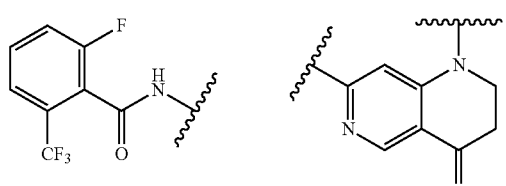 | 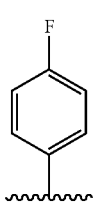 |

TABLE 2-continued
| No. | Y | | Z |
|---|---|---|---|
| II-43 | 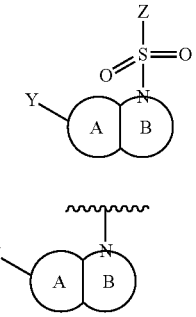 | 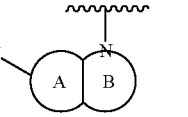 | 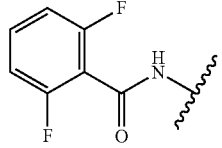 [SMILES: *NC(=O)c1c(F)cccc1F] |
| II-44 | 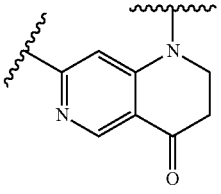 | 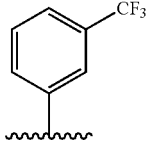 [SMILES: *c1cccc(C(F)(F)F)c1] | 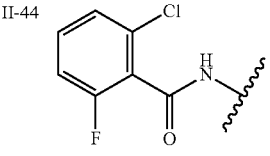 |
| II-45 | 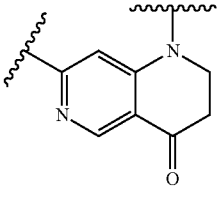 [SMILES: *c1cc2c(cn1)C(=O)CCN2*] | 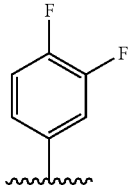 [SMILES: *c1ccc(F)c(F)c1] | 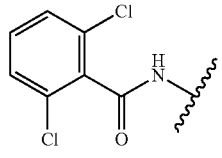 |
| II-46 | 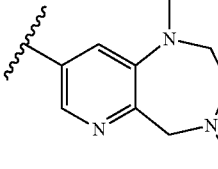 | 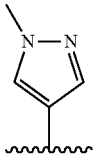 | 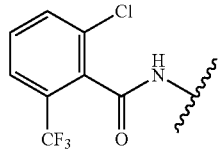 |
| II-47 | 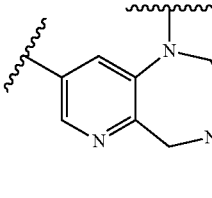 | 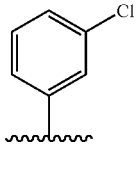 | 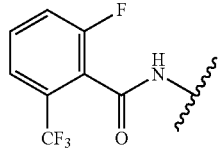 |
| II-48 | 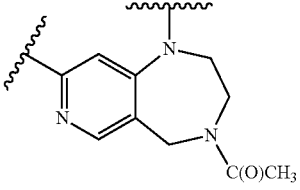 | 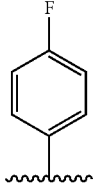 | 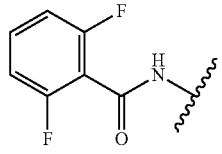 [SMILES: *NC(=O)c1c(F)cccc1F] |

TABLE 2-continued
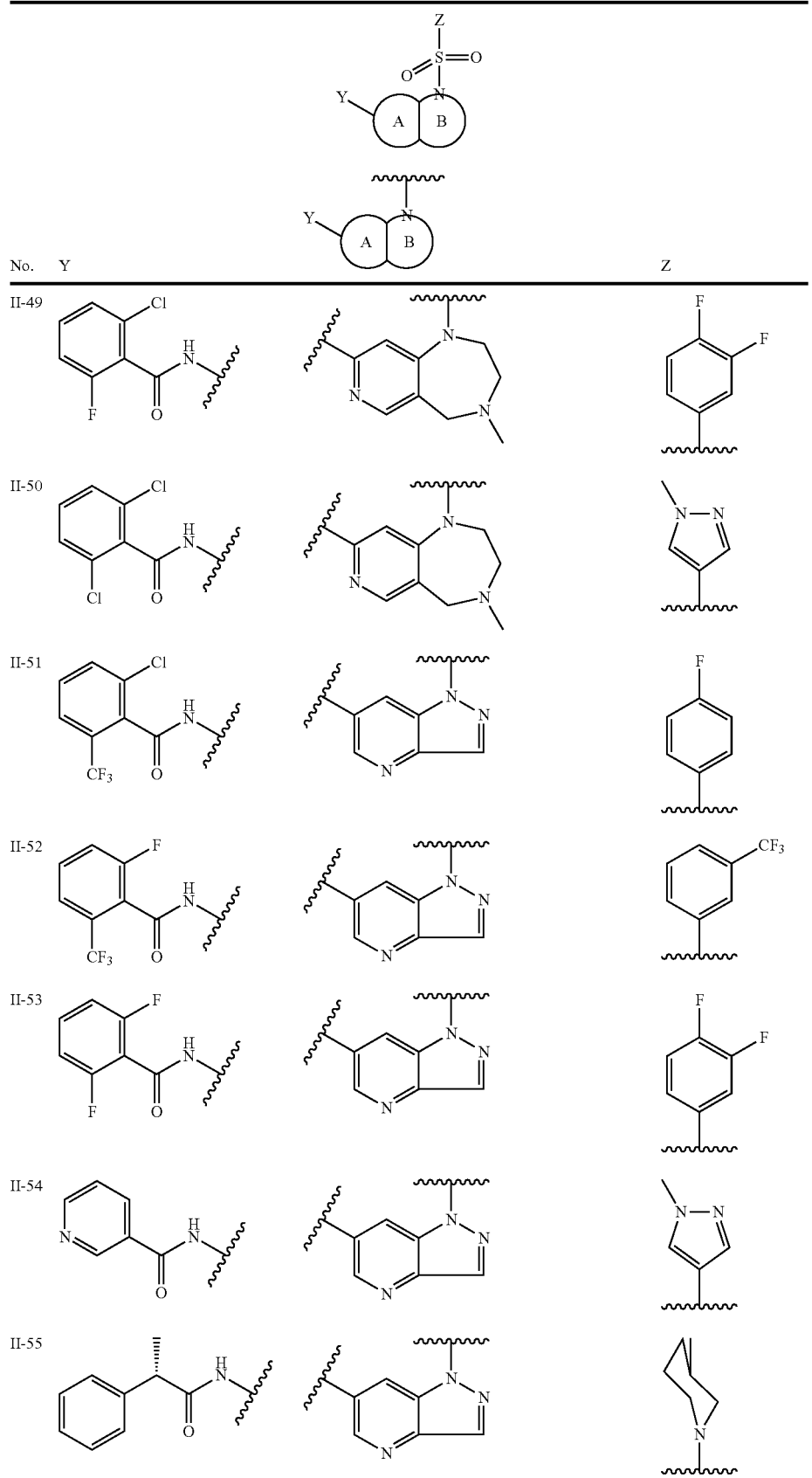

TABLE 2-continued
| No. | Y | | Z |
|---|---|---|---|
| II-56 | 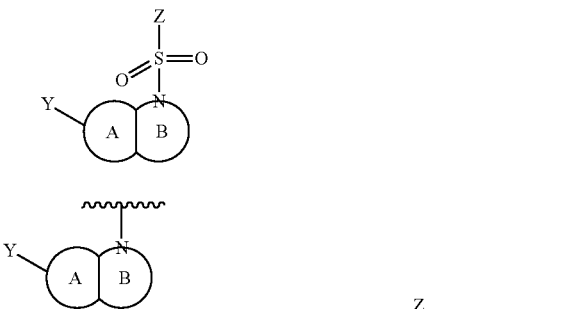 | 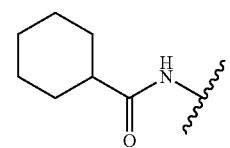 [SMILES: *NC(=O)C1CCCCC1] | 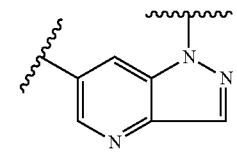 [SMILES: *c1cnc2cnn(*)c2c1] |
| II-57 | 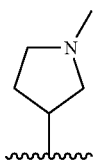 [SMILES: *C1CCN(C)C1] | 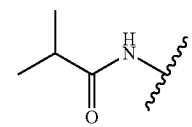 [SMILES: *NC(=O)C(C)C] | 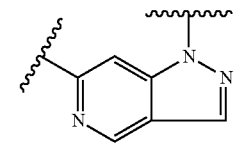 [SMILES: *c1cc2c(cn1)cnn2*] |
| II-58 | 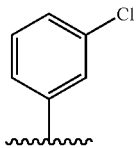 | 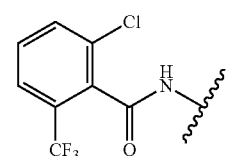 | 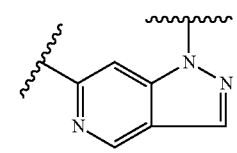 [SMILES: *c1cc2c(cn1)cnn2*] |
| II-59 | 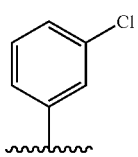 [SMILES: *c1cccc(Cl)c1] | 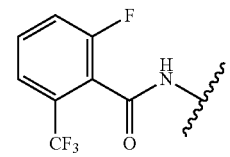 | 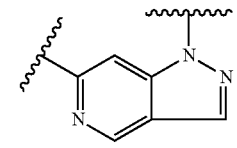 [SMILES: *c1cc2c(cn1)cnn2*] |
| II-60 |  | 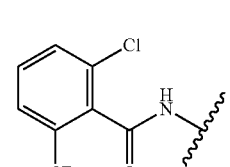 | 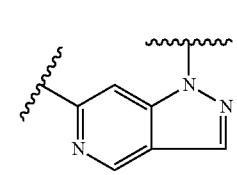 |
| II-61 | 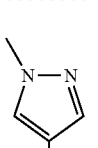 | 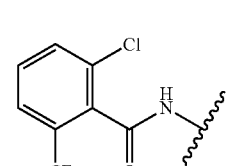 | 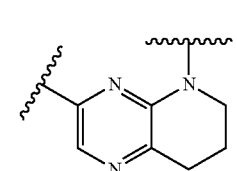 |
| II-62 | 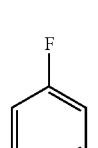 | 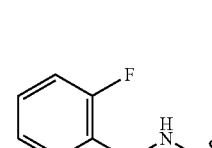 | 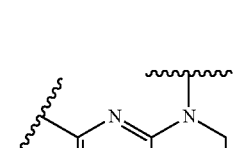 |

TABLE 2-continued

| No. | Y | | Z |
|---|---|---|---|
| II-63 | 2,6-difluorobenzamide | tetrahydropyrido[3,2-b]pyrazine (N-linked) | 3,4-difluorophenyl |
| II-64 | 2-chloro-6-fluorobenzamide | tetrahydropyrido[3,2-b]pyrazine (N-linked) | 1-methyl-1H-pyrazol-4-yl |
| II-65 | 2,6-dichlorobenzamide | tetrahydropyrido[3,2-b]pyrazine (N-linked) | piperidin-4-yl |
| II-66 | 2-chloro-6-(trifluoromethyl)benzamide | tetrahydropyrido[3,2-b]pyrazine (N-linked) | 1-methylpyrrolidin-3-yl |
| II-67 | 2-chloro-6-(trifluoromethyl)benzamide | hydroxymethyl-substituted tetrahydropyrido[3,2-b]pyrazine | 4-fluorophenyl |
| II-68 | 2-fluoro-6-(trifluoromethyl)benzamide | hydroxymethyl-substituted tetrahydropyrido[3,2-b]pyrazine | 3-(trifluoromethyl)phenyl |
| II-69 | 2,6-difluorobenzamide | N(H)C(O)CH₃-methyl-substituted tetrahydropyrido[3,2-b]pyrazine | 3,4-difluorophenyl |

TABLE 2-continued
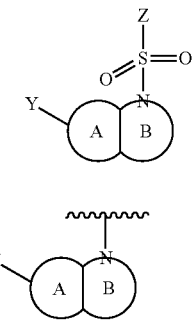
| No. | Y | | Z |
|---|---|---|---|
| II-70 | 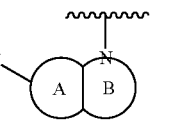 | 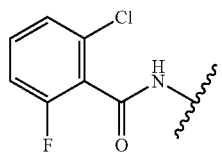 | 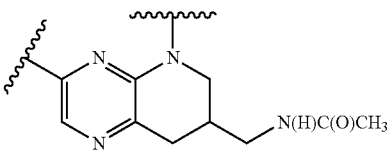 |
TABLE 3
| No. | Compound |
|---|---|
| III-1 | 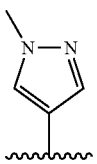 |
| III-2 | 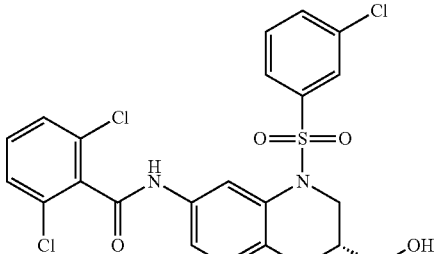 |
| III-3 | 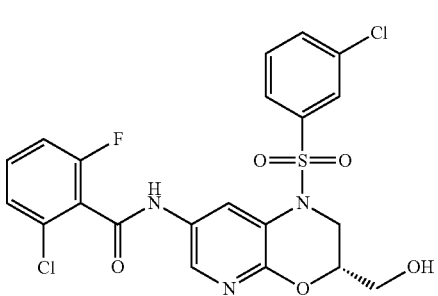 [SMILES: O=C(Nc1cnc2c(c1)N(S(=O)(=O)c1cccc(Cl)c1)C[C@H](CO)O2)c1c(Cl)cccc1Cl] |

TABLE 3-continued

| No. | Compound |
|---|---|
| III-4 | |
| III-5 | |
| III-6 | |
| III-7 | |
| III-8 | |

TABLE 3-continued

| No. | Compound |
|---|---|
| III-9 | |
| III-10 | |
| III-11 | |
| III-12 | |
| III-13 | |

TABLE 3-continued

| No. | Compound |
|---|---|
| III-14 | (structure) |
| III-15 | (structure) |
| III-16 | (structure) |
| III-17 | (structure) |
| III-18 | (structure) |

TABLE 3-continued
| No. | Compound |
|---|---|
| III-19 | 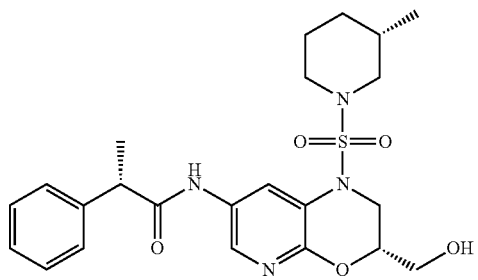 [SMILES: C[C@H]1CCCN(S(=O)(=O)N2C[C@H](CO)Oc3ncc(NC(=O)[C@@H](C)c4ccccc4)cc32)C1] |
| III-20 | 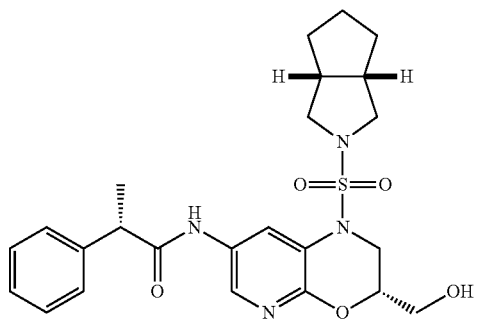 [SMILES: C[C@H](C(=O)Nc1cnc2c(c1)N(S(=O)(=O)N1C[C@H]3CCC[C@H]3C1)C[C@H](CO)O2)c1ccccc1] |
| III-21 | 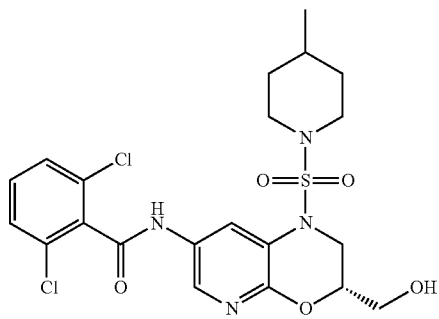 [SMILES: CC1CCN(S(=O)(=O)N2C[C@H](CO)Oc3ncc(NC(=O)c4c(Cl)cccc4Cl)cc32)CC1] |
| III-22 | 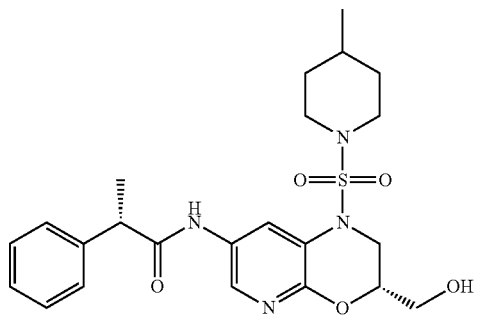 [SMILES: CC1CCN(S(=O)(=O)N2C[C@H](CO)Oc3ncc(NC(=O)[C@@H](C)c4ccccc4)cc32)CC1] |
| III-23 | 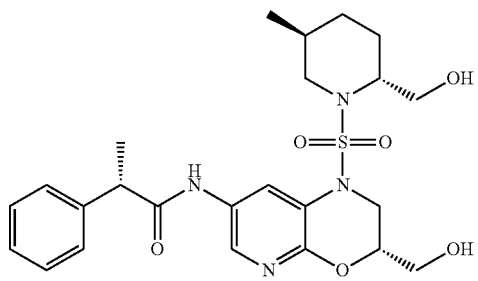 [SMILES: C[C@H]1CC[C@H](CO)N(S(=O)(=O)N2C[C@H](CO)Oc3ncc(NC(=O)[C@@H](C)c4ccccc4)cc32)C1] |

TABLE 3-continued
| No. | Compound |
|---|---|
| III-24 | 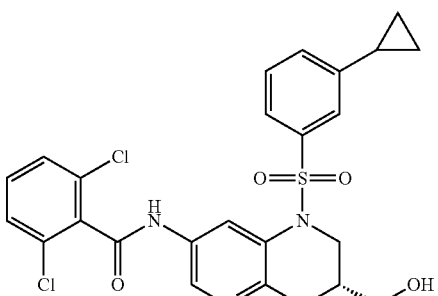 |
| III-25 | 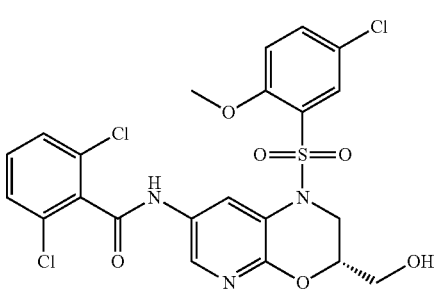 [SMILES: COc1ccc(Cl)cc1S(=O)(=O)N1C[C@H](CO)Oc2ncc(NC(=O)c3c(Cl)cccc3Cl)cc21] |
| III-26 | 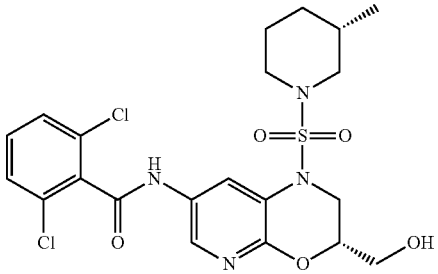 [SMILES: C[C@H]1CCCN(S(=O)(=O)N2C[C@H](CO)Oc3ncc(NC(=O)c4c(Cl)cccc4Cl)cc32)C1] |
| III-27 | 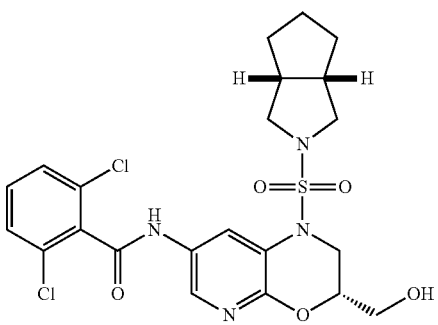 [SMILES: O=C(Nc1cnc2c(c1)N(S(=O)(=O)N1C[C@H]3CCC[C@H]3C1)C[C@H](CO)O2)c1c(Cl)cccc1Cl] |
| III-28 | 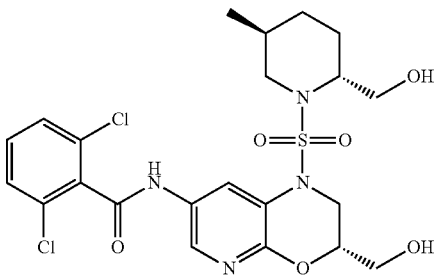 [SMILES: C[C@H]1CC[C@H](CO)N(S(=O)(=O)N2C[C@H](CO)Oc3ncc(NC(=O)c4c(Cl)cccc4Cl)cc32)C1] |

TABLE 3-continued

| No. | Compound |
|---|---|
| III-29 | |
| III-30 | |
| III-31 | |
| III-32 | |
| III-33 | |

TABLE 3-continued

| No. | Compound |
|---|---|
| III-34 | |
| III-35 | |
| III-36 | |
| III-37 | |
| III-38 | |

TABLE 3-continued
| No. | Compound |
|---|---|
| III-39 | 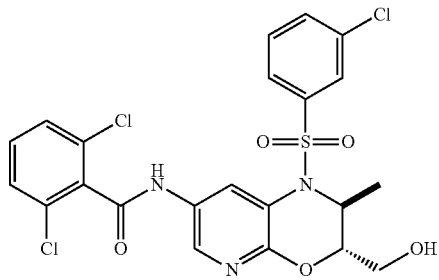 [SMILES: C[C@H]1[C@H](CO)Oc2ncc(NC(=O)c3c(Cl)cccc3Cl)cc2N1S(=O)(=O)c1cccc(Cl)c1] |
| III-40 | 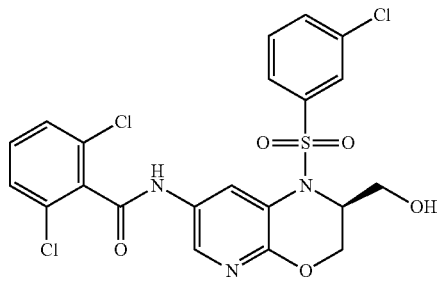 [SMILES: O=C(Nc1cnc2c(c1)N(S(=O)(=O)c1cccc(Cl)c1)[C@@H](CO)CO2)c1c(Cl)cccc1Cl] |
| III-41 | 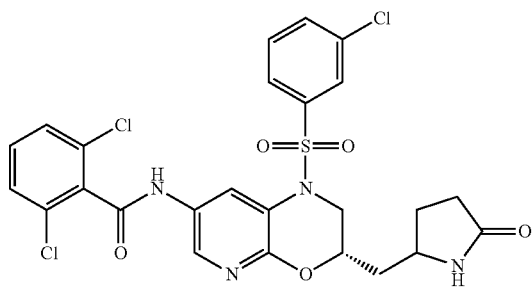 [SMILES: O=C1CCC(C[C@H]2CN(S(=O)(=O)c3cccc(Cl)c3)c3cc(NC(=O)c4c(Cl)cccc4Cl)cnc3O2)N1] |
| III-42 | 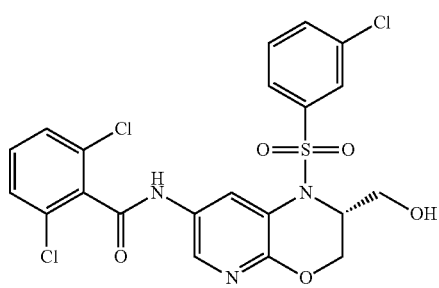 [SMILES: O=C(Nc1cnc2c(c1)N(S(=O)(=O)c1cccc(Cl)c1)[C@H](CO)CO2)c1c(Cl)cccc1Cl] |
| III-43 | 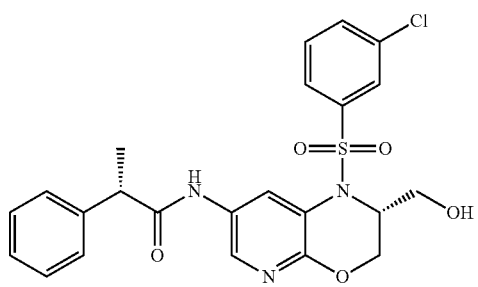 [SMILES: C[C@H](C(=O)Nc1cnc2c(c1)N(S(=O)(=O)c1cccc(Cl)c1)[C@H](CO)CO2)c1ccccc1] |

TABLE 3-continued

| No. | Compound |
|---|---|
| III-44 | |
| III-45 | |
| III-46 | |
| III-47 | |
| III-48 | |

TABLE 3-continued

| No. | Compound |
|---|---|
| III-49 | |
| III-50 | |
| III-51 | |
| III-52 | |
| III-53 | |

TABLE 3-continued

| No. | Compound |
|---|---|
| III-54 | |
| III-55 | |
| III-56 | |
| III-57 | |
| III-58 | |

TABLE 3-continued

| No. | Compound |
| --- | --- |
| III-59 | |
| III-60 | |
| III-61 | |
| III-62 | |
| III-63 | |

TABLE 3-continued

| No. | Compound |
|---|---|
| III-64 | |
| III-65 | |
| III-66 | |
| III-67 | |

TABLE 3-continued

| No. | Compound |
|---|---|
| III-68 | |
| III-69 | |
| III-70 | |
| III-71 | |
| III-72 | |

TABLE 3-continued
| No. | Compound |
|---|---|
| III-73 | 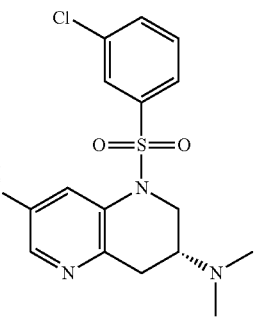 |
| III-74 | 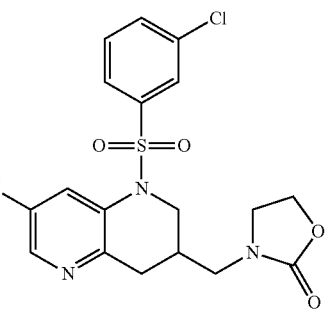 |
| III-75 | 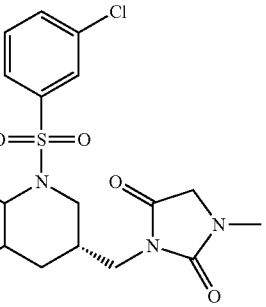 |
| III-76 | 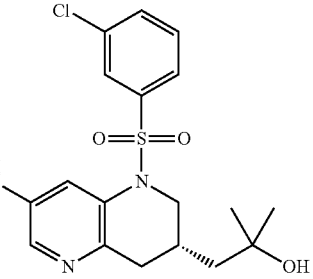 |
| III-77 | 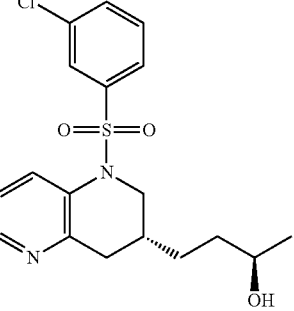 |

TABLE 3-continued
| No. | Compound |
|---|---|
| III-78 | 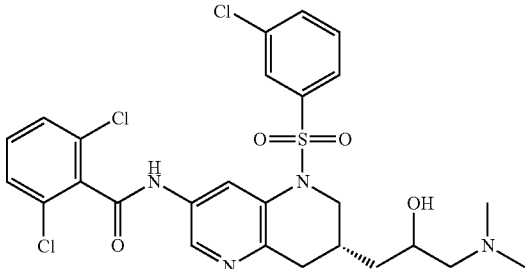 |
| III-79 | 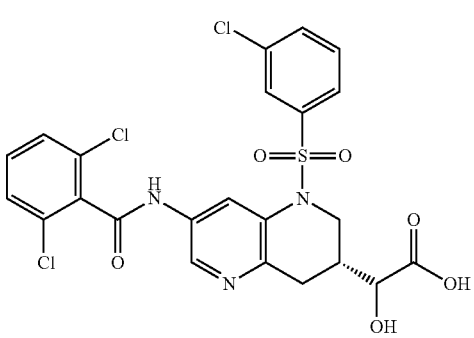 [SMILES: O=C(Nc1cnc2c(c1)N(S(=O)(=O)c1cccc(Cl)c1)C[C@H](C(O)C(=O)O)C2)c1c(Cl)cccc1Cl] |
| III-80 | 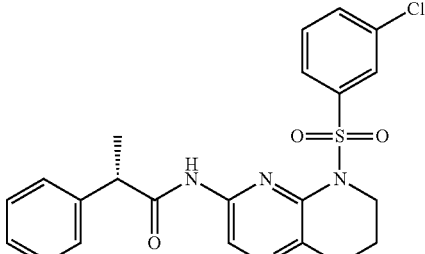 |
| III-81 | 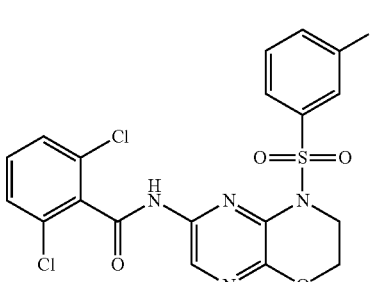 |
| III-82 | 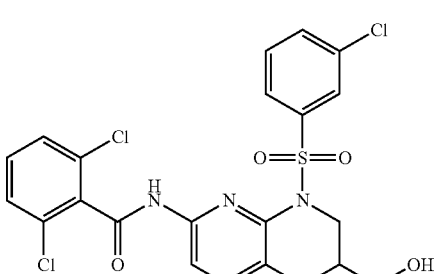 |

TABLE 3-continued
| No. | Compound |
|---|---|
| III-83 | 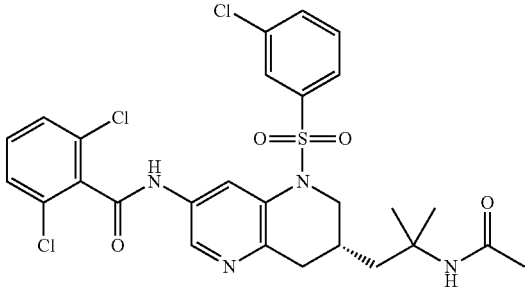 [SMILES: CC(=O)NC(C)(C)C[C@@H]1Cc2ncc(NC(=O)c3c(Cl)cccc3Cl)cc2N(S(=O)(=O)c2cccc(Cl)c2)C1] |
| III-84 | 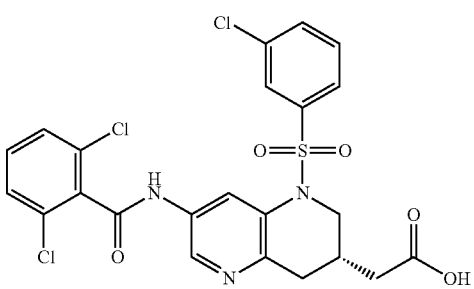 [SMILES: O=C(O)C[C@@H]1Cc2ncc(NC(=O)c3c(Cl)cccc3Cl)cc2N(S(=O)(=O)c2cccc(Cl)c2)C1] |
| III-85 | 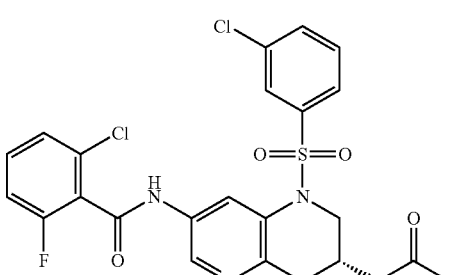 |
| III-86 | 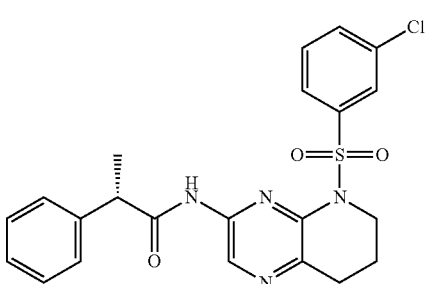 |
| III-87 | 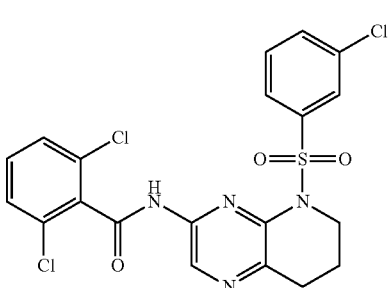 |

TABLE 3-continued

| No. | Compound |
|---|---|
| III-88 | |

Methods for preparing compounds described herein are illustrated in the following synthetic schemes. The schemes are given for the purpose of illustrating the invention, and are not intended to limit the scope or spirit of the invention. Starting materials shown in the schemes can be obtained from commercial sources or be prepared based on procedures described in the literature.

The synthetic route illustrated in Scheme 1 is a general method for preparing various 3-amido-5,6,7,8-tetrahydro-1,5-naphthyridine compounds. Reaction of bromo-aminopyridine A with glycerin in the presence of sulfuric acid provides bromo-1,5-naphthyridine B. For further description of exemplary procedures for this transformation, see, for example, Skraup, Z. H. *Berichte* 1880, 13, 2086; and Li et al. in *Org. Lett.* 2000, 2, 875-878. Bromo-1,5-naphthyridine B can be converted to amino-1,5-naphthyridine C using procedures known in the art, such as (1) Ullmann $CuSO_4$ mediated addition of ammonia (Hauser et al. in *J. Org. Chem.* 1950, 15, 1224-1232); (2) Pd-mediated addition of a carbamate (Bhagwanth et al. in *J. Org Chem.* 2009, 74, 4634-4637) followed by deprotection; (3) Pd-mediated addition of hexamethyldisilazide (Stefko et al. in *J. Org. Chem.* 2011, 76, 6619-6635), and (4) Pd-mediated addition of diphenylmethanimine followed by deprotection with acid (Grasa et al. in *J. Org. Chem.* 2001, 66, 7729-7737). Reaction of amino-1,5-naphthyridine C with an acid chloride provides amido-1,5-naphthyridine D. Reduction of amido-1,5-naphthyridine D using, for example, hydrogenation conditions, provides substituted-tetrahydro-1,5-naphthyridine E. Reaction of a sulphonyl chloride or a sulfamoyl chloride with substituted-tetrahydro-1,5-naphthyridine E provides the final amido-tetrahydro-1,5-naphthyridine F.

The reaction procedures in Scheme 1 are contemplated to be amenable to preparing a wide variety of amide-substituted 5,6,7,8-tetrahydro-1,5-naphthyridine compounds having different substituents at the R, $R^I$, and $R^{II}$ positions. For example, numerous substituted 5-bromo-3-aminopyridines are known in the literature and/or are commercially available, such as 5-bromo-6-methyl-pyridin-3-amine, 5-bromo-4-methyl-pyridin-3-amine, 5-amino-3-bromo-2-methoxylpyridine, and 5-bromo-4,6-dimethyl-pyridin-3-amine. Furthermore, if a functional group that is part of R, $R^I$, or $R^{II}$ would not be amenable to a reaction condition described in Scheme 1, it is contemplated that the functional group can first be protected using standard protecting group chemistry and strategies, and then the protecting group is removed after completing the desired synthetic transformation. See, for example, Greene, T. W.; Wuts, P. G. M. *Protective Groups in Organic Synthesis*, $2^{nd}$ ed.; Wiley: New York, 1991, for further description of protecting chemistry and strategies. In certain other embodiments, a functional group in substituent R, $R^I$, and $R^{II}$ in tetrahydro-1,5-naphthyridine F can converted to another functional group using standard functional group manipulation procedures known in the art. See, for example, "Comprehensive Organic Synthesis" (B. M. Trost & I. Fleming, eds., 1991-1992)

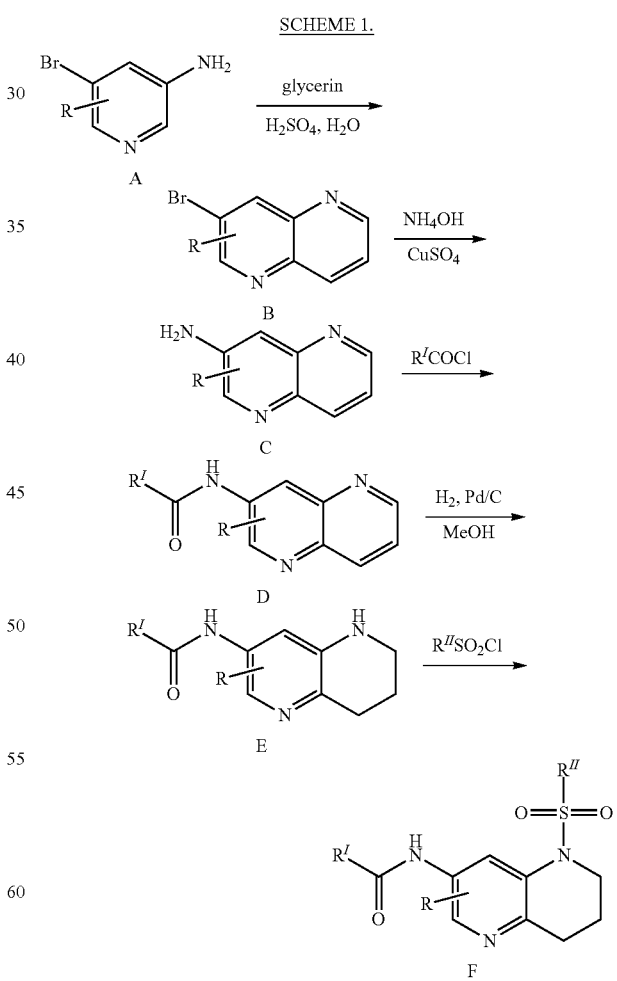

SCHEME 1.

R may be, for example, hydrogen or a substituent, such as methyl; and $R^I$ and $R^{II}$ may be, for example, a cyclic group, such as phenyl.

Scheme 2 illustrates an alternative general method for preparing substituted 5,6,7,8-tetrahydro-1,5-naphthyridine compounds. Reduction of halo-nitro-pyridine A by dissolving metal reduction provides halo-amino-pyridine B. Exemplary dissolving metal reduction conditions include using, for example, (1) $SnCl_2$ in HCl as described by Adams et al. in WO 2008/150827, or (2) Fe in HCl or $NH_4Cl$ as described by Carroll et al. in *J. Med. Chem.* 2002, 45, 4755-4761 and Oalmann et al. in WO 2010/071853. Reaction of halo-amino-pyridine B with a sulphonyl chloride or sulfamoyl chloride provides halo-pyridinyl sulfonamide C. Reaction of halo-pyridinyl sulfonamide C with a vinyl boronic acid or vinyl stannane provides alkene D, which can be allylated using, for example, an allyl halide under basic conditions or an allyl alcohol under Mitsunobu conditions to provide di-alkene E. Di-alkene E can be subjected to ring closing metathesis conditions to provide dihydro-1,5-naphthyridine F. For exemplary ring closing metathesis conditions, see, for example, Mitsuhiro et al. in *J. Org. Chem.* 2006, 71, 4255-4261. Reduction of dihydro-1,5-naphthyridine F provides saturated tetrahydro-1,5-naphthyridine G. The methyl ester on tetrahydro-1,5-naphthyridine G can be converted to a carboxylic acid under hydrolytic conditions, and the resulting carboxylic acid is subjected to reaction conditions that facilitate Curtius rearrangement (see, for example, Ninomiya in *Tetrahedron* 1974, 30, 2151-2157) to provide tetrahydronaphthyridinyl carbamate H. The carbamate functional group of tetrahydronaphthyridinyl carbamate H can be converted to an amino group using standard carbamate protecting group removal procedures, and the resulting amino-tetrahydronaphthyridine can be reacted with an acid ($R^ICO_2H$) using standard amide coupling conditions (e.g., using amide coupling reagents HATU or PyBop) to provide amido-tetrahydro-1,5-naphthyridine I. It is understood that an acid chloride ($R^IC(O)Cl$) can be used in lieu of an acid ($R^ICO_2H$) and amide coupling reagent in the step used to produce amido-tetrahydro-1,5-naphthyridine I.

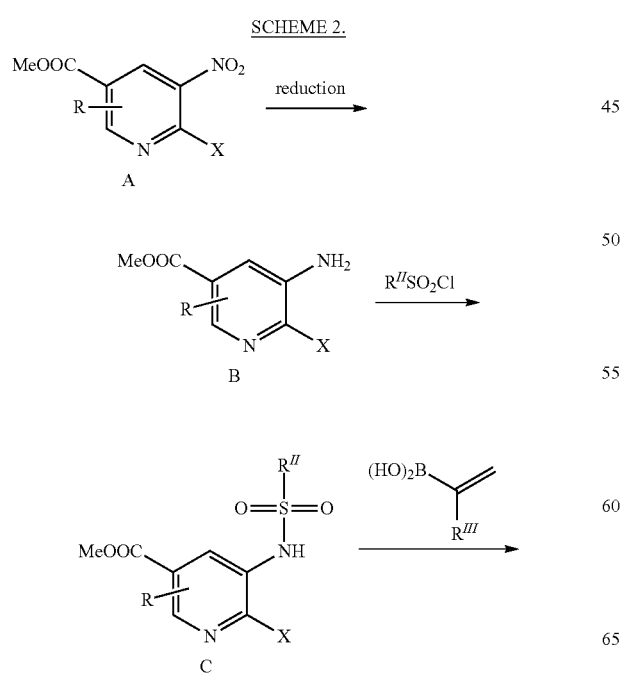

SCHEME 2.

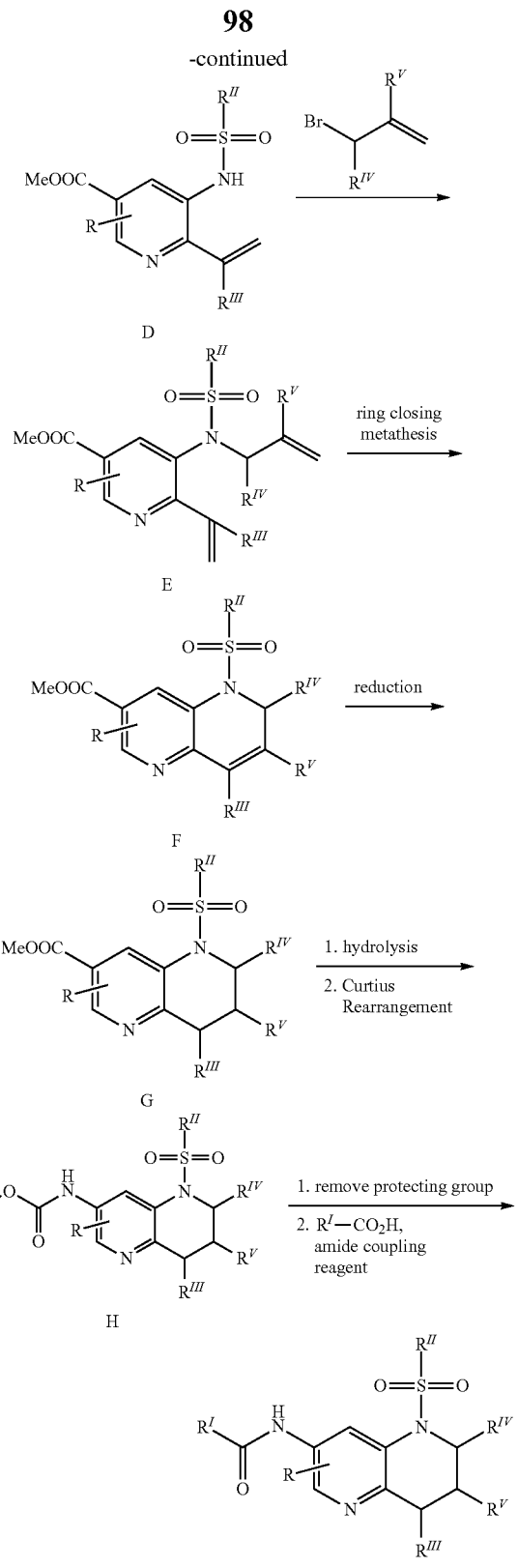

R may be, for example, hydrogen or a substituent, such as methyl; $R^I$ and $R^{II}$ may be, for example, a cyclic group, such as phenyl; $R^{III}$-$R^{VI}$ are substituents, such as methyl; and X may be, for example, halogen.

Scheme 3 illustrates a general route to providing oxygenated 5,6,7,8-tetrahydro-1,5-naphthyridine compounds. Chiral osmylation of alkene A provides diol B. For exemplary chiral osmylation procedures, see, for example, Noe et al. in *Org. Reactions* 2005, 66, 109. Reduction of diol B provides alcohol C. The hydroxyl group in compound C can be alkylated to provide ether D, or the hydroxyl group can be converted to other functional groups using functional group conversion procedures known in the art.

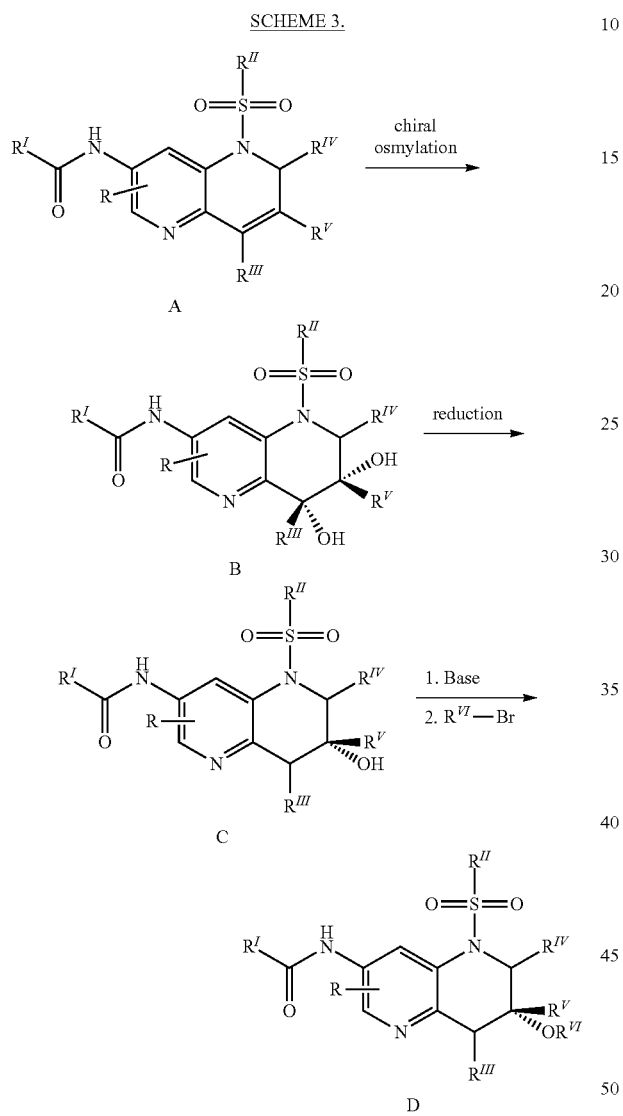

R may be, for example, hydrogen or a substituent, such as methyl; $R^I$ and $R^{II}$ may be, for example, a cyclic group, such as phenyl; and $R^{III}$-$R^{VI}$ are substituents, such as methyl.

Scheme 4 illustrates another general procedure for preparing 5,6,7,8-tetrahydro-1,5-naphthyridine compounds. Treatment of halo-nitro-pyridine A with a Negishi reagent under Pd-mediated conditions provides diester B. For additional description of related procedures, see, for example, Zhu et al. in *J. Org. Chem.* 1991, 56, 1445-1453. Dissolving metal reduction of diester B with in situ cyclization affords dihydro-1,5-naphthyridin-2(1H)-one C. Reaction of dihydro-1,5-naphthyridin-2(1H)-one C with a protecting group installation reagent (e.g., benzylbromide (Bn-Br)) provides protected amide D, which after hydrolysis and in situ formation of the azide and Curtius rearrangement provides carbamate E. A substituent can be installed alpha to the amide group by reaction of carbamate E with base and an electrophile (e.g., $R^V$-halide) to provide substituted-dihydro-1,5-naphthyridin-2(1H)-one F. Reduction of substituted-dihydro-1,5-naphthyridin-2(1H)-one F can be performed by reaction with a hydride (e.g., a borane or lithium aluminum hydride) to provide tetrahydro-1,5-naphthyridine G. Next, protecting groups (e.g., the benzyl and carbamate protecting group) are removed and the resulting amine is reacted with a desired carbonxylic acid, acid chloride, sulphonyl chloride, and/or sulfamoyl chloride to provide the final amido-tetrahydro-1,5-naphthyridine H.

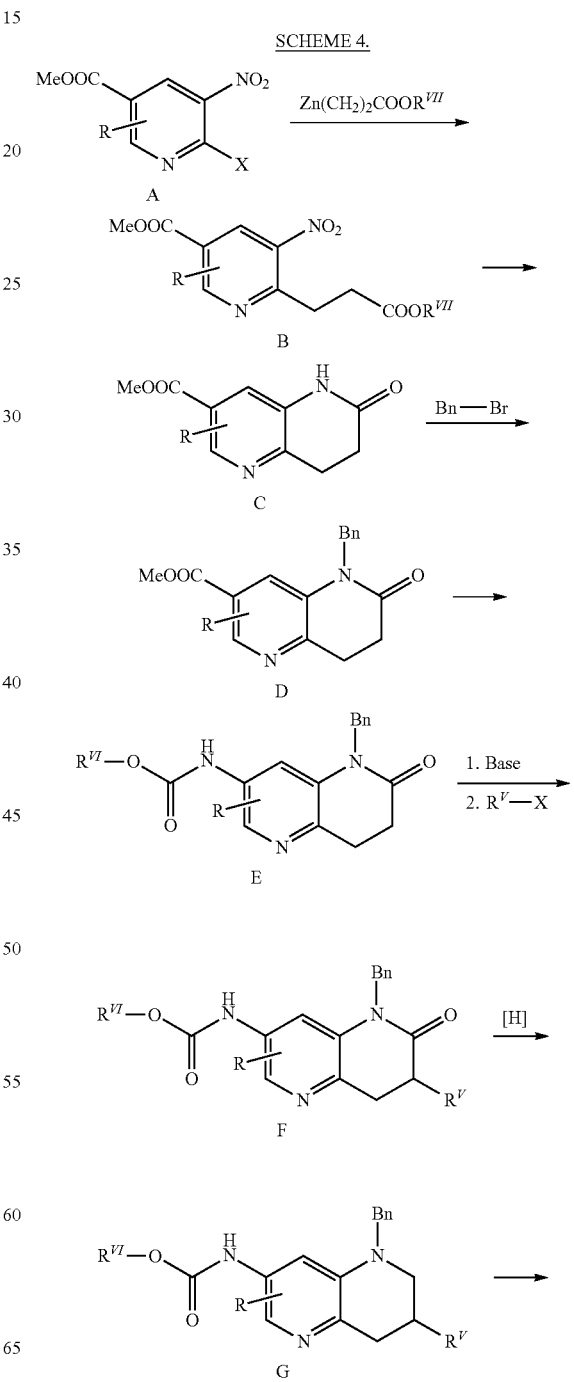

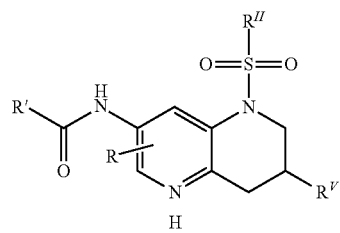

R may be, for example, hydrogen or a substituent, such as methyl; $R^I$ and $R^{II}$ may be, for example, a cyclic group, such as phenyl; $R^V$ and $R^{VII}$ are substituents, such as methyl; and X may be, for example, halogen.

Scheme 5 illustrates another procedure for preparing substituted tetrahydro-1,5-naphthyridines. Reacting halo-nitro-pyridine A with a Negishi reagent (formed from a 2-((tert-butoxycarbonyl)amino)-3-iodopropanoate) provides amino acid B. Then, amino acid B is subjected to dissolving metal reduction conditions with in situ cyclization to provide dihydro-1,5-naphthyridin-2(1H)-one C. Subjecting dihydro-1,5-naphthyridin-2(1H)-one C to hydrolysis conditions provides a carboxylic acid (not shown), that after in situ formation of an acyl azide followed by a Curtius rearrangement provides bis-carbamate D. Selective reduction of the amide group in bis-carbamate D using borane or lithium aluminum hydride provides tetrahydro-1,5-naphthyridine E. Reaction of tetrahydro-1,5-naphthyridine E with a sulphonyl chloride or sulfamoyl chloride provides sulfonamide F. Next, the benzylcarbamate protecting group is removed from sulfonamide F to provide an amino-tetrahydro-1,5-naphthyridine (not shown) that can be subjected to amide coupling conditions using a carboxylic acid and an amide coupling agent to provide amido-tetrahydro-1,5-naphthyridine G. The remaining Boc protecting group on amido-tetrahydro-1,5-naphthyridine G can be removed by treatment with acid to provide amino-tetrahydro-1,5-naphthyridine H. It is understood that the amino group on amino-tetrahydro-1,5-naphthyridine H can be converted to other functional groups (e.g., by reaction with an alkylating agent(s), aldehyde (reductive alkylations), acyl halide, sulphonyl chloride, isocyanate, and the like) to afford the compound I.

SCHEME 5.

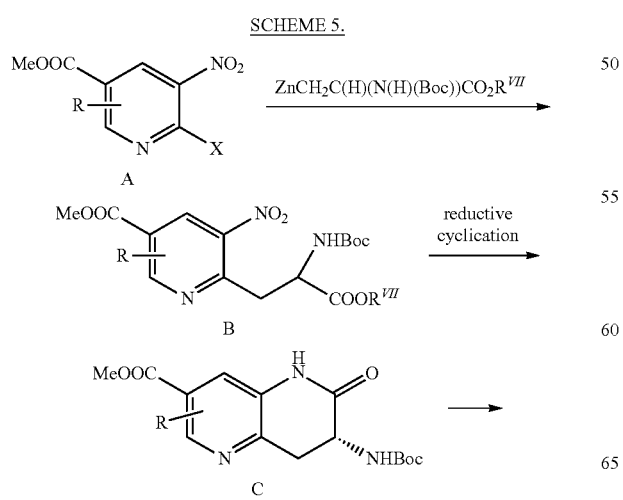

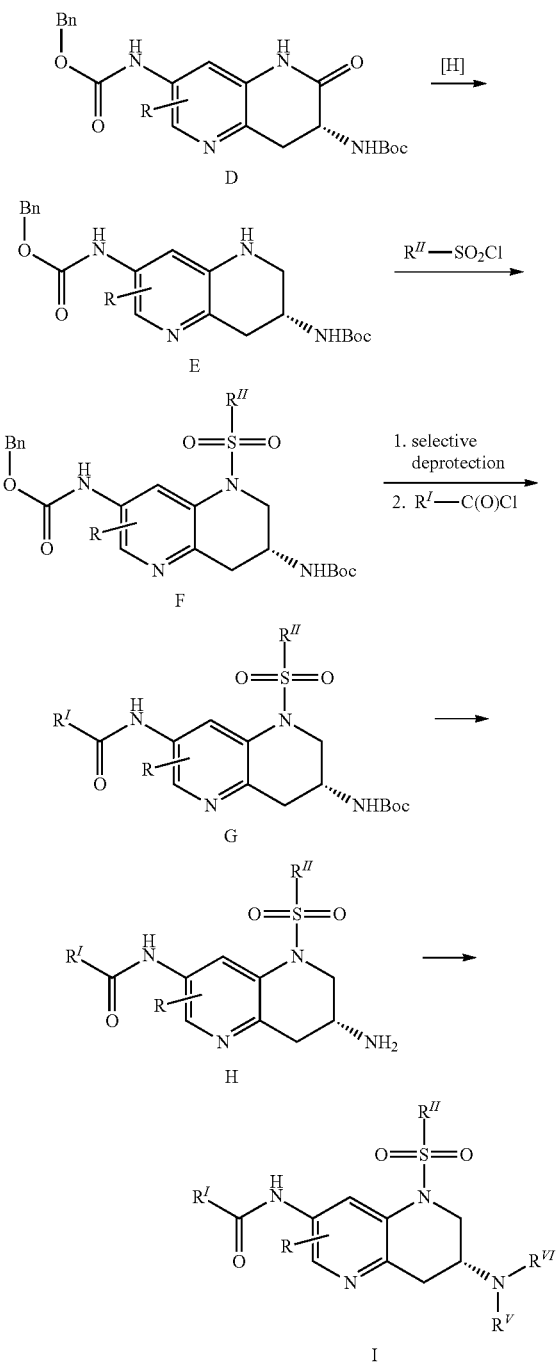

R may be, for example, hydrogen or a substituent, such as methyl; $R^I$ and $R^{II}$ may be, for example, a cyclic group, such as phenyl; $R^V$ and $R^{VII}$ are substituents, such as methyl; and X may be, for example, halogen.

Scheme 6 illustrates a general procedure for preparing tetrahydro-5H-pyrido[3,2-b]azepines. Reaction of halo-nitro-pyridine A with a Negishi reagent under Pd-mediated conditions provides diester B. For additional description of related procedures, see, for example, Zhu et al. in *J. Org. Chem.* 1991, 56, 1445-1453. Dissolving metal reduction of diester B with in situ cyclization provides tetrahydro-5H-pyrido[3,2-b]azepine C, which can be converted to final product D using procedures described in Scheme 4 above.

SCHEME 6.

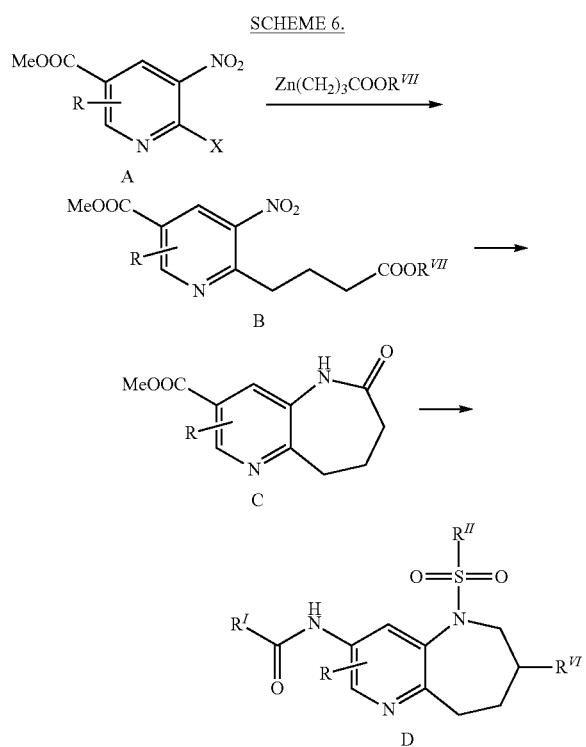

R may be, for example, hydrogen or a substituent, such as methyl; $R^I$ and $R^{II}$ may be, for example, a cyclic group, such as phenyl; $R^{VI}$ and $R^{VII}$ are substituents, such as methyl; and X may be, for example, halogen.

Scheme 7 illustrates a general method for preparing tetrahydro-5H-pyrido[3,2-b]azepines having an amino group at the 7-position. Reacting halo-nitro-pyridine A with a Negishi reagent (formed from a 2-((tert-butoxycarbonyl) amino)-3-iodopropanoate) provides amino acid B. Then, amino acid B is subjected to dissolving metal reduction conditions with in situ cyclization to provide tetrahydro-5H-pyrido[3,2-b]azepine C, which can be converted to final product D using procedures described in Scheme 5 above.

SCHEME 7.

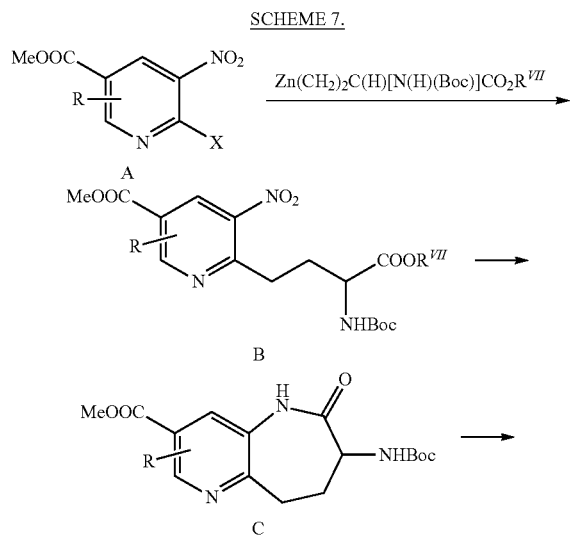

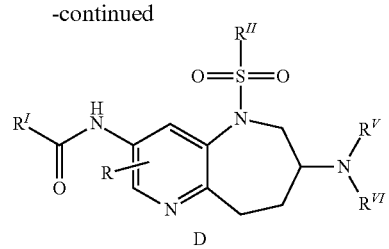

R may be, for example, hydrogen or a substituent, such as methyl; $R^I$ and $R^{II}$ may be, for example, a cyclic group, such as phenyl; $R^{VI}$-$R^{VII}$ are substituents, such as methyl; and X may be, for example, halogen.

Scheme 8 illustrates a general method for preparing substituted tetrahydro-1,6-naphthyridines. Acylation of pyridyl-amine A provides pyridyl-amide B, which is treated with an allylic alcohol under Heck conditions to afford compound C. For exemplary description of such Heck reaction conditions, see, for example, Colbon et al. in *J. Org. Letters* 2011, 13, 5456-5459. Subjecting compound C to reductive cyclization followed by treatment with a sulphonyl chloride or a sulfamoyl chloride provides sulfonamido-tetrahydro-1,6-naphthyridine D.

SCHEME 8.

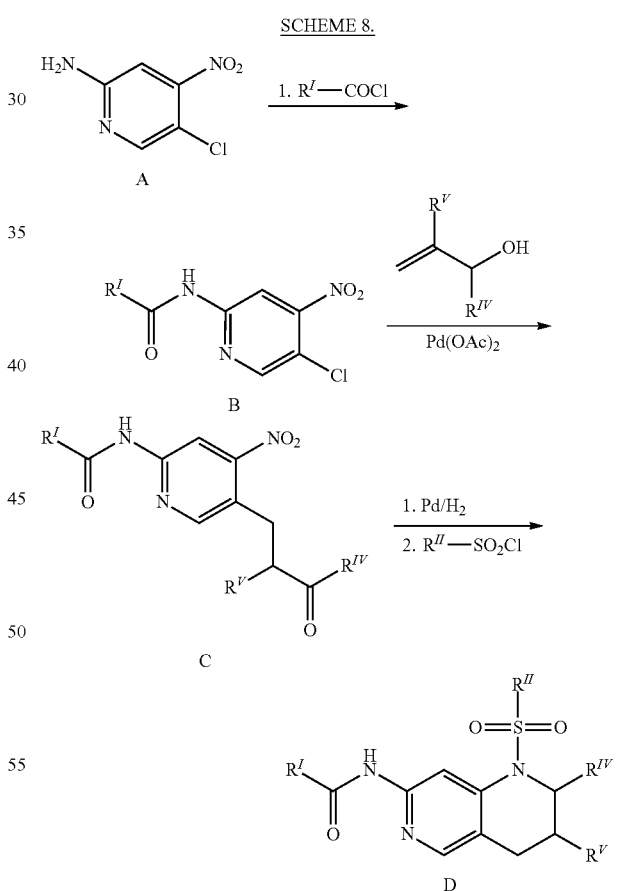

$R^I$ and $R^{II}$ may be, for example, a cyclic group, such as phenyl; and $R^{IV}$ and $R^V$ may be, for example, H or a substituent, such as methyl.

Scheme 9 illustrates another general method for preparing substituted tetrahydro-1,5-naphthyridines. Acylation of amino-pyridine A provides amido-pyridine B, which is treated with an allylic alcohol under Heck conditions to provide compound C. For exemplary description of such Heck reaction conditions, see, for example, Colbon et al. in *J. Org. Letters* 2011, 13, 5456-5459. Subjecting Compound C to reductive cyclization conditions followed by treatment with a sulphonyl chloride or sulfamoyl chloride provides sulfonamide-tetrahydro-1,5-naphthyridine D.

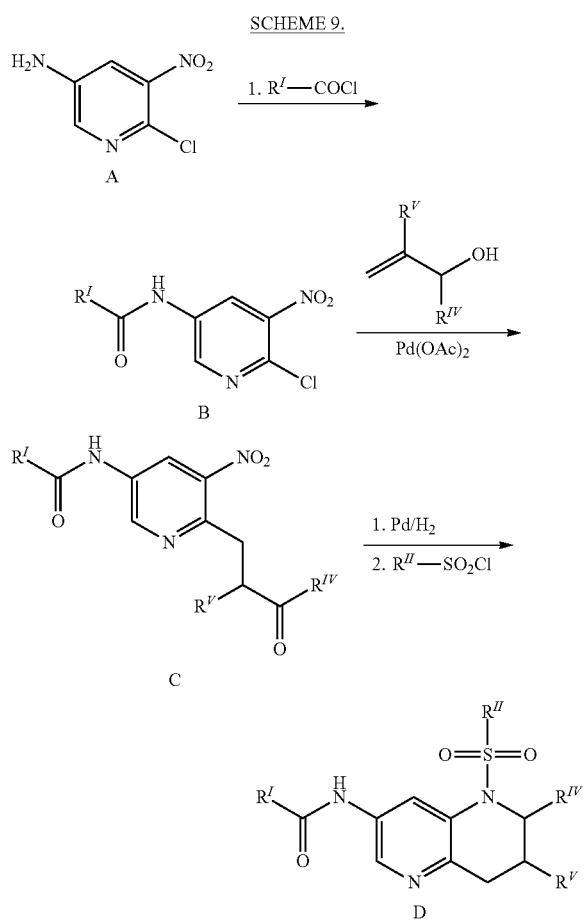

$R^I$ and $R^{II}$ may be, for example, a cyclic group, such as phenyl; and $R^{IV}$ and $R^V$ may be, for example, H or a substituent, such as methyl.

Scheme 10 illustrates a general method for preparing 2-substituted-2,3-dihydro-1H-pyrido[2,3-b]oxazines. Reaction of chloro-pyridine A with hydroxy-ketone B provides nitro-pyridyl ether C. Exhaustive reduction (e.g., using Raney Nickel) of compound C provides amino-dihydro-1H-pyrido[2,3-b]oxazine D. Acylation of pyrido[2,3-b]oxazine D provides amido-pyrido[2,3-b]oxazine E, which is treated with a sulphonyl chloride or sulfamoyl chloride to afford final compound F.

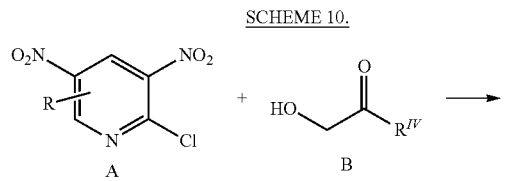

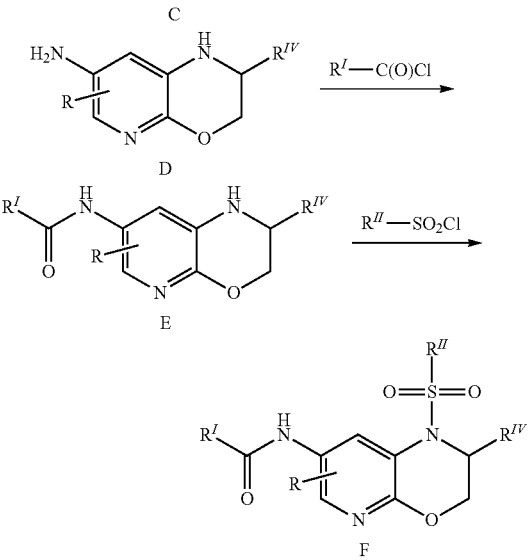

R may be, for example, hydrogen or a substituent, such as methyl; $R^I$ and $R^{II}$ may be, for example, a cyclic group, such as phenyl; and $R^{IV}$ is a substituent, such as methyl.

Scheme 11 illustrates a general method for preparing substituted-2,3-dihydro-1H-pyrido[2,3-b]oxazines. Reacting chloro-pyridine A with protected hydroxyketone (or a protected hydroxyaldehyde) B provides an aryl-alkyl ether intermediate (not shown) that upon acid hydrolysis provides dinitropyridyl-ketone (or dinitropyridyl-aldehyde) C. Exhaustive reduction (e.g., using Raney Nickel) of compound C provides amino-dihydro-1H-pyrido[2,3-b]oxazine D. Acylation of the amino group in compound D affords amido-dihydro-1H-pyrido[2,3-b]oxazine E, which is treated with a sulphonyl chloride or a sulfamoyl chloride to afford the final compound F.

In embodiments where it is desirable to prepare pyridooxazines F in chiral form, a protected chiral hydroxyketone B can be used as starting material.

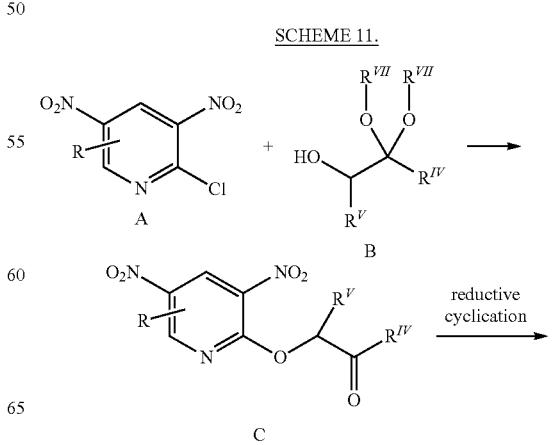

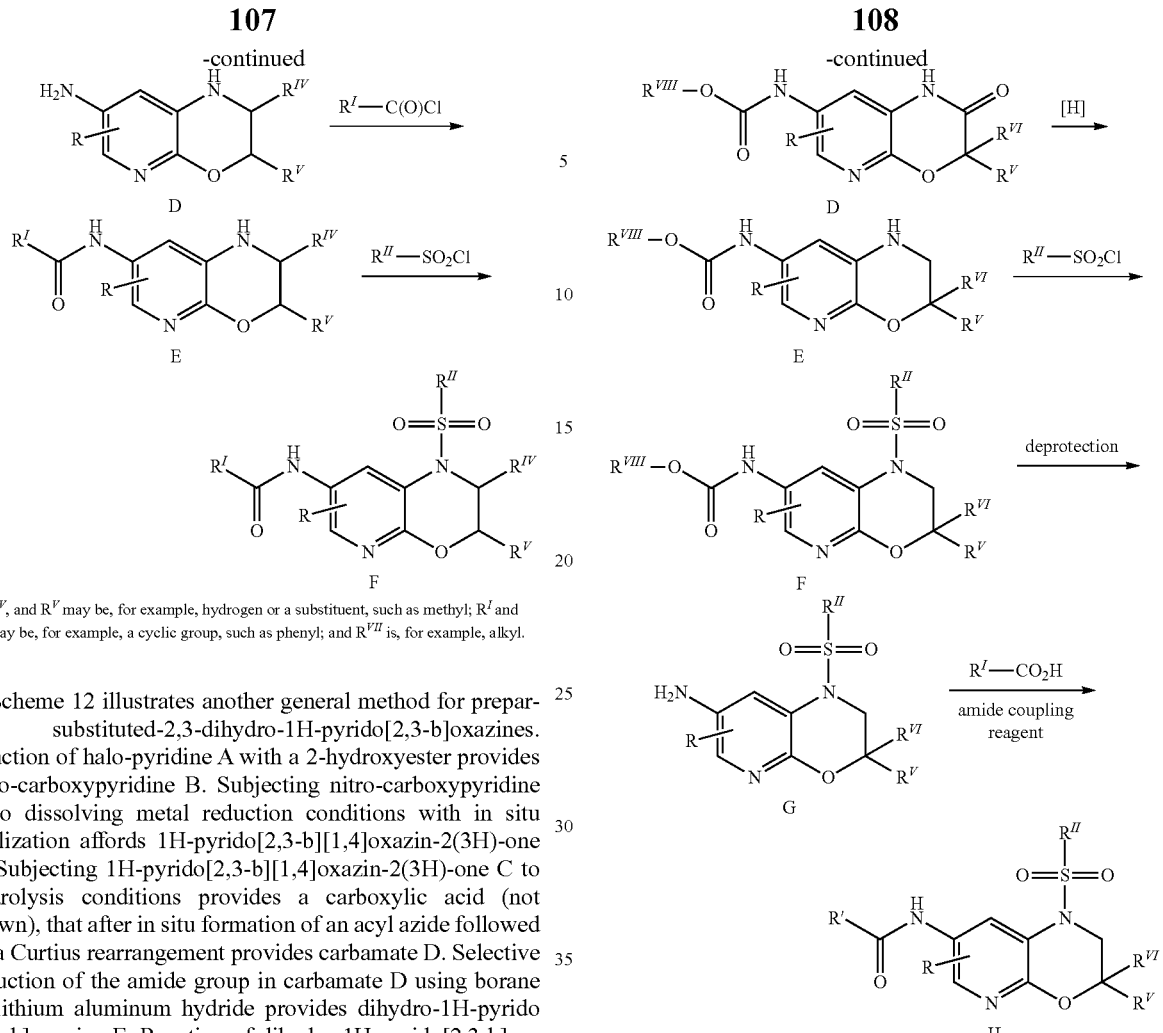

R, $R^{IV}$, and $R^V$ may be, for example, hydrogen or a substituent, such as methyl; $R^I$ and $R^{II}$ may be, for example, a cyclic group, such as phenyl; and $R^{VII}$ is, for example, alkyl.

Scheme 12 illustrates another general method for preparing substituted-2,3-dihydro-1H-pyrido[2,3-b]oxazines. Reaction of halo-pyridine A with a 2-hydroxyester provides nitro-carboxypyridine B. Subjecting nitro-carboxypyridine B to dissolving metal reduction conditions with in situ cyclization affords 1H-pyrido[2,3-b][1,4]oxazin-2(3H)-one C. Subjecting 1H-pyrido[2,3-b][1,4]oxazin-2(3H)-one C to hydrolysis conditions provides a carboxylic acid (not shown), that after in situ formation of an acyl azide followed by a Curtius rearrangement provides carbamate D. Selective reduction of the amide group in carbamate D using borane or lithium aluminum hydride provides dihydro-1H-pyrido[2,3-b]oxazine E. Reaction of dihydro-1H-pyrido[2,3-b]oxazine E with a sulphonyl chloride or sulfamoyl chloride provides sulfonamide F. Next, the carbamate protecting group is removed from sulfonamide F to provide amino-dihydro-1H-pyrido[2,3-b]oxazine G that can be subjected to amide coupling conditions using a carboxylic acid and a coupling agent to provide amido-dihydro-1H-pyrido[2,3-b]oxazine H.

R may be, for example, hydrogen or a substituent, such as methyl; $R^I$ and $R^{II}$ may be, for example, a cyclic group, such as phenyl; $R^V$-$R^{VIII}$ are substituents, such as methyl; and X may be, for example, halogen.

Scheme 13 illustrates an alternate general method for preparing substituted-2,3-dihydro-1H-pyrido[2,3-b]oxazines. Reaction of halo-nitropyridine A with a hydroxyalkyl-epoxide provides nitro-pyridyl ether B. Subjecting nitro-pyridyl ether B to dissolving metal reduction conditions with in situ cyclization affords a bicyclic alkoxide intermediate (not shown) that is reacted with an alcohol protecting group reagent (e.g., a trialkylsilylchloride or with an alkyl halide if the final target is an ether) to provide bicyclic ether C. Reaction of bicyclic ether C with a sulphonyl chloride or sulfamoyl chloride provides sulfonamide-pyrido-oxazine D. The methyl ester on sulfonamide-pyrido-oxazine D can be converted to a carboxylic acid using hydrolytic conditions to provide an intermediate carboxylic acid compound (not shown), that is converted to an acyl azide followed by a Curtius rearrangement to provide carbamate E. The carbamate protecting group may be removed using standard deprotection conditions to provide a bicyclic amine (not shown) that can be subjected to amide coupling conditions using a carboxylic acid and an amide coupling agent to provide amide-substituted 5,6,7,8-tetrahydro-1,5-naphthryridine F. In embodiments, where $R^{IX}$ is protecting group (e.g., a trialkylsilyl group), $R^{IX}$ may be removed using standard deprotection conditions (e.g., using tetra-n-butylammonium fluoride) to provide alcohol G.

SCHEME 12.

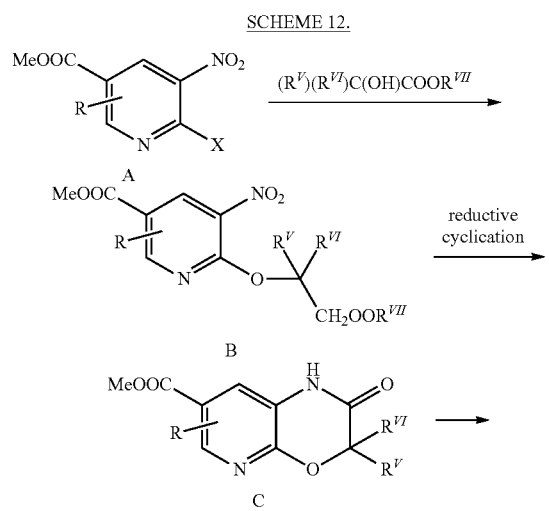

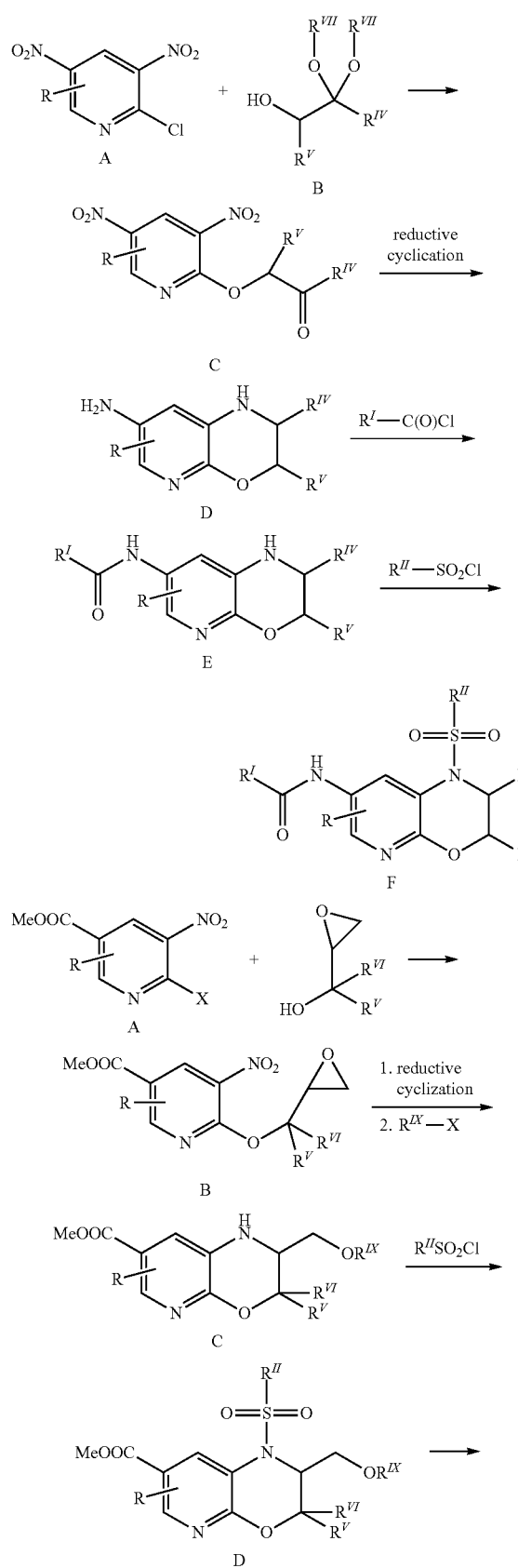
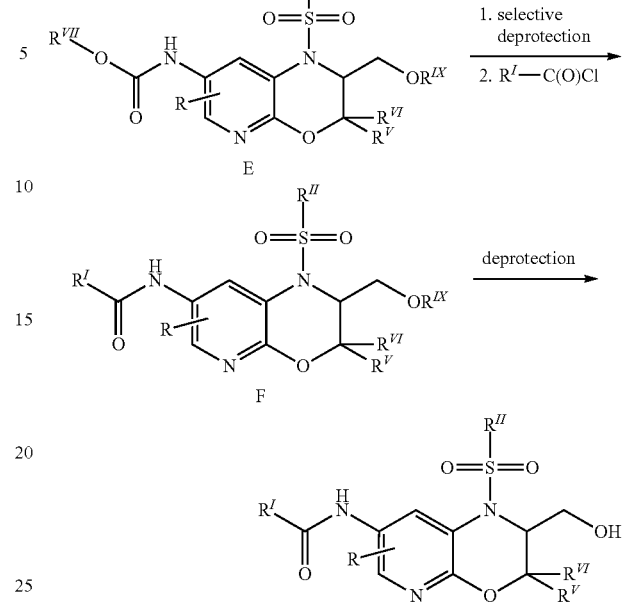
R may be, for example, hydrogen or a substituent, such as methyl; $R^I$ and $R^{II}$ may be, for example, a cyclic group, such as phenyl; $R^V$-$R^{VII}$ are substituents, such as methyl; $R^{IX}$ is a protecting group or alkyl; and X may be, for example, halogen.
Scheme 14 illustrates a general method for preparing substituted 1,2,3,4-tetrahydropyrido[2,3-b][1,4]oxazepines.
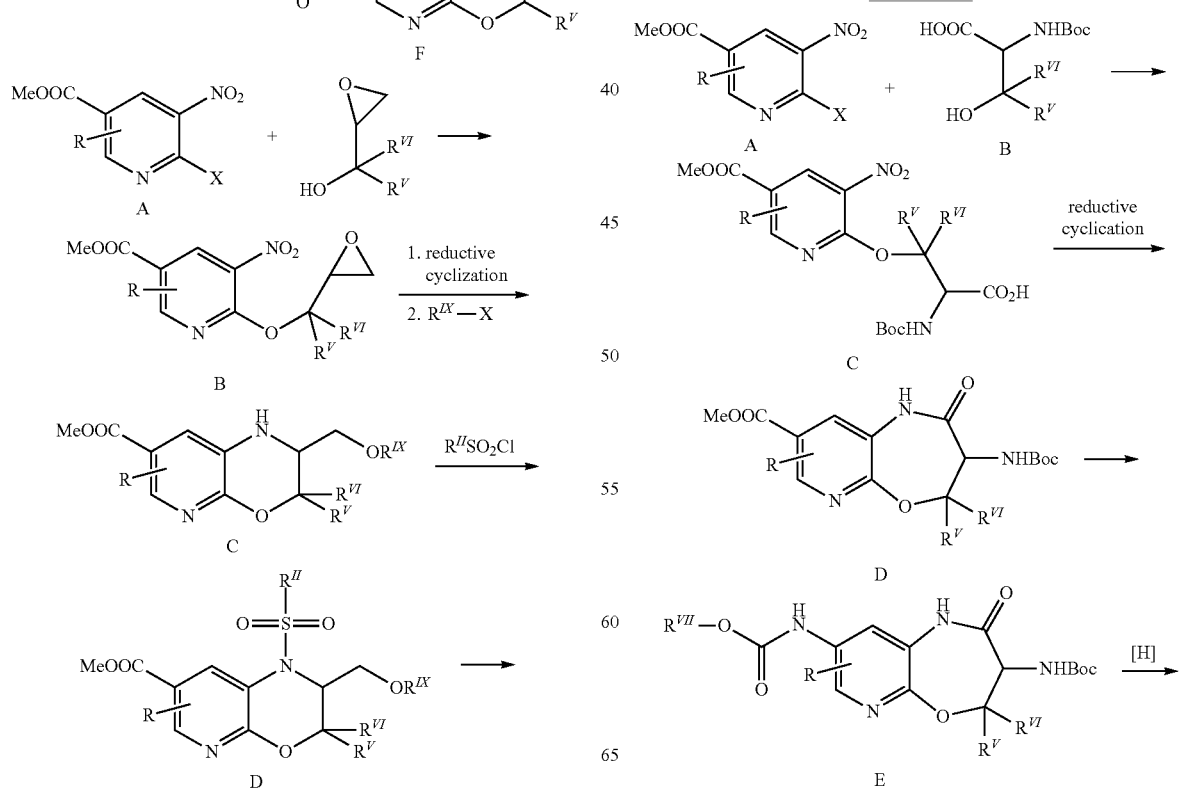

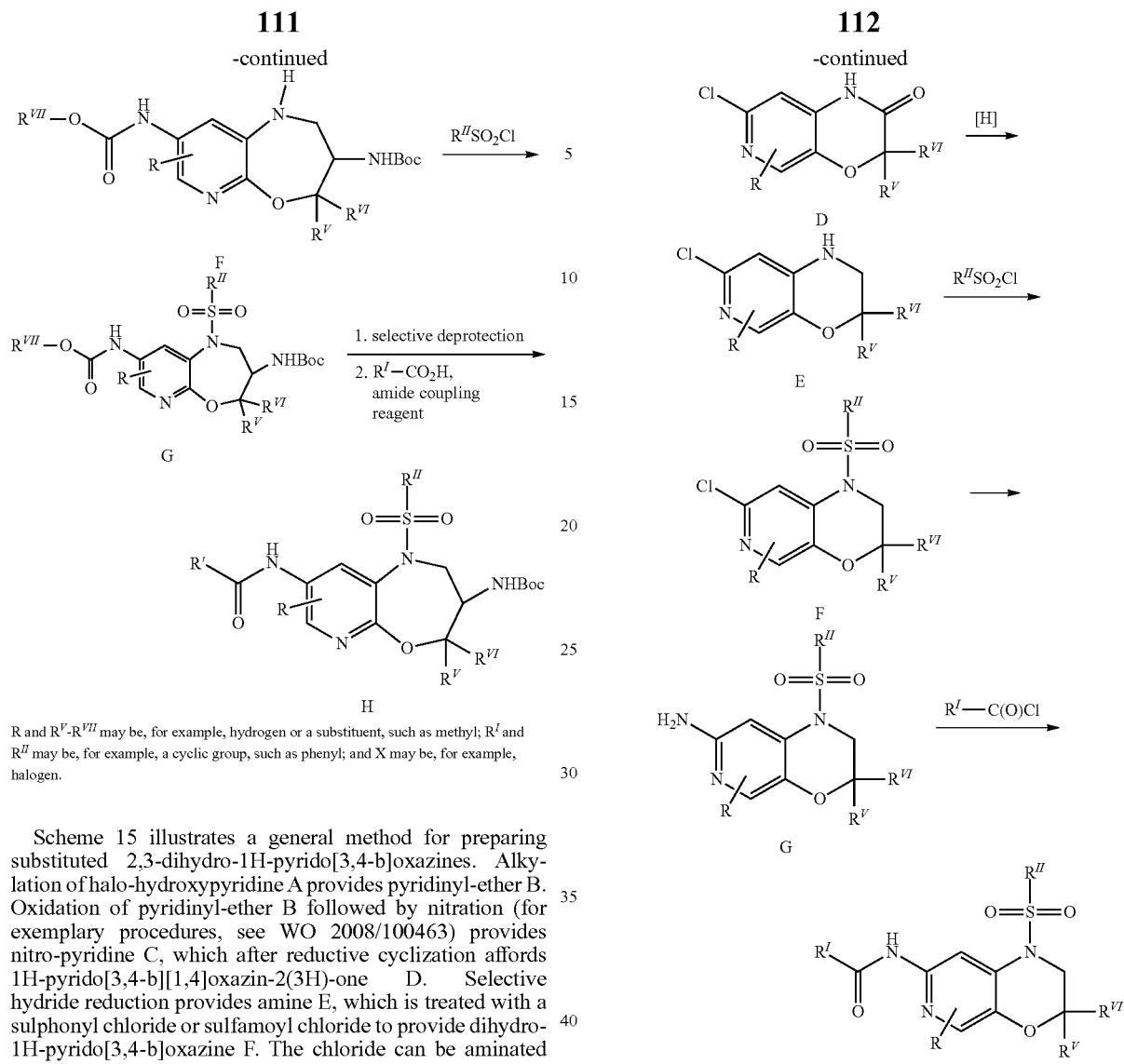

Scheme 15 illustrates a general method for preparing substituted 2,3-dihydro-1H-pyrido[3,4-b]oxazines. Alkylation of halo-hydroxypyridine A provides pyridinyl-ether B. Oxidation of pyridinyl-ether B followed by nitration (for exemplary procedures, see WO 2008/100463) provides nitro-pyridine C, which after reductive cyclization affords 1H-pyrido[3,4-b][1,4]oxazin-2(3H)-one D. Selective hydride reduction provides amine E, which is treated with a sulphonyl chloride or sulfamoyl chloride to provide dihydro-1H-pyrido[3,4-b]oxazine F. The chloride can be aminated (such as using procedures shown in Scheme 1) to provide amine G, which allows functionalization with an acyl moiety to provide the final amide-substituted 2,3-dihydro-1H-pyrido[3,4-b]oxazine H.

R and $R^V$-$R^{VII}$ may be, for example, hydrogen or a substituent, such as methyl; and $R^I$ and $R^{II}$ may be, for example, a cyclic group, such as phenyl.

SCHEME 15.

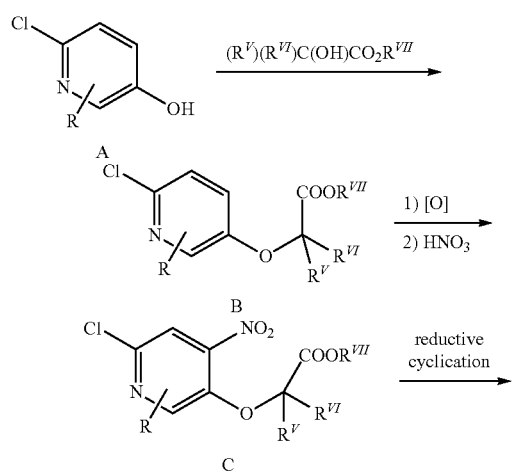

Scheme 16 illustrates a general method for preparing amido-dihydro-5H-pyridazino[3,4-b][1,4]oxazines. Reaction of halo-nitro-pyridazine A with a 2-hydroxyester provides pyridazine ether B. Reductive cyclization of pyridazine ether B affords 5H-pyridazino[3,4-b][1,4]oxazin-6(7H)-one C. Reaction of a protected amine (Pg-NH$_2$, such as NH$_2$COOtBu) with oxazinone C in the presence of a palladium catalyst provides protected amino-dihydro-5H-pyridazino[3,4-b][1,4]oxazine D. Selective hydride reduction affords amino-oxazine E, and treatment of amino-oxazine E with a sulphonyl chloride or a sulfamoyl chloride provides sulfonamido-dihydro-5H-pyridazino[3,4-b][1,4]oxazine F. The amino protecting group (Pg) can be removed using standard protecting group removal procedures, and the resulting amine can be used in an amide coupling reaction (such as with a carboxylic acid an amide coupling reagent) to provide final oxazine G.

SCHEME 16.

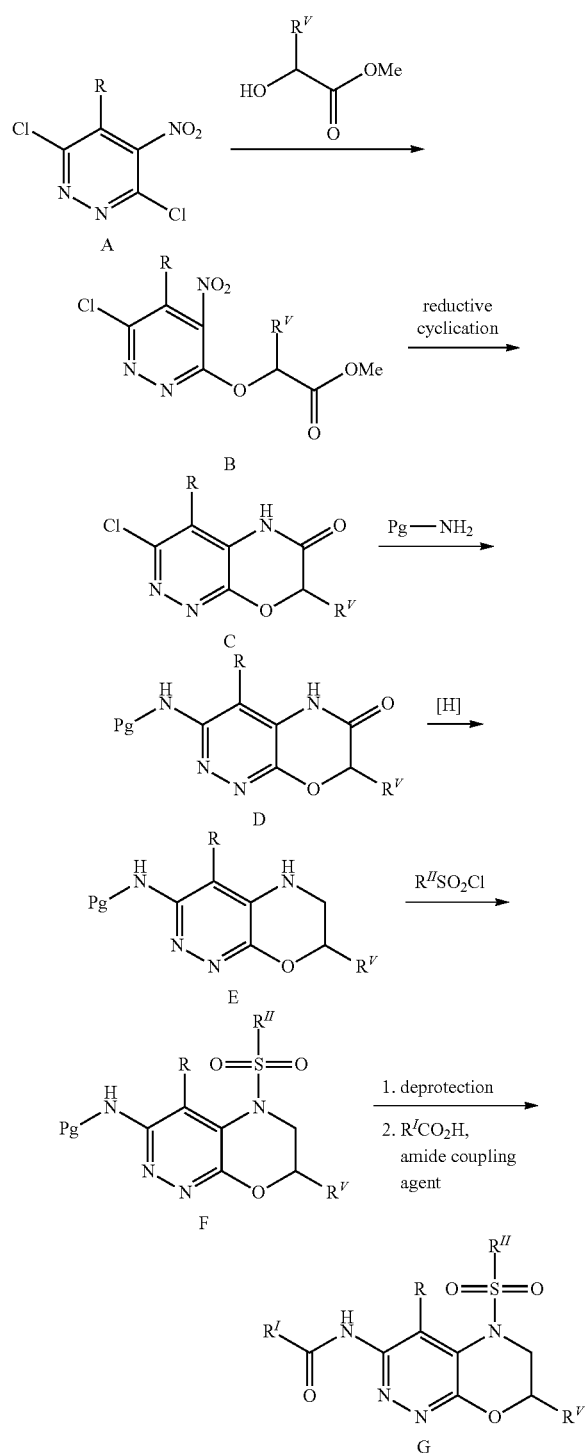

R and R$^V$ may be, for example, hydrogen or a substituent, such as methyl; and R$^I$ and R$^{II}$ may be, for example, a cyclic group, such as phenyl.

Scheme 17 illustrates another general method for preparing amido-dihydro-5H-pyridazino[3,4-b][1,4]oxazines. Reaction of halopyridazine A with amino alcohol B provides the halo-dihydro-5H-pyridazino[3,4-b][1,4]oxazine C. For further description of related reaction procedures, see, for example, Nyrkova et al. in *Zh. Org. Khimii* 1965, 1, 1688–1691. Reaction of protected amine (Pg-NH$_2$, such as para-methoxybenzylamine (PMB-NH$_2$)) with oxazine C in the presence of a palladium catalyst provides protected amino-dihydro-5H-pyridazino[3,4-b][1,4]oxazine D. Reaction of oxazine D with a sulphonyl chloride or a sulfamoyl chloride provides sulfonamido-dihydro-5H-pyridazino[3,4-b][1,4] oxazine E. The para-methoxybenzyl (PMB) protecting group on oxazine E can be removed using standard PMB deprotection conditions to provide an amino-oxazine (not shown), which can be used in an amide coupling reaction (such as with a carboxylic acid an amide coupling reagent) to provide oxazine F.

SCHEME 17.

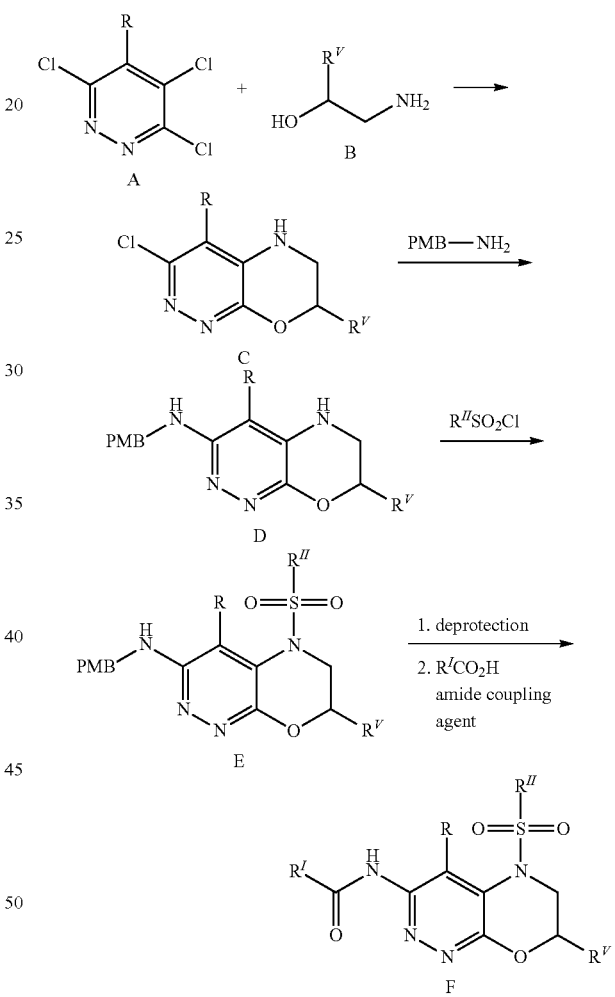

R and R$^V$ may be, for example, hydrogen or a substituent, such as methyl; and R$^I$ and R$^{II}$ may be, for example, a cyclic group, such as phenyl.

Scheme 18 illustrates a general method for preparing amido-dihydro-1,5-naphthyridin-4(1H)-ones. Alkylation of amino-pyridine A with halo-alkyl nitrile B provides nitrile C. For additional description of related procedures, see, for example, Santilli et al. in *J. Het. Chem.* 1975, vol. 12, pages 311-316. Base catalyzed intramolecular condensation of nitrile C provides dihydro-1,5-naphthyridin-4(1H)-one D. Reaction of dihydro-1,5-naphthyridin-4(1H)-one D with base and an alkylhalide provides nitrile E. Reaction of nitrile E with base provides a carboxylic acid which decarboxylates to provide dihydro-1,5-naphthyridin-4(1H)-one F. Reaction of dihydro-1,5-naphthyridin-4(1H)-one F with a sulphonyl chloride or a sulfamoyl chloride provides sulfonamido-dihydro-1,5-naphthyridin-4(1H)-one G. Metal-catalyzed coupling of amide H with sulfonamido-dihydro-1,5-naphthyridin-4(1H)-one G provides final compound I.

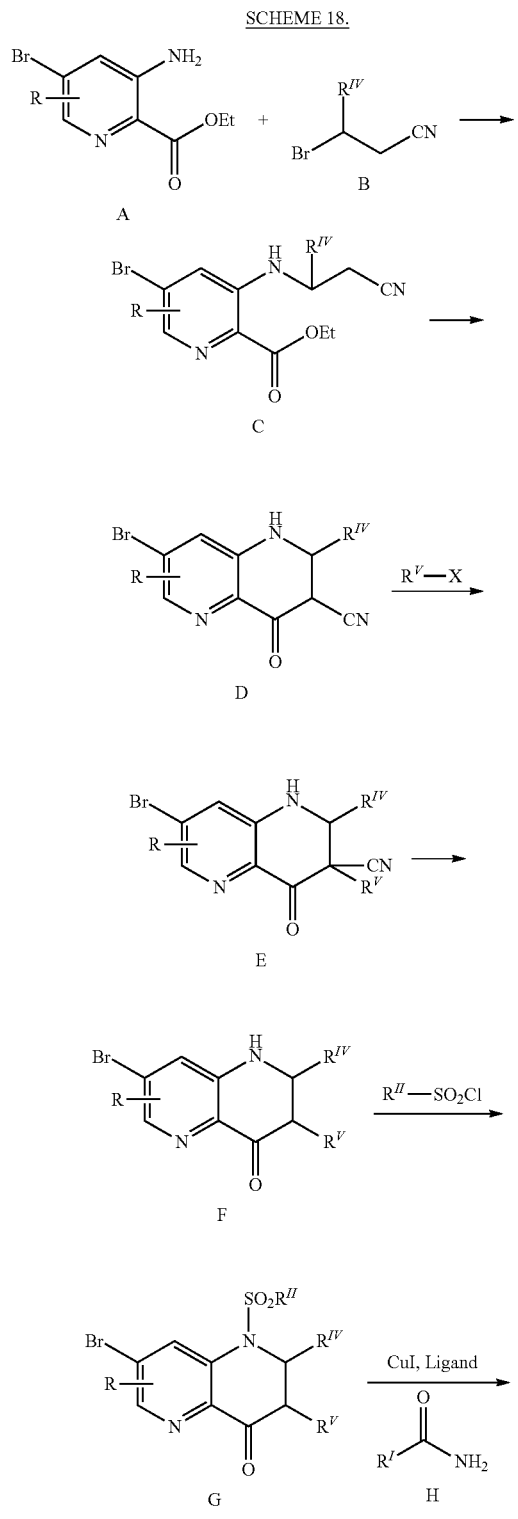

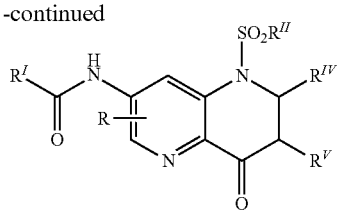

R, $R^{IV}$, and $R^V$ may be, for example, hydrogen or a substituent, such as methyl; $R^I$ and $R^{II}$ may be, for example, a cyclic group, such as phenyl; and X is a leaving group, such as bromide.

Scheme 19 illustrates a general method for preparing amido-dihydro-2H-pyrazino[2,3-b][1,4]oxazines. Reaction of halo-nitro-pyrazine A with a 2-hydroxyester provides pyrazine ether B. Reductive cyclization of pyrazine ether B affords 2H-pyrazino[2,3-b][1,4]oxazin-3(4H)-one C. Reaction of a protected amine (Pg-$NH_2$, such as $NH_2COOtBu$) with oxazinone C in the presence of a palladium catalyst provides protected amino-oxazin-3(4H)-one D. Selective hydride reduction affords amino-oxazinone E, and treatment of amino-oxazinone E with a sulphonyl chloride or a sulfamoyl chloride provides sulfonamido-dihydro-2H-pyrazino[2,3-b][1,4]oxazine F. The amino protecting group (Pg) can be removed using standard protecting group removal procedures, and the resulting amine can be used in an amide coupling reaction (such as with a carboxylic acid an amide coupling reagent) to provide final oxazine G.

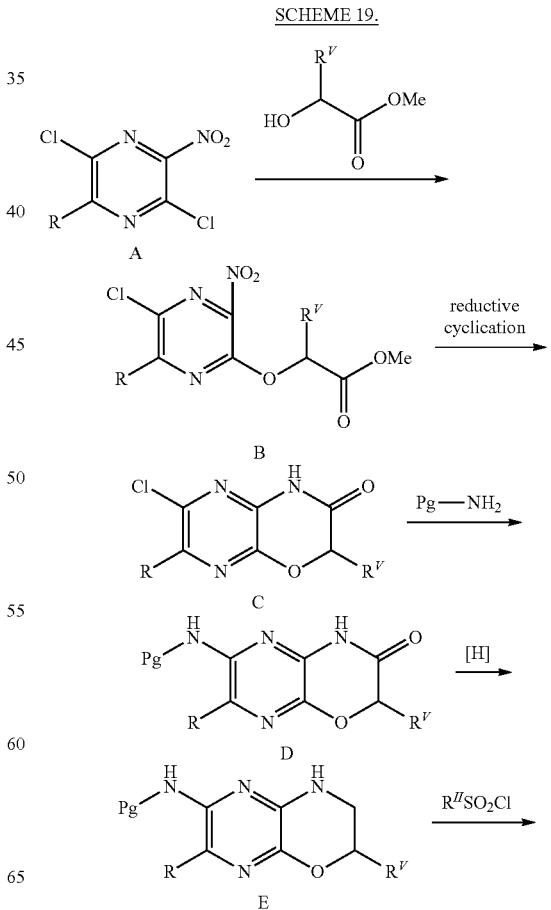

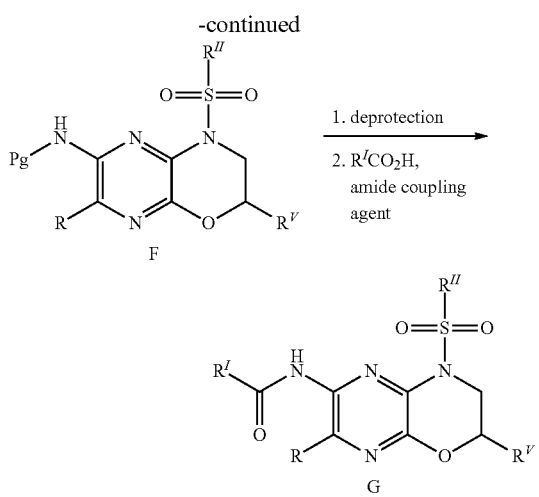

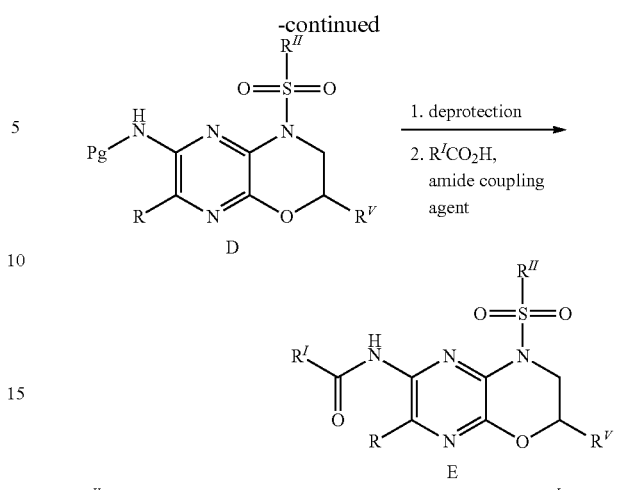

R and R$^V$ may be, for example, hydrogen or a substituent, such as methyl; and R$^I$ and R$^{II}$ may be, for example, a cyclic group, such as phenyl.

R and R$^V$ may be, for example, hydrogen or a substituent, such as methyl; and R$^I$ and R$^{II}$ may be, for example, a cyclic group, such as phenyl.

Scheme 20 illustrates an alternative general method for preparing amido-substituted 3,4-dihydro-2H-pyrazino[2,3-b][1,4]oxazines. Alkylation of amino-pyrazinol A with an di-haloalkane provides chloro-dihydro-2H-pyrazino[2,3-b][1,4]oxazine B. For additional description of related procedures, see, for example, WO 2011/059839. Reaction of a protected amine (Pg-NH$_2$, such as para-methoxybenzylamine (PMB-NH$_2$)) with oxazine B in the presence of a palladium catalyst provides protected amino-dihydro-2H-pyrazino[2,3-b][1,4]oxazine C. Reaction of oxazine C with a sulphonyl chloride or a sulfamoyl chloride provides sulfonamido-dihydro-2H-pyrazino[2,3-b][1,4]oxazine D. The protecting group (Pg) on oxazine D can be removed using standard deprotection conditions to provide an amino-oxazine (not shown), which is used in an amide coupling reaction (such as with a carboxylic acid an amide coupling reagent) to provide oxazine E.

SCHEME 20.

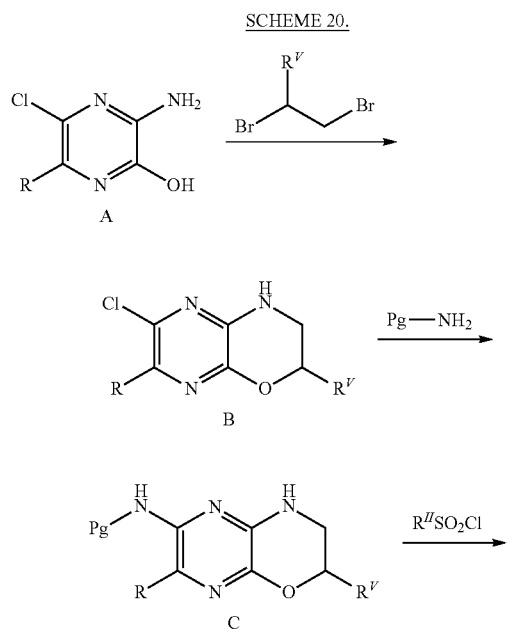

II. Therapeutic Applications of Tetrahydronaphthyridine and Related Compounds

It is contemplated that the tetrahydronaphthyridine and related compounds described herein, such as a compound of Formula I, I-A, II, II-A, III, III-A, IV, V, or VI, provide therapeutic benefits to subjects suffering from an immune disorder or inflammatory disorder. Accordingly, one aspect of the invention provides a method of treating a disorder selected from the group consisting of an immune disorder or inflammatory disorder. The method comprises administering a therapeutically effective amount of a tetrahydronaphthyridine or related compound described herein, such as a compound of Formula I, I-A, II, II-A, III, III-A, IV, V, or VI, to a subject in need thereof to ameliorate a symptom of the disorder, wherein Formula I, I-A, II, II-A, III, III-A, IV, V, or VI are as described above. In certain embodiments, the particular compound of Formula I, I-A, II, II-A, III, III-A, IV, V, or VI is the compound defined by one of the embodiments described above.

In certain embodiments, the disorder is an immune disorder. In certain other embodiments, the disorder is an inflammatory disorder. In certain other embodiments, the disorder is an autoimmune disorder. In certain other embodiments, the disorder is rheumatoid arthritis, psoriasis, chronic graft-versus-host disease, acute graft-versus-host disease, Crohn's disease, inflammatory bowel disease, multiple sclerosis, systemic lupus erythematosus, Celiac Sprue, idiopathic thrombocytopenic thrombotic purpura, myasthenia gravis, Sjogren's syndrome, scleroderma, ulcerative colitis, asthma, or epidermal hyperplasia.

In certain other embodiments, the disorder is cartilage inflammation, bone degradation, arthritis, juvenile arthritis, juvenile rheumatoid arthritis, pauciarticular juvenile rheumatoid arthritis, polyarticular juvenile rheumatoid arthritis, systemic onset juvenile rheumatoid arthritis, juvenile ankylosing spondylitis, juvenile enteropathic arthritis, juvenile reactive arthritis, juvenile Reter's Syndrome, SEA Syndrome, juvenile dermatomyositis, juvenile psoriatic arthritis, juvenile scleroderma, juvenile systemic lupus erythematosus, juvenile vasculitis, pauciarticular rheumatoid arthritis, polyarticular rheumatoid arthritis, systemic onset rheumatoid arthritis, ankylosing spondylitis, enteropathic arthritis, reactive arthritis, Reter's Syndrome, dermatomyositis, psoriatic arthritis, vasculitis, myolitis, polymyolitis, dermatomyolitis, osteoarthritis, polyarteritis nodossa, Wegener's granulomatosis, arteritis, polymyalgia rheumatica, sarcoidosis, sclerosis, primary biliary sclerosis, sclerosing cholangitis, dermatitis, atopic dermatitis, atherosclerosis, Still's disease, chronic obstructive pulmonary disease, Guillain-Barre disease, Type I diabetes mellitus, Graves' disease, Addison's disease, Raynaud's phenomenon, autoimmune hepatitis, psoriatic epidermal hyperplasia, plaque psoriasis, guttate psoriasis, inverse psoriasis, pustular psoriasis, erythrodermic psoriasis, or an immune disorder associated with or arising from activity of pathogenic lymphocytes. In certain embodiments, the psoriasis is plaque psoriasis, guttate psoriasis, inverse psoriasis, pustular psoriasis, or erythrodermic psoriasis.

In certain other embodiments, the disorder is rheumatoid arthritis.

In certain embodiments, the subject is a human.

Another aspect of the invention provides for the use of a compound described herein (such as a compound of Formula I, I-A, II, II-A, III, III-A, IV, V, or VI) in the manufacture of a medicament. In certain embodiments, the medicament is for treating a disorder described herein, such as rheumatoid arthritis.

Another aspect of the invention provides for the use of a compound described herein (such as a compound of Formula I, I-A, II, II-A, III, III-A, IV, V, or VI) for treating a medical disorder, such a medical disorder described herein (e.g., rheumatoid arthritis).

Further, it is contemplated that tetrahydronaphthyridine and related compounds described herein, such as a compound of Formula I, I-A, II, II-A, III, III-A, IV, V, or VI, can inhibit the activity of RORγ. Accordingly, another aspect of the invention provides a method of inhibiting the activity of RORγ. The method comprises exposing a RORγ to an effective amount of a tetrahydronaphthyridine or related compound described herein, such as a compound of Formula I, I-A, II, II-A, III, III-A, IV, V, or VI, to inhibit said RORγ, wherein Formula I, I-A, II, II-A, III, III-A, IV, V, and VII are as described above. In certain embodiments, the particular compound of Formula I, I-A, II, II-A, III, III-A, IV, V, or VI is the compound defined by one of the embodiments described above.

Further, it is contemplated that tetrahydronaphthyridine and related compounds described herein, such as a compound of Formula I, I-A, II, II-A, III, III-A, IV, V, or VI, can reduce the amount of interleukin-17 (IL-17) in a subject. IL-17 is a cytokine that affects numerous biological functions, including inducing and mediating pro-inflammatory responses. Accordingly, another aspect of the invention provides a method of reducing the amount of IL-17 in a subject. The method comprises administering to a subject an effective amount of a tetrahydronaphthyridine or related compound described herein, such as a compound of Formula I, I-A, II, II-A, III, III-A, IV, V, or VI, to reduce the amount of IL-17 in the subject, wherein Formula I, I-A, II, II-A, III, III-A, IV, V, and VI are as described above. In certain embodiments, the particular compound of Formula I, I-A, II, II-A, III, III-A, IV, V, or VI is the compound defined by one of the embodiments described above.

In certain embodiments, the subject is a human. In certain embodiments, administering the compound reduces the amount of IL-17 produced by Th-17 cells in the subject. A change in the amount of IL-17 produced by, for example, Th-17 cells can be measured using procedures described in the literature, such as an ELISA assay or intracellular staining assay.

Further, it is contemplated that tetrahydronaphthyridine and related compounds described herein, such as a compound of Formula I, I-A, II, II-A, III, III-A, IV, V, or VI, may inhibit the synthesis of IL-17 in a subject. Accordingly, another aspect of the invention provides a method of inhibiting the synthesis of IL-17 in a subject. The method comprises administering to a subject an effective amount of a compound described herein, e.g., a compound of Formula I, I-A, II, II-A, III, III-A, IV, V, or VI, to inhibit the synthesis of IL-17 in the subject, wherein Formula I, I-A, II, II-A, III, III-A, IV, V, and VI are as described above. In certain embodiments, the particular compound of Formula I, I-A, II, II-A, III, III-A, IV, V, or VI is a compound defined by one of the embodiments described above.

The description above describes multiple embodiments providing definitions for variables used herein. The application specifically contemplates all combinations of such variables, e.g., particular combinations of the definitions set forth for variables A and X.

Compounds can be tested for inhibition of ROR using procedures described in the literature. Exemplary procedures for testing a compound for ability to inhibit RORγ activity include (i) a RORγ-Ligand Binding Domain (LBD) TR-FRET Assay, and (ii) a RORγ Reporter Assay. The RORγ-Ligand Binding Domain (LBD) TR-FRET Assay is described in Example 21 herein. The RORγ Reporter Assay is described below:

General Procedures for RORγ Reporter Assay

Inhibition of RORγt in cells is determined using a reporter system in HEK293 cells employing a luciferase readout. The RORγt DNA binding domain (DBD) is replaced with heterologous yeast GAL4 DBD using standard recombinant DNA methods. The resulting GAL4-RORγt-LBD fusion construct is placed under the control of a constitutive cytomegalovirus (CMV) promoter by cloning it into the CMV-driven mammalian expression vector pCDNA3.1+— (Promega Corporation, Madison, Wis.).

A transcriptional reporter expression construct is used to monitor GAL4-RORγ activity, which contains five copies of the GAL4 binding sequence (UAS) controlling expression of a firefly luciferase reporter gene. This construct, pGL4.31, is commercially available from Promega Corporation, Madison Wis. Both constructs are transfected in bulk into HEK-293 cells using standard lipid-based transfection techniques, which allows the GAL4-RORγ-LBD fusion protein to drive expression of the luciferase reporter. Control transfections are performed with an empty pCDN3.1+ vector.

The next day, cells are plated into 384 well plates, test compounds are added, and the plates are incubated overnight. Test compounds capable of blocking the GAL4-RORg fusion protein from initiating expression of the luciferase signal are identified. Promega firefly assays kits are used to stabilize the luciferase signal, and the intensity of the luciferase signal is measured using an EnVision Multilabel Plate Reader (Perkin Elmer, Waltham, Mass.).

Detailed Description of the HEK293 Gal4 Rporter Assay

HEK 293 cells are transfected with GAL4-RORγτ-LBD construct (pcDNA3.1neo) and the pGL4.31 GAL4-luciferase reporter construct (Promega). For a background control, use empty pcDNA3.1neo and pGL4.31. Transfection protocol is for a single T75 flask performed with Mirus Trans-It 293 reagent. A 60 μL aliquot of Trans-IT reagent at room temperature is added drop wise to 1.5 mL of Optimem (Invitrogen). The resulting solution is mixed by inversion and incubated for 5-20 minutes at room temperature. This reagent mixture is added to 10 μg of DNA (5 μg of each expression vector). The solution is mixed by inversion and incubated at room temperature for 20 minutes.

While the Trans-IT reagent and DNA are incubating, harvest HEK-293 cells. Remove media from flasks via aspiration and add enough TrypLE Express (stable Trypsin-like reagent, Invitrogen) to cover the bottom of the flask. The mixture is incubated at room temperature until the cells are visibly loose in the flask (approximately 2-5 minutes). Add an equal volume of complete growth media, and then pipette to achieve a single cell suspension. Spin down $1 \times 10^7$ cells and re-suspend the cells in 10 mL of complete growth media (DMEM high glucose/10% dialyzed FBS/pen/strep; Invitrogen). The cells and transfection mixture are added to one T75 flask. The contents of the T75 flask are mixed and incubated overnight at 37° C. and 5% $CO_2$.

After 16-24 hours, cells are harvested and plated for test compound screening. Cells may be harvested as described above. Next, cells are counted and an appropriate number of cells are spun down. Then, cells are aspirated and re-suspended in complete growth media at a concentration of $0.5 \times 10^6$ cells/mL. Plate 20 μL of the cell suspension into a white, tissue-culture treated 384 well plate. (10,000-20,000 cells/well).

A 10 mM stock solution of test compound in dimethylsulfoxide (DMSO) is diluted to 500× the final test concentration in DMSO, then diluted to 5× the final test concentration with complete growth medium to provide the Test Compound Solution. The concentration of DMSO in the Test Compound Solution is 0.2%. A 5 μL aliquot of Test Compound Solution is added to each test well in the 384 well plate previously plated with the cell suspension. Next, plates are spun briefly and incubated overnight at 37° C. and 5% $CO_2$.

After 16-24 hours, the luciferase assay is performed. Plates and luciferase reagent (e.g. One-Glo® or Dual Glo®; Promega, Madison, Wis.) are brought to room temperature. Next, a 25 μL aliquot of luciferase reagent is added to each well. Plates are spun down briefly and incubated at room temperature for 10 minutes. The luciferase signal is measured on an Envision plate reader (Perkin Elmer) set to the ultra sensitive luminescence setting.

$EC_{50}$ values for test compounds are calculated from the luciferase signal data using GraphPad Prism software.

III. Combination Therapy

Another aspect of the invention provides for combination therapy. Tetrahydronaphthyridine and related compounds (e.g., a compound of Formula I, I-A, II, II-A, III, III-A, IV, V, or VI) or their pharmaceutically acceptable salts may be used in combination with additional therapeutic agents to treat medical disorders, such as medical disorders associated with inappropriate IL-17 pathway activity. Exemplary additional therapeutic agents include, for example, (1) a TNF-α inhibitor; (2) a non-selective COX-1/COX-2 inhibitor; (3) a selective COX-2 inhibitor, such as celecoxib and rofecoxib; (4) other agents for treating inflammatory disease and autoimmune disease including, for example, methotrexate, leflunomide, sulfasalazine, azathioprine, penicillamine, bucillamine, actarit, mizoribine, lobenzarit, hydroxychloroquine, d-penicillamine, aurothiomalate, auranofin, parenteral gold, oral gold, cyclophosphamide, Lymphostat-B, a BAFF/APRIL inhibitor, CTLA-4-Ig, or a mimetic of CTLA-4-Ig; (5) a leukotriene biosynthesis inhibitor, such as a 5-lipoxygenase (5-LO) inhibitor, or a 5-lipoxygenase activating protein (FLAP) antagonist; (6) a LTD4 receptor antagonist; (7) a phosphodiesterase type IV (PDE-IV) inhibitor, such as cilomilast (ariflo) or roflumilast; (8) an antihistamine HI receptor antagonist; (9) an α1- and α2-adrenoceptor agonist; (10) an anticholinergic agent; (11) a β-adrenoceptor agonist; (12) an insulin-like growth factor type I (IGF-1) mimetic; (13) a glucocorticosoid; (14) a kinase inhibitor such as an inhibitor of a Janus Kinase (e.g., JAK 1 and/or JAK2 and/or JAK 3 and/or TYK2), p38 MAPK, Syk or IKK2; (15) a B-cell target biologic such as rituximab; (16) a selective co-stimulation modulator such as abatacept; (17) an interleukin inhibitor or interleukin receptor inhibitor, such as the IL-1 inhibitor anakinra, IL-6 inhibitor tocilizumab, and IL12/IL-23 inhibitor ustekimumab; (18) an anti-IL17 antibody, anti-IL21 antibody, or anti-IL22 antibody (19) a S1P1 agonist, such as fingolimod; (20) an interferon, such as interferon beta 1; (21) an integrin inhibitor such as natalizumab; (22) a mTOR inhibitor such as rapamycin, cyclosporin and tacrolimus; (23) a non-steroidal antiinflammatory agent (NSAID), such as propionic acid derivatives (alminoprofen, benoxaprofen, bucloxic acid, carprofen, fenbufen, fenoprofen, fluprofen, flurbiprofen, ibuprofen, indoprofen, ketoprofen, miroprofen, naproxen, oxaprozin, pirprofen, pranoprofen, suprofen, tiaprofenic acid, and tioxaprofen), acetic acid derivatives (indomethacin, acemetacin, alclofenac, clidanac, diclofenac, fenclofenac, fenclozic acid, fentiazac, furofenac, ibufenac, isoxepac, oxpinac, sulindac, tiopinac, tolmetin, zidometacin, and zomepirac), fenamic acid derivatives (flufenamic acid, meclofenamic acid, mefenamic acid, niflumic acid and tolfenamic acid), biphenylcarboxylic acid derivatives (diflunisal and flufenisal), oxicams (isoxicam, piroxicam, sudoxicam and tenoxican), salicylates (acetyl salicylic acid, sulfasalazine) and pyrazolones (apazone, bezpiperylon, feprazone, mofebutazone, oxyphenbutazone, phenylbutazone); (24) a NRF2 pathway activator, such as the fumaric acid derivative, BG-12; and (25) a chemokine or chemokine receptor inhibitor, such as a CCR9 antagonist.

The amount tetrahydronaphthyridine or related compound (e.g., a compound of Formula I, I-A, II, II-A, III, III-A, IV, V, or VI) and additional therapeutic agent and the relative timing of administration may be selected in order to achieve a desired combined therapeutic effect. For example, when administering a combination therapy to a patient in need of such administration, the therapeutic agents in the combination, or a pharmaceutical composition or compositions comprising the therapeutic agents, may be administered in any order such as, for example, sequentially, concurrently, together, simultaneously and the like. Further, for example, a tetrahydronaphthyridine or related compound (e.g., a compound of any one of Formula I, I-A, II, II-A, III, III-A, IV, V, or VI) may be administered during a time when the additional therapeutic agent(s) exerts its prophylactic or therapeutic effect, or vice versa.

The doses and dosage regimen of the active ingredients used in the combination therapy may be determined by an attending clinician. In certain embodiments, the tetrahydronaphthyridine or related compound (e.g., a compound of any one of Formula I, I-A, II, II-A, III, III-A, IV, V, or VI) and the additional therapeutic agent(s) are administered in doses commonly employed when such agents are used as monotherapy for treating the disorder. In other embodiments, the tetrahydronaphthyridine or related compound (e.g., a compound of any one of Formula I, I-A, II, II-A, III, III-A, IV, V, or VI) and the additional therapeutic agent(s) are administered in doses lower than the doses commonly employed when such agents are used as monotherapy for treating the disorder. In certain embodiments, the tetrahydronaphthyridine or related compound (e.g., a compound of any one of Formula I, I-A, II, II-A, III, III-A, IV, V, or VI) and the additional therapeutic agent(s) are present in the same composition, which is suitable for oral administration.

In certain embodiments, the tetrahydronaphthyridine or related compound (e.g., a compound of any one of Formula I, I-A, II, II-A, III, III-A, IV, V, or VI) and the additional therapeutic agent(s) may act additively or synergistically. A synergistic combination may allow the use of lower dosages of one or more agents and/or less frequent administration of one or more agents of a combination therapy. A lower dosage or less frequent administration of one or more agents may lower toxicity of the therapy without reducing the efficacy of the therapy.

Another aspect of this invention is a kit comprising a therapeutically effective amount of the tetrahydronaphthyridine or related compound (e.g., a compound of any one of Formula I, I-A, II, II-A, III, III-A, IV, V, or VI), a pharmaceutically acceptable carrier, vehicle or diluent, and optionally at least one additional therapeutic agent listed above.

IV. Pharmaceutical Compositions and Dosing Considerations

As indicated above, the invention provides pharmaceutical compositions, which comprise a therapeutically-effective amount of one or more of the compounds described above, formulated together with one or more pharmaceutically acceptable carriers (additives) and/or diluents. The pharmaceutical compositions may be specially formulated for administration in solid or liquid form, including those adapted for the following: (1) oral administration, for example, drenches (aqueous or non-aqueous solutions or suspensions), tablets, e.g., those targeted for buccal, sublingual, and systemic absorption, boluses, powders, granules, pastes for application to the tongue; (2) parenteral administration, for example, by subcutaneous, intramuscular, intravenous or epidural injection as, for example, a sterile solution or suspension, or sustained-release formulation; (3) topical application, for example, as a cream, ointment, or a controlled-release patch or spray applied to the skin; (4) intravaginally or intrarectally, for example, as a pessary, cream or foam; (5) sublingually; (6) ocularly; (7) transdermally; or (8) nasally.

The phrase "therapeutically-effective amount" as used herein means that amount of a compound, material, or composition comprising a compound of the present invention which is effective for producing some desired therapeutic effect in at least a sub-population of cells in an animal at a reasonable benefit/risk ratio applicable to any medical treatment.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

Wetting agents, emulsifiers and lubricants, such as sodium lauryl sulfate and magnesium stearate, as well as coloring agents, release agents, coating agents, sweetening, flavoring and perfuming agents, preservatives and antioxidants can also be present in the compositions.

Examples of pharmaceutically-acceptable antioxidants include: (1) water soluble antioxidants, such as ascorbic acid, cysteine hydrochloride, sodium bisulfate, sodium metabisulfite, sodium sulfite and the like; (2) oil-soluble antioxidants, such as ascorbyl palmitate, butylated hydroxyanisole (BHA), butylated hydroxytoluene (BHT), lecithin, propyl gallate, alpha-tocopherol, and the like; and (3) metal chelating agents, such as citric acid, ethylenediamine tetraacetic acid (EDTA), sorbitol, tartaric acid, phosphoric acid, and the like.

Formulations of the present invention include those suitable for oral, nasal, topical (including buccal and sublingual), rectal, vaginal and/or parenteral administration. The formulations may conveniently be presented in unit dosage form and may be prepared by any methods well known in the art of pharmacy. The amount of active ingredient which can be combined with a carrier material to produce a single dosage form will vary depending upon the host being treated, the particular mode of administration. The amount of active ingredient which can be combined with a carrier material to produce a single dosage form will generally be that amount of the compound which produces a therapeutic effect. Generally, out of one hundred percent, this amount will range from about 0.1 percent to about ninety-nine percent of active ingredient, preferably from about 5 percent to about 70 percent, most preferably from about 10 percent to about 30 percent.

In certain embodiments, a formulation of the present invention comprises an excipient selected from the group consisting of cyclodextrins, celluloses, liposomes, micelle forming agents, e.g., bile acids, and polymeric carriers, e.g., polyesters and polyanhydrides; and a compound of the present invention. In certain embodiments, an aforementioned formulation renders orally bioavailable a compound of the present invention.

Methods of preparing these formulations or compositions include the step of bringing into association a compound of the present invention with the carrier and, optionally, one or more accessory ingredients. In general, the formulations are prepared by uniformly and intimately bringing into association a compound of the present invention with liquid carriers, or finely divided solid carriers, or both, and then, if necessary, shaping the product.

Formulations of the invention suitable for oral administration may be in the form of capsules, cachets, pills, tablets, lozenges (using a flavored basis, usually sucrose and acacia or tragacanth), powders, granules, or as a solution or a suspension in an aqueous or non-aqueous liquid, or as an oil-in-water or water-in-oil liquid emulsion, or as an elixir or syrup, or as pastilles (using an inert base, such as gelatin and glycerin, or sucrose and acacia) and/or as mouth washes and the like, each containing a predetermined amount of a compound of the present invention as an active ingredient. A compound of the present invention may also be administered as a bolus, electuary or paste.

In solid dosage forms of the invention for oral administration (capsules, tablets, pills, dragees, powders, granules, trouches and the like), the active ingredient is mixed with one or more pharmaceutically-acceptable carriers, such as sodium citrate or dicalcium phosphate, and/or any of the following: (1) fillers or extenders, such as starches, lactose, sucrose, glucose, mannitol, and/or silicic acid; (2) binders, such as, for example, carboxymethylcellulose, alginates, gelatin, polyvinyl pyrrolidone, sucrose and/or acacia; (3) humectants, such as glycerol; (4) disintegrating agents, such as agar-agar, calcium carbonate, potato or tapioca starch, alginic acid, certain silicates, and sodium carbonate; (5) solution retarding agents, such as paraffin; (6) absorption accelerators, such as quaternary ammonium compounds and surfactants, such as poloxamer and sodium lauryl sulfate; (7) wetting agents, such as, for example, cetyl alcohol, glycerol monostearate, and non-ionic surfactants; (8) absorbents, such as kaolin and bentonite clay; (9) lubricants, such as talc, calcium stearate, magnesium stearate, solid polyethylene glycols, sodium lauryl sulfate, zinc stearate, sodium stearate, stearic acid, and mixtures thereof; (10) coloring agents; and (11) controlled release agents such as crospovidone or ethyl cellulose. In the case of capsules, tablets and pills, the pharmaceutical compositions may also comprise buffering agents. Solid compositions of a similar type may also be employed as fillers in soft and hard-shelled gelatin capsules using such excipients as lactose or milk sugars, as well as high molecular weight polyethylene glycols and the like.

A tablet may be made by compression or molding, optionally with one or more accessory ingredients. Compressed tablets may be prepared using binder (for example, gelatin or hydroxypropylmethyl cellulose), lubricant, inert diluent, preservative, disintegrant (for example, sodium starch glycolate or cross-linked sodium carboxymethyl cellulose), surface-active or dispersing agent. Molded tablets may be made by molding in a suitable machine a mixture of the powdered compound moistened with an inert liquid diluent.

The tablets, and other solid dosage forms of the pharmaceutical compositions of the present invention, such as dragees, capsules, pills and granules, may optionally be scored or prepared with coatings and shells, such as enteric coatings and other coatings well known in the pharmaceutical-formulating art. They may also be formulated so as to provide slow or controlled release of the active ingredient therein using, for example, hydroxypropylmethyl cellulose in varying proportions to provide the desired release profile, other polymer matrices, liposomes and/or microspheres. They may be formulated for rapid release, e.g., freeze-dried. They may be sterilized by, for example, filtration through a bacteria-retaining filter, or by incorporating sterilizing agents in the form of sterile solid compositions which can be dissolved in sterile water, or some other sterile injectable medium immediately before use. These compositions may also optionally contain opacifying agents and may be of a composition that they release the active ingredient(s) only, or preferentially, in a certain portion of the gastrointestinal tract, optionally, in a delayed manner. Examples of embedding compositions which can be used include polymeric substances and waxes. The active ingredient can also be in micro-encapsulated form, if appropriate, with one or more of the above-described excipients.

Liquid dosage forms for oral administration of the compounds of the invention include pharmaceutically acceptable emulsions, microemulsions, solutions, suspensions, syrups and elixirs. In addition to the active ingredient, the liquid dosage forms may contain inert diluents commonly used in the art, such as, for example, water or other solvents, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor and sesame oils), glycerol, tetrahydrofuryl alcohol, polyethylene glycols and fatty acid esters of sorbitan, and mixtures thereof.

Besides inert diluents, the oral compositions can also include adjuvants such as wetting agents, emulsifying and suspending agents, sweetening, flavoring, coloring, perfuming and preservative agents.

Suspensions, in addition to the active compounds, may contain suspending agents as, for example, ethoxylated isostearyl alcohols, polyoxyethylene sorbitol and sorbitan esters, microcrystalline cellulose, aluminum metahydroxide, bentonite, agar-agar and tragacanth, and mixtures thereof.

Formulations of the pharmaceutical compositions of the invention for rectal or vaginal administration may be presented as a suppository, which may be prepared by mixing one or more compounds of the invention with one or more suitable nonirritating excipients or carriers comprising, for example, cocoa butter, polyethylene glycol, a suppository wax or a salicylate, and which is solid at room temperature, but liquid at body temperature and, therefore, will melt in the rectum or vaginal cavity and release the active compound.

Formulations of the present invention which are suitable for vaginal administration also include pessaries, tampons, creams, gels, pastes, foams or spray formulations containing such carriers as are known in the art to be appropriate.

Dosage forms for the topical or transdermal administration of a compound of this invention include powders, sprays, ointments, pastes, creams, lotions, gels, solutions, patches and inhalants. The active compound may be mixed under sterile conditions with a pharmaceutically-acceptable carrier, and with any preservatives, buffers, or propellants which may be required.

The ointments, pastes, creams and gels may contain, in addition to an active compound of this invention, excipients, such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to a compound of this invention, excipients such as lactose, talc, silicic acid, aluminum hydroxide, calcium silicates and polyamide powder, or mixtures of these substances. Sprays can additionally contain customary propellants, such as chlorofluorohydrocarbons and volatile unsubstituted hydrocarbons, such as butane and propane.

Transdermal patches have the added advantage of providing controlled delivery of a compound of the present invention to the body. Such dosage forms can be made by dissolving or dispersing the compound in the proper medium. Absorption enhancers can also be used to increase the flux of the compound across the skin. The rate of such flux can be controlled by either providing a rate controlling membrane or dispersing the compound in a polymer matrix or gel.

Ophthalmic formulations, eye ointments, powders, solutions and the like, are also contemplated as being within the scope of this invention.

Pharmaceutical compositions of this invention suitable for parenteral administration comprise one or more compounds of the invention in combination with one or more pharmaceutically-acceptable sterile isotonic aqueous or nonaqueous solutions, dispersions, suspensions or emulsions, or sterile powders which may be reconstituted into sterile injectable solutions or dispersions just prior to use, which may contain sugars, alcohols, antioxidants, buffers, bacteriostats, solutes which render the formulation isotonic with the blood of the intended recipient or suspending or thickening agents.

Examples of suitable aqueous and nonaqueous carriers which may be employed in the pharmaceutical compositions of the invention include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

These compositions may also contain adjuvants such as preservatives, wetting agents, emulsifying agents and dispersing agents. Prevention of the action of microorganisms upon the subject compounds may be ensured by the inclusion of various antibacterial and antifungal agents, for example, paraben, chlorobutanol, phenol sorbic acid, and the like. It may also be desirable to include isotonic agents, such as sugars, sodium chloride, and the like into the compositions. In addition, prolonged absorption of the injectable pharmaceutical form may be brought about by the inclusion of agents which delay absorption such as aluminum monostearate and gelatin.

In some cases, in order to prolong the effect of a drug, it is desirable to slow the absorption of the drug from subcutaneous or intramuscular injection. This may be accomplished by the use of a liquid suspension of crystalline or amorphous material having poor water solubility. The rate of absorption of the drug then depends upon its rate of dissolution which, in turn, may depend upon crystal size and crystalline form. Alternatively, delayed absorption of a parenterally-administered drug form is accomplished by dissolving or suspending the drug in an oil vehicle.

Injectable depot forms are made by forming microencapsule matrices of the subject compounds in biodegradable polymers such as polylactide-polyglycolide. Depending on the ratio of drug to polymer, and the nature of the particular polymer employed, the rate of drug release can be controlled. Examples of other biodegradable polymers include poly(orthoesters) and poly(anhydrides). Depot injectable formulations are also prepared by entrapping the drug in liposomes or microemulsions which are compatible with body tissue.

When the compounds of the present invention are administered as pharmaceuticals, to humans and animals, they can be given per se or as a pharmaceutical composition containing, for example, 0.1 to 99% (more preferably, 10 to 30%) of active ingredient in combination with a pharmaceutically acceptable carrier.

The preparations of the present invention may be given orally, parenterally, topically, or rectally. They are of course given in forms suitable for each administration route. For example, they are administered in tablets or capsule form, by injection, inhalation, eye lotion, ointment, suppository, etc. administration by injection, infusion or inhalation; topical by lotion or ointment; and rectal by suppositories. Oral administrations are preferred.

The phrases "parenteral administration" and "administered parenterally" as used herein means modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticulare, subcapsular, subarachnoid, intraspinal and intrasternal injection and infusion.

The phrases "systemic administration," "administered systemically," "peripheral administration" and "administered peripherally" as used herein mean the administration of a compound, drug or other material other than directly into the central nervous system, such that it enters the patient's system and, thus, is subject to metabolism and other like processes, for example, subcutaneous administration.

These compounds may be administered to humans and other animals for therapy by any suitable route of administration, including orally, nasally, as by, for example, a spray, rectally, intravaginally, parenterally, intracisternally and topically, as by powders, ointments or drops, including buccally and sublingually.

Regardless of the route of administration selected, the compounds of the present invention, which may be used in a suitable hydrated form, and/or the pharmaceutical compositions of the present invention, are formulated into pharmaceutically-acceptable dosage forms by conventional methods known to those of skill in the art.

Actual dosage levels of the active ingredients in the pharmaceutical compositions of this invention may be varied so as to obtain an amount of the active ingredient which is effective to achieve the desired therapeutic response for a particular patient, composition, and mode of administration, without being toxic to the patient.

The selected dosage level will depend upon a variety of factors including the activity of the particular compound of the present invention employed, or the ester, salt or amide thereof, the route of administration, the time of administration, the rate of excretion or metabolism of the particular compound being employed, the rate and extent of absorption, the duration of the treatment, other drugs, compounds and/or materials used in combination with the particular compound employed, the age, sex, weight, condition, general health and prior medical history of the patient being treated, and like factors well known in the medical arts.

A physician or veterinarian having ordinary skill in the art can readily determine and prescribe the effective amount of the pharmaceutical composition required. For example, the physician or veterinarian could start doses of the compounds of the invention employed in the pharmaceutical composition at levels lower than that required in order to achieve the desired therapeutic effect and gradually increase the dosage until the desired effect is achieved.

In general, a suitable daily dose of a compound of the invention will be that amount of the compound which is the lowest dose effective to produce a therapeutic effect. Such an effective dose will generally depend upon the factors described above. Preferably, the compounds are administered at about 0.01 mg/kg to about 200 mg/kg, more preferably at about 0.1 mg/kg to about 100 mg/kg, even more preferably at about 0.5 mg/kg to about 50 mg/kg. When the compounds described herein are co-administered with another agent (e.g., as sensitizing agents), the effective amount may be less than when the agent is used alone.

If desired, the effective daily dose of the active compound may be administered as two, three, four, five, six or more sub-doses administered separately at appropriate intervals throughout the day, optionally, in unit dosage forms. Preferred dosing is one administration per day.

The invention further provides a unit dosage form (such as a tablet or capsule) comprising a tetrahydronaphthyridine or related compound described herein (such as a compound of any one of Formulae I-VI, I-A, II-A, and III-A, or a specific compound described herein, such as in Tables 1-9) in a therapeutically effective amount for the treatment of an immune or inflammatory disorder, such as one of the particular immune disorders or inflammatory disorders described herein.

EXAMPLES

The invention now being generally described, will be more readily understood by reference to the following examples, which are included merely for purposes of illustration of certain aspects and embodiments of the present invention, and are not intended to limit the invention. As explained herein, certain compounds were purified and/or characterized using high-performance liquid chromatograph (HPLC). The conditions of HPLC Method A are as follows: Waters C-18 column, 4.6×150 mm, 3.5 micron, 25° C., 2.0 mL/min, 1 min 25% MeCN in $H_2O$ (0.1% TFA), 7 min gradient of 25%-95% MeCN in $H_2O$ (0.1% TFA), 95%

MeCN in H₂O (0.1% TFA) for 2 min, and then equilibration to 25% MeCN in H₂O (0.1% TFA) over 2.0 min.

Example 1—Synthesis of 2-chloro-6-fluoro-N-[1-(3-trifluoromethylbenzenesulfonyl)-1H-pyrazolo[4,3-b]pyridin-6-yl]benzamide (Compound 1)

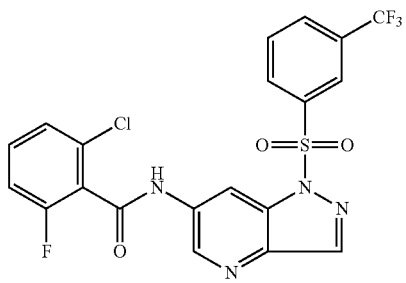 [SMILES: O=C(Nc1cnc2cnn(S(=O)(=O)c3cccc(C(F)(F)F)c3)c2c1)c1c(F)cccc1Cl]

The title compound was prepared according to the procedures described below.

Part I—Synthesis of 1-(6-nitro-1H-pyrazolo[4,3-b]pyridine-1-yl)ethanone

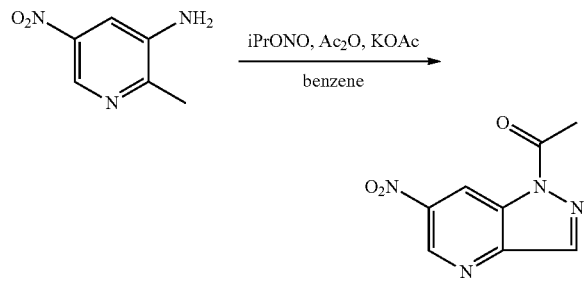

To a refluxing and stirring suspension of 2-methyl-5-nitropyridin-3-amine (0.58 g, 3.78 mmol), acetic anhydride (0.77 g, 7.56 mmol) and KOAc (0.37 g, 3.78 mmol) in benzene (40 mL) was slowly added isopropyl nitrite (0.51 g, 5.67 mmol in benzene (20 mL)). The reaction mixture was then refluxed for 24 hours, cooled to room temperature, and filtered. The mother liquor was washed with water (3×50 mL) and brine, dried over MgSO₄, and concentrated to provide the title compound. Yield 0.32 g (41%). ¹H NMR 250 MHz DMSO-d₆ δ 9.52 (d, J=2.2 Hz, 1H), 9.22 (dd, J=2.2, 0.9 Hz, 1H), 8.97 (d, J=0.9 Hz, 1H), 2.79 (s, 3H). LCMS (ESI): calc. $C_8H_6N_4O_3$=206; obs. M+H=207.

Part II—Synthesis of 6-nitro-1H-pyrazolo[4,3-b]pyridine

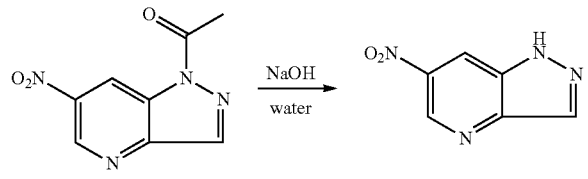

A suspension of 1-(6-nitro-1H-pyrazolo[4,3-b]pyridin-1-yl)ethanone (0.32 g, 1.55 mmol) in 1N NaOH (10 mL, 10 mmol) was stirred at 40° C. for 3 h. Next, the reaction mixture was acidified with 1N HCl and the product was extracted with EtOAc (3×30 mL), washed with brine, dried over MgSO₄, and concentrated to provide the title compound. Yield 0.20 g (78%). LCMS (ESI): calc. $C_6H_4N_4O_2$=164; obs. M+H=165.

Part III—Synthesis of 6-nitro-1-(3-trifluoromethylbenzenesulfonyl)-1H-pyrazolo[4,3-b]pyridine

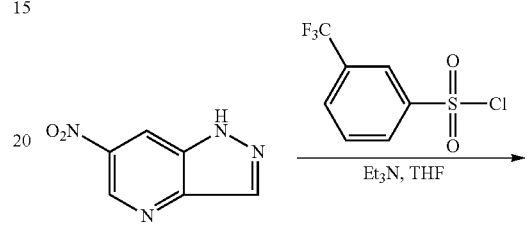

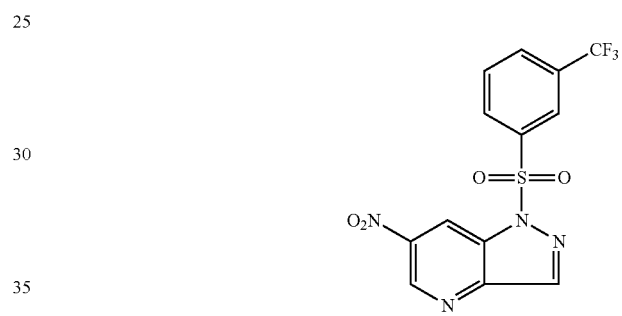

To a solution of 6-nitro-1H-pyrazolo[4,3-b]pyridine (100 mg, 0.61 mmol) and triethylamine (62 mg, 0.61 mmol) in THF (5 mL) was added 3-(trifluoromethyl)benzene-1-sulfonyl chloride (150 mg, 0.61 mmol). The reaction mixture was stirred for 1 hour, then quenched with water (10 mL) and the resulting mixture was extracted with EtOAc (3×20 mL). The combined organic extracts were washed with water (2×50 mL), washed with brine, dried (MgSO₄), and concentrated under reduced pressure to provide the title comound. Yield 100 mg (44%). LCMS (ESI): calc. $C_{13}H_7F_3N_4O_4S$=372; obs. M+H=373.

Part IV—Synthesis of 1-(3-trifluoromethylbenzenesulfonyl)-1H-pyrazolo[4,3-b]pyridin-6-ylamine

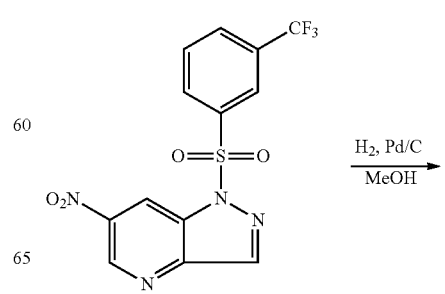

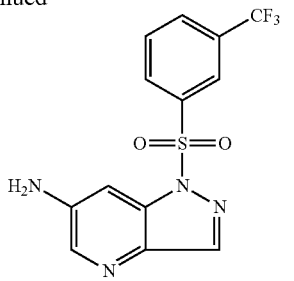

6-Nitro-1-(3-trifluoromethylbenzenesulfonyl)-1H-pyrazolo[4,3-b]pyridine (100 mg, 0.26 mmol) and 10% Pd/C were combined in MeOH (20 mL). The resulting suspension was agitated under a hydrogen atmosphere (60 p.s.i.) for 12 hours in a Parr shaker. Then, the suspension was filtered, and the mother liquor was concentrated under reduced pressure to provide the title compound. Yield 40 mg (42%). LCMS (ESI): calc. $C_{13}H_9F_3N_4O_2S=342$; obs. M+H=343.

Part V—Synthesis of 2-chloro-6-fluoro-N-[1-(3-trifluoromethylbenzenesulfonyl)-1H-pyrazolo[4,3-b]pyridin-6-yl]benzamide

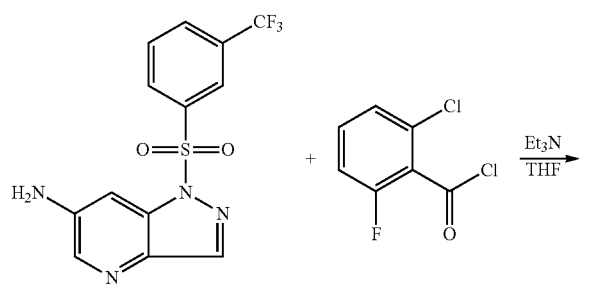

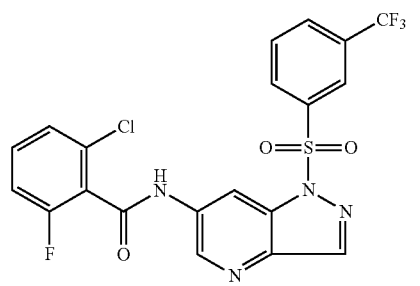

To a solution of 1-(3-trifluoromethylbenzenesulfonyl)-1H-pyrazolo[4,3-b]pyridin-6-ylamine (40 mg, 0.11 mmol) and triethylamine (11 mg, 0.11 mmol) in THF (5 mL) was added 2-chloro-6-fluorobenzoyl chloride (25 mg, 0.11 mmol). The reaction mixture was stirred for one hour, then quenched with water (10 mL), and the resulting mixture was extracted with EtOAc (3×20 mL). The combined organic extracts were washed with water (2×50 mL), washed with brine, dried (MgSO$_4$), and concentrated to provide a residue, which was purified by HPLC to provide the title compound. Yield 18 mg (33%). LCMS (ESI): calc. $C_{20}H_{11}ClF_4N_4O_3S=498$; obs. M+H=499.

Example 2—Synthesis of 2-chloro-6-fluoro-N-[1-(4-fluorobenzenesulfonyl)-1H-pyrazolo-[4,3-c]pyridin-6-yl]benzamide (Compound 2)

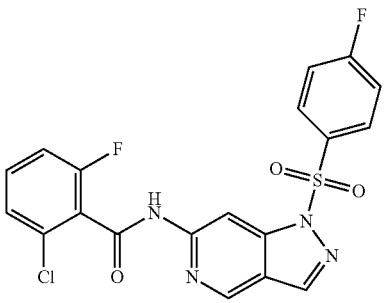

The title compound was prepared according to the procedures described below.

Part I—Synthesis of (4,6-dichloropyridin-3-yl)methanol

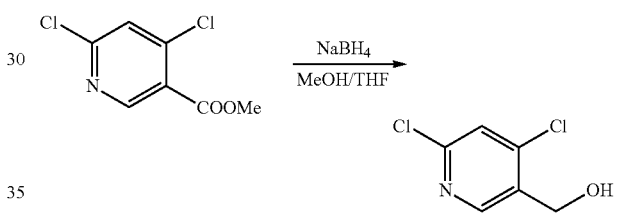

Methyl 4,6-dichloronicotinate (5 g, 24 mmol) was dissolved in THF (140 mL) to form a solution. Next, solid sodium borohydride (4.6 g, 120 mmol) was added to the solution, followed by dropwise addition of MeOH (140 mL) over five minutes. After 2 hours, saturated NH$_4$Cl was added and the resulting mixture was extracted three times with EtOAc. The combined organic extracts were washed with brine, dried (Na$_2$SO$_4$), and concentrated to give (4,6-dichloropyridin-3-yl)methanol. Yield 4.2 g (98%). LCMS (ESI): calc. $C_6H_5Cl_2NO=177$; obs. M+H=178.

Part II—Synthesis of 4,6-dichloropyridine-3-carbaldehyde

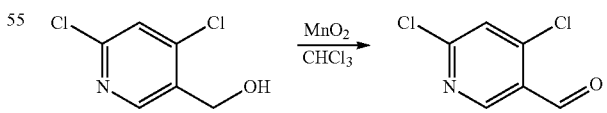

(4,6-Dichloropyridin-3-yl)methanol (4.9 g, 28 mmol) was dissolved in CHCl$_3$ (100 mL). MnO$_2$ (24 g, 280 mmol) was then added and the reaction mixture was stirred at 75° C. for 12 hours. Next, the reaction was cooled to room temperature, filtered through Celite, and concentrated to give 4,6-dichloropyridine-3-carbaldehyde. Yield 2.9 g (90%). LCMS (ESI): calc. $C_6H_3Cl_2NO=175$; obs. M+H=low ionization.

Part III—Synthesis of 6-chloro-1H-pyrazolo[4,3-c]pyridine

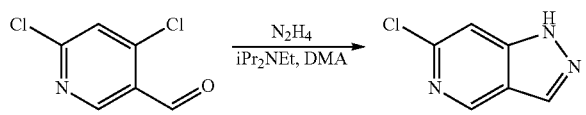

4,6-Dichloropyridine-3-carbaldehyde (3.7 g, 32 mmol), hydrazine (3.5 mL, 110 mmol) and N,N-diisopropylethylamine (20 mL) were combined in DMA (100 mL) and stirred at 80° C. for four hours. Then, the solution was cooled to room temperature, diluted with EtOAc, and washed three times with water and then with brine. The organic solution was concentrated and the resulting mixture was precipitated from dichloromethane to give 6-chloro-1H-pyrazolo[4,3-c]pyridine. Yield 2 g (41%). LCMS (ESI): calc. $C_6H_4ClN_3$=153; obs. M+H=154.

Part IV—Synthesis of 6-chloro-1-(4-fluorobenzenesulfonyl)-1H-pyrazolo[4,3-c]pyridine

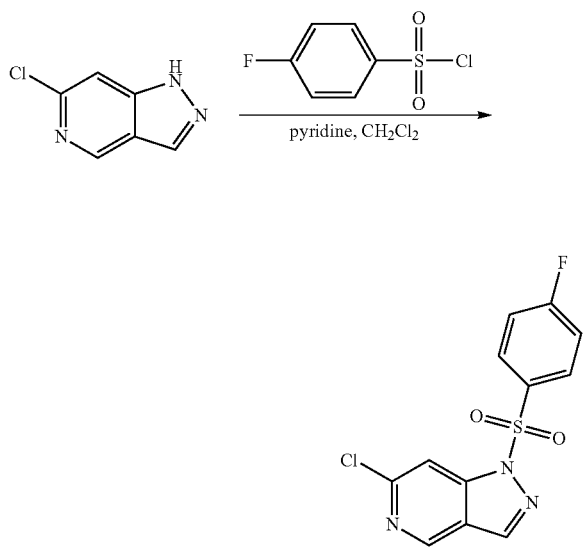

6-Chloro-1H-pyrazolo[4,3-c]pyridine (150 mg, 1.0 mmol) was dissolved in dichloromethane (2 mL) and pyridine (2 mL) to form a solution. 4-Fluorobenzenesulfonyl chloride (300 mg, 1.5 mmol) was added to the solution and the resulting reaction mixture was stirred at 50° C. for 16 hours. Next, the reaction mixture was washed with water, washed with brine, and then concentrated and purified by column chromatography (EtOAc/hexanes) to give 6-chloro-1-(4-fluorobenzenesulfonyl)-1H-pyrazolo[4,3-c]pyridine. Yield 184 mg (59%). LCMS (ESI): calc. $C_{12}H_7ClFN_3O_2S$=311; obs. M+H=312.

Part V—Synthesis of (2,4-dimethoxybenzyl)-[1-(4-fluorobenzenesulfonyl)-1H-pyrazolo[4,3-c]pyridine-6-yl]amine

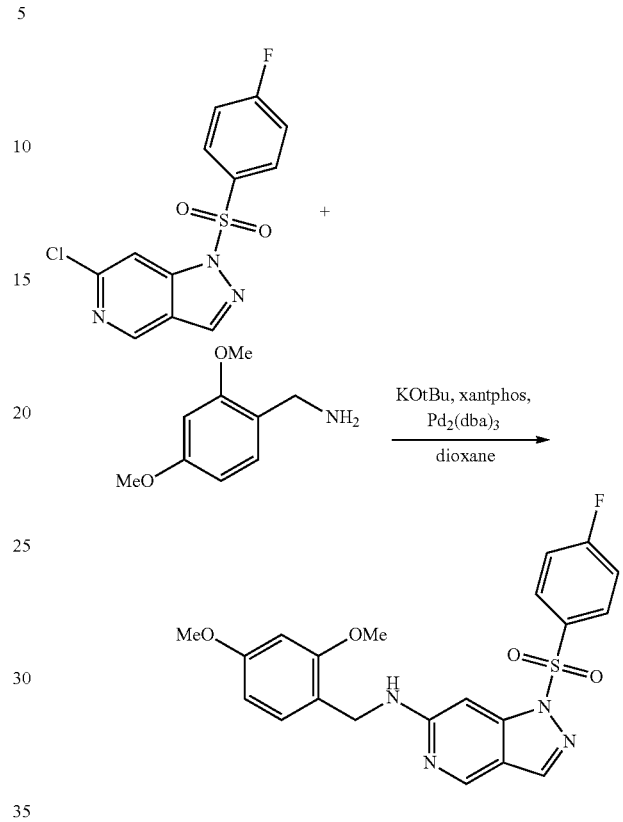

6-Chloro-1-(4-fluorobenzenesulfonyl)-1H-pyrazolo[4,3-c]pyridine (60 mg, 0.19 mmol), 2,4-dimethoxybenzylamine (0.10 mL, 0.66 mmol), $Pd_2(dba)_3$ (30 mg, 0.033 mmol), Xantphos (4,5-Bis(diphenylphosphino)-9,9-dimethylxanthene) (15 mg, 0.026 mmol), and KOtBu (90 mg, 0.80 mmol) were suspended in dioxane (2 mL) and stirred at 110° C. for 12 hours. Then, the reaction mixture was cooled to room temperature, diluted with EtOAc, and washed with 1 N HCl, saturated $NaHCO_3$, and then brine. The resulting organic solution was then dried ($Na_2SO_4$), concentrated, and purified by column chromatography (EtOAc/hexanes) to give (2,4-dimethoxybenzyl)-[1-(4-fluorobenzenesulfonyl)-1H-pyrazolo[4,3-c]pyridin-6-yl]amine. Yield 17 mg (20%). LCMS (ESI): calc. $C_{21}H_{19}FN_4O_4S$=442; obs. M+H=443.

Part VI—Synthesis of 1-(4-fluorobenzenesulfonyl)-1H-pyrazolo[4,3-c]pyridin-6-yl]amine

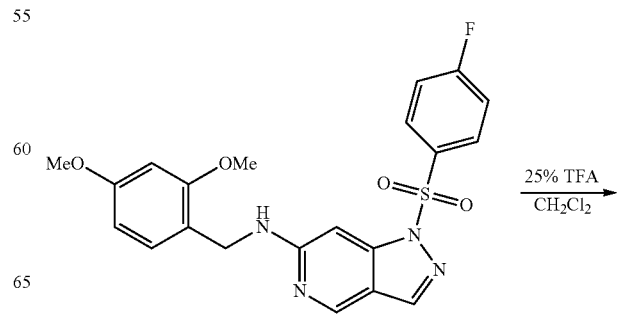

-continued

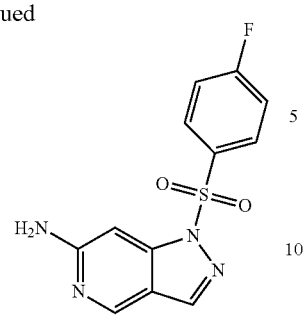

(2,4-Dimethoxybenzyl)-[1-(4-fluorobenzenesulfonyl)-1H-pyrazolo[4,3-c]pyridin-6-yl]amine (20 mg, 0.045 mmol) was dissolved in 25% trifluoroacetic acid/dichloromethane and stirred at 50° C. for 30 minutes. Then, the solvent was removed under reduced pressure and the resulting residue was basified with a minimal amount of saturated $K_2CO_3$ and extracted three times with EtOAc. The resulting organic solution was dried ($Na_2SO_4$) and concentrated under reduced pressure to give 1-(4-fluorobenzenesulfonyl)-1H-pyrazolo[4,3-c]pyridin-6-ylamine. Yield 20 mg crude. LCMS (ESI): calc. $C_{12}H_9FN_4O_2S=292$; obs. M+H=293.

Part VII—Synthesis of 2-chloro-6-fluoro-N-[1-(4-fluorobenzenesulfonyl)-1H-pyrazolo[4,3-c]pyridin-6-yl]benzamide

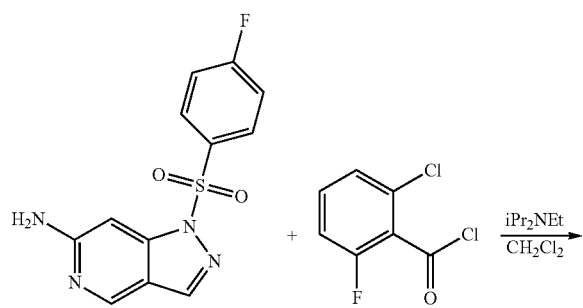

-continued

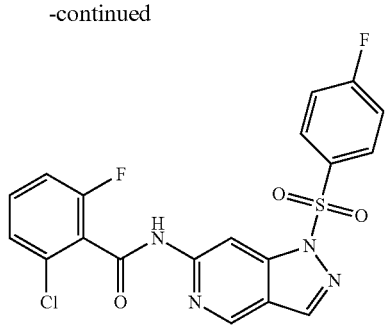

1-(4-Fluorobenzenesulfonyl)-1H-pyrazolo[4,3-c]pyridin-6-ylamine (20 mg, 0.068 mmol) and N,N-diisopropylethylamine (0.05 mL, 0.3 mmol) were dissolved in dichloromethane (1 mL). 2-Chloro-6-fluorobenzoyl chloride (26 mg, 0.14 mmol) was then added and the reaction mixture was stirred for 30 minutes. Next, 2 M LiOH (0.3 mL) and THF (0.3 mL) was added and the reaction mixture was stirred at 60° C. for 12 hours. Then, the reaction mixture was neutralized with 1N HCl, extracted with EtOAc, and purified by HPLC to give 2-chloro-6-fluoro-N-[1-(4-fluorobenzenesulfonyl)-1H-pyrazolo[4,3-c]pyridin-6-yl]benzamide. LCMS (ESI): calc. $C_{19}H_{11}ClF_2N_4O_3S=448$; obs. M+H=449.

Example 3—Preparation of additional N-(1-arylsulfonyl)-1H-pyrazolo[4,3-b]pyridin-6-yl)benzamide Compounds The compounds in Table 4 below were prepared based on the experimental procedures described in Examples 1 and 2 and in the detailed description. Starting materials can be obtained from commercial sources or readily prepared from commercially available materials.

TABLE 4

| Compound No. | Chemical Structure | LCMS (ESI): Calculated m/z | Observed m/z |
| --- | --- | --- | --- |
| 3 |  | 455 | M + H = 456 |

TABLE 4-continued

| Compound No. | Chemical Structure | LCMS (ESI): Calculated m/z | Observed m/z |
|---|---|---|---|
| 4 | 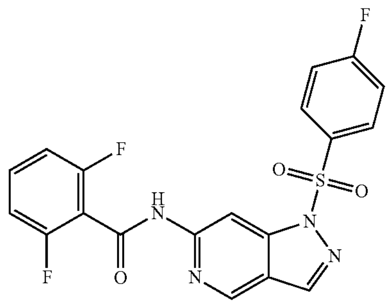 [SMILES: O=C(Nc1cc2c(cn1)cnn2S(=O)(=O)c1ccc(F)cc1)c1c(F)cccc1F] | 432 | M + H = 433 |
| 5 | 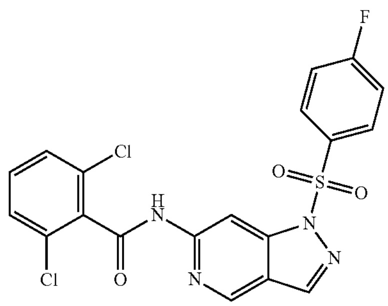 [SMILES: O=C(Nc1cc2c(cn1)cnn2S(=O)(=O)c1ccc(F)cc1)c1c(Cl)cccc1Cl] | 464 | M + H = 465 |
| 6 | 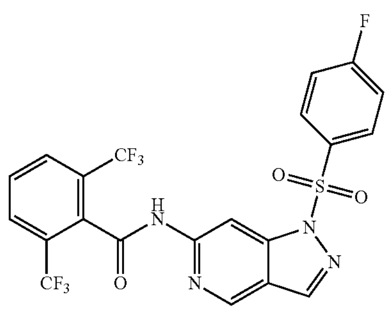 [SMILES: O=C(Nc1cc2c(cn1)cnn2S(=O)(=O)c1ccc(F)cc1)c1c(C(F)(F)F)cccc1C(F)(F)F] | 498 | M + H = 499 |
| 7 | 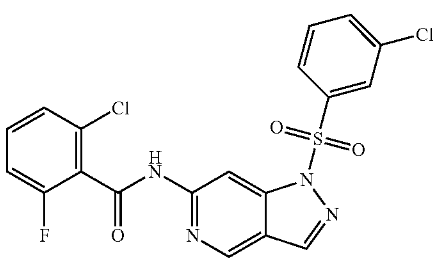 [SMILES: O=C(Nc1cc2c(cn1)cnn2S(=O)(=O)c1cccc(Cl)c1)c1c(F)cccc1Cl] | 464 | M + H = 465 |
| 8 | 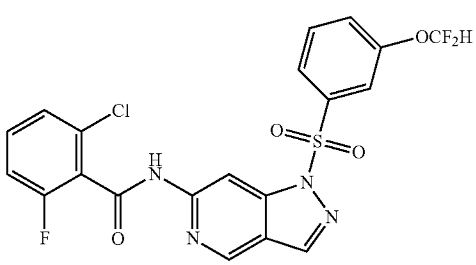 | 496 | M + H = 497 |

TABLE 4-continued

| Compound No. | Chemical Structure | LCMS (ESI): Calculated m/z | Observed m/z |
|---|---|---|---|
| 9 | 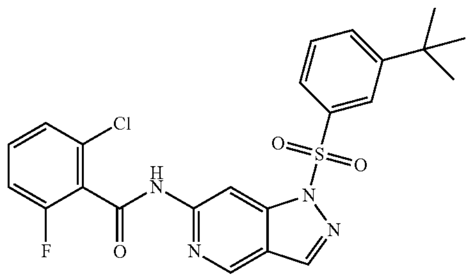 [SMILES: CC(C)(C)c1cccc(S(=O)(=O)n2ncc3cnc(NC(=O)c4c(F)cccc4Cl)cc32)c1] | 486 | M + H = 487 |
| 10 | 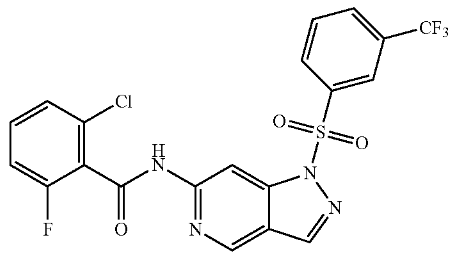 [SMILES: O=C(Nc1cc2c(cn1)cnn2S(=O)(=O)c1cccc(C(F)(F)F)c1)c1c(F)cccc1Cl] | 498 | M + H = 499 |
| 11 | 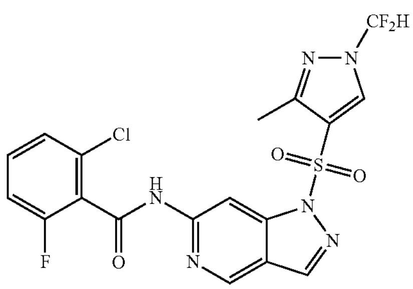 [SMILES: Cc1nn(C(F)F)cc1S(=O)(=O)n1ncc2cnc(NC(=O)c3c(F)cccc3Cl)cc21] | 484 | M + H = 485 |

Example 4—Synthesis of 2-chloro-6-fluoro-N-[1-(4-fluorobenzenesulfonyl)-2-methyl-2,3-dihydro-1H-pyrido[2,3-b][1,4]oxazin-7-yl]benzamide (Compound 12)

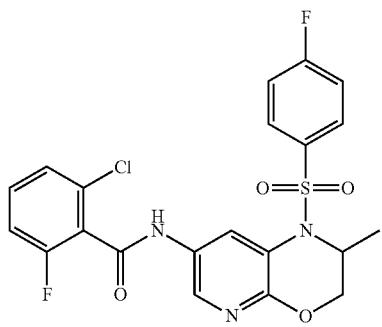 [SMILES: CC1COc2ncc(NC(=O)c3c(F)cccc3Cl)cc2N1S(=O)(=O)c1ccc(F)cc1]

The title compound was prepared according to the procedures described below.

Part I—Synthesis of 1-(3,5-dinitropyridin-2-yloxy)propan-2-one

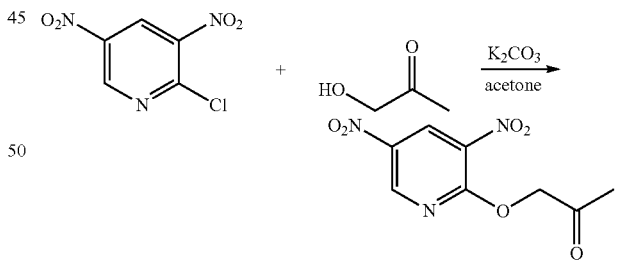

1-Chloro-3,5-dinitropyridine (0.46 g, 2.3 mmol) and hydroxyacetone (0.31 mL, 4.6 mmol) were dissolved in DMF (3 mL) to provide a solution. Potassium carbonate (0.95 g, 6.8 mmol) was added to the solution and the resulting reaction mixture was stirred at room temperature for 1 hour. Then, the reaction mixture was diluted with EtOAc and washed with water and then brine. The resulting organic mixture was purified by column chromatography (EtOAc/hexanes) to give 1-(3,5-dinitropyridin-2-yloxy)propan-2-one. Yield 0.11 g (19%). LCMS (ESI): calc. $C_8H_7N_3O_6$=241; obs. low ionization.

Part II—Synthesis of 2-methyl-2,3-dihydro-1H-pyrido[2,3-b][1,4]oxazin-7-ylamine

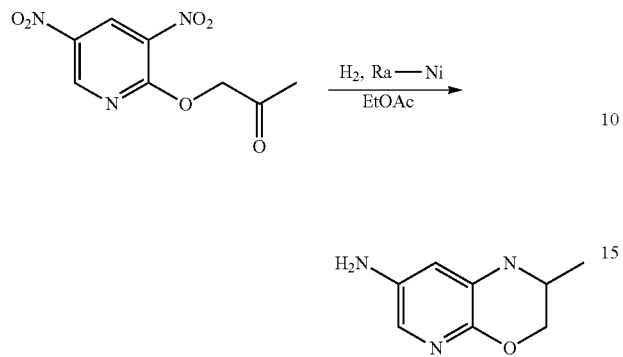

1-(3,5-Dinitropyridin-2-yloxy)propan-2-one (55 mg, 0.23 mmol) was dissolved in EtOAc (5 mL), and then Raney nickel (~50 mg) was added and the reaction mixture was agitated under hydrogen (50 p.s.i.) for 12 hours. Next, the reaction mixture was filtered over celite, and the filtrate was concentrated to give 2-methyl-2,3-dihydro-1H-pyrido[2,3-b][1,4]oxazin-7-ylamine. Yield 25 mg (66%). $^1$H NMR 250 MHz CDCl$_3$ δ 7.12 (d, J=2.5 Hz, 1H), 6.29 (d, J=2.5 Hz, 1H), 4.26 (dd, J=10.8, 2.9 Hz, 1H), 3.86 (dd, J=10.7, 8.2 Hz, 1H), 3.62-3.45 (m, 1H), 1.17 (d, J=6.5 Hz, 3H). LCMS (ESI): calc. $C_8H_{11}N_3O$=165; obs. M+H=166.

Part III—Synthesis of 2-chloro-6-fluoro-N-(2-methyl-2,3-dihydro-1H-pyrido[2,3-b][1,4]oxazin-7-yl)benzamide

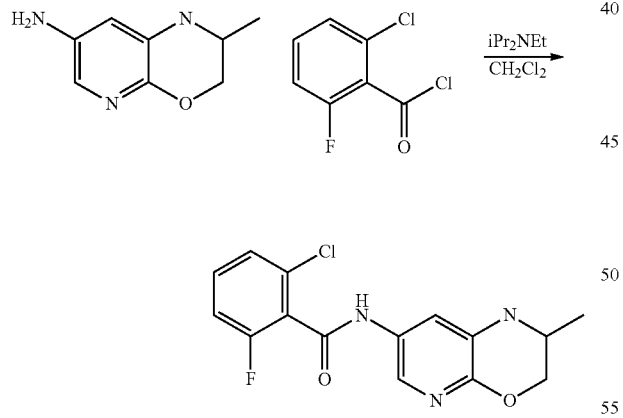

2-Methyl-2,3-dihydro-1H-pyrido[2,3-b][1,4]oxazin-7-ylamine (53 mg, 0.32 mmol) was dissolved in a mixture of N,N-diisopropylethylamine (0.084 mL, 0.48 mmol) and dichloromethane (1 mL) to form a solution. 2-Chloro-6-fluorobenzoyl chloride (0.043 mL, 0.32 mmol) was added to the solution, and the resulting reaction mixture was stirred at room temperature for 12 hours. Next, the reaction mixture was concentrated to give 2-chloro-6-fluoro-N-(2-methyl-2,3-dihydro-1H-pyrido[2,3-b][1,4]oxazin-7-yl)benzamide. LCMS (ESI): calc. $C_{15}H_{13}ClFN_3O_2$=321; obs. M+H=322.

Part IV—Synthesis of 2-chloro-6-fluoro-N-[1-(4-fluorobenzenesulfonyl)-2-methyl-2,3-dihydro-1H-pyrido[2,3-b][1,4]oxazin-7-yl]benzamide

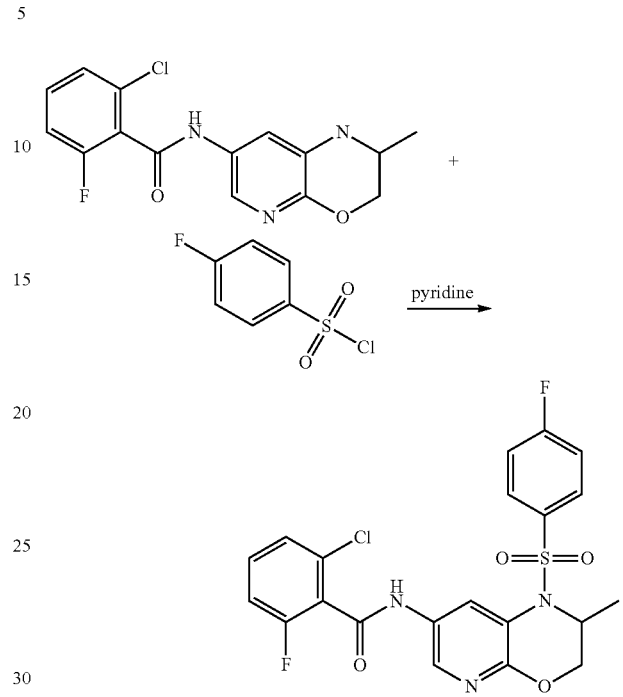

2-Chloro-6-fluoro-N-(2-methyl-2,3-dihydro-1H-pyrido[2,3-b][1,4]oxazin-7-yl)benzamide (crude, ~0.16 mmol) was dissolved in pyridine (1 mL) to form a solution. 4-Fluorobenzenesulfonyl chloride (46 mg, 0.24 mmol) was added to the solution, and the resulting reaction mixture was stirred at room temperature for 12 hours. Next, the reaction mixture was subjected to HPLC purification to provide 2-chloro-6-fluoro-N-[1-(4-fluorobenzenesulfonyl)-2-methyl-2,3-dihydro-1H-pyrido[2,3-b][1,4]oxazin-7-yl]benzamide. LCMS (ESI): calc. $C_{21}H_{16}ClF_2N_3O_4S$=479; obs. M+H=480.

Example 5—Synthesis of 2-chloro-6-fluoro-N-[1-(4-fluorobenzenesulfonyl)-2,3-dihydro-1H-pyrido[2,3-b][1,4]oxazin-7-yl]benzamide (Compound 13)

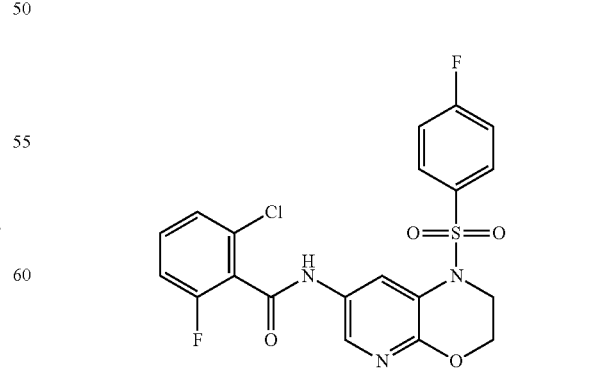

The title compound was prepared according to the procedures described below.

Part I—Synthesis of 2-(2,2-diethoxy-ethoxy)-3,5-dinitropyridine

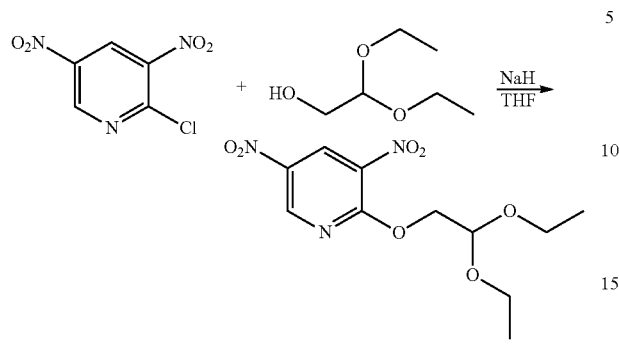

2,2'-Diethoxyethanol (0.27 g, 2.5 mmol) was dissolved in THF to form a solution. NaH (60% in mineral oil, 0.13 g, 3.4 mmol) was added to the solution, and the resulting reaction mixture was stirred at room temperature for 30 minutes. Next, 1-chloro-2,5-dinitropyridine (0.34 g, 1.7 mmol) was added, and the reaction mixture was heated to 50° C. for 90 minutes. Next, the reaction mixture was cooled to room temperature, diluted with EtOAc, and washed with water and brine. The resulting organic solution was concentrated and purified by column chromatography (EtOAc/hexanes) to provide 2-(2,2-diethoxy-ethoxy)-3,5-dinitropyridine. Yield 0.18 g (35%). LCMS (ESI): calc. $C_{11}H_{15}N_3O_7=301$; obs. low ionization.

Part II—Synthesis of (3,5-dinitropyridin-2-yloxy)acetaldehyde

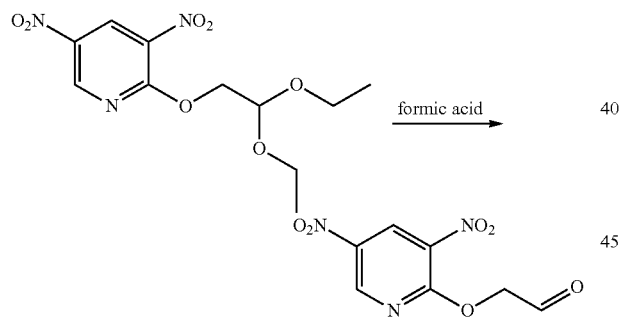

2-(2,2-diethoxy-ethoxy)-3,5-dinitropyridine (136 mg, 0.45 mmol) was dissolved in formic acid (2 mL) and stirred at room temperature for 1 hour. The resulting solution was concentrated and purified by column chromatography (EtOAc/hexanes) to provide (3,5-dinitropyridin-2-yloxy)acetaldehyde. Yield 89 mg (87%). LCMS (ESI): calc. $C_7H_5N_3O_6=227$; obs. low ionization.

Part III—Synthesis of 2-chloro-6-fluoro-N-[1-(4-fluorobenzenesulfonyl)-2,3-dihydro-1H-pyrido[2,3-b][1,4]oxazin-7-yl]benzamide

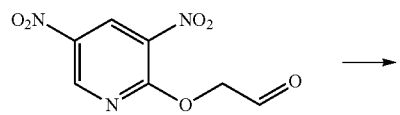

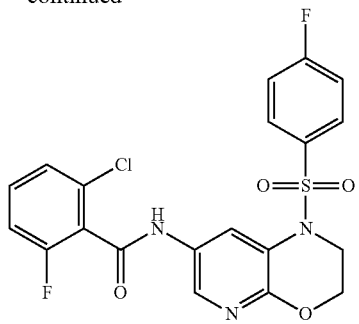

The title compound was prepared based on procedures described in Example 4. LCMS (ESI): calc. $C_{20}H_{14}ClF_2N_3O_4S=465$; obs. M+H=466.

Example 6—Synthesis of (S)-2-chloro-6-fluoro-N-(3-methyl-1-(m-tolylsulfonyl)-2,3-dihydro-1H-pyrido[2,3-b][1,4]oxazin-7-yl)benzamide (Compound 14)

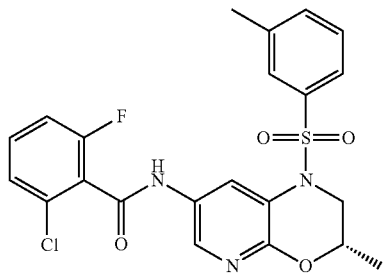 [SMILES: Cc1cccc(S(=O)(=O)N2C[C@H](C)Oc3ncc(NC(=O)c4c(F)cccc4Cl)cc32)c1]

The title compound was prepared according to the procedures described below.

Part I—Synthesis of (S)-methyl 6-((1-methoxy-1-oxopropan-2-yl)oxy)-5-nitronicotinate

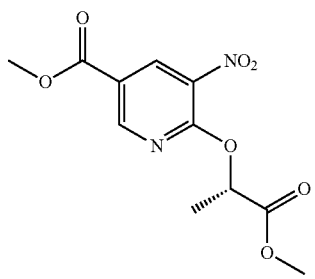

To methyl (S)-lactate (0.56 g, 5.4 mmol) and methyl 6-chloro-5-nitro-pyridine-3-carboxylate (0.8 g, 3.7 mmol) in anhydrous tetrahydrofuran (15 mL) under nitrogen at 0° C. was added 1,8-diazabicyclo[5.4.0]undec-7-ene (0.88 mL, 5.9 mmol). The solution quickly turned dark. The reaction mixture was stirred at 0° C. for 30 minutes, then allowed to stir at ambient temperature for one hour. A solid precipitated out of solution. Next, the reaction mixture was diluted with ethyl acetate (15 mL), solids were removed by filtration, and the filtrate was concentrated in the presence of silica to provide a crude product, which was purified by column chromatography eluting with a gradient of 10-50% ethyl acetate in hexanes to provide the title compound (0.68 g, 64% yield); HPLC retention time Method A: 5.46 minutes (98.9% pure).

Part II—Synthesis of (S)-methyl 3-methyl-2-oxo-2,3-dihydro-1H-pyrido[2,3-b][1,4]oxazine-7-carboxylate

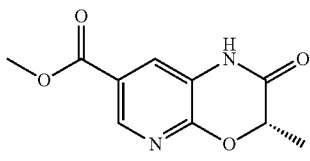 [SMILES: COC(=O)c1cnc2c(c1)NC(=O)[C@H](C)O2]

To a solution of (5)-methyl 6-((1-methoxy-1-oxopropan-2-yl)oxy)-5-nitronicotinate (0.68 g, 2.4 mmol) in glacial acetic acid (10 mL) was added powdered iron (0.67 g, 12 mmol). The resulting suspension was heated to 80° C. for 2 hours. Then, the resulting reaction mixture was cooled, filtered through celite, and washed with ethyl acetate. The filtrates were washed with water, washed with brine, dried with sodium sulfate, filtered and concentrated in vacuo to yield title compound. (420 mg, 79% yield); HPLC retention time Method A: 1.83 minutes (>99% pure).

Part III—Synthesis of (S)-3-methyl-2-oxo-2,3-dihydro-1H-pyrido[2,3-b][1,4]oxazine-7-carboxylic acid

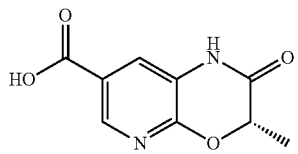

To (5)-methyl 3-methyl-2-oxo-2,3-dihydro-1H-pyrido[2,3-b][1,4]oxazine-7-carboxylate (0.42 g, 1.9 mmol) in tetrahydrofuran (5 mL) and methanol (1 mL) was added 2M sodium hydroxide (2.8 mL, 5.6 mmol). The reaction mixture was stirred at ambient temperature for 6 hours. Next, an aliquot (6 mL) of 1M hydrogen chloride was added to the reaction mixture. A solid formed slowly. The reaction mixture was stirred at ambient temperature for 30 minutes, then solids were removed by filtration and dried in a vacuum oven at 60° C. overnight to yield title compound. (340 mg, 86% yield); HPLC retention time Method A: 1.1 minutes (>99% pure).

Part IV—Synthesis of (S)-tert-butyl(3-methyl-2-oxo-2,3-dihydro-1H-pyrido[2,3-b][1,4]oxazin-7-yl)carbamate

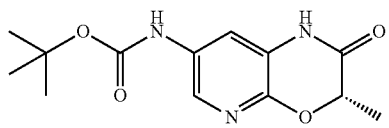 [SMILES: C[C@@H]1Oc2ncc(NC(=O)OC(C)(C)C)cc2NC1=O]

To a solution of (S)-3-methyl-2-oxo-2,3-dihydro-1H-pyrido[2,3-b][1,4]oxazine-7-carboxylic acid (2.39 g, 11.5 mmol) in anhydrous toluene (20 mL) and anhydrous tert-butanol (20 mL) with triethylamine (3.5 mL, 25.2 mmol) was added activated 4 Å molecular sieves. The resulting mixture was stirred for 15 minutes before adding diphenylphosphorazide (3 mL, 13.8 mmol). The resulting reaction mixture was heated to reflux under nitrogen for 2 hours. Then, the reaction mixture was cooled, filtered over filter paper, diluted with ethyl acetate, washed with water, washed with brine, dried with sodium sulfate, filtered, and concentrated in vacuo in the presence of silica to provide a crude product, which was purified by column chromatography eluting with a gradient of 0.5-5% methanol in dichloromethane to provide the title compound as a mixture with an impurity (1.88 g, 58% yield); HPLC retention time Method A: 3.56 minutes (83% pure).

Part V—Synthesis of (S)-tert-butyl(3-methyl-2,3-dihydro-1H-pyrido[2,3-b][1,4]oxazin-7-yl)carbamate

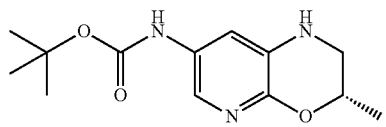 [SMILES: C[C@H]1CNc2cc(NC(=O)OC(C)(C)C)cnc2O1]

To a solution of (S)-tert-butyl (3-methyl-2-oxo-2,3-dihydro-1H-pyrido[2,3-b][1,4]oxazin-7-yl)carbamate (1.88 g, 26.9 mmol) in anhydrous tetrahydrofuran (30 mL) under nitrogen at 0° C. was added 1M lithium aluminum hydride in tetrahydrofuran (27 mL, 27 mmol) dropwise. The resulting reaction mixture was stirred at 0° C. for 3 hours, then at ambient temperature for 1 hour. Next, the reaction mixture was recooled to 0° C. before carefully quenching with sodium sulfate decahydrate. The resulting slurry was stirred at ambient temperature for two hours, and then solids were removed by filtration over celite. The solids were washed with tetrahydrofuran, and the filtrates were concentrated in the presence of silica to provide a crude product, which was purified via column chromatography eluting with a gradient of 0.5-5% methanol in dichloromethane to provide the title compound. (1.1 g, 62% yield); HPLC retention time Method A: 2.36 minutes (96.4% pure).

Part VI—Synthesis of (S)-tert-butyl(3-methyl-1-(m-tolylsulfonyl)-2,3-dihydro-1H-pyrido[2,3-b][1,4]oxazin-7-yl)carbamate

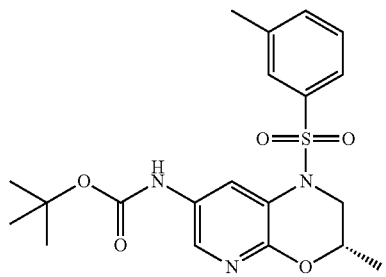 [SMILES: Cc1cccc(S(=O)(=O)N2C[C@H](C)Oc3ncc(NC(=O)OC(C)(C)C)cc32)c1]

To (S)-tert-butyl (3-methyl-2,3-dihydro-1H-pyrido[2,3-b][1,4]oxazin-7-yl)carbamate (0.5 g, 1.9 mmol) in 2,6-lutidine (5 mL) was added m-toluenesulfonyl chloride (0.33 mL, 2.3 mmol). The resulting mixture was stirred at 100° C. for 24 hours. Then, the reaction mixture was cooled, diluted with ethyl acetate, and the organic layer was washed with 1M hydrogen chloride (3×40 mL), washed with brine, dried with sodium sulfate, filtered and concentrated in the presence of silica to provide a crude product, which was purified by column chromatography eluting with a gradient of 20-70% ethyl acetate in hexanes to provide the title compound. (540 mg, 68% yield); HPLC retention time Method A: 6.46 minutes (95% pure).

Part VII—Synthesis of (S)-3-methyl-1-(m-tolylsulfonyl)-2,3-dihydro-1H-pyrido[2,3-b][1,4]oxazin-7-amine

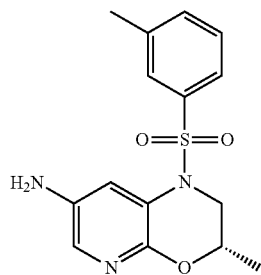 [SMILES: Cc1cccc(S(=O)(=O)N2C[C@H](C)Oc3ncc(N)cc32)c1]

To a solution of (S)-tert-butyl (3-methyl-1-(m-tolylsulfonyl)-2,3-dihydro-1H-pyrido[2,3-b][1,4]oxazin-7-yl)carbamate (0.54 g, 1.3 mmol) in dichloromethane (10 mL) was added trifluoroacetic acid (5 mL). The resulting mixture was stirred at ambient temperature for 90 minutes. Then, the reaction mixture was concentrated in vacuo to provide a residue, which was dissolved in ethyl acetate and washed with saturated sodium bicarbonate, washed with brine, dried with sodium sulfate, filtered and concentrated in vacuo to yield title compound. (430 mg, crude quantitative yield); HPLC retention time Method A: 3.17 minutes (95% pure).

Part VIII—Synthesis of (S)-2-chloro-6-fluoro-N-(3-methyl-1-(m-tolylsulfonyl)-2,3-dihydro-1H-pyrido[2,3-b][1,4]oxazin-7-yl)benzamide

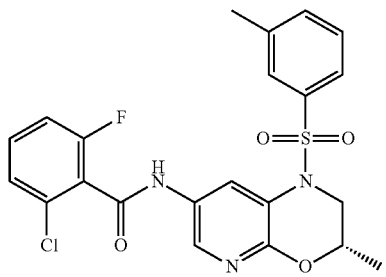

To a solution of (S)-3-methyl-1-(m-tolylsulfonyl)-2,3-dihydro-1H-pyrido[2,3-b][1,4]oxazin-7-amine (75 mg, 0.23 mmol) in tetrahydrofuran (2 mL) was added N,N-diisopropylethylamine (49 μL, 0.28 mmol) followed by 2-chloro-6-fluorobenzoyl chloride (34 μL, 0.26 mmol). The resulting solution was shaken at ambient temperature for 1 hour, diluted with ethyl acetate, washed with 1M hydrogen chloride, washed with brine, dried with sodium sulfate, filtered and concentrated in the presence of silica to provide a crude product, which was purified by column chromatography eluting with a gradient of 20-70% ethyl acetate in hexanes to provide the title compound (60 mg, 54% yield); HPLC retention time Method A: 6.10 minutes (>99% pure).

Example 7—Synthesis of (S)-2-chloro-N-(1-((3-ethylphenyl)sulfonyl)-3-methyl-2,3-dihydro-1H-pyrido-[2,3-b][1,4]oxazin-7-yl)-6-fluorobenzamide (Compound 15)

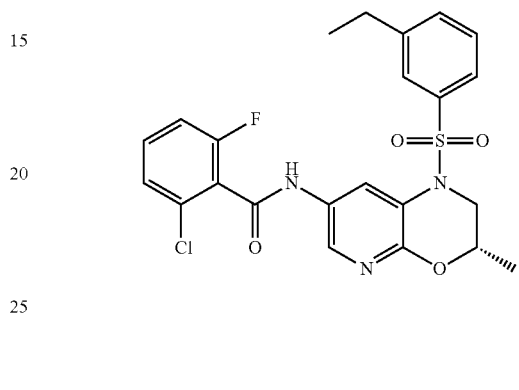

The title compound was prepared according to the procedures described below.

Part I—Synthesis of (S)-tert-butyl(3-methyl-1-((3-vinylphenyl)sulfonyl)-2,3-dihydro-1H-pyrido[2,3-b][1,4]oxazin-7-yl)carbamate

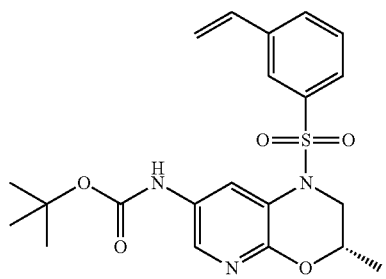 [SMILES: C=Cc1cccc(S(=O)(=O)N2C[C@H](C)Oc3ncc(NC(=O)OC(C)(C)C)cc32)c1]

In a microwave tube was combined (S)-tert-butyl(1-((3-bromophenyl)sulfonyl)-3-methyl-2,3-dihydro-1H-pyrido[2,3-b][1,4]oxazin-7-yl)carbamate (75 mg, 0.15 mmol), tributylvinyltin (68 μL, 0.23 mmol), and tetrakistriphenylphosphine palladium(0) (18 mg, 0.016 mmol) in anhydrous 1,4-dioxane (1.5 mL). The resulting mixture was heated in the microwave at 130° C. for 20 minutes, then concentrated onto silica in vacuo to provide a crude product that was purified by column chromatography eluting with a gradient of ethyl acetate in hexanes to provide the title compound. (65 mg, 97% yield); HPLC retention time Method A: 6.65 minutes (99% pure).

Part II—Synthesis of (S)-tert-butyl(1-((3-ethylphenyl)sulfonyl)-3-methyl-2,3-dihydro-1H-pyrido[2,3-b][1,4]oxazin-7-yl)carbamate

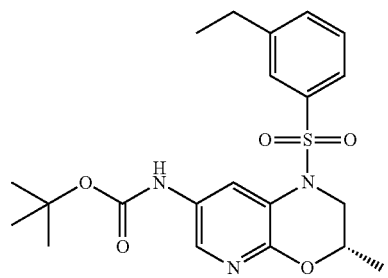 [SMILES: CCc1cccc(S(=O)(=O)N2C[C@H](C)Oc3ncc(NC(=O)OC(C)(C)C)cc32)c1]

A solution of (S)-tert-butyl(3-methyl-1-((3-vinylphenyl)sulfonyl)-2,3-dihydro-1H-pyrido[2,3-b][1,4]oxazin-7-yl)carbamate (65 mg, 0.15 mmol) in anhydrous methanol (5 mL) was degassed by bubbling nitrogen into the reaction solution for 10 minutes. Next, 10% palladium on carbon (50 mg) was added to the degassed solution, and the resulting reaction mixture was placed in a Parr shaker apparatus. The container holding the reaction mixture was evacuated and refilled with nitrogen three times, followed by repeated purging with hydrogen gas. Next, the reaction mixture was shaken at ambient temperature under a 60 PSI hydrogen atmosphere for 4 hours. Then, after purging the reaction vessel of hydrogen gas under vacuum and refilling with nitrogen three times, the suspension was filtered through celite, washed with methanol, and concentrated in vacuo to provide the title compound. (50 mg, 77% yield); HPLC retention time Method A: 6.98 minutes (98% pure yield).

Part III—Synthesis of (S)-2-chloro-N-(1-((3-ethylphenyl)sulfonyl)-3-methyl-2,3-dihydro-1H-pyrido-[2,3-b][1,4]oxazin-7-yl)-6-fluorobenzamide

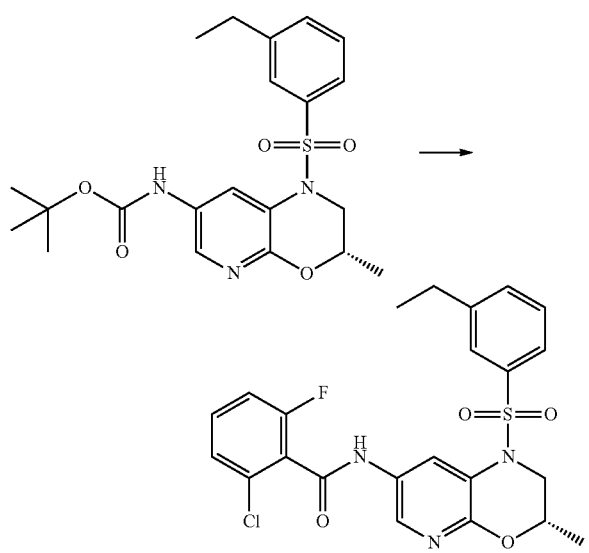

(S)-tert-Butyl (1-((3-ethylphenyl)sulfonyl)-3-methyl-2,3-dihydro-1H-pyrido[2,3-b][1,4]oxazin-7-yl)carbamate was converted to the title compound using procedures based on those described in Example 6.

Example 8—Synthesis of (S)—N-(3-(acetamidomethyl)-1-(m-tolylsulfonyl)-2,3-dihydro-1H-pyrido[2,3-b][1,4]oxazin-7-yl)-2-chloro-6-fluorobenzamide (Compound 16)

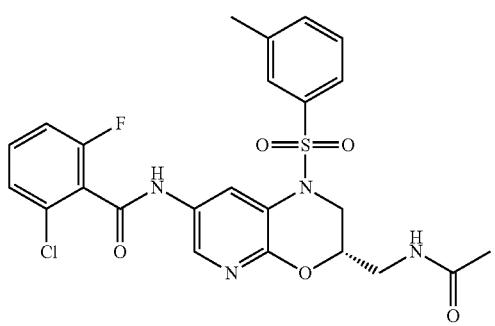 [SMILES: CC(=O)NC[C@H]1CN(S(=O)(=O)c2cccc(C)c2)c2cc(NC(=O)c3c(F)cccc3Cl)cnc2O1]

The title compound was prepared according to the procedures described below.

Part I—Synthesis of (S)-3-((tert-butoxycarbonyl)amino)-2-hydroxypropanoic acid

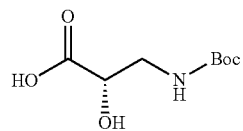

To (L)-isoserine (1.0 g, 9.5 mmol) in tetrahydrofuran (10 mL) and 2M sodium hydroxide (9.75 mL, 19.5 mmol) was added di-tert-butyl dicarbonate (0.78 g, 10 mmol). The resulting mixture was stirred vigorously at ambient temperature overnight. Then, the reaction mixture was acidified with 1M hydrogen chloride (20 mL) and stirred for 20 minutes until gas evolution ceased. The resulting mixture was partitioned between ethyl acetate and water, washed with brine, dried with sodium sulfate, filtered and concentrated in vacuo to yield title compound. (1.57 g, 80% yield)

Part II—Synthesis of (S)-methyl 3-((tert-butoxycarbonyl)amino)-2-hydroxypropanoate

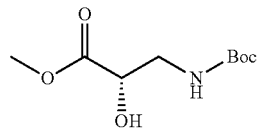

To (S)-3-((tert-butoxycarbonyl)amino)-2-hydroxypropanoic acid (1.57 g, 7.65 mmol) in N,N-dimethylformamide (15 mL) was added sodium bicarbonate (1.3 g, 15.3 mmol), followed by addition of iodomethane (0.57 mL, 9.2 mmol). The resulting mixture was stirred at ambient temperature for 6 hours. Then, another 0.2 mL of iodomethane was added, and the reaction mixture was stirred at ambient temperature overnight. Next, the reaction mixture was diluted with ethyl acetate, washed with saturated sodium bicarbonate, washed with brine, dried with sodium sulfate, filtered, and concentrated in vacuo to yield title compound. (0.78 g, 47% yield).

Part III—Synthesis of (S)-methyl 6-((3-((tert-butoxycarbonyl)amino)-1-methoxy-1-oxopropan-2-yl)oxy)-5-nitronicotinate

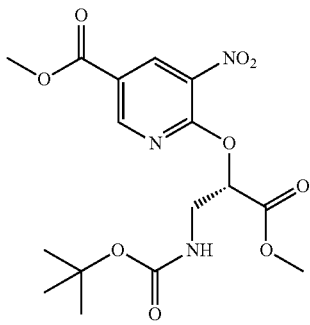 [SMILES: COC(=O)c1cnc(O[C@@H](CNC(=O)OC(C)(C)C)C(=O)OC)c([N+](=O)[O-])c1]

To (S)-methyl 3-((tert-butoxycarbonyl)amino)-2-hydroxypropanoate (0.78 g, 3.6 mmol) and methyl 6-chloro-5-nitro-pyridine-3-carboxylate (0.77 g, 3.6 mmol) in anhydrous tetrahydrofuran (15 mL) under nitrogen with activated 4 Å molecular sieves at 0° C. was added 1,8-diazabicyclo[5.4.0]undec-7-ene (0.69 mL, 4.6 mmol). Then, the cooling bath was removed from the reaction container and the reaction mixture was stirred at ambient temperature for 1 hour. A solid was observed to precipitate out of the solution. The reaction mixture was diluted with ethyl acetate (15 mL), solids were removed by filtration, and the filtrates were concentrated in the presence of silica to provide a crude product that was purified by column chromatography eluting with a gradient of 5-50% ethyl acetate in hexanes to provide the title compound. (0.98 g, 69% yield).

Part IV—Synthesis of (S)-methyl 3-(((tert-butoxycarbonyl)amino)methyl)-2-oxo-2,3-dihydro-1H-pyrido[2,3-b][1,4]oxazine-7-carboxylate

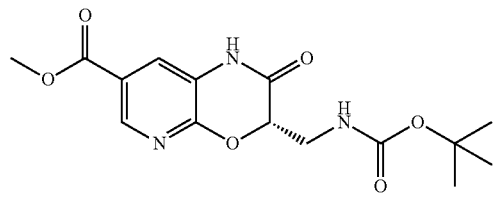 [SMILES: COC(=O)c1cnc2c(c1)NC(=O)[C@H](CNC(=O)OC(C)(C)C)O2]

A suspension of (S)-methyl 6-((3-((tert-butoxycarbonyl)amino)-1-methoxy-1-oxopropan-2-yl)oxy)-5-nitronicotinate (0.97 g, 2.43 mmol) and powdered iron (0.68 g, 12.1 mmol) in glacial acetic acid (15 mL) was heated to 70° C. for 2 hours. Then, the reaction mixture was cooled, filtered through celite, and the celite was washed with tetrahydrofuran. The filtrates were concentrated to a volume of approximately 3 mL in vacuo. Then, tetrahydrofuran (10 mL) was added to the concentrated mixture. Next, water (30 mL) was added slowly to the mixture in order to crash out the solids. The resulting mixture was slurried at ambient temperature for 15 minutes, solids were removed by filtration, and the solids were washed with water and air dried to provide the title compound. (0.58 g, 71% yield); HPLC retention time Method A: 3.52 minutes (>99% pure).

Part V—Synthesis of (S)-3-(((tert-butoxycarbonyl)amino)methyl)-2-oxo-2,3-dihydro-1H-pyrido[2,3-b][1,4]oxazine-7-carboxylic acid

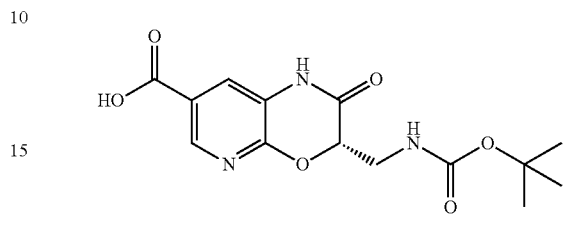

To (S)-methyl 3-(((tert-butoxycarbonyl)amino)methyl)-2-oxo-2,3-dihydro-1H-pyrido[2,3-b][1,4]oxazine-7-carboxylate (3.5 g, 10.4 mmol) in tetrahydrofuran (40 mL) and methanol (10 mL) was added 2M sodium hydroxide (16 mL, 31.1 mmol). The resulting mixture was stirred at ambient temperature overnight. Then, the solution was acidified with 1M hydrogen chloride (35 mL), diluted with water (250 mL), and the resulting mixture was slurried for 20 minutes before filtering off the solids to yield the title compound (3.12 g, 93% yield).

Part VI—Synthesis of bis-carbamate of 3-(aminomethyl)-2-oxo-2,3-dihydro-1H-pyrido[2,3-b][1,4]oxazine (hereinafter Compound A')

(Compound A')

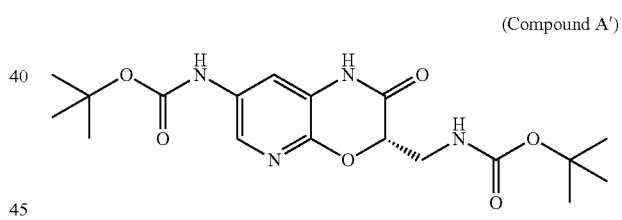

To a solution of (S)-3-(((tert-butoxycarbonyl)amino)methyl)-2-oxo-2,3-dihydro-1H-pyrido[2,3-b][1,4]oxazine-7-carboxylic acid (3.12 g, 9.65 mmol) in anhydrous toluene (30 mL) with activated 4 Å molecular sieves was added tert-butyl alcohol (10 mL), followed by triethylamine (3 mL, 21 mmol). The resulting suspension was stirred for 15 minutes before adding diphenylphosphorylazide (2.5 mL, 11.6 mmol). Next, the reaction mixture was heated to reflux under a nitrogen atmosphere for 3 hours. Then, the reaction mixture was cooled, filtered, diluted with ethyl acetate, and then washed with 1M hydrogen chloride, saturated sodium bicarbonate, and brine. The resulting organic solution was dried with sodium sulfate, filtered, and concentrated in vacuo in the presence of silica to provide the crude product that was purified by column chromatography eluting with a gradient of 30-100% ethyl acetate in hexanes to provide the title compound. (3.1 g, 81% yield); HPLC retention time Method A: 4.55 minutes (95% pure).

Part VII—Synthesis of bis-carbamate of 3-(aminomethyl)-2,3-dihydro-1H-pyrido[2,3-b][1,4]oxazine (hereinafter Compound B')

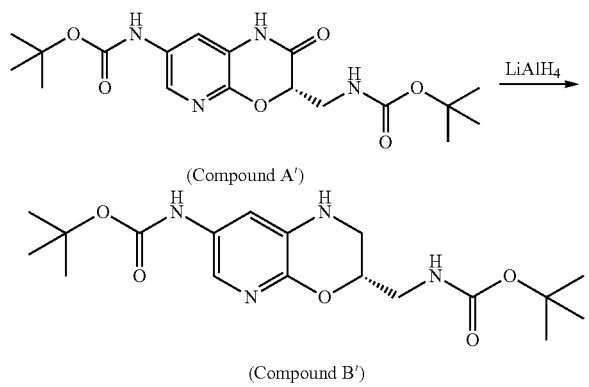

(Compound A')

(Compound B')

To a solution of Compound A' (3.1 g, 7.9 mmol) in anhydrous tetrahydrofuran (30 mL) under nitrogen at 0° C. was added lithium aluminum hydride (1M in tetrahydrofuran, 31.4 mL, 31.4 mmol) dropwise. Next, the reaction mixture was stirred at 0° C. for 2 hours, and then at ambient temperature for 2 hours. Next, the reaction mixture was cooled to 0° C., and excess sodium sulfate decahydrate was added carefully to quench the reaction. The resulting slurry was stirred at ambient temperature for 30 minutes before adding anhydrous sodium sulfate. Solids were removed by filtering the reaction nmixture through celite. The solids were washed with tetrahydrofuran and the filtrates were concentrated in the presence of silica to provide a crude product that was purified by column chromatography eluting with a gradient of 30-100% ethyl acetate in hexanes to provide the title compound. (1.8 g, 60% yield); HPLC retention time Method A: 3.88 minutes (95% pure).

Part VIII—Synthesis of Bis-carbamate of 3-(aminomethyl)-1-(m-tolylsulfonyl)-2,3-dihydro-1H-pyrido[2,3-b][1,4]oxazine (hereinafter Compound C')

To Compound B' (0.5 g, 1.3 mmol) in 2,6-lutidine (5 mL) was added m-toluenesulfonyl chloride (0.25 mL, 1.7 mmol). Then, the reaction mixture was stirred and heated at 100° C. for 24 hours. Next, since analytical HPLC showed that a significant amount of starting material remained, an aliquot of m-toluenesulfonyl chloride (50 μL, 0.34 mmol) was added to the reaction mixture, and the reaction mixture was heated for 6 hours. Then, the resulting suspension was cooled, diluted with ethyl acetate, and washed with 1M hydrogen chloride, then brine. The resulting organic solution was dried with sodium sulfate, filtered, and concentrated in the presence of silica to provide a crude product that was purified by column chromatography eluting with a gradient of 20-80% ethyl acetate in hexanes to provide the title compound. (460 mg, 65% yield); HPLC retention time Method A: 6.96 minutes (96% pure).

Part IX—Synthesis of (S)-3-(aminomethyl)-1-(m-tolylsulfonyl)-2,3-dihydro-1H-pyrido[2,3-b][1,4]oxazin-7-amine

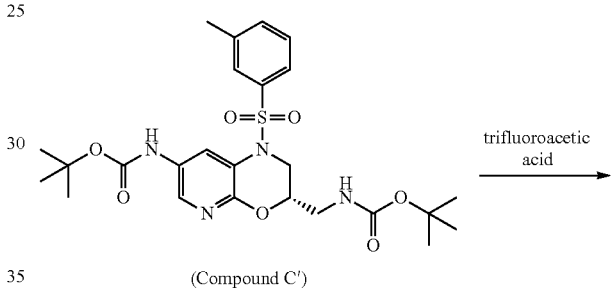

(Compound C')

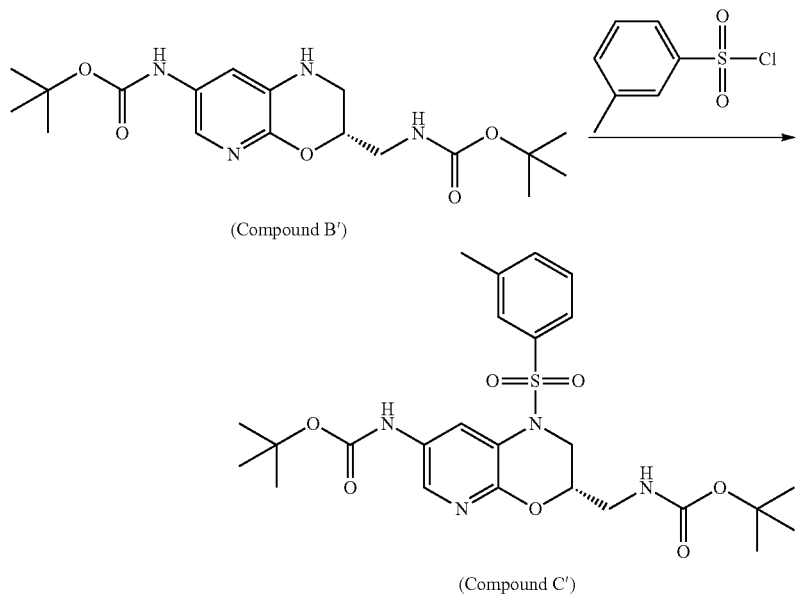

(Compound B')

(Compound C')

-continued

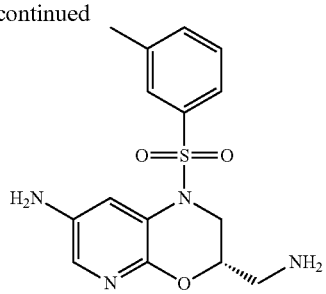

To a solution of Compound C' (0.46 g, 0.86 mmol) in dichloromethane (5 mL) was added trifluoroacetic acid (5 mL). The resulting mixture was stirred at ambient temperature for 1 hour. Then, the solution was concentrated in vacuo to produce a residue that was redissolved in ethyl acetate. The resulting solution was washed with saturated sodium bicarbonate, washed with brine, dried with sodium sulfate, filtered and concentrated in vacuo to yield title compound (220 mg, 76% yield); HPLC retention time Method A: 3.95 minutes (82% pure).

Part X—Synthesis of (S)—N-((7-Amino-1-(m-tolylsulfonyl)-2,3-dihydro-1H-pyrido[2,3-b][1,4]oxazin-3-yl)methyl)acetamide

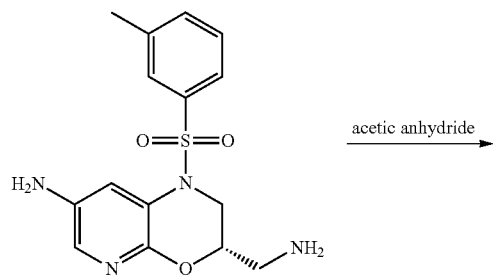

To (S)-3-(aminomethyl)-1-(m-tolylsulfonyl)-2,3-dihydro-1H-pyrido[2,3-b][1,4]oxazin-7-amine (220 mg, 0.63 mmol) in tetrahydrofuran (4 mL) was added acetic anhydride (59 μL, 0.63 mmol). The resulting mixture was stirred at ambient temperature for 2 hours, then the mixture was subjected to column chromatography purification eluting with a gradient of ethyl acetate in hexanes to provide the title compound as a mixture (130 mg; 55% yield); HPLC retention time Method A: 4.28 minutes (62% pure).

Part XI—Synthesis of (S)—N-(3-(Acetamidomethyl)-1-(m-tolylsulfonyl)-2,3-dihydro-1H-pyrido[2,3-b][1,4]oxazin-7-yl)-2-chloro-6-fluorobenzamide

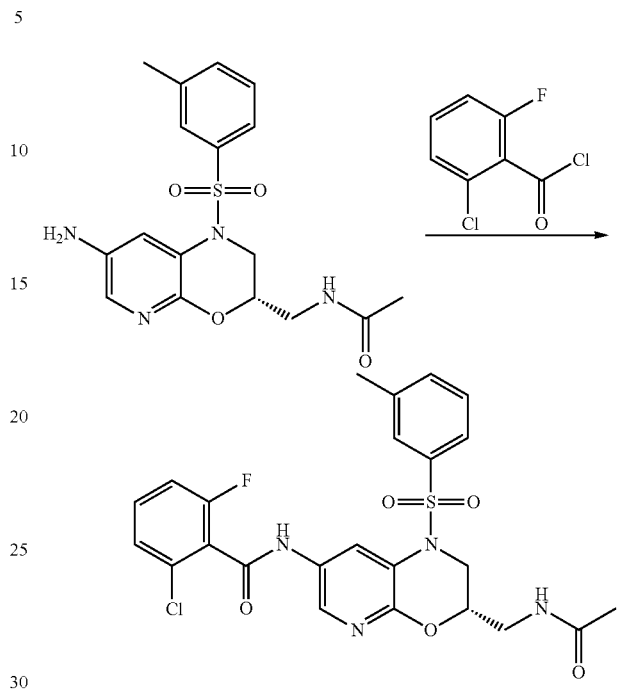

To (S)—N-((7-amino-1-(m-tolylsulfonyl)-2,3-dihydro-1H-pyrido[2,3-b][1,4]oxazin-3-yl)methyl)acetamide (40 mg, 0.11 mmol) in tetrahydrofuran (1 mL) was added N,N-diisopropylethylamine (37 μL, 0.21 mmol) followed by 2-chloro-6-fluorobenzoyl chloride (17 μL, 0.13 mmol). Then, the reaction solution was shaken at ambient temperature for 1 hour. The resulting mixture was subjected to column chromatography purification eluting with a gradient of ethyl acetate in hexanes to provide the title compound. (31 mg, 52% yield); HPLC retention time Method A: 5.01 minutes (95.9% pure).

Example 9—Synthesis of (S)—N—((S)-3-(Acetamidomethyl)-1-(m-tolylsulfonyl)-2,3-dihydro-1H-pyrido[2,3-b][1,4]oxazin-7-yl)-2-phenylpropanamide (Compound 17)

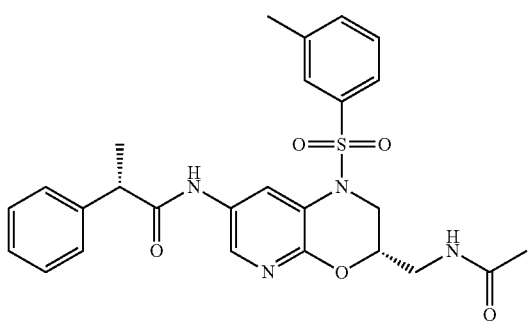 [SMILES: CC(=O)NC[C@H]1CN(S(=O)(=O)c2cccc(C)c2)c2cc(NC(=O)[C@@H](C)c3ccccc3)cnc2O1]

To a solution of (S)—N-((7-amino-1-(m-tolylsulfonyl)-2,3-dihydro-1H-pyrido[2,3-b][1,4]oxazin-3-yl)methyl)acetamide (40 mg, 0.11 mmol) in N,N-dimethylformamide (0.4 mL) was added (2S)-2-phenylpropanoic acid (24 mg, 0.16 mmol) and N,N-diisopropylethylamine (56 µL, 0.32 mmol), followed by O-(7-azabenzotriazol-1-yl)-N,N,N',N'-tetramethyluroniumhexafluorophosphate (61 mg, 0.16 mmol). The reaction mixture was shaken at ambient temperature for 2 hours, diluted with ethyl acetate, and washed with 1M hydrogen chloride and brine. The resulting organic solution was dried with sodium sulfate, filtered, and concentrated in the presence of silica to provide a crude product that was purified by column chromatography eluting with a gradient of 0.5-10% methanol in dichloromethane to provide the title compound. (29 mg, 51% yield); HPLC retention time Method A: 5.36 minutes (95% pure).

Example 10—Synthesis of (S)—N-(3-(acetamidomethyl)-1-((3-cyclopropylphenyl)sulfonyl)-2,3-dihydro-1H-pyrido[2,3-b][1,4]oxazin-7-yl)-2,6-dichlorobenzamide (Compound 18)

The title compound was prepared according to the procedures described below.

Part I—Synthesis of bis-carbamate of (S)-3-(aminomethyl)-1-(3-bromophenylsulfonyl)-2,3-dihydro-1H-pyrido[2,3-b][1,4]oxazin-7-amine (hereinafter Compound A")

Part II—Synthesis of bis-carbamate of (S)-3-(aminomethyl)-1-(3-cyclopropylphenylsulfonyl)-2,3-dihydro-1H-pyrido[2,3-b][1,4]oxazin-7-amine (hereinafter Compound B")

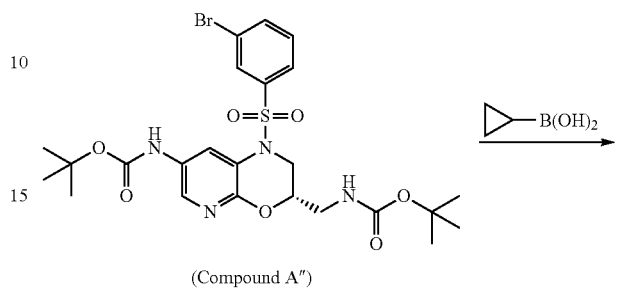

(Compound A")

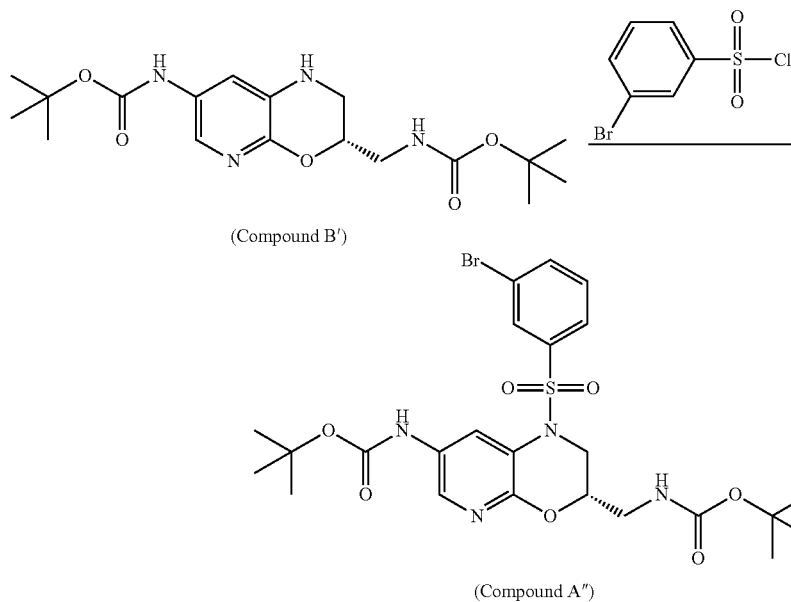

(Compound B')

(Compound A")

To Compound B' (from Example 8) (1.4 g, 3.7 mmol) in 2,6-lutidine (25 mL) was added 3-bromosulfonyl chloride (0.69 mL, 4.8 mmol) and the resulting mixture was stirred at 100° C. for 24 hours. Then, the resulting suspension was cooled, diluted with ethyl acetate, and washed with 10% citric acid (3×50 mL), water, and brine. The resulting organic solution was dried with sodium sulfate, filtered, and concentrated in the presence of silica to provide a crude product that was purified by column chromatography eluting with a gradient of 25-100% ethyl acetate in hexanes to provide the title compound. (750 mg, 34% yield); HPLC retention time Method A: 7.4 minutes (96% pure).

-continued

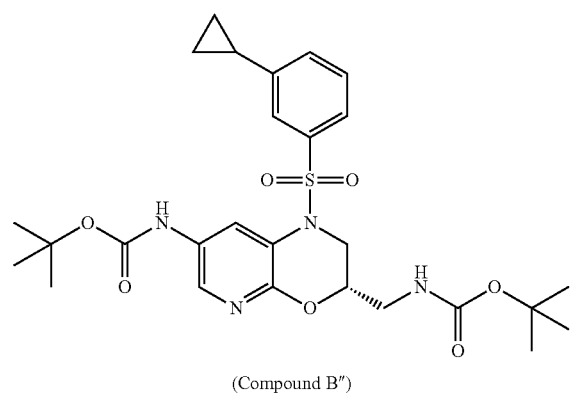

(Compound B")

In a 100 mL round bottomed flask was combined Compound A" (750 mg, 1.25 mmol), cyclopropylboronic acid (215 mg, 2.50 mmol), tricyclohexyl phosphine (35 mg, 0.13 mmol), potassium phosphate tribasic (930 mg, 4.4 mmol), palladium (II) acetate (14 mg, 0.063 mmol) in toluene (15 mL), and water (5 mL). The resulting solution was refluxed for 18 hours. Then, the reaction mixture was partitioned between ethyl acetate and brine, the organic layer was separated and dried with sodium sulfate, filtered and concentrated in vacuo to provide a crude product that was purified by column chromatography eluting with a gradient of ethyl acetate in hexanes to produce the title compound. (520 mg, 74% yield); HPLC retention time Method A: 7.43 minutes (95% pure).

Part III—Synthesis of (S)—N-((7-amino-1-((3-cyclopropylphenyl)sulfonyl)-2,3-dihydro-1H-pyrido[2,3-b][1,4]oxazin-3-yl)methyl)acetamide

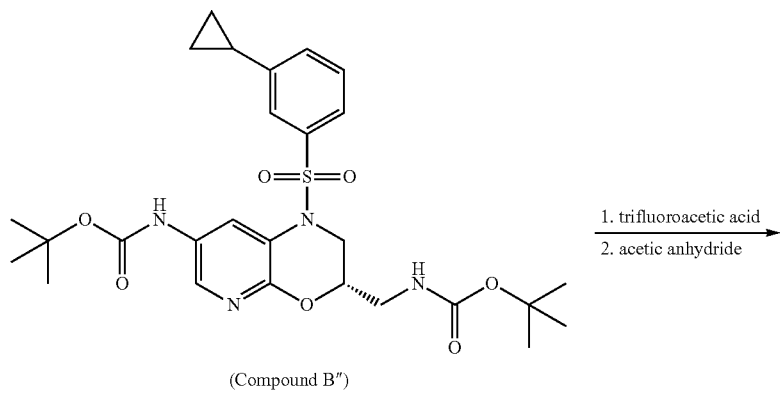

(Compound B")

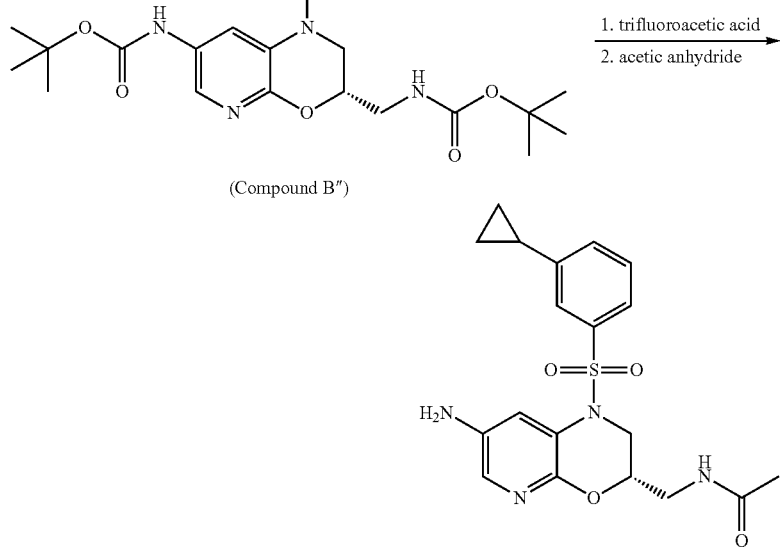

To a solution of Compound B" (0.52 g, 0.93 mmol) in dichloromethane (5 mL) was added trifluoroacetic acid (5 mL). The resulting mixture was stirred at ambient temperature for 1 hour. Then, the resulting solution was concentrated in vacuo to provide a residue. The residue was dissolved in tetrahydrofuran (5 mL) and N,N-diisopropylethylamine (0.81 mL, 4.6 mmol) was added, followed by the dropwise addition of a solution of acetic anhydride (79 μL, 0.83 mmol) in tetrahydrofuran (2 mL). The resulting reaction mixture was stirred at ambient temperature for 18 hours. Then, the reaction solution was diluted with ethyl acetate and washed with water and brine. The resulting organic solution was dried with sodium sulfate, filtered, and concentrated in the presence of silica to provide a crude product that was purified by column chromatography eluting with a gradient of methanol in dichloromethane to provide the title compound. (250 mg, 67% yield); HPLC retention time Method A: 2.65 minutes (95% pure).

Part IV—Synthesis of (S)—N-(3-(acetamidomethyl)-1-((3-cyclopropylphenyl)sulfonyl)-2,3-dihydro-1H-pyrido[2,3-b][1,4]oxazin-7-yl)-2,6-dichlorobenzamide

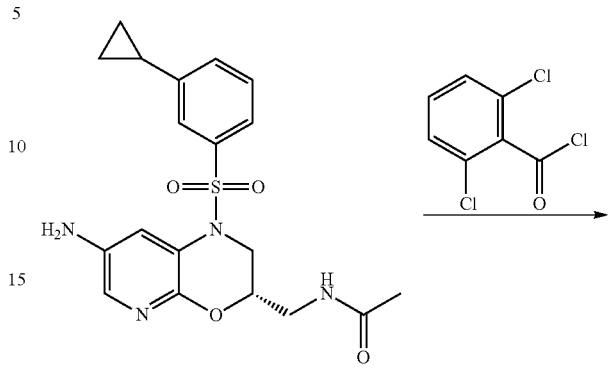

-continued

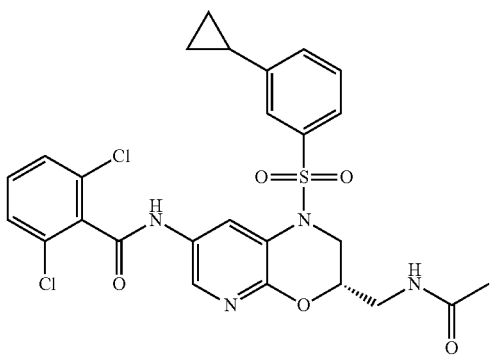

To a solution of (S)—N-((7-amino-1-((3-cyclopropylphenyl)sulfonyl)-2,3-dihydro-1H-pyrido[2,3-b][1,4]oxazin-3-yl)methyl)acetamide (75 mg, 0.19 mmol) in tetrahydrofuran (2 mL) was added N,N-diisopropylethylamine (65 µL, 0.37 mmol) followed by 2,6-dichlorobenzoyl chloride (29 µL, 0.21 mmol). The reaction mixture was stirred at ambient temperature for 30 minutes. Then, the solution was diluted with dichloromethane, silica was added, and the resulting mixture was concentrated in vacuo to provide a crude product that was purified by column chromatography eluting with a gradient of 1-7% methanol in dichloromethane to produce the title compound. (45 mg, 40% yield); HPLC retention time Method A: 5.55 minutes (95% pure).

Example 11—Preparation of Additional N-(1-(arylsulfonyl)-2,3-dihydro-1H-pyrido[2,3-b][1,4]oxazin-7-yl)benzamide Compounds The compounds in Table 5 below were prepared based on the experimental procedures described in Examples 4-10 and in the detailed description. Starting materials can be obtained from commercial sources or readily prepared from commercially available materials. The abbreviation "NA" indicates that no data was available.

TABLE 5

| Compound No. | Chemical Structure | LCMS (ESI): Calculated m/z | Observed m/z |
|---|---|---|---|
| 19 | 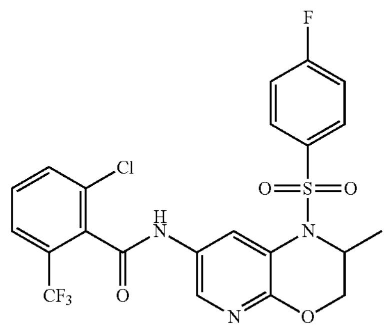 [SMILES: CC1COc2ncc(NC(=O)c3c(Cl)cccc3C(F)(F)F)cc2N1S(=O)(=O)c1ccc(F)cc1] | 529 | M + H = 530 |
| 20 | 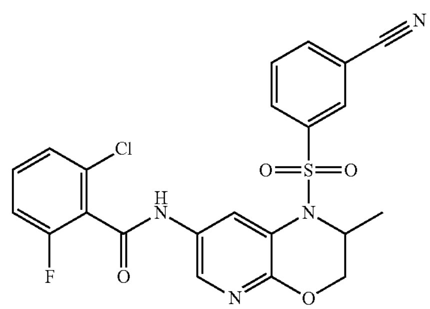 [SMILES: CC1COc2ncc(NC(=O)c3c(F)cccc3Cl)cc2N1S(=O)(=O)c1cccc(C#N)c1] | 486 | M + H = 487 |
| 21 | 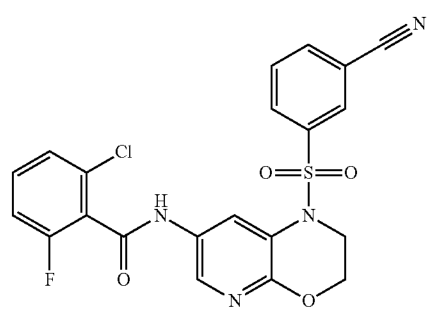 [SMILES: N#Cc1cccc(S(=O)(=O)N2CCOc3ncc(NC(=O)c4c(F)cccc4Cl)cc32)c1] | 472 | M + H = 473 |

TABLE 5-continued

| Compound No. | Chemical Structure | LCMS (ESI): Calculated m/z | LCMS (ESI): Observed m/z |
|---|---|---|---|
| 22 | 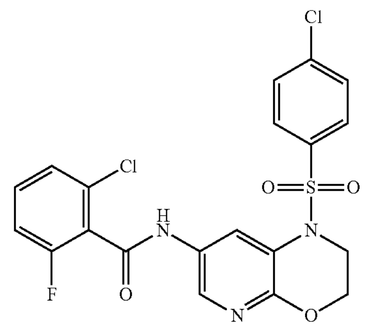 [SMILES: O=C(Nc1cnc2c(c1)N(S(=O)(=O)c1ccc(Cl)cc1)CCO2)c1c(F)cccc1Cl] | 481 | M + H = 482 |
| 23 | 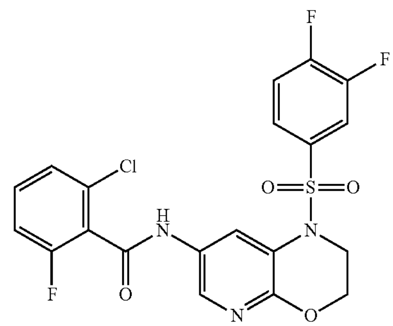 [SMILES: O=C(Nc1cnc2c(c1)N(S(=O)(=O)c1ccc(F)c(F)c1)CCO2)c1c(F)cccc1Cl] | 481 | M + H = 484 |
| 24 | 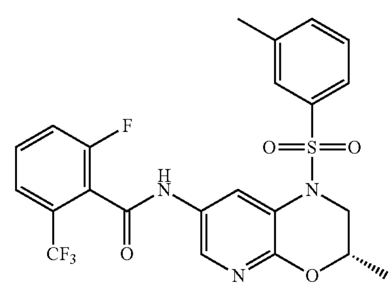 | 509 | M + H + Na = 532 |
| 25 | 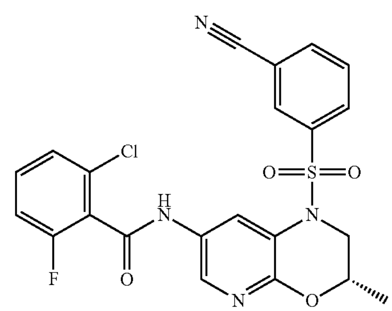 [SMILES: C[C@H]1CN(S(=O)(=O)c2cccc(C#N)c2)c2cc(NC(=O)c3c(F)cccc3Cl)cnc2O1] | 486 | M + H + Na = 509, 511 |
| 26 | 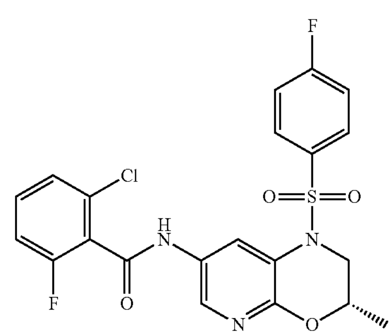 [SMILES: C[C@H]1CN(S(=O)(=O)c2ccc(F)cc2)c2cc(NC(=O)c3c(F)cccc3Cl)cnc2O1] | 479 | M + H + Na = 502, 504 |

TABLE 5-continued

| Compound No. | Chemical Structure | LCMS (ESI): Calculated m/z | Observed m/z |
|---|---|---|---|
| 27 | 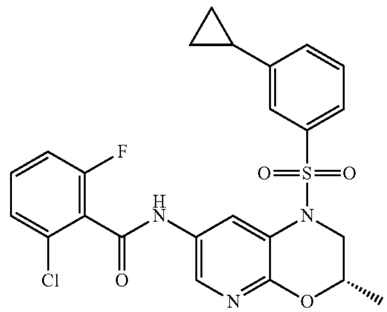 [SMILES: C[C@H]1CN(S(=O)(=O)c2cccc(C3CC3)c2)c2cc(NC(=O)c3c(F)cccc3Cl)cnc2O1] | 501 | M + H = 502, 504 |
| 28 | 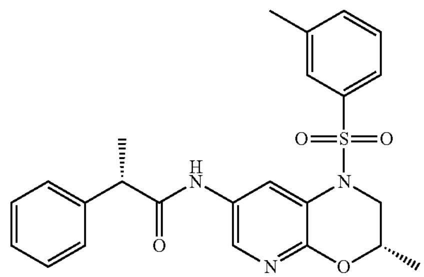 [SMILES: Cc1cccc(S(=O)(=O)N2C[C@H](C)Oc3ncc(NC(=O)[C@@H](C)c4ccccc4)cc32)c1] | 451 | M + H + Na = 474 |
| 29 | 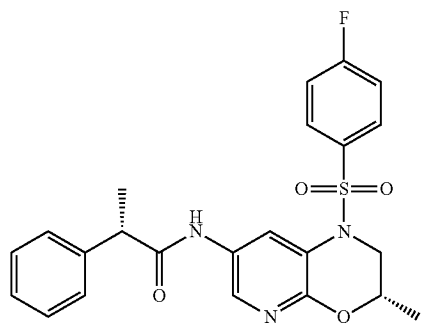 [SMILES: C[C@H](C(=O)Nc1cnc2c(c1)N(S(=O)(=O)c1ccc(F)cc1)C[C@H](C)O2)c1ccccc1] | 455 | M + H + Na = 478 |
| 30 | 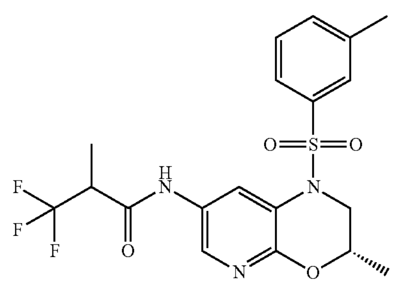 [SMILES: Cc1cccc(S(=O)(=O)N2C[C@H](C)Oc3ncc(NC(=O)C(C)C(F)(F)F)cc32)c1] | | M + H = 444 |
| 31 | 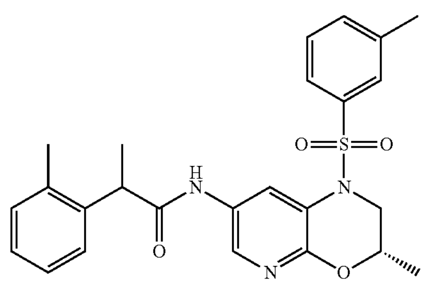 [SMILES: Cc1cccc(S(=O)(=O)N2C[C@H](C)Oc3ncc(NC(=O)C(C)c4ccccc4C)cc32)c1] | | M + H = 466 |

TABLE 5-continued

| Compound No. | Chemical Structure | LCMS (ESI): Calculated m/z | Observed m/z |
|---|---|---|---|
| 32 | 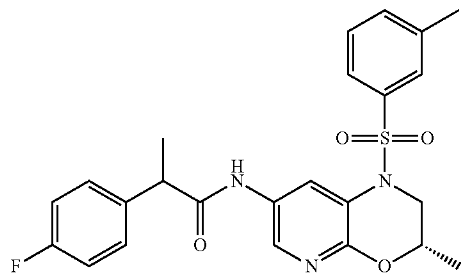 [SMILES: Cc1cccc(S(=O)(=O)N2C[C@H](C)Oc3ncc(NC(=O)C(C)c4ccc(F)cc4)cc32)c1] | M + H = 470 | |
| 33 | 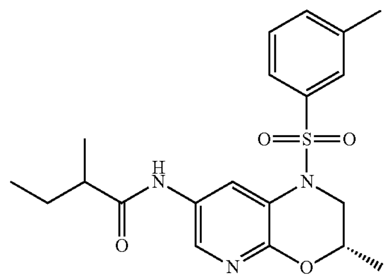 [SMILES: CCC(C)C(=O)Nc1cnc2c(c1)N(S(=O)(=O)c1cccc(C)c1)C[C@H](C)O2] | M + H = 404 | |
| 34 | 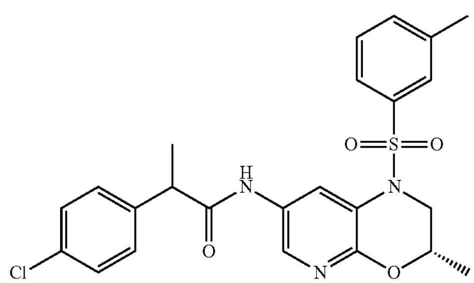 [SMILES: Cc1cccc(S(=O)(=O)N2C[C@H](C)Oc3ncc(NC(=O)C(C)c4ccc(Cl)cc4)cc32)c1] | M + H = 486 | |

Example 12—Synthesis of (S)-2,6-dichloro-N-((3-cyclopropylphenyl)sulfonyl)-3-methyl-2,3-dihydro[2,3,b][1,4]oxazin-yl)benzamide (Compound 35)

The title compound was prepared according to the procedures described below.

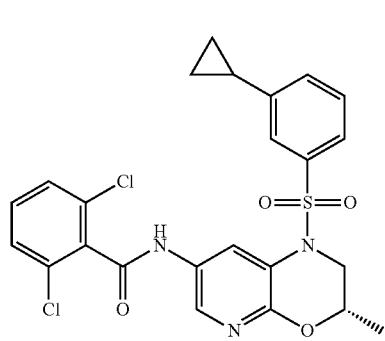 [SMILES: C[C@H]1CN(S(=O)(=O)c2cccc(C3CC3)c2)c2cc(NC(=O)c3c(Cl)cccc3Cl)cnc2O1]

Part I—Synthesis of (S)-tert-butyl(1-((3-bromophenyl)sulfonyl)-3-methyl-2,3-dihydro-1H-pyrido[2,3-b][1,4]oxazin-7-yl)carbamate

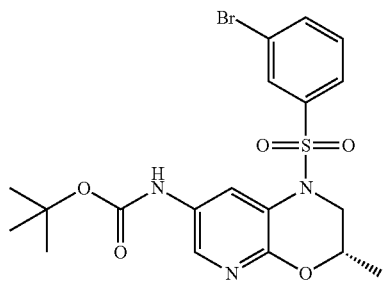 [SMILES: C[C@H]1CN(S(=O)(=O)c2cccc(Br)c2)c2cc(NC(=O)OC(C)(C)C)cnc2O1]

To a solution of (S)-tert-butyl (3-methyl-2,3-dihydro-1H-pyrido[2,3-b][1,4]oxazin-7-yl)carbamate (520 mg, 1.96 mmol) in 2,6-lutidine (8 mL) under a nitrogen atmosphere was added 3-bromobenzenesulfonyl chloride. The resulting mixture was stirred at 100° C. for 24 hours. Then, the resulting suspension was cooled, diluted with ethyl acetate, and washed with 1M hydrogen chloride (3×40 mL), washed with brine, dried with sodium sulfate, filtered, and concentrated in the presence of silica to provide a crude product that was purified by column chromatography eluting with a gradient of 20-70% ethyl acetate in hexanes to provide the title compound. (267 mg, 28% yield); HPLC retention time Method A: 6.76 minutes (95% pure).

Part II—Synthesis of (S)-tert-butyl(1-((3-cyclopropylphenyl)sulfonyl)-3-methyl-2,3-dihydro-1H-pyrido[2,3-b][1,4]oxazin-7-yl)carbamate

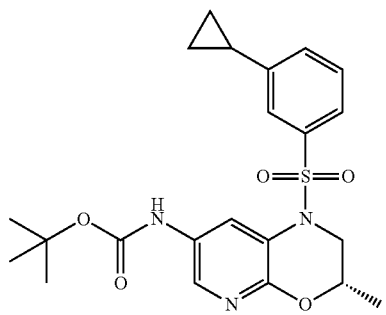 [SMILES: C[C@H]1CN(S(=O)(=O)c2cccc(C3CC3)c2)c2cc(NC(=O)OC(C)(C)C)cnc2O1]

In a microwave tube was combined (S)-tert-butyl (1-((3-bromophenyl)sulfonyl)-3-methyl-2,3-dihydro-1H-pyrido[2,3-b][1,4]oxazin-7-yl)carbamate (75 mg, 0.15 mmol), cyclopropylboronic acid (27 mg, 0.31 mmol), tricyclohexylphosphine (4 mg, 0.016 mmol), potassium phosphate tribasic (115 mg, 0.54 mmol), palladium (II) acetate (2 mg, 0.08 mmol) in toluene (1 mL), and water (0.5 mL). The tube was then heated in the microwave at 130° C. for 20 minutes. The resulting reaction mixture was partitioned between ethyl acetate and brine, separated, dried with sodium sulfate, filtered and concentrated in vacuo to provide a crude product that was purified by column chromatography eluting with a gradient of ethyl acetate in hexanes to provide title compound. (37 mg, 54% yield); HPLC retention time Method A: 6.8 minutes (95% pure).

Part III—Synthesis of (S)-2,6-dichloro-N-((3-cyclopropylphenyl)sulfonyl)-3-methyl-2,3-dihydro[2,3,b][1,4]oxazin-yl)benzamide

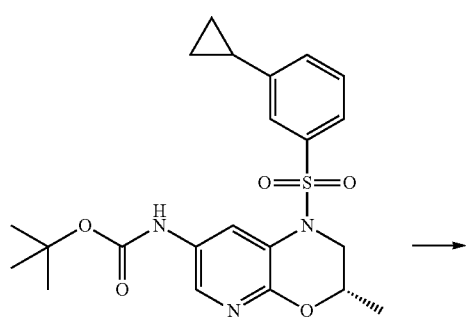

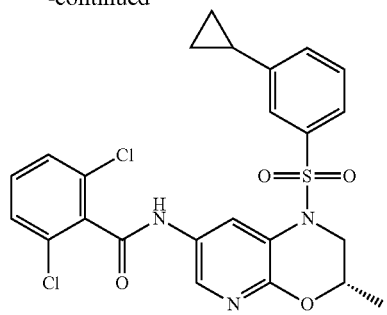

(S)-tert-Butyl (14(3-cyclopropylphenyl)sulfonyl)-3-methyl-2,3-dihydro-1H-pyrido[2,3-b][1,4]oxazin-7-yl)carbamate was converted to the title compound using procedures based on those described in Example 6 above.

Example 13—Synthesis of 2,6-difluoro-N-(5-(4-fluorobenzenesulfonyl)-5,6,7,8-tetrahydro-[1,5]naphthyridin-3-yl)benzamide (Compound 36)

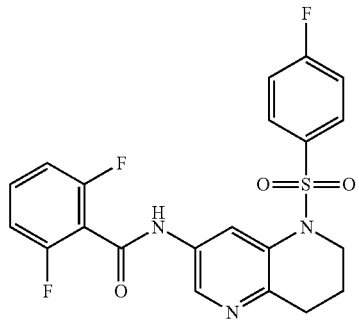 [SMILES: O=C(Nc1cnc2c(c1)N(S(=O)(=O)c1ccc(F)cc1)CCC2)c1c(F)cccc1F]

The title compound was prepared according to the procedures described below.

Part I—Synthesis of 3-bromo-[1,5]naphthyridine

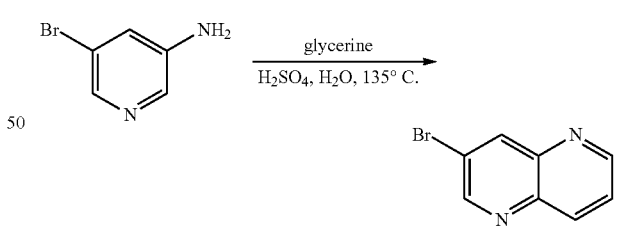

A mixture of 5-bromo-3-aminopyridine (2.00 g, 11.6 mmol), 3-nitrobenzenesulfonic acid sodium salt (5.10 g, 22.6 mmol), glycerine (4.16 mL, 5.26 g, 57.0 mmol), sulfuric acid (12.00 g, 122.4 mmol) and water (6.5 mL) was stirred at 135° C. overnight. Next, the reaction mixture was cooled and then poured in water (200 mL). To the resulting mixture was added saturated NaHCO$_3$ to bring the pH of the mixture to 8. Then, the aqueous mixture was extracted three times with EtOAc (50 mL each). The organic extracts were combined and washed with water (2×50 mL), then brine, and then dried (MgSO$_4$) and concentrated to provide a residue that was purified by SiO$_2$ chromatography (EtOAc/ hexanes) to provide the title compound. Yield 1.25 g (52%). LCMS (ESI): calc. $C_8H_5BrN_2$, 208; obs. M+H=209.

Part II—Synthesis of [1,5]naphthyridin-3-ylamine

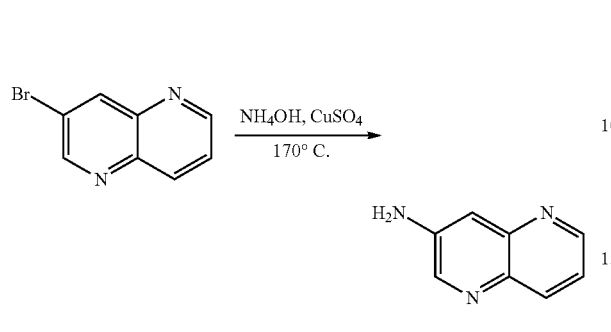

A suspension of 3-bromo-[1,5]naphthyridine (1.25 g, 5.98 mmol) and $CuSO_4$ (0.48 g, 3.00 mmol) in $NH_4OH$ (50 mL) was heated in a sealed flask at 170° C. for two days. Then, the reaction mixture was extracted with EtOAc (3×30 mL). The organic extracts were combined and washed with water (2×50 mL), washed with brine, dried ($MgSO_4$), and concentrated under reduced pressure to provide the title compound. Yield 0.37 g (43%). LCMS (ESI): calc. $C_8H_7N_3$=145; obs. M+H=146.

Part III—Synthesis of 2,6-difluoro-N-[1,5]naphthyridin-3-yl-benzamide

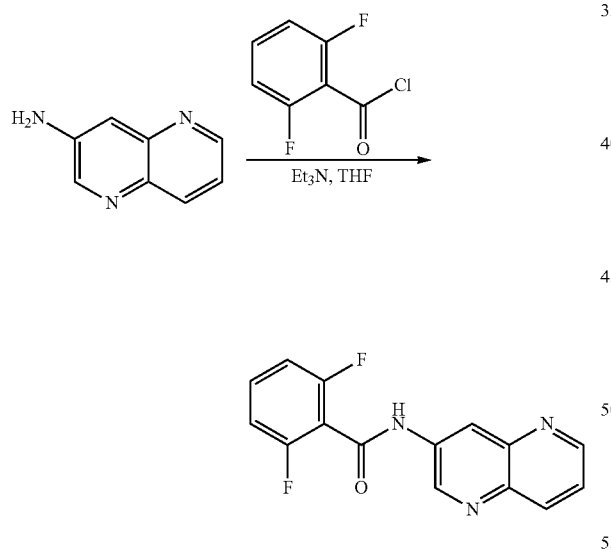

To a solution of [1,5]naphthyridin-3-ylamine (0.37 g, 2.55 mmol) and triethylamine (0.27 g, 2.67 mmol) in THF (5 mL) was added 2,6-difluorobenzoyl chloride (0.53 g, 2.55 mmol) dropwise. Next, the reaction mixture was stirred for one hour, then quenched with water (50 mL), and the resulting mixture was extracted with EtOAc (3×20 mL). The organic extracts were combined and washed with water (2×50 mL), washed with brine, dried ($MgSO_4$), and concentrated under reduced pressure to provide the title compound. Yield 0.45 g (62%). LCMS (ESI): calc. $C_{15}H_9F_2N_3O$=285; obs. M+H=286.

Part IV—Synthesis of 2,6-difluoro-N-(5,6,7,8-tetrahydro[1,5]naphthyridin-3-yl)benzamide

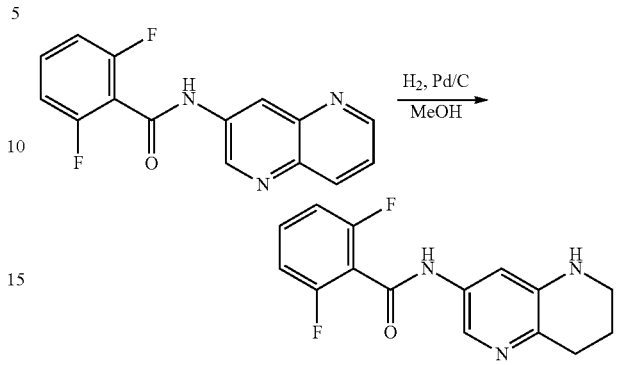

2,6-Difluoro-N-[1,5]naphthyridin-3-yl-benzamide (0.45 g, 1.6 mmol) and 10% Pd/C were combined in MeOH (50 mL). The resulting suspension was agitated under a hydrogen atmosphere (60 p.s.i.) for 12 hours in a Parr shaker. Then, the resulting suspension was filtered and the mother liquor was concentrated under reduced pressure to provide a residue, which was used in next step without further purification. Yield 0.4 g (87%). LCMS (ESI): calc. $C_{15}H_{13}F_2N_3O$=289; obs. M+H=290.

Part V—Synthesis of 2,6-difluoro-N-(5-(4-fluorobenzenesulfonyl)-5,6,7,8-tetrahydro-[1,5]naphthyridin-3-yl)benzamide

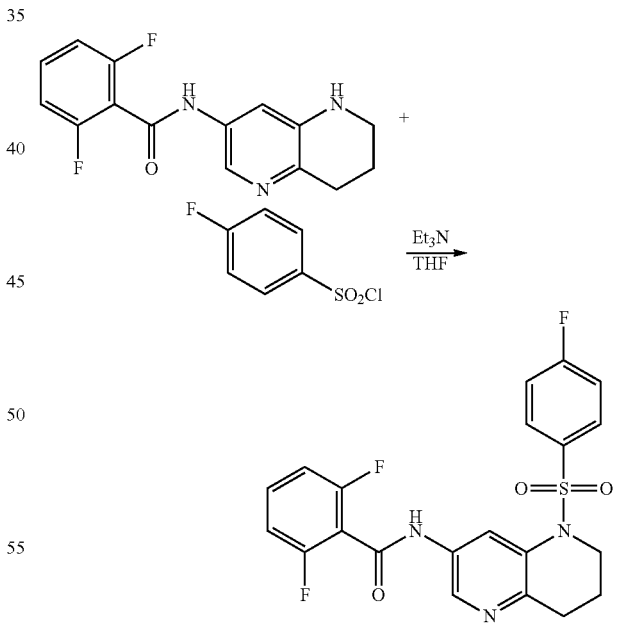

To a solution of 2,6-difluoro-N-(5,6,7,8-tetrahydro[1,5]naphthyridin-3-yl)benzamide (50 mg, 0.17 mmol) and triethylamine (17 mg, 0.17 mmol) in THF (1 mL) was added 4-fluorobenzenesulfonyl chloride (34 mg, 0.17 mmol). The resulting reaction mixture was stirred for one hour, and then concentrated to provide a crude mixture that was purified by HPLC to provide the title compound. Yield 42 mg (55%). $^1$H NMR 250 MHz $CDCl_3$ δ 9.24 (s, 1H), 9.11 (s, 1H), 8.82 (s, 1H), 7.91 (dd, J=7.7, 4.7 Hz, 2H), 7.45 (p, J=6.4 Hz, 1H), 7.23 (t, J=7.5 Hz, 2H), 7.05 (t, J=8.0 Hz, 2H), 3.91 (m, 2H), 3.01 (t, J=6.8 Hz, 2H), 1.91 (m, 2H). LCMS (ESI): calc. $C_{21}H_{16}F_3N_3O_3S$=447; obs. M+H=448.

Example 14—Synthesis of 2-chloro-6-fluoro-N-(5-(m-tolylsulfonyl)-5,6,7,8-tetrahydro-1,5-naphthyridin-3-yl)benzamide (Compound 37)

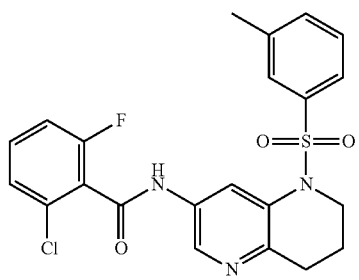

The title compound was prepared according to the procedures described below.

Part I—Synthesis of methyl 5-amino-6-chloronicotinate

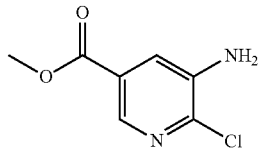

To methyl 6-chloro-5-nitro-pyridine-3-carboxylate (2.0 g, 9.2 mmol) in anhydrous methanol (30 mL) under nitrogen was added tin (II) chloride (5.3 g, 28 mmol). The resulting mixture was refluxed for 18 hours. Then, the reactiom mixture was cooled and then poured carefully into a stirred slurry of celite in saturated sodium bicarbonate at 0° C. The resulting suspension was stirred for 20 minutes before filtering the mixture through celite to remove the solids. The solids were washed with ethyl acetate, and the filtrates were collected, washed with water, and washed with brine. The resulting organic solution was dried with sodium sulfate, filtered, and concentrated in vacuo to provide the title compound as a crude mixture. (1.7 g, 92% yield); HPLC retention time Method A: 2.99 minutes (91.8% pure).

Part II—Synthesis of methyl 6-chloro-5-(3-methylphenylsulfonamido)nicotinate

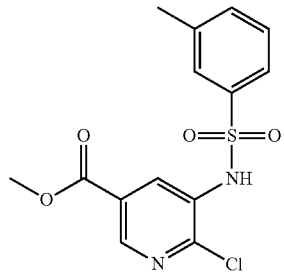 [SMILES: COC(=O)c1cnc(Cl)c(NS(=O)(=O)c2cccc(C)c2)c1]

To a solution of methyl 5-amino-6-chloronicotinate (1.7 g, 9.3 mmol) in dichloromethane (30 mL) was added pyridine (0.9 mL, 11 mmol) followed by m-benzenesulfonyl chloride (1.5 mL, 10.2 mmol). The resulting reaction mixture was stirred at ambient temperature for 24 hours. Then, a catalytic amout of 4-dimethylaminopyridine (~30 mg) was added to the reaction mixture, and the resulting mixture was stirred at ambient temperature for another 24 hours. Next, the reaction solution was diluted with dichloromethane and washed with saturated ammonium chloride. The organic solution was dried with sodium sulfate, filtered, and concentrated in the presence of silica to provide a crude product that was purified by column chromatography eluting with a gradient of ethyl acetate in hexanes to provide the title compound as a crude mixture. (2.44 g, 77% yield); HPLC retention time Method A: 5.72 minutes (76% pure).

Part III—Synthesis of methyl 5-(3-methylphenylsulfonamido)-6-vinylnicotinate

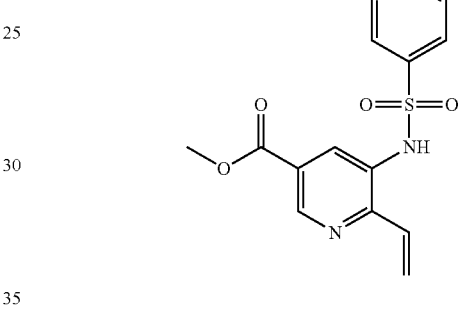

To a solution of methyl 6-chloro-5-(3-methylphenylsulfonamido)nicotinate (1.5 g, 4.4 mmol) in anhydrous 1,4-dioxane (15 mL) under nitrogen was added tributylvinyltin (1.5 mL, 5.3 mmol) followed by tetrakistriphenylphosphine palladium(0) (0.25 g, 0.22 mmol). The resulting solution was refluxed for 3 hours. Then, the solution was diluted with ethyl acetate and concentrated in the presence of silica to provide a crude product that was purified via column chromatography eluting with a gradient of ethyl acetate in hexanes to provide the title compound. (530 mg, 36% yield); HPLC retention time Method A: 5.55 minutes (>99% pure).

Part IV—Synthesis of methyl 5-(N-allyl-3-methylphenylsulfonamido)-6-vinylnicotinate

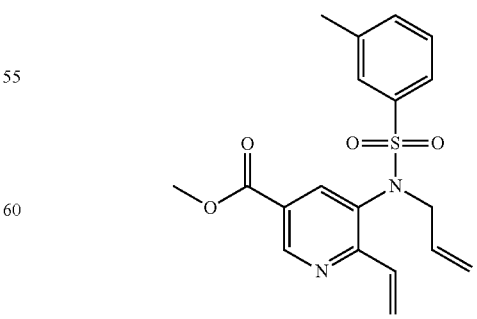

To a solution of methyl 5-(3-methylphenylsulfonamido)-6-vinylnicotinate (0.53 g, 1.6 mmol) in acetonitrile (10 mL)

was added potassium carbonate (0.66 g, 4.8 mmol) and allyl iodide (0.18 mL, 1.9 mmol). The resulting mixture was stirred at 60° C. for 18 hours. Next, the reaction mixture was cooled, diluted with ethyl acetate, and washed with water and brine. The resulting organic solution was dried with sodium sulfate, filtered, and concentrated in the presence of silica to provide the crude product that was purified by column chromatography eluting with a gradient of ethyl acetate in hexanes to provide the title compound. (480 mg, 81% yield); HPLC retention time Method A: 7.01 minutes (>99% pure).

Part V—Synthesis of methyl 5-(m-tolylsulfonyl)-5,6-dihydro-1,5-naphthyridine-3-carboxylate

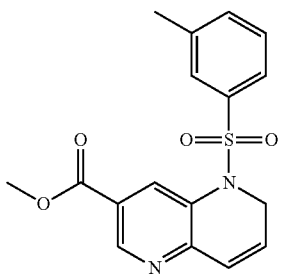 [SMILES: COC(=O)c1cnc2c(c1)N(S(=O)(=O)c1cccc(C)c1)CC=C2]

To a solution of methyl 5-(N-allyl-3-methylphenylsulfonamido)-6-vinylnicotinate (0.50 g, 1.34 mmol) in anhydrous 1,2-dichloroethane (6 mL) under nitrogen was added Grubbs 2nd Generation catalyst (28 mg, 0.034 mmol). The resulting mixture was heated to 80° C. overnight. Next, the reaction mixture was concentrated in the presence of silica and the resulting mixture was subjected to column chromatography purification eluting with a gradient of 0-60% ethyl acetate in hexanes to provide the title compound. (385 mg, 83% yield); HPLC retention time Method A: 5.87 minutes (>99% pure).

Part VI—Synthesis of methyl 5-(m-tolylsulfonyl)-5,6,7,8-tetrahydro-1,5-naphthyridine-3-carboxylate

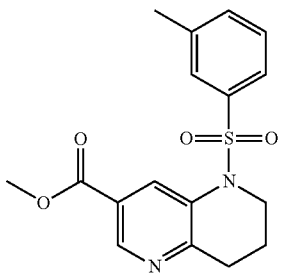 [SMILES: COC(=O)c1cnc2c(c1)N(S(=O)(=O)c1cccc(C)c1)CCC2]

A solution of methyl 5-(m-tolylsulfonyl)-5,6-dihydro-1,5-naphthyridine-3-carboxylate (385 mg, 1.1 mmol) in methanol (10 mL) was first degassed by bubbling nitrogen into the solution for 10 minutes, then 10% palladium on carbon (300 mg) was added while keeping the reaction vessel under a nitrogen atmosphere. Next, the suspension was transferred to a Parr shaker. The reaction vessel was evacuated and refilled with nitrogen three times. Then, the reaction vessel was evacuated and refilled with hydrogen gas three times. Next, the reaction mixture was shaken under a 60 PSI hydrogen atmosphere at ambient temperature for 3 hours. Then, the reaction vessel was evacuated and refilled with nitrogen three times before filtering the reaction mixture over celite to remove the solids. The solids were washed with methanol, and the organic solution was concentrated in vacuo to yield title compound as a crude mixture. (0.34 g, 88% yield); HPLC retention time Method A: 5.46 minutes (95% pure).

Part VII—Synthesis of 5-(m-tolylsulfonyl)-5,6,7,8-tetrahydro-1,5-naphthyridine-3-carboxylic acid

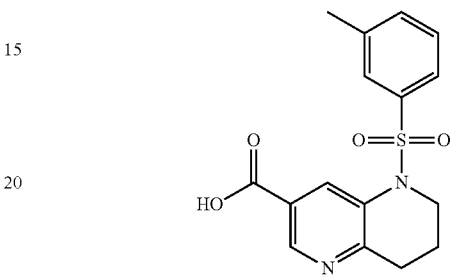

To a solution methyl 5-(m-tolylsulfonyl)-5,6,7,8-tetrahydro-1,5-naphthyridine-3-carboxylate (390 mg, 1.13 mmol) in methanol (4 mL) and tetrahydrofuran (2 mL) was added 2M sodium hydroxide (1.7 mL, 3.4 mmol). The reaction mixture was stirred at ambient temperature for 2 hours. Then, the reaction mixture was acidified with 10% citric acid, and extracted with ethyl acetate twice. The organic extracts were combined and washed with water, washed with brine, dried with sodium sulfate, filtered, and concentrated in vacuo to provide the title compound as a crude mixture. (380 mg, quantitative crude); HPLC retention time Method A: 4.07 minutes (>99% pure).

Part VIII—Synthesis of tert-butyl(5-(m-tolylsulfonyl)-5,6,7,8-tetrahydro-1,5-naphthyridin-3-yl)carbamate

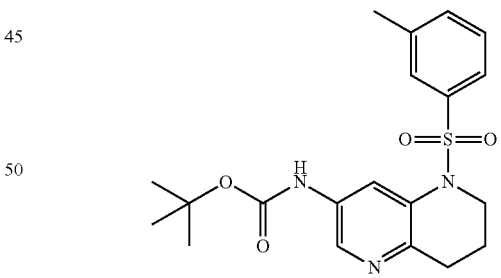

To a solution of 5-(m-tolylsulfonyl)-5,6,7,8-tetrahydro-1,5-naphthyridine-3-carboxylic acid (0.38 g, 1.1 mmol) in anhydrous toluene (4 mL) and anhydrous tert-butanol (4 mL) with triethylamine (0.35 mL, 2.5 mmol) was added activated 4 Å molecular sieves. The resulting mixture was stirred for 15 minutes, then diphenylphosphorylazide (0.3 mL, 1.4 mmol) was added to the mixture. Next, the reaction mixture was heated to reflux under nitrogen for 2 hours. Then, the reaction mixture was cooled, filtered, diluted with ethyl acetate, and washed with saturated ammonium chloride, saturated sodium bicarbonate, and brine. The resulting organic solution was dried with sodium sulfate, filtered, and concentrated in vacuo in the presence of silica to provide the crude product that was purified by column chromatography eluting with a gradient of 15-80% ethyl acetate in hexanes to provide the title compound. (250 mg, 54% yield); HPLC retention time Method A: 4.80 minutes (95.6% pure). HPLC: 95.6% pure @ 4.80 minutes.

Part IX—Synthesis of 5-(m-tolylsulfonyl)-5,6,7,8-tetrahydro-1,5-naphthyridin-3-amine

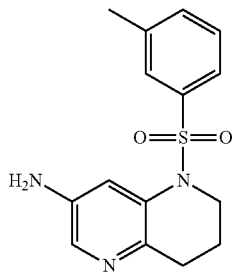 [SMILES: Cc1cccc(S(=O)(=O)N2CCCc3ncc(N)cc32)c1]

To a solution of tert-butyl (5-(m-tolylsulfonyl)-5,6,7,8-tetrahydro-1,5-naphthyridin-3-yl)carbamate (0.25 g, 0.62 mmol) in dichloromethane (2 mL) was added trifluoroacetic acid (2 mL). The resulting mixture was stirred at ambient temperature for 1 hour and then concentrated in vacuo to yield title compound as a crude mixture. (180 mg, quantitative crude yield); HPLC retention time Method A: 2.88 minutes (95% pure).

Part X—Synthesis of 2-chloro-6-fluoro-N-(5-(m-tolylsulfonyl)-5,6,7,8-tetrahydro-1,5-naphthyridin-3-yl)benzamide

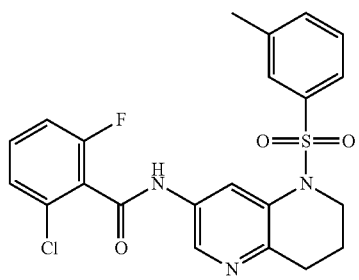

To a solution of 5-(m-tolylsulfonyl)-5,6,7,8-tetrahydro-1,5-naphthyridin-3-amine (64 mg, 0.21 mmol) in tetrahydrofuran (1 mL) was added N,N-diisopropylethylamine (0.18 mL, 1.1 mmol) followed by 2-chloro-6-fluorobenzoyl chloride (31 µL, 0.23 mmol). The resulting mixture was stirred at ambient temperature for 1 hour, diluted with ethyl acetate, and washed with 1M hydrogen chloride and brine. The resulting organic solution was dried with sodium sulfate, filtered, and concentrated in the presence of silica to provide the crude product that was purified by column chromatography eluting with a gradient of 20-70% ethyl acetate in hexanes to provide the title compound. (45 mg, 44% yield); HPLC retention time Method A: 5.01 minutes (94.2% pure).

Example 15—Synthesis of (S)-2-phenyl-N-(5-(m-tolylsulfonyl)-5,6,7,8-tetrahydro-1,5-naphthyridin-3-yl)propanamide (Compound 38)

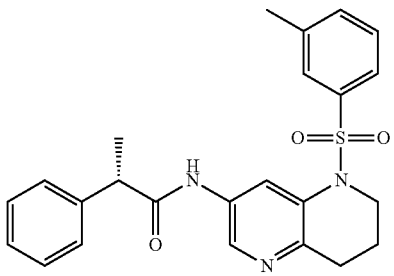 [SMILES: Cc1cccc(S(=O)(=O)N2CCCc3ncc(NC(=O)[C@@H](C)c4ccccc4)cc32)c1]

To a solution of 5-(m-tolylsulfonyl)-5,6,7,8-tetrahydro-1,5-naphthyridin-3-amine (64 mg, 0.21 mmol) in N,N-dimethylformamide (1 mL) was added (2S)-2-phenylpropanoic acid (47 mg, 0.32 mmol) and N,N-diisopropylethylamine (0.18 mL, 1.1 mmol) followed by O-(7-azabenzotriazol-1-yl)-N,N,N',N'-tetramethyluroniumhexafluorophosphate (120 mg, 0.32 mmol). The reaction mixture was stirred at ambient temperature for 2 hours, then diluted with ethyl acetate. The resulting organic solution was washed with 1M hydrogen chloride and brine. Next, the organic solution was dried with sodium sulfate, filtered, and concentrated in the presence of silica to provide the crude product that was purified by column chromatography eluting with a gradient of 20-70% ethyl acetate in hexanes to provide the title compound. (39 mg, 43% yield); HPLC retention time Method A: 4.98 minutes (>99% pure).

Example 16—Synthesis of (R)-tert-butyl(7-(2,6-dichlorobenzamido)-1-(m-tolylsulfonyl)-1,2,3,4-tetrahydro-1,5-naphthyridin-3-yl)carbamate (Compound 39)

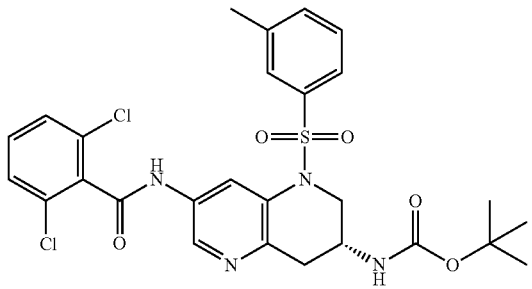 [SMILES: Cc1cccc(S(=O)(=O)N2C[C@H](NC(=O)OC(C)(C)C)Cc3ncc(NC(=O)c4c(Cl)cccc4Cl)cc32)c1]

The title compound was prepared according to the procedures described below.

Part I—Synthesis of (R)-methyl 7-((tert-butoxycarbonyl)amino)-6-oxo-5,6,7,8-tetrahydro-1,5-naphthyridine-3-carboxylate

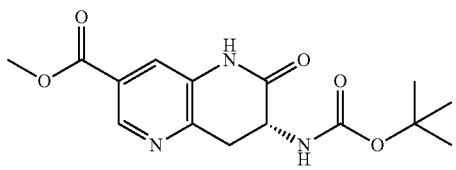 [SMILES: COC(=O)c1cnc2c(c1)NC(=O)[C@H](NC(=O)OC(C)(C)C)C2]

An oven-dried flask was charged with zinc powder (2.0 g, 30 mmol) and iodine (0.12 g, 0.46 mmol), and flushed with nitrogen. Next, the flask was cooled in an ice bath and a solution of methyl (2S)-2-(tert-butoxycarbonylamino)-3-iodo-propanoate (5.0 g, 15 mmol) in anhydrous N,N-dimethylformamide (20 mL) was added to the flask. The resulting reaction mixture was stirred at 0° C. for 90 minutes. Then, solid methyl 5-amino-6-chloronicotinate (3.7 g, 19.7 mmol) was added followed by addition of dichlorobistriphenyl-phosphine palladium (II) (0.53 g, 0.76 mmol). Then, the reaction mixture was heated to 40° C. for 18 hours. Next, the reaction mixture was filtered through celite, washing with ethyl acetate. The resulting organic solution was concentrated in vacuo to provide a residue that was redissolved in N,N-dimethylformamide (20 mL). To the resulting organic solution, potassium carbonate (2.5 g, 18 mmol) was added and the rection mixture was heated to 80° C. for 2 hours. The resulting solution was partitioned between ethyl acetate and saturated ammonium chloride. The organic layer was separated and washed with water and brine. The resulting organic solution was dried with sodium sulfate, filtered, and concentrated in vacuo to provide the crude product that was purified by column chromatography eluting with a gradient of 20-100% ethyl acetate in hexanes to provide the title compound. (2.63 g, 54% yield); HPLC retention time Method A: 3.49 minutes (>99% pure).

Part II—Synthesis of (R)-7-((tert-butoxycarbonyl)amino)-6-oxo-5,6,7,8-tetrahydro-1,5-naphthyridine-3-carboxylic acid

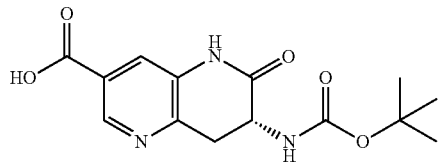 [SMILES: CC(C)(C)OC(=O)N[C@@H]1Cc2ncc(C(=O)O)cc2NC1=O]

To (R)-methyl 7-((tert-butoxycarbonyl)amino)-6-oxo-5,6,7,8-tetrahydro-1,5-naphthyridine-3-carboxylate (2.63 g, 8.2 mmol) in tetrahydrofuran (20 mL) and methanol (20 mL) was added 2M sodium hydroxide (12 mL, 24 mmol). The reaction mixture was stirred at ambient temperature for 2 hours. Then, the volume of the reaction mixture was reduced in vacuo. The resulting solution was partitioned between ethyl acetate and 10% citric acid. The organic layer was isolated, washed with brine, dried with sodium sulfate, filtered, and concentrated in vacuo to yield title compound. (2.07 g, 82% yield); HPLC retention time Method A: 2.05 minutes (98% pure).

Part III—Synthesis of (R)-benzyl tert-butyl(2-oxo-1,2,3,4-tetrahydro-1,5-naphthyridine-3,7-diyl)dicarbamate

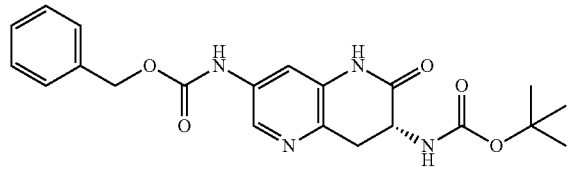 [SMILES: CC(C)(C)OC(=O)N[C@@H]1Cc2ncc(NC(=O)OCc3ccccc3)cc2NC1=O]

To (R)-7-((tert-butoxycarbonyl)amino)-6-oxo-5,6,7,8-tetrahydro-1,5-naphthyridine-3-carboxylic acid (2.07 g, 6.74 mmol) in anhydrous toluene (20 mL) and benzyl alcohol (2.1 mL, 20 mmol) was added activated 4 Å molecular sieves and triethylamine (2.1 mL, 14.8 mmol). The resulting mixture was stirred at ambient temperature for 10 minutes, then diphenylphosphorylazide (1.7 mL, 8.1 mmol) was added. Next, the resulting suspension was refluxed for 2 hours. Then, the reaction mixture was filtered hot through celite, washing with ethyl acetate. The resulting organic solution was concentrated onto silica in vacuo to provide a crude product that was purified by column chromatography eluting with a gradient of methanol in dichloromethane to provide the title compound. (1.1 g, 40% yield); HPLC retention time Method A: 4.05 minutes (97.6% pure).

Part IV—Synthesis of (R)-benzyl tert-butyl(1,2,3,4-tetrahydro-1,5-naphthyridine-3,7-diyl)dicarbamate

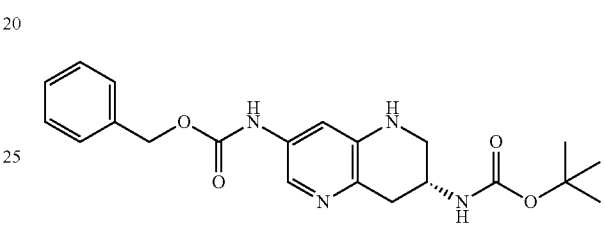

To a solution of (R)-benzyl tert-butyl (2-oxo-1,2,3,4-tetrahydro-1,5-naphthyridine-3,7-diyl)dicarbamate (900 mg, 2.2 mmol) in anhydrous tetrahydrofuran (20 mL) under nitrogen at 0° C. was added 1M lithium aluminum hydride in tetrahydrofuran (8.7 mL, 8.7 mmol) dropwise. The resulting mixture was stirred at ambient temperature for 3 hours. Then, the reaction mixture was cooled to 0° C. and sodium sulfate decahydrate was added carefully to quench the reaction. The resulting mixture was slurried at ambient temperature, then the mixture was filtered through celite to remove solids. The solids were washed with tetrahydrofuran. The resulting organic solution was concentrated in vacuo to provide the title compound as a crude mixture, which was used directly in the next step (810 mg).

Part V—Synthesis of (R)-benzyl tert-butyl(1-(m-tolylsulfonyl)-1,2,3,4-tetrahydro-1,5-naphthyridine-3,7-diyl)dicarbamate

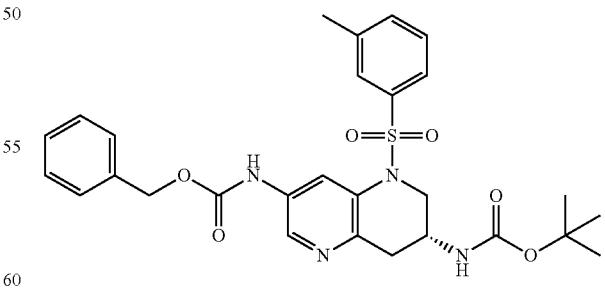

To a solution of (R)-benzyl tert-butyl (1,2,3,4-tetrahydro-1,5-naphthyridine-3,7-diyl)dicarbamate (150 mg, 0.38 mmol) in pyridine (2 mL) was added m-toluenesulfonyl chloride (66 µL mL, 0.45 mmol). The resulting reaction mixture was stirred at ambient temperature for 18 hours. Then, the volume of the reaction mixture was reduced in vacuo. The resulting mixture was re-dissolved in ethyl acetate and washed with 10% citric acid, water, and brine. The resulting organic solution was dried with sodium sulfate, filtered, and concentrated in vacuo to provide a crude product that was purified by column chromatography eluting with a gradient of ethyl acetate in hexanes to provide the title compound. (90 mg, 43% yield); HPLC retention time Method A: 6.25 minutes (88% pure).

Part VI—Synthesis of (R)-tert-butyl(7-amino-1-(m-tolylsulfonyl)-1,2,3,4-tetrahydro-1,5-naphthyridin-3-yl)carbamate

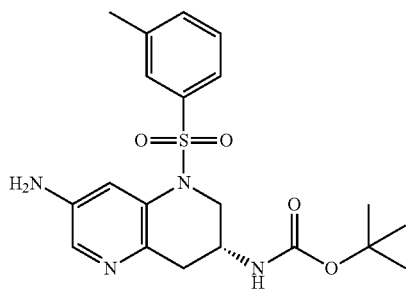 [SMILES: Cc1cccc(S(=O)(=O)N2C[C@H](NC(=O)OC(C)(C)C)Cc3ncc(N)cc32)c1]

A suspension of ammonium formate (0.2 g, 3.3 mmol) and (R)-benzyl tert-butyl (1-(m-tolylsulfonyl)-1,2,3,4-tetrahydro-1,5-naphthyridine-3,7-diyl)dicarbamate (180 mg, 0.33 mmol) in anhydrous methanol (4 mL) was placed into a reaction vessel under nitrogen. The reaction vessel was evacuated and refilled with nitrogen three times before adding 10% palladium on carbon (34 mg, 0.03 mmol). Next, the reaction mixture refluxed under a nitrogen atmosphere for 40 minutes. Then, the reaction mixture was cooled to ambient temperature, and filtered through celite, washing with methanol. The resulting organic solution was concentrated in vacuo to provide a mixture that was re-dissolved in ethyl acetate. The resulting organic solution was washed with water, washed with brine, dried with sodium sulfate, filtered, and concentrated in vacuo to yield title compound as a crude mixture. (125 mg, 92% yield); HPLC retention time Method A: 4.32 minutes (95% pure).

Part VII—Synthesis of (R)-tert-butyl(7-(2,6-dichlorobenzamido)-1-(m-tolylsulfonyl)-1,2,3,4-tetrahydro-1,5-naphthyridin-3-yl)carbamate

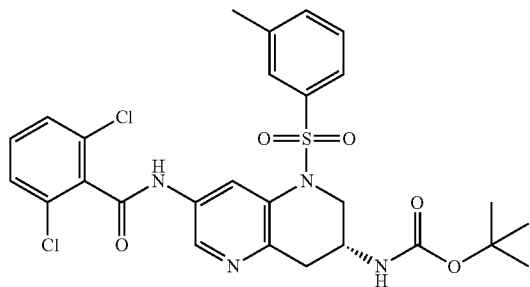 [SMILES: Cc1cccc(S(=O)(=O)N2C[C@H](NC(=O)OC(C)(C)C)Cc3ncc(NC(=O)c4c(Cl)cccc4Cl)cc32)c1]

To a solution of (R)-tert-butyl (7-amino-1-(m-tolylsulfonyl)-1,2,3,4-tetrahydro-1,5-naphthyridin-3-yl)carbamate (75 mg, 0.18 mmol) in tetrahydrofuran (3 mL) was added N,N-diisopropylethylamine (0.14 mL, 0.54 mmol) followed by 2,6-dichlorobenzoyl chloride (36 µL, 0.25 mmol). The resulting reaction mixture was stirred at ambient temperature overnight. Then, the reaction mixture was concentrated in vacuo in the presence of silica to provide a crude product that was purified by column chromatography eluting with a gradient of ethyl acetate in hexanes to provide the title compound. (50 mg, 47% yield); HPLC retention time Method A: 6.46 minutes (86% pure).

Example 17—Synthesis of (R)—N-(7-amino-5-(m-tolylsulfonyl)-5,6,7,8-tetrahydro-1,5-naphthyridin-3-yl)-2,6-dichlorobenzamide trifluoroacetic acid salt (Compound 40)

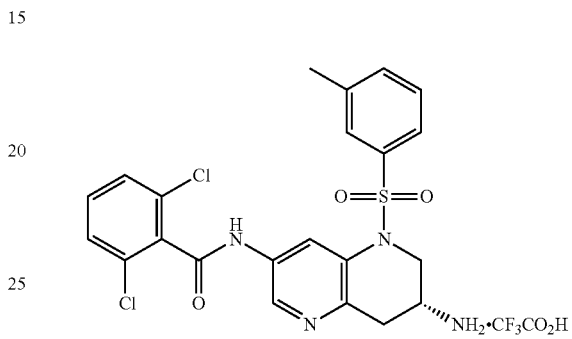

To a solution of (R)-tert-butyl (7-(2,6-dichlorobenzamido)-1-(m-tolylsulfonyl)-1,2,3,4-tetrahydro-1,5-naphthyridin-3-yl)carbamate (50 mg, 0.085 mmol) in dichloromethane (1 mL) was added trifluoroacetic acid (1 mL). The reaction mixture was stirred at ambient temperature for 1 hour. Then, the reaction mixture was concentrated in vacuo to provide the crude product that was purified by preparatory HPLC. Pure fractions were concentrated to provide the title compound in it's trifluoroacetic acid salt form. (22 mg, 43% yield); HPLC retention time Method A: 4.00 minutes (99% pure).

Example 18—Synthesis of (R)—N-(7-acetamido-5-(m-tolylsulfonyl)-5,6,7,8-tetrahydro-1,5-naphthyridin-3-yl)-2,6-dichlorobenzamide (Compound 41)

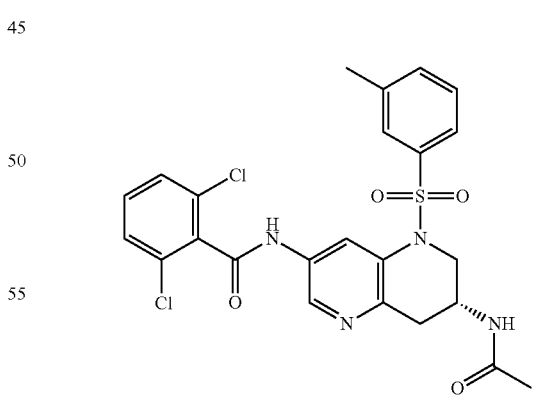

To a solution of (R)—N-(7-amino-5-(m-tolylsulfonyl)-5,6,7,8-tetrahydro-1,5-naphthyridin-3-yl)-2,6-dichlorobenzamide (64 mg, 0.13 mmol) in tetrahydrofuran (0.5 mL) was added acetic anhydride (12 µL, 0.13 mmol). The reaction mixture was stirred at ambient temperature for 2 hours. Then, the reaction mixture was concentrated in vacuo in the presence of silica to provide the crude product that was purified by column chromatography eluting with a gradient of ethyl acetate in hexanes to provide the title compound. (21 mg, 30% yield); HPLC retention time Method A: 4.84 minutes (99% pure).

Example 19—Synthesis of (R)-methyl(7-(2,6-dichlorobenzamido)-1-(m-tolylsulfonyl)-1,2,3,4-tetrahydro-1,5-naphthyridin-3-yl)carbamate (Compound 42)

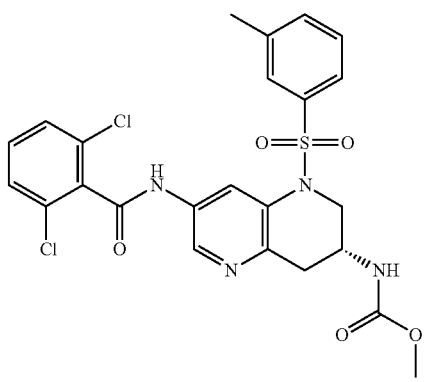 [SMILES: COC(=O)N[C@@H]1Cc2ncc(NC(=O)c3c(Cl)cccc3Cl)cc2N(S(=O)(=O)c2cccc(C)c2)C1]

To a solution of (R)—N-(7-amino-5-(m-tolylsulfonyl)-5,6,7,8-tetrahydro-1,5-naphthyridin-3-yl)-2,6-dichlorobenzamide (30 mg, 0.061 mmol) in tetrahydrofuran (0.5 mL) was added methyl chloroformate (5 μL, 0.067 mmol). The resulting reaction mixture was stirred at ambient temperature for 2 hours. Then, triethylamine (50 μL) was added to neutralize the reaction. Next, the reaction mixture was concentrated in vacuo in the presence of silica to provide a mixture that was purified by column chromatography eluting with a gradient of EtOAc in hexanes to provide the title compound. (5 mg, 15% yield); HPLC retention time Method A: 5.4 minutes (98% pure).

Example 20—Preparation of Additional N-(1-(arylsulfonyl)-2,3-dihydro-1H-pyrido[2,3-b][1,4]oxazin-7-yl)benzamide and N-(5-(Arylsulfonyl)-5,6,7,8-tetrahydro-1,5-naphthyridin-3-yl)benzamide Compounds The compounds in Table 6 below were prepared based on the experimental procedures described in Examples 4-10 and 12-14 and in the detailed description. Starting materials can be obtained from commercial sources or readily prepared from commercially available materials.

TABLE 6

| Compound No. | Chemical Structure | LCMS (ESI): Calculated m/z | Observed m/z |
|---|---|---|---|
| 43 |  | NA | NA |
| 44 |  | 475 | 476, 478 |

TABLE 6-continued

| Compound No. | Chemical Structure | LCMS (ESI): Calculated m/z | Observed m/z |
|---|---|---|---|
| 45 | 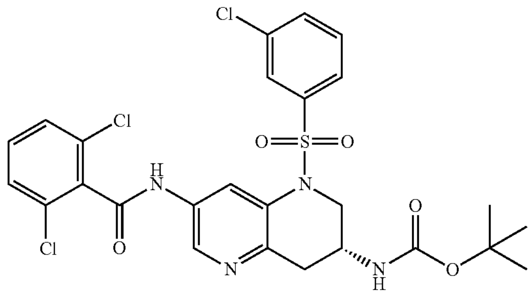 | 610 | M + H = 611, 613 |
| 46 | 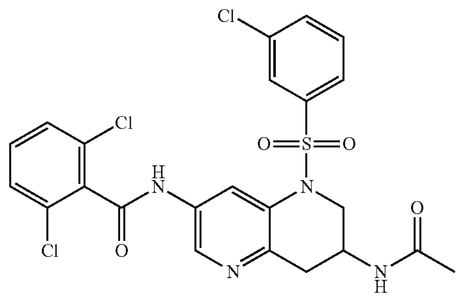 [SMILES: CC(=O)NC1Cc2ncc(NC(=O)c3c(Cl)cccc3Cl)cc2N(S(=O)(=O)c2cccc(Cl)c2)C1] | 552 | M + H = 553, 555 |
| 47 | 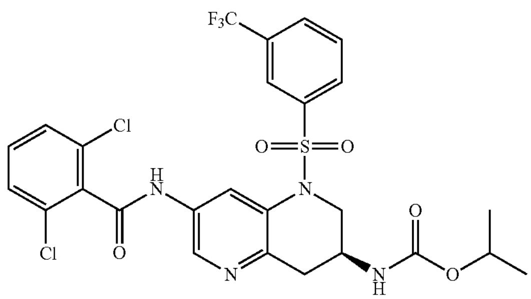 [SMILES: CC(C)OC(=O)N[C@H]1Cc2ncc(NC(=O)c3c(Cl)cccc3Cl)cc2N(S(=O)(=O)c2cccc(C(F)(F)F)c2)C1] | 630 | M + H + Na = 653, 655 |
| 48 | 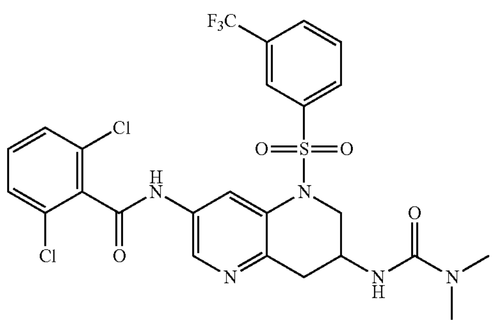 [SMILES: CN(C)C(=O)NC1Cc2ncc(NC(=O)c3c(Cl)cccc3Cl)cc2N(S(=O)(=O)c2cccc(C(F)(F)F)c2)C1] | 615 | M + H + Na = 638, 640 |
| 49 | 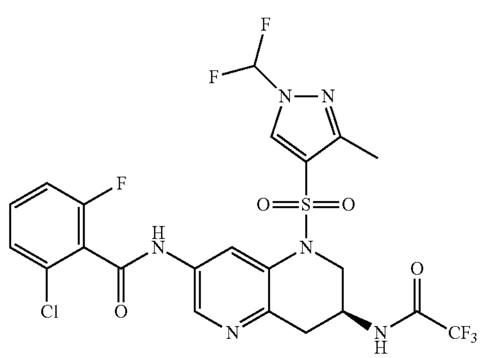 [SMILES: Cc1nn(C(F)F)cc1S(=O)(=O)N1C[C@@H](NC(=O)C(F)(F)F)Cc2ncc(NC(=O)c3c(F)cccc3Cl)cc21] | 610 | M + H + Na = 633, 635 |

TABLE 6-continued

| Compound No. | Chemical Structure | LCMS (ESI): Calculated m/z | Observed m/z |
|---|---|---|---|
| 50 | 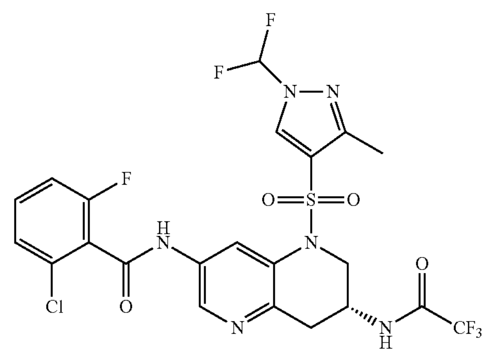 [SMILES: Cc1nn(C(F)F)cc1S(=O)(=O)N1C[C@H](NC(=O)C(F)(F)F)Cc2ncc(NC(=O)c3c(F)cccc3Cl)cc21] | 610 | M + H + Na = 633, 635 |
| 51 | 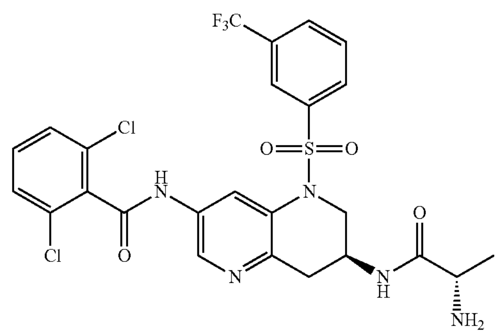 [SMILES: C[C@H](N)C(=O)N[C@H]1Cc2ncc(NC(=O)c3c(Cl)cccc3Cl)cc2N(S(=O)(=O)c2cccc(C(F)(F)F)c2)C1] | 615 | M + H = 616, 618 |
| 52 | 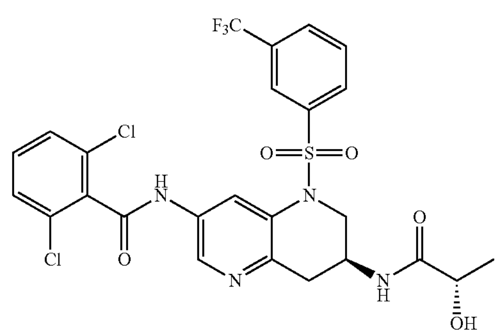 [SMILES: C[C@H](O)C(=O)N[C@H]1Cc2ncc(NC(=O)c3c(Cl)cccc3Cl)cc2N(S(=O)(=O)c2cccc(C(F)(F)F)c2)C1] | 616 | M + H + Na = 639, 641 |
| 53 | 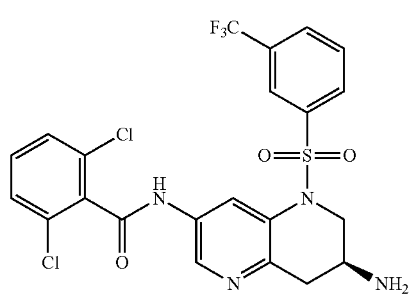 [SMILES: N[C@H]1Cc2ncc(NC(=O)c3c(Cl)cccc3Cl)cc2N(S(=O)(=O)c2cccc(C(F)(F)F)c2)C1] | 544 | M + H = 545, 547 |

TABLE 6-continued

| Compound No. | Chemical Structure | LCMS (ESI): Calculated m/z | Observed m/z |
|---|---|---|---|
| 54 | 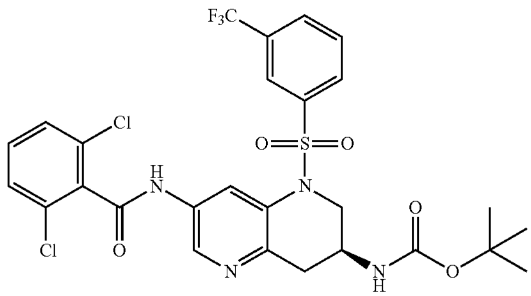 [SMILES: CC(C)(C)OC(=O)N[C@H]1Cc2ncc(NC(=O)c3c(Cl)cccc3Cl)cc2N(S(=O)(=O)c2cccc(C(F)(F)F)c2)C1] | 644 | M + H + Na = 667, 669 |
| 55 | 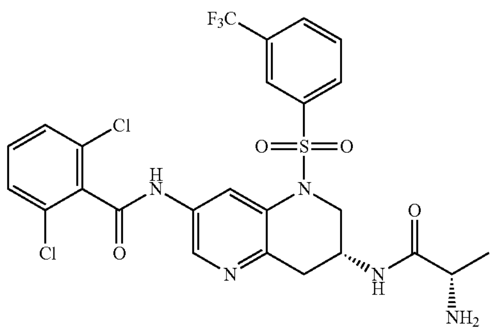 [SMILES: C[C@H](N)C(=O)N[C@@H]1Cc2ncc(NC(=O)c3c(Cl)cccc3Cl)cc2N(S(=O)(=O)c2cccc(C(F)(F)F)c2)C1] | 615 | M + H = 616, 618 |
| 56 | 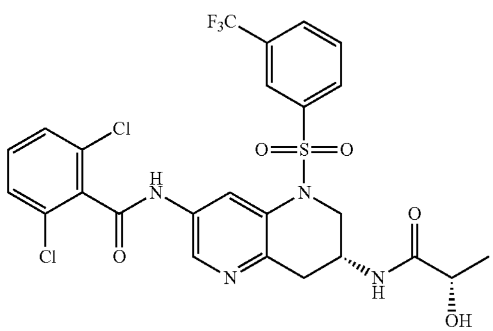 [SMILES: C[C@H](O)C(=O)N[C@@H]1Cc2ncc(NC(=O)c3c(Cl)cccc3Cl)cc2N(S(=O)(=O)c2cccc(C(F)(F)F)c2)C1] | 616 | M + H + Na = 639, 641 |
| 57 | 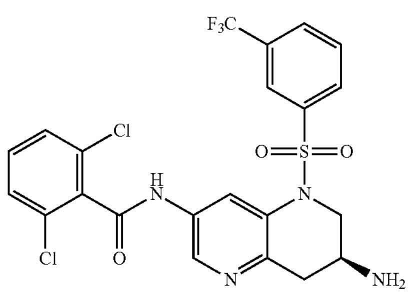 [SMILES: N[C@H]1Cc2ncc(NC(=O)c3c(Cl)cccc3Cl)cc2N(S(=O)(=O)c2cccc(C(F)(F)F)c2)C1] | 544 | M + H = 545, 547 |
| 58 | 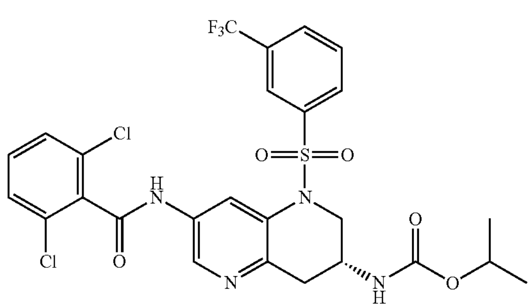 [SMILES: CC(C)OC(=O)N[C@@H]1Cc2ncc(NC(=O)c3c(Cl)cccc3Cl)cc2N(S(=O)(=O)c2cccc(C(F)(F)F)c2)C1] | 630 | M + H + Na = 653, 655 |

TABLE 6-continued

| Compound No. | Chemical Structure | LCMS (ESI): Calculated m/z | Observed m/z |
|---|---|---|---|
| 59 | 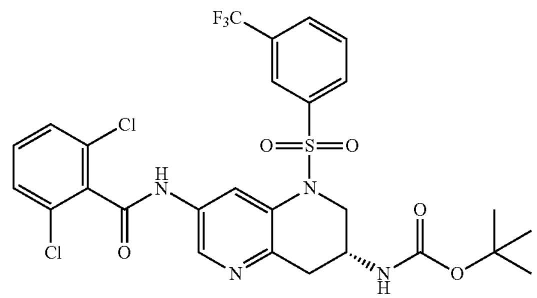 [SMILES: CC(C)(C)OC(=O)N[C@@H]1Cc2ncc(NC(=O)c3c(Cl)cccc3Cl)cc2N(S(=O)(=O)c2cccc(C(F)(F)F)c2)C1] | 644 | M + H + Na = 667, 669 |
| 60 | 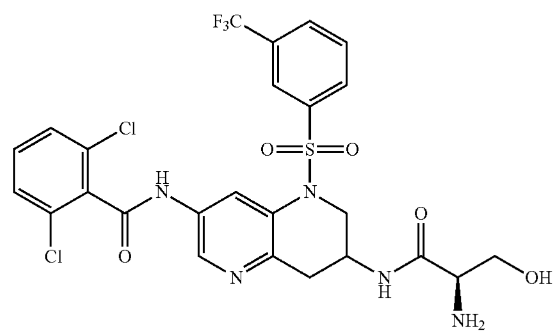 [SMILES: N[C@H](CO)C(=O)NC1Cc2ncc(NC(=O)c3c(Cl)cccc3Cl)cc2N(S(=O)(=O)c2cccc(C(F)(F)F)c2)C1] | 631 | M + Na = 654, 656 |
| 61 | 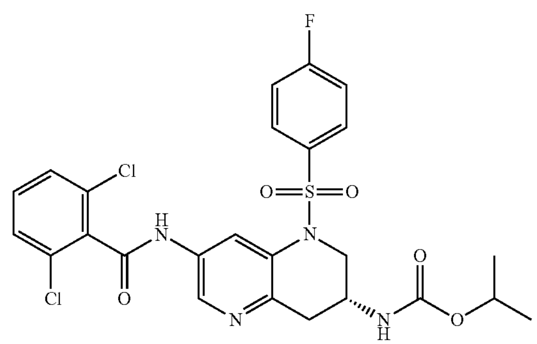 [SMILES: CC(C)OC(=O)N[C@@H]1Cc2ncc(NC(=O)c3c(Cl)cccc3Cl)cc2N(S(=O)(=O)c2ccc(F)cc2)C1] | 630 | M + Na = 653, 655 |
| 62 | 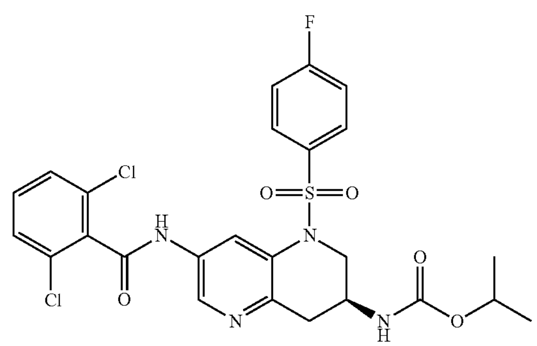 [SMILES: CC(C)OC(=O)N[C@H]1Cc2ncc(NC(=O)c3c(Cl)cccc3Cl)cc2N(S(=O)(=O)c2ccc(F)cc2)C1] | 630 | M + Na 653, 655 |

TABLE 6-continued

| Compound No. | Chemical Structure | LCMS (ESI): Calculated m/z | Observed m/z |
|---|---|---|---|
| 63 | 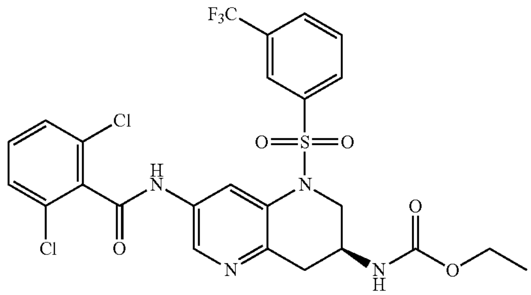 [SMILES: CCOC(=O)N[C@H]1Cc2ncc(NC(=O)c3c(Cl)cccc3Cl)cc2N(S(=O)(=O)c2cccc(C(F)(F)F)c2)C1] | 616 | M + Na = 639, 641 |
| 64 | 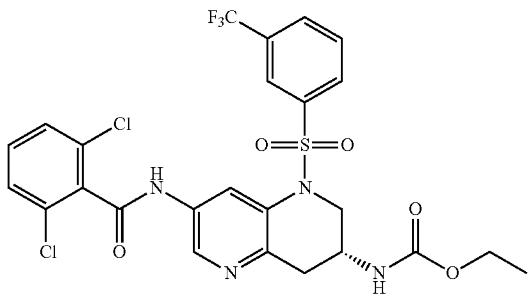 [SMILES: CCOC(=O)N[C@@H]1Cc2ncc(NC(=O)c3c(Cl)cccc3Cl)cc2N(S(=O)(=O)c2cccc(C(F)(F)F)c2)C1] | 616 | M + Na = 639, 641 |
| 65 | 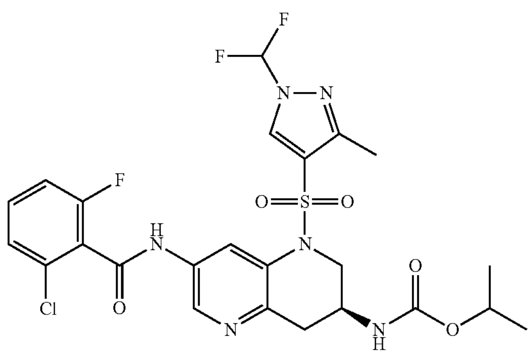 [SMILES: Cc1nn(C(F)F)cc1S(=O)(=O)N1C[C@@H](NC(=O)OC(C)C)Cc2ncc(NC(=O)c3c(F)cccc3Cl)cc21] | 600 | M + Na = 623, 625 |
| 66 | 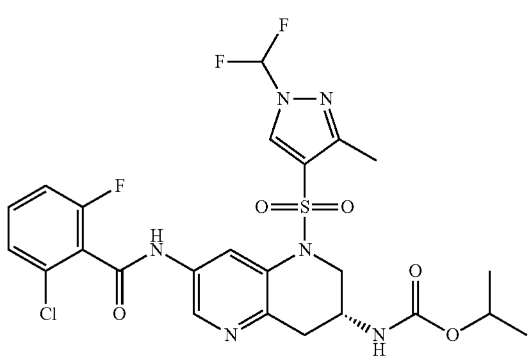 [SMILES: Cc1nn(C(F)F)cc1S(=O)(=O)N1C[C@H](NC(=O)OC(C)C)Cc2ncc(NC(=O)c3c(F)cccc3Cl)cc21] | 600 | M + Na = 623, 625 |

TABLE 6-continued
| Compound No. | Chemical Structure | LCMS (ESI): Calculated m/z | Observed m/z |
|---|---|---|---|
| 67 | 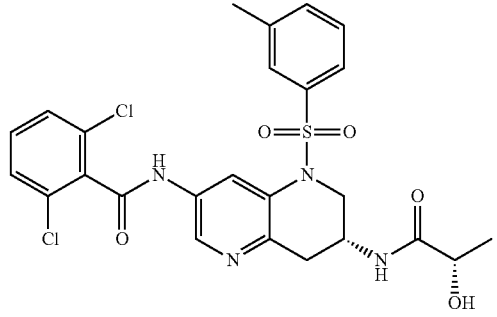 [SMILES: Cc1cccc(S(=O)(=O)N2C[C@H](NC(=O)[C@H](C)O)Cc3ncc(NC(=O)c4c(Cl)cccc4Cl)cc32)c1] | 562 | M + H = 563, 564 |
| 68 | 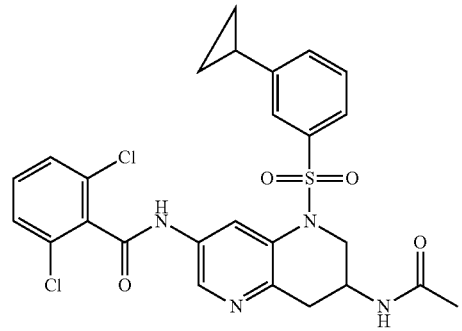 [SMILES: CC(=O)NC1Cc2ncc(NC(=O)c3c(Cl)cccc3Cl)cc2N(S(=O)(=O)c2cccc(C3CC3)c2)C1] | 558 | M + Na = 581, 583 |
| 69 | 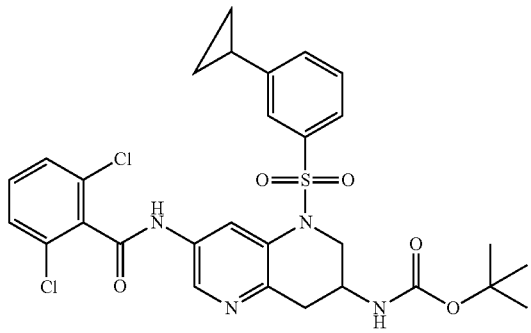 [SMILES: CC(C)(C)OC(=O)NC1Cc2ncc(NC(=O)c3c(Cl)cccc3Cl)cc2N(S(=O)(=O)c2cccc(C3CC3)c2)C1] | 616 | M + Na = 639, 641 |
| 70 | 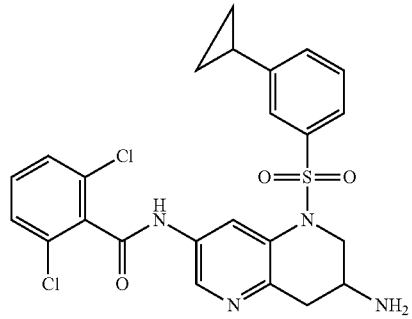 [SMILES: NC1Cc2ncc(NC(=O)c3c(Cl)cccc3Cl)cc2N(S(=O)(=O)c2cccc(C3CC3)c2)C1] | 516 | M + H = 517, 519 |

Example 21—Synthesis of N-[7-amino-5-(toluene-3-sulfonyl)-5,6,7,8-tetrahydro-9-oxa-1,5-diaza-benzocyclohepten-3-yl]-2,2,2-trifluoro-acetamide (Compound 71)

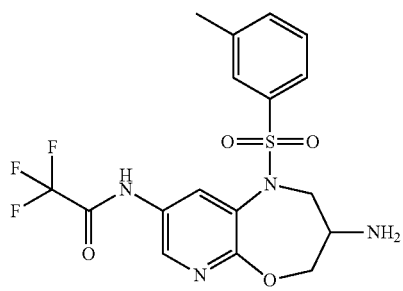 [SMILES: Cc1cccc(S(=O)(=O)N2CC(N)COc3ncc(NC(=O)C(F)(F)F)cc32)c1]

The title compound was prepared according to the procedures described below.

Part I—Synthesis of 2-dibenzylamino-propane-1,3-diol

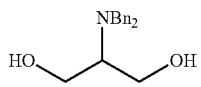

Serinol (2.0 g, 22 mmol) and potassium carbonate (9.1 g, 66 mmol) were combined in ethanol (50 mL). Benzyl bromide (5.2 mL, 44 mmol) was added and the reaction was stirred at reflux for 12 hours. The reaction mixture was concentrated, re-suspended in ethyl acetate, and washed with water and brine, dried ($Na_2SO_4$), concentrated, and precipitated from ether to give 2-dibenzylamino-propane-1,3-diol. LCMS (ESI): calc. $C_{17}H_{21}NO_2$=271; obs. M+H=272.

Part II—Synthesis of 3-(tert-butyl-dimethyl-silanyloxy)-2-dibenzylamino-propan-1-ol

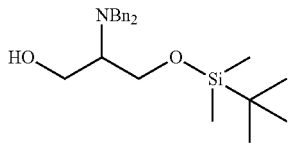

2-Dibenzylamino-propane-1,3-diol (4.0 g, 15 mmol) and imidazole (1.8 g, 27 mmol) were combined in DMF (2.5 mL) and dichloromethane (100 mL). tert-Butyldimethylsilyl chloride (3.34 g, 22.1 mmol) was added and the reaction was stirred for one hour at room temperature. The reaction mixture was diluted with ethyl acetate and washed three times with water and brine, dried ($Na_2SO_4$), concentrated, and purified by column chromatography (EtOAc/hexanes) to give 3-(tert-butyl-dimethyl-silanyloxy)-2-dibenzylamino-propan-1-ol. LCMS (ESI): calc. $C_{23}H_{35}NO_2Si$=385; obs. M+H=386.

Part III—Synthesis of N-(5-bromo-2-chloro-pyridin-3-yl)-N-[3-(tert-butyl-dimethyl-silanyloxy)-2-dibenzylamino-propyl]-3-methyl-benzenesulfonamide

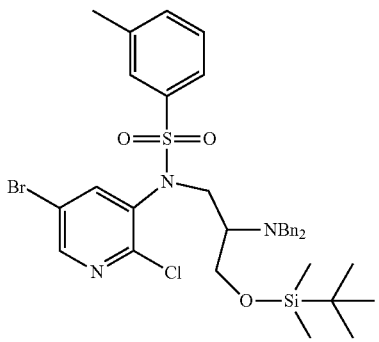

N-(5-Bromo-2-chloro-pyridin-3-yl)-3-methyl-benzenesulfonamide (2.24 g, 6.2 mmol), 3-(tert-butyl-dimethyl-silanyloxy)-2-dibenzylamino-propan-1-ol (2.87 g, 7.4 mmol), and triphenyl phosphine (2.43 g, 9.3 mmol) were dissolved in dichloromethane:THF (1:1, 100 mL) and cooled to 0° C. Diisopropylazodicarboxylate (1.8 mL, 9.3 mmol) was added dropwise over 2 minutes. The reaction was allowed to come to room temperature and stir for 12 hours. The reaction mixture was diluted with ether and the solids were removed by filtration. The filtrate was concentrated and purified by column chromatography (EtOAc/hexanes) to give N-(5-bromo-2-chloro-pyridin-3-yl)-N-[3-(tert-butyl-dimethyl-silanyloxy)-2-dibenzylamino-propyl]-3-methyl-benzenesulfonamide. LCMS (ESI): calc. $C_{35}H_{43}BrClN_3O_3SSi$=728; obs. M+H=729.

Part IV—Synthesis of dibenzyl-[3-bromo-5-(toluene-3-sulfonyl)-5,6,7,8-tetrahydro-9-oxa-1,5-diaza-benzocyclohepten-7-yl]-amine

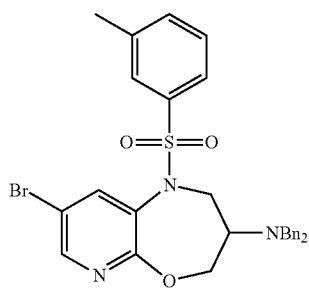

N-(5-Bromo-2-chloro-pyridin-3-yl)-N-[3-(tert-butyl-dimethyl-silanyloxy)-2-dibenzylamino-propyl]-3-methyl-benzenesulfonamide (4.44 g, 6.09 mmol) was dissolved in THF (120 mL). Tetrabutylammonium fluoride (1M in THF, 7.3 mL, 7.3 mmol) was added and the reaction was stirred for 8 hours at 60° C. Additional TBAF (1M in THF, 3 mL, 3 mmol) was added and the reaction was stirred for 2 hours at 70° C. The reaction mixture was concentrated under reduced pressure and the residue was dissolved in ether: dichoromethane (1:1) and washed with saturated $NaHCO_3$ (aq), dried ($Na_2SO_4$), concentrated, and purified by column chromatography (EtOAc/hexanes/TEA) to give dibenzyl-[3- bromo-5-(toluene-3-sulfonyl)-5,6,7,8-tetrahydro-9-oxa-1,5-diaza-benzocyclohepten-7-yl]-amine. LCMS (ESI): calc. $C_{29}H_{28}BrN_3O_3S=578$; obs. M+H=579.

Part V—Synthesis of $N^3,N^3$-dibenzyl-1-(m-tolylsulfonyl)-1,2,3,4-tetrahydropyrido[2,3-b][1,4]oxazepine-3,8-diamine

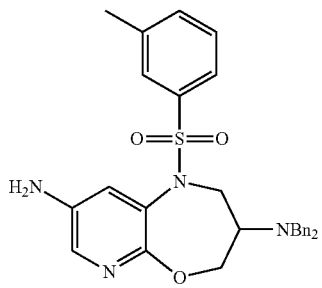

Dibenzyl-[3-bromo-5-(toluene-3-sulfonyl)-5,6,7,8-tetrahydro-9-oxa-1,5-diaza-benzocyclohepten-7-yl]-amine (700 mg, 1.2 mmol), Xantphos (91 mg, 0.16 mmol), sodium tert-butoxide (365 mg, 3.8 mmol), and $Pd_2(dba)_3$ (61 mg, 0.067 mmol) were combined in NMP (2 mL). Benzophenone imine (0.43 mL, 2.6 mmol) was added and nitrogen was bubbled through the reaction mixture for 1 minute. The vial was sealed and the reaction was stirred for 1 hour at 90° C. 1M Hydrochloric acid (aq) (1 mL) was added and the reaction was stirred for 1 hour at 40 C. The reaction mixture was diluted with ethyl acetate and washed with water, saturated $NaHCO_3(aq)$, and brine, dried ($Na_2SO_4$), concentrated, and purified by column chromatography (EtOAc/hexanes) to give $N^3,N^3$-dibenzyl-1-(m-tolylsulfonyl)-1,2,3,4-tetrahydropyrido[2,3-b][1,4]oxazepine-3,8-diamine. LCMS (ESI): calc. $C_{29}H_{30}N_4O_3S=514$; obs. M+H=515.

Part VI—Synthesis of N-[7-dibenzylamino-5-(toluene-3-sulfonyl)-5,6,7,8-tetrahydro-9-oxa-1,5-diazabenzocyclohepten-3-yl]-2,2,2-trifluoro-acetamide

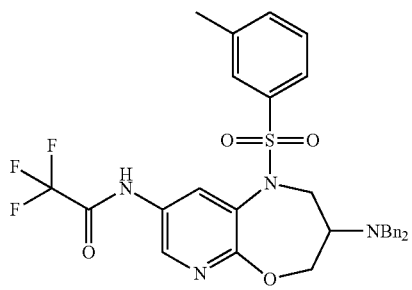

$N^3,N^3$-Dibenzyl-1-(m-tolylsulfonyl)-1,2,3,4-tetrahydropyrido[2,3-b][1,4]oxazepine-3,8-diamine (500 mg, 0.97 mmol) and disopropylethylamine (0.60 mL, 3.4 mmol) were combined in dichloromethane (10 mL) and cooled to 0° C. Trifluoroacetic anhydride (0.30 mL, 2.1 mmol) was then added dropwise over 1 minute and the reaction was stirred for 10 minutes at 0° C. Water (5 mL) was added and the reaction was stirred at room temperature for 30 minutes. The reaction mixture was diluted with ethyl acetate and washed with brine, dried ($Na_2SO_4$), concentrated, and purified by column chromatography (EtOAc/hexanes) to give N-[7-dibenzylamino-5-(toluene-3-sulfonyl)-5,6,7,8-tetrahydro-9-oxa-1,5-diaza-benzocyclohepten-3-yl]-2,2,2-trifluoro-acetamide. LCMS (ESI): calc. $C_{31}H_{29}F_3N_4O_4S=610$; obs. M+H=611.

Part VII—Synthesis of N-[7-amino-5-(toluene-3-sulfonyl)-5,6,7,8-tetrahydro-9-oxa-1,5-diaza-benzocyclohepten-3-yl]-2,2,2-trifluoro-acetamide

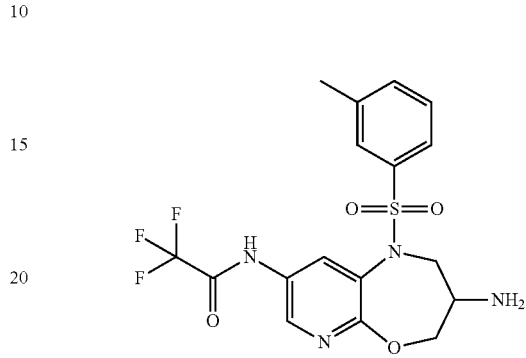

N-[7-dibenzylamino-5-(toluene-3-sulfonyl)-5,6,7,8-tetrahydro-9-oxa-1,5-diazabenzocyclo hepten-3-yl]-2,2,2-trifluoro-acetamide (475 mg, 0.78 mmol, 1.0 equiv.) was dissolved in 50 mL methanol. 10% Palladium on carbon (712 mg) was added and the resulting mixture was transferred to a Parr apparatus and hydrogenated at 80 PSI for 18 hours. The reaction mixture was filtered through a pad of Celite and concentrated under vacuum to obtain N-[7-amino-5-(toluene-3-sulfonyl)-5,6,7,8-tetrahydro-9-oxa-1,5-diaza-benzocyclohepten-3-yl]-2,2,2-trifluoro-acetamide (200 mg, 60%) LCMS (ESI): calc. $C_{17}H_{17}F_3N_4O_4S=430$; obs. M+H=431.

Example 22—Synthesis of [5-(toluene-3-sulfonyl)-3-(2,2,2-trifluoro-acetylamino)-5,6,7,8-tetrahydro-9-oxa-1,5-diaza-benzocyclohepten-7-yl]-carbamic acid tert-butyl ester (Compound 72)

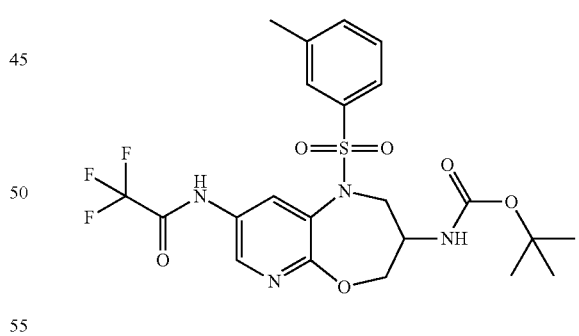

N-[7-amino-5-(toluene-3-sulfonyl)-5,6,7,8-tetrahydro-9-oxa-1,5-diaza-benzocyclohepten-3-yl]-2,2,2-trifluoro-acetamide (200 mg, 0.46 mmol, 1.0 equiv) was dissolved in p-dioxane (2 mL), then sodium bicarbonate (98 mg, 1.2 mmol, 2.5 equiv), di-tert-butyl dicarbonate (152 mg, 0.70 mmol, 1.5 equiv), and water (1 mL) were added and the resulting mixture stirred at room temperature. The reaction was concentrated and purified by flash chromatography (EtOAc/hexane) to obtain [5-(toluene-3-sulfonyl)-3-(2,2,2-trifluoro-acetylamino)-5,6,7,8-tetrahydro-9-oxa-1,5-diaza-benzocyclohepten-7-yl]-carbamic acid tert-butyl ester. LCMS (ESI): calc. $C_{22}H_{25}F_3N_4O_6S=530$; obs. M+H=531.

Example 23—Synthesis of [3-(2,6-dichloro-benzoylamino)-5-(toluene-3-sulfonyl)-5,6,7,8-tetrahydro-9-oxa-1,5-diaza-benzocyclohepten-7-yl]-carbamic acid tert-butyl ester (Compound 73)

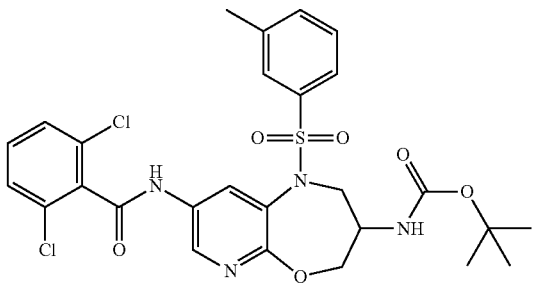 [SMILES: Cc1cccc(S(=O)(=O)N2CC(NC(=O)OC(C)(C)C)COc3ncc(NC(=O)c4c(Cl)cccc4Cl)cc32)c1]

The title compound was prepared according to the procedures described below.

Part I—Synthesis of [3-amino-5-(toluene-3-sulfonyl)-5,6,7,8-tetrahydro-9-oxa-1,5-diaza-benzocyclohepten-7-yl]-carbamic acid tert-butyl ester

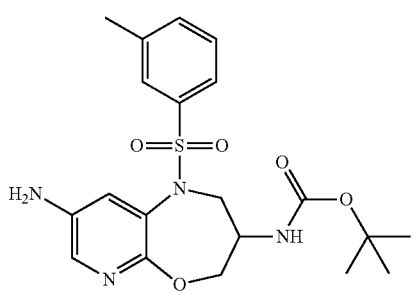 [SMILES: Cc1cccc(S(=O)(=O)N2CC(NC(=O)OC(C)(C)C)COc3ncc(N)cc32)c1]

[5-(Toluene-3-sulfonyl)-3-(2,2,2-trifluoro-acetylamino)-5,6,7,8-tetrahydro-9-oxa-1,5-diaza-benzocyclohepten-7-yl]-carbamic acid tert-butyl ester. (200 mg, 0.38 mmol, 1.0 equiv) was dissolved in p-dioxane (2 mL), then sodium hydroxide (60 mg, 1.5 mmol, 4 equiv) and water (1 mL) were added and the resulting mixture heated to 60° C. for three hours. The reaction was concentrated and purified by flash chromatography (EtOAc/hexane) to obtain [3-amino-5-(toluene-3-sulfonyl)-5,6,7,8-tetrahydro-9-oxa-1,5-diaza-benzocyclohepten-7-yl]-carbamic acid tert-butyl ester. LCMS (ESI): calc. $C_{20}H_{26}N_4O_5S=434$; obs. M+H=435.

Part II—Synthesis of [3-(2,6-dichloro-benzoylamino)-5-(toluene-3-sulfonyl)-5,6,7,8-tetrahydro-9-oxa-1,5-diaza-benzocyclohepten-7-yl]-carbamic acid tert-butyl ester

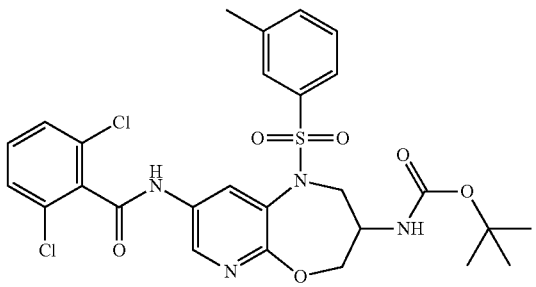 [SMILES: Cc1cccc(S(=O)(=O)N2CC(NC(=O)OC(C)(C)C)COc3ncc(NC(=O)c4c(Cl)cccc4Cl)cc32)c1]

[3-Amino-5-(toluene-3-sulfonyl)-5,6,7,8-tetrahydro-9-oxa-1,5-diaza-benzocyclohepten-7-yl]-carbamic acid tert-butyl ester (97 mg, 0.23 mmol, 1.0 equiv) was dissolved in p-dioxane. (0.5 mL) 2,6-dichlorobenzoyl chloride (94 mg, 0.45 mmol, 2.0 equiv), sodium hydroxide (36 mg, 0.90 mmol, 4.0 equiv), and water (0.5 mL) were added and the mixture was stirred for one hour at 60° C. The reaction mixture was concentrated and purified by flash chromatography to get [3-(2,6-dichloro-benzoylamino)-5-(toluene-3-sulfonyl)-5,6,7,8-tetrahydro-9-oxa-1,5-diaza-benzocyclohepten-7-yl]-carbamic acid tert-butyl ester. LCMS (ESI): calc. $C_{27}H_{28}Cl_2N_4O_6S=606$; obs. M+H=607.

Example 24—Synthesis of N-[7-amino-5-(toluene-3-sulfonyl)-5,6,7,8-tetrahydro-9-oxa-1,5-diaza-benzocyclohepten-3-yl]-2,6-dichloro-benzamide (Compound 74)

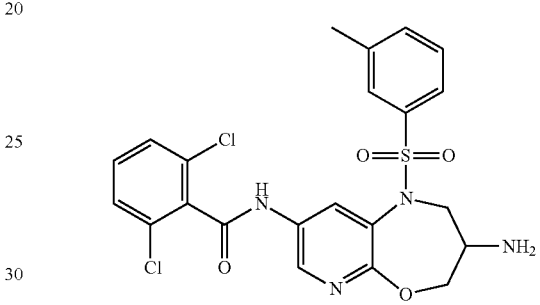

[3-(2,6-Dichloro-benzoylamino)-5-(toluene-3-sulfonyl)-5,6,7,8-tetrahydro-9-oxa-1,5-diaza-benzocyclohepten-7-yl]-carbamic acid tert-butyl ester (approx. 70 mg, 0.14 mmol) was dissolved in p-dioxane (1 mL). Hydrochloric acid (4 M in p-dioxane, 5 mL) was added and the resulting solution was stirred at room temperature for four hours. The reaction was concentrated under vacuum and submitted for HPLC purification to obtain N-[7-amino-5-(toluene-3-sulfonyl)-5,6,7,8-tetrahydro-9-oxa-1,5-diaza-benzocyclohepten-3-yl]-2,6-dichloro-benzamide. LCMS (ESI): calc. $C_{22}H_{20}Cl_2N_4O_4S=506$; obs. M+H=507.

Example 25—Synthesis of N-[7-acetylamino-5-(toluene-3-sulfonyl)-5,6,7,8-tetrahydro-9-oxa-1,5-diaza-benzocyclohepten-3-yl]-2,6-dichloro-benzamide (Compound 75)

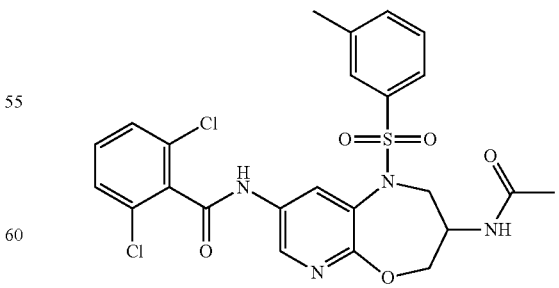

N-[7-Amino-5-(toluene-3-sulfonyl)-5,6,7,8-tetrahydro-9-oxa-1,5-diaza-benzocyclohepten-3-yl]-2,6-dichloro-benzamide (15 mg, 0.028 mmol, 1.0 equiv) was dissolved in pyridine (250 μL). Acetic anhydride (0.003 mL, 0.30 mmol, 1.1 equiv) was added and the resulting mixture was stirred at room temperature for 24 hours and submitted for HPLC purification to obtain N-[7-acetylamino-5-(toluene-3-sulfonyl)-5,6,7,8-tetrahydro-9-oxa-1,5-diaza-benzocyclohepten-3-yl]-2,6-dichloro-benzamide. LCMS (ESI): calc. $C_{24}H_{22}Cl_2N_4O_5S=548$; obs. M+H=551.

Example 26—Synthesis of 2,6-dichloro-N-[7-dimethylamino-5-(toluene-3-sulfonyl)-5,6,7,8-tetrahydro-9-oxa-1,5-diaza-benzocyclohepten-3-yl]-benzamide (Compound 76)

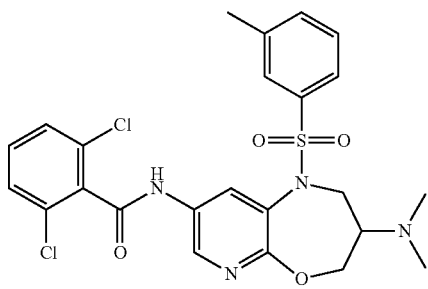 [SMILES: Cc1cccc(S(=O)(=O)N2CC(N(C)C)COc3ncc(NC(=O)c4c(Cl)cccc4Cl)cc32)c1]

N-[7-Amino-5-(toluene-3-sulfonyl)-5,6,7,8-tetrahydro-9-oxa-1,5-diaza-benzocyclohepten-3-yl]-2,6-dichloro-benzamide (15 mg, 0.028 mmol, 1.0 equiv) was dissolved in 1:1 tetrahydrofuran/ethanol (0.5 mL). Formalin (0.015 mL, 0.174 mmol, 6.3 equiv) was added and the mixture was stirred at room temperature for 15 minutes. Sodium triacetoxyborohydride (45 mg, 0.207 mmol, 7.5 equiv) was then added and the mixture stirred overnight at room temperature. The reaction was quenched with a small amount of water, then concentrated under reduced pressure. HPLC purification provided 2,6-dichloro-N-[7-dimethylamino-5-(toluene-3-sulfonyl)-5,6,7,8-tetrahydro-9-oxa-1,5-diaza-benzocyclohepten-3-yl]-benzamide. LCMS (ESI): calc. $C_{24}H_{24}Cl_2N_4O_4S=534$; obs. M+H=535.

Example 27—Preparation of Additional Compounds Via Reductive Amination

The compounds in Table 7 below were prepared using acetaldehyde based on the experimental procedures described in Example 26 with an amine prepared as in Example 17. Starting materials can be obtained from commercial sources or are readily prepared from commercially available materials.

TABLE 7

| Compound No. | Chemical Structure | LCMS (ESI): Calculated m/z | Observed m/z |
|---|---|---|---|
| 77 | | 518 | M + H = 519, 521 |
| 78 | | 546 | M + H = 547, 549 |

TABLE 7-continued

| Compound No. | Chemical Structure | LCMS (ESI): Calculated m/z | Observed m/z |
|---|---|---|---|
| 79 | | 546 | M + H = 547, 549 |

Example 28—Synthesis of 2,6-dichloro-N—[(S)-4-(3-chloro-benzenesulfonyl)-2-(2-oxo-pyrrolidin-1-ylmethyl)-3,4-dihydro-2H-benzo[1,4]oxazin-6-yl]-benzamide (Compound 80)

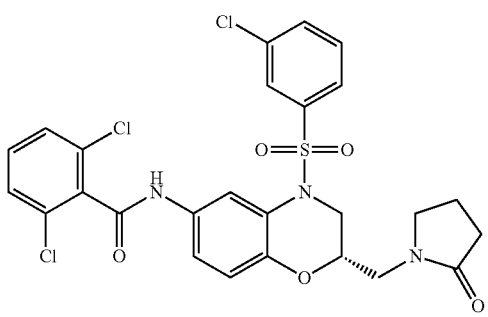 [SMILES: O=C(Nc1ccc2c(c1)N(S(=O)(=O)c1cccc(Cl)c1)C[C@H](CN1CCCC1=O)O2)c1c(Cl)cccc1Cl]

Toluene-4-sulfonic acid (R)-4-(3-chlorobenzenesulfonyl)-6-(2,6-dichlorobenzoylamino)-3,4-dihydro-2H-benzo[1,4]oxazin-2-ylmethyl ester (25 mg, 0.037 mmol) and 4-aminobutyric acid (19 mg, 0.19 mmol) were combined in N-methylpyrrolidinone (0.2 mL) and stirred at 100° C. for 3 hours. The reaction was cooled to room temperature and the product was purified by HPLC to give 2,6-dichloro-N—[(S)-4-(3-chlorobenzenesulfonyl)-2-(2-oxopyrrolidin-1-ylmethyl)-3,4-dihydro-2H-benzo[1,4]oxazin-6-yl]benzamide. LCMS (ESI): calc. $C_{26}H_{22}Cl_3N_3O_5S$=593; obs. 594.

Example 29—Preparation of Additional Pyrrolidinones

The compounds in Table 8 below were prepared based on the experimental procedures described in Example 28. Starting materials can be obtained from commercial sources or are readily prepared from commercially available materials.

TABLE 8

| Compound No. | Chemical Structure | LCMS (ESI): Calculated m/z | Observed m/z |
|---|---|---|---|
| 81 | | 613 | M + Na = 635, 637 |

TABLE 8-continued

| Compound No. | Chemical Structure | LCMS (ESI): Calculated m/z | Observed m/z |
|---|---|---|---|
| 82 | 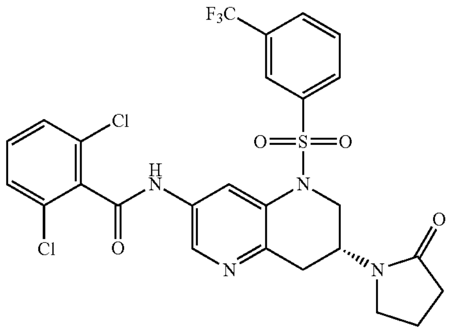 | 613 | M + H + Na = 635, 637 |
| 83 | 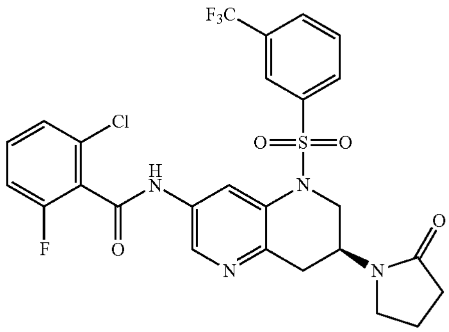 [SMILES: O=C(Nc1cnc2c(c1)N(S(=O)(=O)c1cccc(C(F)(F)F)c1)C[C@@H](N1CCCC1=O)C2)c1c(Cl)cccc1Cl] | 545 | M + H + Na = 569, 571 |
| 84 | 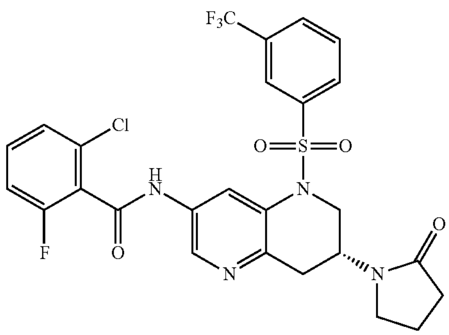 [SMILES: O=C(Nc1cnc2c(c1)N(S(=O)(=O)c1cccc(C(F)(F)F)c1)C[C@H](N1CCCC1=O)C2)c1c(Cl)cccc1Cl] | 545 | M + H + Na = 569, 571 |

Example 30—(S)-2,6-dichloro-N-(1-((3-chlorophenyl)sulfonyl)-3-((2,4-dioxooxazolidin-3-yl)methyl)-2,3-dihydro-1H-pyrido[2,3-b][1,4]oxazin-7-yl)benzamide (Compound 85)

The title compound was prepared according to the procedures described below.

Part I—Synthesis of (R)-tert-butyl(1-((3-chlorophenyl)sulfonyl)-3-(hydroxymethyl)-2,3-dihydro-1H-pyrido[2,3-b][1,4]oxazin-7-yl)carbamate

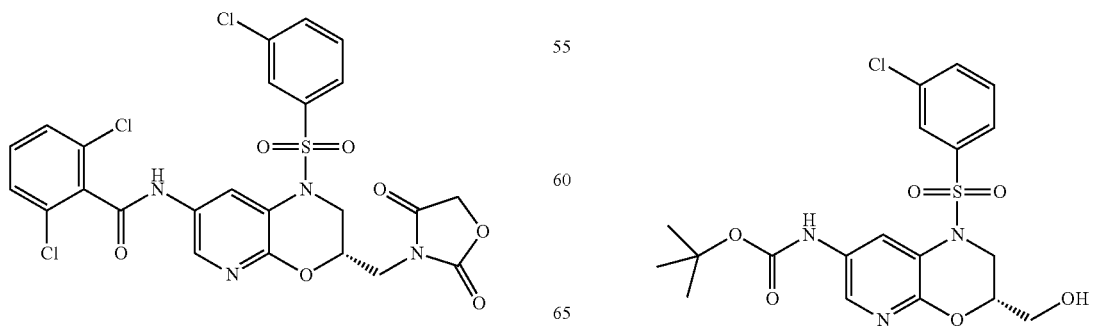

To a solution ((R)-3-hydroxymethyl-2,3-dihydro-1H-pyrido[2,3-b][1,4]oxazin-7-yl)-carbamic acid tert-butyl ester (0.56 g, 2 mmol) in pyridine (5 mL) at 0° C. was added 3-chloro phenyl sulfonyl chloride (0.42 g, 2 mmol) at 0° C. The reaction mixture was stirred at room temperature for 2 hours. The reaction mixture was diluted with ethyl acetate, washed with brine, saturated sodium bicarbonate and water. The organic layer was separated, dried (Na$_2$SO$_4$) and concentrated. The crude product was purified by column chromatography on silica gel eluting with a gradient of hexanes/ethyl acetate (2:1 to 1:3) to afford the title compound (0.45 g) as white foam. LCMS (ESI) m/z 456.

Part II—Synthesis of [(S)-1-(3-chloro-benzenesulfonyl)-3-(2,4-dioxo-oxazolidin-3-ylmethyl)-2,3-dihydro-1H-pyrido[2,3-b][1,4]oxazin-7-yl]-carbamic acid tert-butyl ester

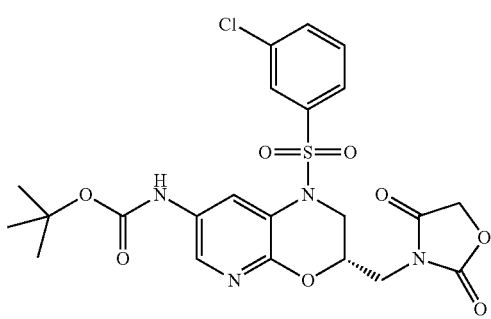 [SMILES: CC(C)(C)OC(=O)Nc1cnc2c(c1)N(S(=O)(=O)c1cccc(Cl)c1)C[C@H](CN1C(=O)COC1=O)O2]

To a solution of (91 mg, 0.2 mmol) [(R)-1-(3-chloro-benzenesulfonyl)-3-hydroxymethyl-2,3-dihydro-1H-pyrido[2,3-b][1,4]oxazin-7-yl]-carbamic acid tert-butyl ester), oxazolidine-2,4-dione (20 mg, 0.20 mmol), triphenylphosphine (78.6 mg, 0.30 mmol) in THF (2 mL) was added diisopropylazodicarboxylate (60.6 mg, 0.30 mmol) and the mixture was stirred for 12 hours at room temperature. The solvent was removed under reduced pressure and the residue was purified by silica gel chromatography eluting with a gradient of hexane:ethyl acetate (5:1 to 1:1) to afford the title compound (ESI) m/z 539.1.

Part III—Synthesis of (S)-2,6-dichloro-N-(1-((3-chlorophenyl)sulfonyl)-3-((2,4-dioxooxazolidin-3-yl)methyl)-2,3-dihydro-1H-pyrido[2,3-b][1,4]oxazin-7-yl)benzamide

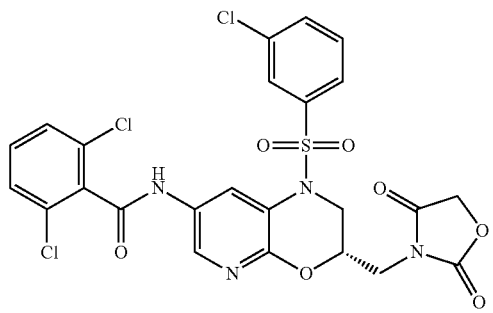 [SMILES: O=C(Nc1cnc2c(c1)N(S(=O)(=O)c1cccc(Cl)c1)C[C@H](CN1C(=O)COC1=O)O2)c1c(Cl)cccc1Cl]

[(S)-1-(3-Chloro-benzenesulfonyl)-3-(2,4-dioxo-oxazolidin-3-ylmethyl)-2,3-dihydro-1H-pyrido[2,3-b][1,4]oxazin-7-yl]-carbamic acid tert-butyl ester (92 mg) was dissolved in a solution 4 M HCl in dioxane, then stirred at 40° C. for 1 hour. The solvent was removed under reduced pressure. The HCl salt was washed with ether and the ether was decanted to afford a white precipitate (62 mg, 0.14 mmol). To the residue was added dichloromethane (1 mL) and triethylamine (0.062 mL, 0.45 mmol). The resulting mixture was stirred for 5 minutes after which 2,6-dichlorobenzoyl chloride (31.5 mg, 0.15 mmol) was added and the reaction was stirred for an additional 30 minutes. The solvent was removed under reduced pressure and the residue was diluted with ethyl acetate and washed with saturated aqueous NaHCO$_3$ and brine. The organic layer was dried (Na$_2$SO$_4$) and concentrated. The residue was purified by HPLC to provide the title compound. LCMS (ESI) m/z 611, 613.

Example 31—(S)-2,6-dichloro-N-(1-((3-chlorophenyl)sulfonyl)-3-((3-methyl-2,5-dioxoimidazolidin-1-yl)methyl)-2,3-dihydro-1H-pyrido[2,3-b][1,4]oxazin-7-yl)benzamide (Compound 86)

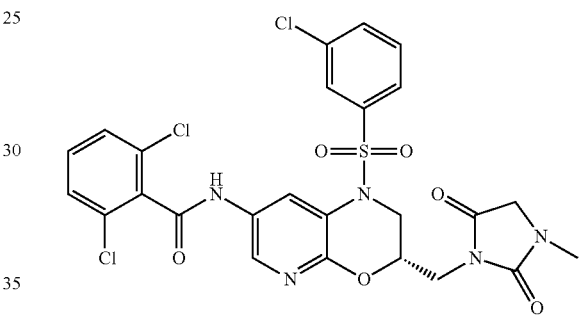

The title compound was prepared following the procedure of Example 30, substituting 1-methylimidazolidine-2,4-dione for oxazolidine-2,4-dione in part. calc. C$_{25}$H$_{20}$Cl$_3$N$_5$O$_6$S=623; obs. M+H=624, 626.

Example 32—(S)-2,6-dichloro-N-(1-((3-chlorophenyl)sulfonyl)-3-((4-methyl-3-oxopiperazin-1-yl)methyl)-2,3-dihydro-1H-pyrido[2,3-b][1,4]oxazin-7-yl)benzamide (Compound 87)

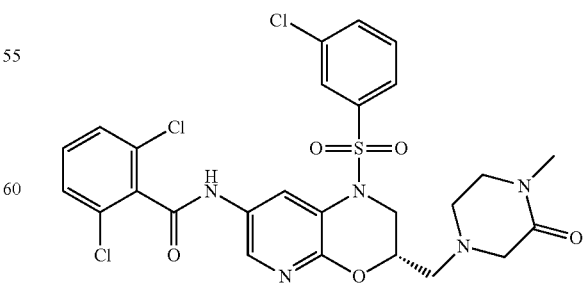

The title compound was prepared according to the procedures described below.

Part I—Synthesis of 3-chloro-benzenesulfonic acid (R)-7-tert-butoxycarbonylamino-1-(3-chloro-benzenesulfonyl)-2,3-dihydro-1H-pyrido[2,3-b][1,4]oxazin-3-yl methyl ester

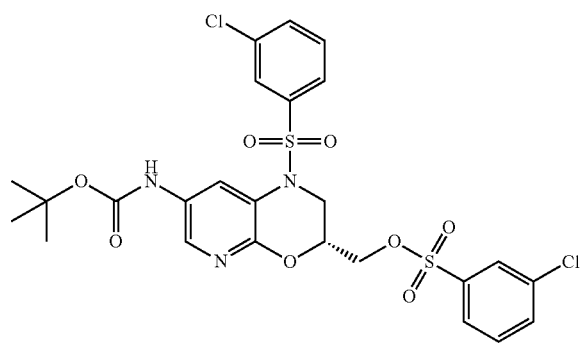 [SMILES: CC(C)(C)OC(=O)Nc1cnc2c(c1)N(S(=O)(=O)c1cccc(Cl)c1)C[C@H](COS(=O)(=O)c1cccc(Cl)c1)O2]

To a solution ((R)-3-hydroxymethyl-2,3-dihydro-1H-pyrido[2,3-b][1,4]oxazin-7-yl)-carbamic acid tert-butyl ester (0.56 g, 2 mmol) in pyridine (5 mL) was added 3-chlorobenzenesulfonyl chloride (0.42 g, 2 mmol). The resulting mixture was stirred for 15 minutes at 0° C., and additional sulfonyl chloride (0.42 mmol, 2 mmol) was added and stirring continued for 1 hour at room temperature. The reaction mixture was diluted with ethyl acetate, washed with water, dried (Na$_2$SO$_4$) and concentrated. The crude product was purified by column chromatography eluting with hexanes/ethyl acetate (2:1) to afford the title compound. LCMS (ESI) m/z 630.3.

Part II—Synthesis of [(S)-4-(3-chloro-benzenesulfonyl)-2-(4-methyl-3-oxo-piperazin-1-ylmethyl)-3,4-dihydro-2H-benzo[1,4]oxazin-6-yl]-carbamic acid tert-butyl ester

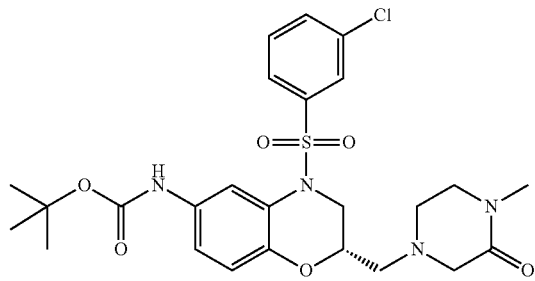 [SMILES: CN1CCN(C[C@H]2CN(S(=O)(=O)c3cccc(Cl)c3)c3cc(NC(=O)OC(C)(C)C)ccc3O2)CC1=O]

A suspension of 3-chloro-benzenesulfonic acid (R)-6-tert-butoxycarbonylamino-4-(3-chloro-benzenesulfonyl)-3,4-dihydro-2H-benzo[1,4]oxazin-2-yl methyl ester (63 mg, 0.1 mmol), N,N-diisopropylethylamine (0.2 mmol), 1-methyl-piperazin-2-one, hydrochloride salt (30 mg, 0.2 mmol) and potassium iodide (5 mg) in THF (0.5 mL) and N-methyl pyrrolidinone (0.5 mL) was heated in a sealed tube for 12 hours at 80° C. After cooling, the mixture was partitioned between water and ethyl acetate. The organic layer was separated, washed with brine, saturated aqueous NaHCO$_3$ and concentrated. The residue was purified by column chromatography on silica gel to provide [(S)-4-(3-chloro-benzenesulfonyl)-2-(4-methyl-3-oxo-piperazin-1-ylmethyl)-3,4-dihydro-2H-benzo[1,4]oxazin-6-yl]-carbamic acid tert-butyl ester. LCMS (ESI) m/z 551.

Part III—Synthesis of 4-[(S)-6-amino-4-(3-chloro-benzenesulfonyl)-3,4-dihydro-2H-benzo[1,4]oxazin-2-yl methyl]-1-methyl-piperazin-2-one, hydrochloride

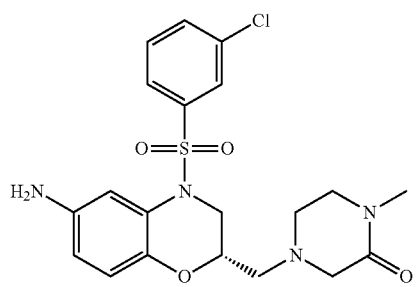 [SMILES: CN1CCN(C[C@H]2CN(S(=O)(=O)c3cccc(Cl)c3)c3cc(N)ccc3O2)CC1=O]

[(S)-4-(3-Chloro-benzenesulfonyl)-2-(4-methyl-3-oxo-piperazin-1-ylmethyl)-3,4-dihydro-2H-benzo[1,4]oxazin-6-yl]-carbamic acid tert-butyl ester was dissolved in 4 M HCl in p-dioxane, followed by stirring at 40° C. for one hour. The volatiles were removed and the product was used in the next step without further purification. LC/MS (ESI) 451.

Part IV—Synthesis of 2,6-dichloro-N—[(S)-4-(3-chloro-benzenesulfonyl)-2-(4-methyl-3-oxo-piperazin-1-ylmethyl)-3,4-dihydro-2H-benzo[1,4]oxazin-6-yl]-benzamide To a stirred solution of 4-[(S)-6-amino-4-(3-chloro-benzenesulfonyl)-3,4-dihydro-2H-benzo[1,4]oxazin-2-yl methyl]-1-methyl-piperazin-2-one (40 mg, 0.1 mmol) and triethyl amine (0.4 mmol) in dichloromethane (2 mL) was added 2,6-dichloro benzoyl chloride (24.4 mg, 0.12 mmol). The reaction mixture was stirred for 12 hours at 40° C. then concentrated. The product was recovered after purification by HPLC eluting with a gradient of water and acetonitrile with trifluoroacetic acid. LC/MS (ESI) 623.51.

Example 33—Preparation of Additional Amines

The compounds in Table 9 below were prepared based on the experimental procedures described in Example 32 with the appropriate amine in place of 1-methyl-piperazin-2-one. Starting materials can be obtained from commercial sources or are readily prepared from commercially available materials.

TABLE 9

| Compound No. | Chemical Structure | LCMS (ESI): Calculated m/z | Observed m/z |
|---|---|---|---|
| 88 | 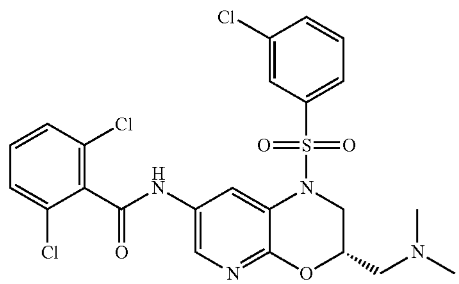 [SMILES: CN(C)C[C@H]1CN(S(=O)(=O)c2cccc(Cl)c2)c2cc(NC(=O)c3c(Cl)cccc3Cl)cnc2O1] | 554 | M + H = 555, 557 |
| 89 | 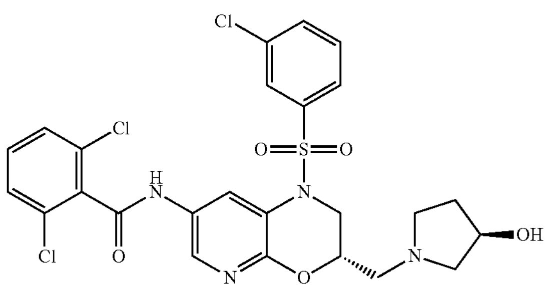 [SMILES: O=C(Nc1cnc2c(c1)N(S(=O)(=O)c1cccc(Cl)c1)C[C@H](CN1CC[C@@H](O)C1)O2)c1c(Cl)cccc1Cl] | 596 | M + H = 597 |
| 90 | 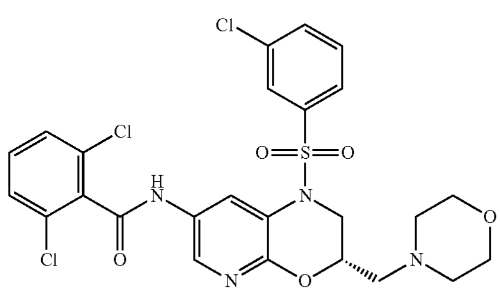 [SMILES: O=C(Nc1cnc2c(c1)N(S(=O)(=O)c1cccc(Cl)c1)C[C@H](CN1CCOCC1)O2)c1c(Cl)cccc1Cl] | 596 | M + H = 597 |
| 91 | 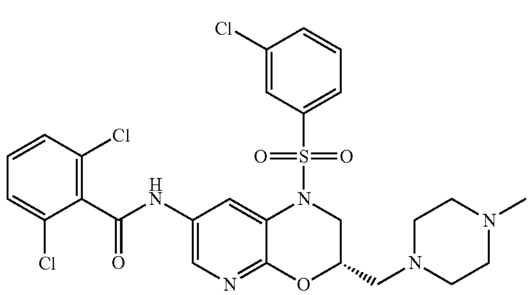 [SMILES: CN1CCN(C[C@H]2CN(S(=O)(=O)c3cccc(Cl)c3)c3cc(NC(=O)c4c(Cl)cccc4Cl)cnc3O2)CC1] | 609 | M + H = 610, 612 |

Example 34—Synthesis of (S)—N—((R)-5-((1-(difluoromethyl)-3-methyl-1H-pyrazol-4-yl)sulfonyl)-7-(hydroxymethyl)-5,6,7,8-tetrahydro-1,5-naphthyridin-3-yl)-2,3,3-trimethylbutanamide (Compound 92)

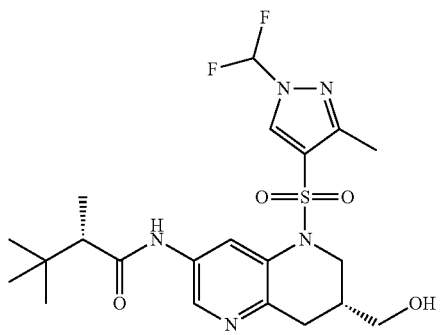 [SMILES: Cc1nn(C(F)F)cc1S(=O)(=O)N1C[C@H](CO)Cc2ncc(NC(=O)[C@@H](C)C(C)(C)C)cc21]

The title compound was prepared according to the procedures described below.

Part I—Synthesis of 1-benzyl-7-bromo-3,4-dihydro-1,5-naphthyridin-2(1H)-one

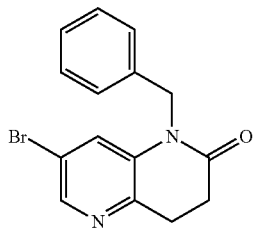 [SMILES: O=C1CCc2ncc(Br)cc2N1Cc1ccccc1]

To 7-bromo-3,4-dihydro-1,5-naphthyridin-2(1H)-one (8.1 g, 35.7 mmol) in N,N-dimethylformamide (50 mL) was added cesium carbonate (23.2 g, 71.4 mmol) followed by benzyl bromide (5.1 mL, 42.8 mmol). This mixture was stirred at 70° C. overnight. The solution was cooled, diluted with ethyl acetate, washed with water, brine, dried with sodium sulfate, filtered and concentrated. The product was recrystallized from ethyl acetate/hexanes, and rinsed with hexanes to afford the title compound (4.4 g, 39%).

Part II—Synthesis of methyl 1-benzyl-7-bromo-2-oxo-1,2,3,4-tetrahydro-1,5-naphthyridine-3-carboxylate

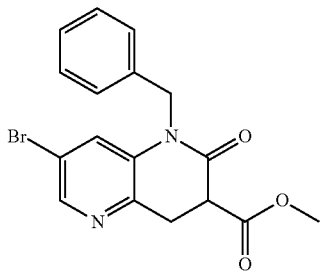 [SMILES: COC(=O)C1Cc2ncc(Br)cc2N(Cc2ccccc2)C1=O]

To 1-benzyl-7-bromo-3,4-dihydro-1,5-naphthyridin-2(1H)-one (4.6 g, 14.5 mmol) in anhydrous tetrahydrofuran (50 mL) under nitrogen at −78° C. was added lithium hexamethyldisilazane (1 M in tetrahydrofuran, 29 mL, 29 mmol), and the mixture was stirred for 5 minutes at −78° C. To the anion formed was added methyl chloroformate (1.2 mL, 16 mmol) and this mixture was stirred at −78° C. for an additional 30 minutes. The mixture was allowed to warm to ambient temperature, quenched with saturated aqueous ammonium chloride, extracted with ethyl acetate, washed with brine, dried with sodium sulfate, filtered and concentrated to yield the title compound. (5.35 g, 98%).

Part III—Synthesis of (1-benzyl-7-bromo-1,2,3,4-tetrahydro-1,5-naphthyridin-3-yl)methanol To a solution of methyl 1-benzyl-7-bromo-2-oxo-1,2,3,4-tetrahydro-1,5-naphthyridine-3-carboxylate (5.35 g, 14.3 mmol) in anhydrous tetrahydrofuran (40 mL) under nitrogen at ambient temperature was carefully added $BH_3$—$SMe_2$ (10 M in tetrahydrofuran, 5.7 mL, 57 mmol). After addition, the reaction was refluxed for 90 minutes, then cooled to 0° C. and carefully quenched with methanol (30 mL), then refluxed for a further 10 minutes. The solution was cooled and concentrated. The residue was diluted in ethyl acetate, washed with water, brine, dried with sodium sulfate, and concentrated to yield the title compound (4.6 g, 97%).

Part IV—Synthesis of 1-benzyl-7-bromo-3-(((tert-butyldimethylsilyl)oxy)methyl)-1,2,3,4-tetrahydro-1,5-naphthyridine

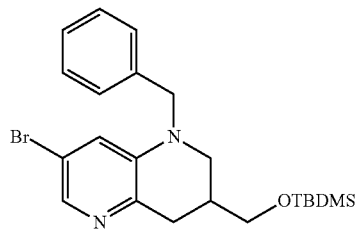 [SMILES: CC(C)(C)[Si](C)(C)OCC1Cc2ncc(Br)cc2N(Cc2ccccc2)C1]

To a solution of (1-benzyl-7-bromo-1,2,3,4-tetrahydro-1,5-naphthyridin-3-yl)methanol (4.6 g, 13.8 mmol) in dichloromethane (50 mL) was added diisopropylethylamine (5.4 mL, 20.7 mmol), tert-butyldimethylsilyl chloride (2.5 g, 16.6 mmol) and catalytic 4-dimethylaminopyridine (0.17 g, 1.4 mmol) and the resulting mixture was stirred at ambient temperature overnight. The solution was washed with saturated aqueous ammonium chloride, dried ($Na_2SO_4$), and concentrated in the presence of silica gel. The residue was purified by column chromatography eluting with a gradient of 0-30% ethyl acetate in hexanes to yield the title compound (3.98 g, 64%).

Part V—Synthesis of 5-benzyl-7-(((tert-butyldimethylsilyl)oxy)methyl)-N-(diphenylmethylene)-5,6,7,8-tetrahydro-1,5-naphthyridin-3-amine

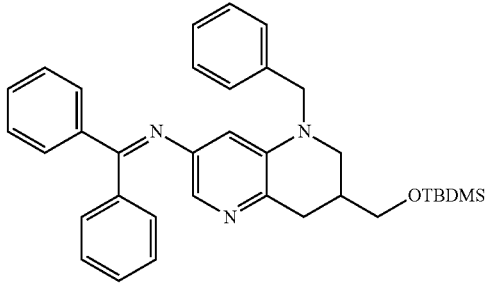 [SMILES: CC(C)(C)[Si](C)(C)OCC1Cc2ncc(N=C(c3ccccc3)c3ccccc3)cc2N(Cc2ccccc2)C1]

A suspension 1-benzyl-7-bromo-3-(((tert-butyldimethylsilyl)oxy)methyl)-1,2,3,4-tetrahydro-1,5-naphthyridine (3.98 g, 8.9 mmol), benzophenone imine (1.8 mL, 10.7 mmol), cesium carbonate (4.3 g, 13.3 mmol), X-Phos (0.21 g, 0.44 mmol), and tris(dibenzylideneacetone)dipalladium (0) (0.4 g, 0.44 mmoL) in anhydrous 1,4-dioxane (50 mL) was first degassed, then heated to 110° C. under nitrogen for 24 hours. The solution was cooled, diluted with ethyl acetate, filtered through celite, and concentrated in the presence of silica gel. The residue was purified by column chromatography eluting with a gradient of 5-40% ethyl acetate in hexanes to yield the title compound (3.7 g, 76%).

Part VI—Synthesis of 5-benzyl-7-(((tert-butyldimethylsilyl)oxy)methyl)-5,6,7,8-tetrahydro-1,5-naphthyridin-3-amine

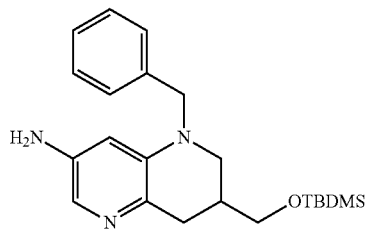 [SMILES: CC(C)(C)[Si](C)(C)OCC1Cc2ncc(N)cc2N(Cc2ccccc2)C1]

To a degassed suspension of 5-benzyl-7-(((tert-butyldimethylsilyl)oxy)methyl)-N-(diphenylmethylene)-5,6,7,8-tetrahydro-1,5-naphthyridin-3-amine (3.7 g, 6.8 mmol) and ammonium formate (8.5 g, 135 mmol) under nitrogen in methanol (75 mL) was added 10% palladium on carbon (0.7 g, 0.68 mmol). This mixture was refluxed under nitrogen for 2 hours. The reaction was cooled to ambient temperature and filtered through Celite, rinsing with methanol. The filtrates were concentrated under reduced pressure, redissolved in ethyl acetate, washed with water, then brine, dried with sodium sulfate, filtered and concentrated in the presence of silica gel. Purification by column chromatography eluting with a gradient of ethanol in dichloromethane yielded the title compound.

Part VII—Synthesis of tert-butyl(5-benzyl-7-(((tert-butyldimethylsilyl)oxy)methyl)-5,6,7,8-tetrahydro-1,5-naphthyridin-3-yl)carbamate

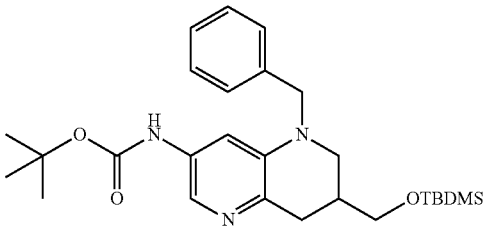 [SMILES: CC(C)(C)OC(=O)Nc1cnc2c(c1)N(Cc1ccccc1)CC(CO[Si](C)(C)C(C)(C)C)C2]

A mixture of 5-benzyl-7-(((tert-butyldimethylsilyl)oxy)methyl)-5,6,7,8-tetrahydro-1,5-naphthyridin-3-amine (3.83 g, 10 mmol), triethylamine (2.02 g, 20 mmol), and di-tert-butyl dicarbonate (2.73 g, 12.5 mmol) in dichloromethane (50 mL) was stirred at room temperature for 2 days. The reaction mixture was partitioned between dichloromethane and water. The aqueous layer was re-extracted with dichloromethane, and the combined organic layers were dried ($Na_2SO_4$) and concentrated to afford the title compound, which was used without further purification.

Part VIII—Synthesis of [7-(tert-butyl-dimethyl-silanyloxymethyl)-5,6,7,8-tetrahydro-[1,5]naphthyridin-3-yl]-carbamic acid tert-butyl ester

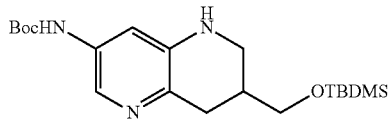 [SMILES: CC(C)(C)OC(=O)Nc1cnc2c(c1)NCC(CO[Si](C)(C)C(C)(C)C)C2]

[5-Benzyl-7-(tert-butyl-dimethyl-silanyloxymethyl)-5,6,7,8-tetrahydro-[1,5]naphthyridin-3-yl]-carbamic acid tert-butyl ester (5.9 g, 12.2 mmol) was dissolved in methanol (100 mL) and 10% Pd/C catalyst (1.0 g) was added, followed by ammonium formate (5 g). The mixture was heated at reflux for 24 hours. The cooled mixture was filtered through a pad of Celite and the filtrate was evaporated. The residue was purified by $SiO_2$ chromatography to afford the title compound (4.18 g, 87.1%). LC/MS (ESI) m/z 394.4 This material was separated by chiral SPC chromatography into its two enantiomers. The following experimental procedures are illustrative of the chemistry employed separately for each of the two enantiomers.

Part IX—Synthesis of [7-(tert-butyl-dimethyl-silanyloxymethyl)-5-(4-fluoro-benzenesulfonyl)-5,6,7,8-tetrahydro-[1,5]naphthyridin-3-yl]-carbamic acid tert-butyl ester

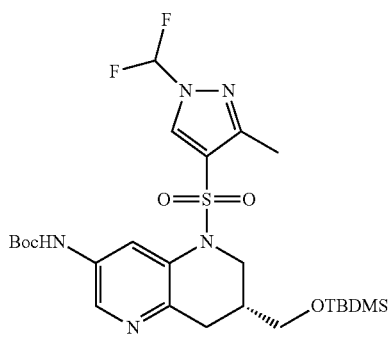 [SMILES: Cc1nn(C(F)F)cc1S(=O)(=O)N1C[C@H](CO[Si](C)(C)C(C)(C)C)Cc2ncc(NC(=O)OC(C)(C)C)cc21]

To a solution [7-(tert-butyl-dimethyl-silanyloxymethyl)-5,6,7,8-tetrahydro-[1,5]naphthyridin-3-yl]-carbamic acid tert-butyl ester (0.394 g, 1 mmol), 4-dimethylaminopyridine (0.061 g, 0.5 mmol) in pyridine (15 mL) was added 1-difluoromethyl-3-methyl-1H-pyrazole-4-sulfonyl chloride (0.277 g, 1.2 mmol). The reaction was heated at 60° C. for 4 hours. The reaction was cooled and partitioned between ethyl acetate and water. The organic layer was washed with brine, dried ($Na_2SO_4$) and concentrated. The product was purified by chromatography on silica gel to give [7-(tert-butyl-dimethyl-silanyloxymethyl)-5-(1-difluoromethyl-3-methyl-1H-pyrazole-4-sulfonyl)-5,6,7,8-tetrahydro-[1,5]naphthyridin-3-yl]-carbamic acid tert-butyl ester (0.387 g, 66%). LC/MS(ESI) m/z 588.5.

The enantiomeric compound was prepared in an analogous manner.

Part X—Synthesis of [7-amino-1-(1-difluoromethyl-3-methyl-1H-pyrazole-4-sulfonyl)-1,2,3,4-tetrahydro-[1,5]naphthyridin-3-yl]-methanol

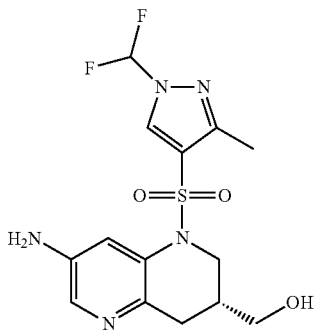 [SMILES: Cc1nn(C(F)F)cc1S(=O)(=O)N1C[C@H](CO)Cc2ncc(N)cc21]

[7-(tert-Butyl-dimethyl-silanyloxymethyl)-5-(1-difluoromethyl-3-methyl-1H-pyrazole-4-sulfonyl)-5,6,7,8-tetrahydro-[1,5]naphthyridin-3-yl]-carbamic acid tert-butyl ester (50 mg, 0.085 mmol) was treated with 4 N HCl in dioxane (0.5 mL) and the mixture was stirred at room temperature for an hour. The solvent was removed, and the residual white solid was washed with ethyl ether and dried under vacuo for 12 hours to provide [7-amino-1-(1-difluoromethyl-3-methyl-1H-pyrazole-4-sulfonyl)-1,2,3,4-tetrahydro-[1,5]-naphthyridin-3-yl]-methanol (30 mg). LC/MC (ESI) m/z 374.2.5.

The enantiomeric compound was prepared in analogous manner.

Part XI—Synthesis of (S)—N—((R)-5-((1-(difluoromethyl)-3-methyl-1H-pyrazol-4-yl)sulfonyl)-7-(hydroxymethyl)-5,6,7,8-tetrahydro-1,5-naphthyridin-3-yl)-2,3,3-trimethylbutanamide

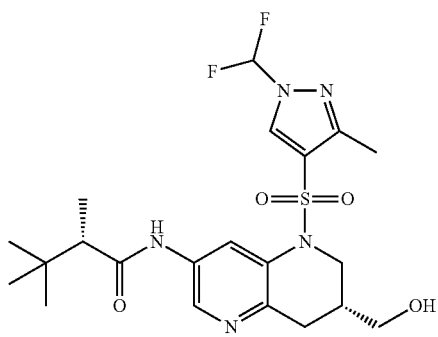 [SMILES: Cc1nn(C(F)F)cc1S(=O)(=O)N1C[C@H](CO)Cc2ncc(NC(=O)[C@@H](C)C(C)(C)C)cc21]

[7-Amino-1-(1-difluoromethyl-3-methyl-1H-pyrazole-4-sulfonyl)-1,2,3,4-tetrahydro-[1,5] naphthyridin-3-yl]-methanol (37.3 mg, 0.1 mmol), 2,3,3-trimethylbutyric acid (19.8 mg, 1.5 mmol) and HATU (49.4 mg, 0.13 mmol) were dissolved in DMF (0.2 ml). N,N-diisopropylethyl amine (0.07 mL, 0.4 mmol) was added and the reaction mixture was stirred at 60° C. for 12 hours. The mixture was partitioned between ethyl acetate and brine. The organic layer was dried ($Na_2SO_4$) and concentrated. The residue was purified by HPLC to provide the title compound. LC/MS (ESI) m/z 486.

Example 35—Synthesis of (S)—N—((S)-5-((1-(difluoromethyl)-3-methyl-1H-pyrazol-4-yl)sulfonyl)-7-(hydroxymethyl)-5,6,7,8-tetrahydro-1,5-naphthyridin-3-yl)-2,3,3-trimethylbutanamide (Compound 93)

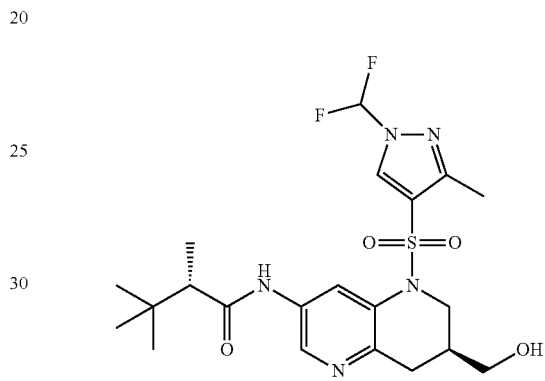

The title compound was prepared following the methods of Example 34.

Example 36—Synthesis of 2,6-dichloro-N-(7-(hydroxymethyl)-5-(m-tolylsulfonyl)-5,6,7,8-tetrahydro-1,5-naphthyridin-3-yl)benzamide (Compound 94)

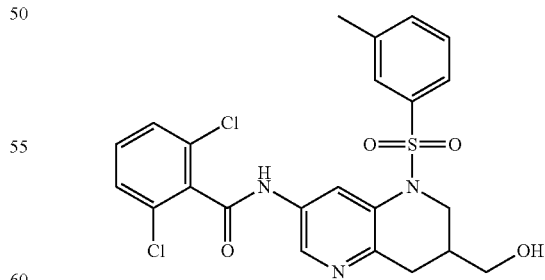

The title compound was prepared following the method of Example 34.

Example 37—Synthesis of (S)—N—((S)-5-((1-(difluoromethyl)-3-methyl-1H-pyrazol-4-yl)sulfonyl)-7-(((R)-3-hydroxypyrrolidin-1-yl)methyl)-5,6,7,8-tetrahydro-1,5-naphthyridin-3-yl)-2,3,3-trimethylbutanamide (Compound 95)

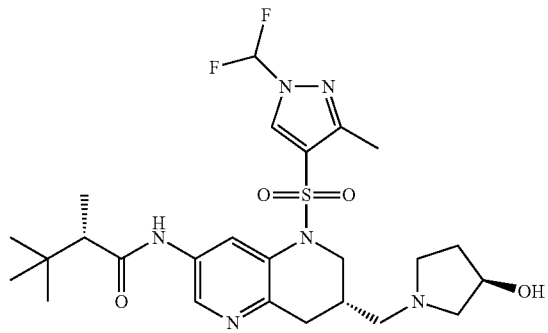 [SMILES: Cc1nn(C(F)F)cc1S(=O)(=O)N1C[C@H](CN2CC[C@@H](O)C2)Cc2ncc(NC(=O)[C@@H](C)C(C)(C)C)cc21]

The title compound was prepared according to the procedures described below.

Part I—Synthesis of (R)-(7-((tert-butoxycarbonyl)amino)-1-((1-(difluoromethyl)-3-methyl-1H-pyrazol-4-yl)sulfonyl)-1,2,3,4-tetrahydro-1,5-naphthyridin-3-yl)methyl methanesulfonate

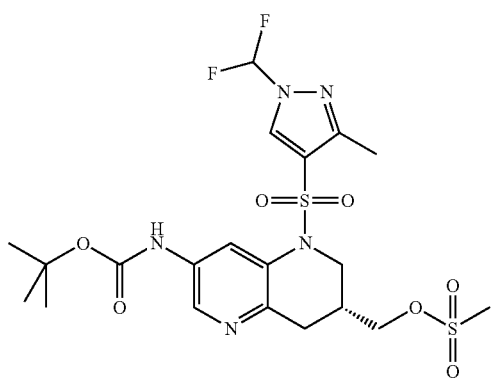 [SMILES: Cc1nn(C(F)F)cc1S(=O)(=O)N1C[C@H](COS(C)(=O)=O)Cc2ncc(NC(=O)OC(C)(C)C)cc21]

To a solution (R)-tert-butyl (5-((1-(difluoromethyl)-3-methyl-1H-pyrazol-4-yl)sulfonyl)-7-(hydroxymethyl)-5,6,7,8-tetrahydro-1,5-naphthyridin-3-yl)carbamate (0.28 g, 0.59 mmol) in dichloromethane (5 mL) was added triethylamine (0.248 mL, 1.77 mmol) and methanesulfonic acid anhydride (0.153 g, 0.88 mmol). The mixture was stirred at room temperature for four hours, then concentrated, and the residue was partitioned between ethyl acetate and water. The organic layer was dried (Na$_2$SO$_4$) and concentrated to afford the title compound (0.325 g, 99%). LC/MS(ESI) m/z 552.6.

Part II—Synthesis of tert-butyl((S)-5-((1-(difluoromethyl)-3-methyl-1H-pyrazol-4-yl)sulfonyl)-7-(((R)-3-hydroxypyrrolidin-1-yl)methyl)-5,6,7,8-tetrahydro-1,5-naphthyridin-3-yl)carbamate

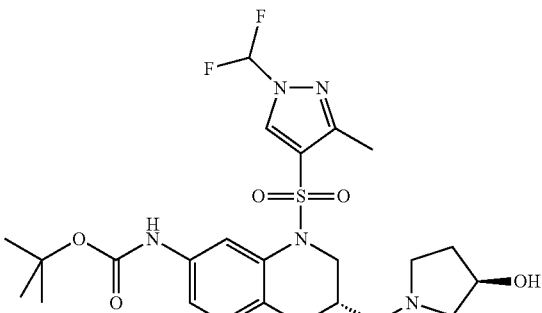

A mixture methanesulfonic acid 7-tert-butoxycarbonylamino-1-(1-difluoromethyl-3-methyl-1H-pyrazole-4-sulfonyl)-1,2,3,4-tetrahydro-[1,5]naphthyridin-3-yl methyl ester (0.10 g, 0.18 mmol) and (R)-pyrrolidine-3-ol (31.3 mg, 0.36 mmol) in THF with triethylamine (10 uL) was heated at 70° C. for 12 hours. The reaction mixture was diluted with dichloromethane and washed with water. The organic layer was dried (Na$_2$SO$_4$) and concentrated. The residue was purified by column chromatography eluting with dichloromethane/MeOH/triethylamine (89:10:1) to give the title compound (80 mg, 81.3%). LC/MS(ESI) m/z 543.2.

Part III—Synthesis of (R)-1-[(S)-7-amino-1-(1-difluoromethyl-3-methyl-1H-pyrazole-4-sulfonyl)-1,2,3,4-tetrahydro-[1,5]naphthyridin-3-ylmethyl]-pyrrolidin-3-ol

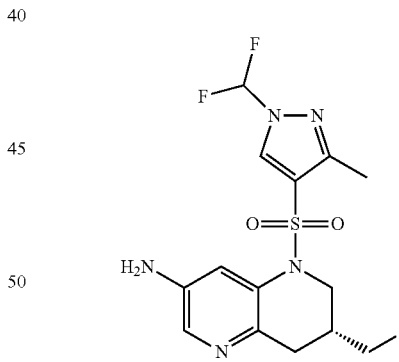

tert-Butyl ((S)-5-((1-(difluoromethyl)-3-methyl-1H-pyrazol-4-yl)sulfonyl)-7-(((R)-3-hydroxypyrrolidin-1-yl)methyl)-5,6,7,8-tetrahydro-1,5-naphthyridin-3-yl)carbamate (100 mg, 0.18 mmol) was treated with 4 N HCl in dioxane (1 mL) and the mixture was stirred at room temperature for one hour. The solvent was removed under reduced pressure, and the residual white precipitate was washed with ethyl ether to provide the title compound as a hydrochloride salt (80 mg). LC/MS(ESI) m/z 443.2. The hydrochloride salt was suspended in ethyl acetate then saturated aqueous potassium bicarbonate was added. The organic layer was separated, dried (Na$_2$SO$_4$), and concentrated in vacuo to afford the title compound.

Part IV—Synthesis of (S)—N—[(S)-5-(1-difluoromethyl-3-methyl-1H-pyrazole-4-sulfonyl)-7-((R)-3-hydroxy-pyrrolidin-1-yl methyl)-5,6,7,8-tetrahydro-[1,5]naphthyridin-3-yl]-2,3,3-trimethyl-butyramide

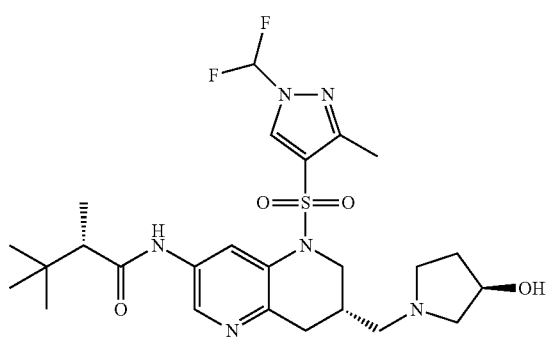 [SMILES: Cc1nn(C(F)F)cc1S(=O)(=O)N1C[C@H](CN2CC[C@@H](O)C2)Cc2ncc(NC(=O)[C@@H](C)C(C)(C)C)cc21]

(R)-1-[(S)-7-Amino-1-(1-difluoromethyl-3-methyl-1H-pyrazole-4-sulfonyl)-1,2,3,4-tetrahydro-[1,5]naphthyridin-3-ylmethyl]-pyrrolidin-3-ol (80 mg, 0.18 mmol), (S)-2,3,3-trimethylbutyric acid (46.6 mg, 0.36 mmol) and HATU (76.0 mg, 0.20 mmol) were dissolved in DMF (0.2 ml). N,N-diisopropylethylamine (0.07 mL, 0.4 mmol) was added and the reaction mixture was stirred at 60° C. for 12 hours, then cooled and partititioned between brine and ethyl acetate. The organic layer was dried (Na$_2$SO$_4$), concentrated and purified by HPLC to provide the title compound. LC/MS (ESI) m/z 555.

Example 38—Synthesis of (S)—N—((R)-5-((1-(difluoromethyl)-3-methyl-1H-pyrazol-4-yl)sulfonyl)-7-(((R)-3-hydroxypyrrolidin-1-yl)methyl)-5,6,7,8-tetrahydro-1,5-naphthyridin-3-yl)-2,3,3-trimethylbutanamide (Compound 96)

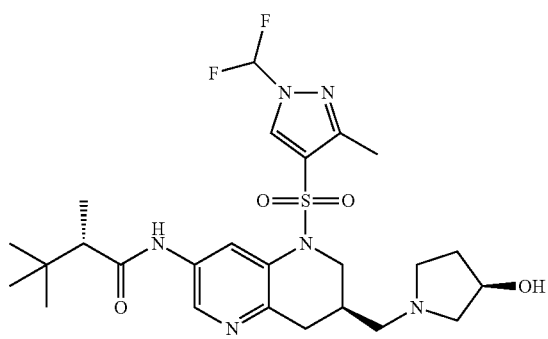 [SMILES: Cc1nn(C(F)F)cc1S(=O)(=O)N1C[C@@H](CN2CC[C@@H](O)C2)Cc2ncc(NC(=O)[C@@H](C)C(C)(C)C)cc21]

The title compound was prepared following the method of Example 35.

Example 39—Synthesis of (S)-2,6-dichloro-N-(7-(2-oxooxazolidin-3-yl)-5-((3-(trifluoromethyl)phenyl)sulfonyl)-5,6,7,8-tetrahydro-1,5-naphthyridin-3-yl)benzamide (Compound 97)

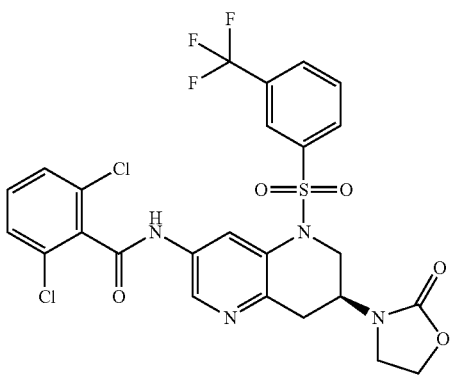 [SMILES: O=C(Nc1cnc2c(c1)N(S(=O)(=O)c1cccc(C(F)(F)F)c1)C[C@@H](N1CCOC1=O)C2)c1c(Cl)cccc1Cl]

To a solution of (S)—N-(7-amino-5-((3-(trifluoromethyl)phenyl)sulfonyl)-5,6,7,8-tetrahydro-1,5-naphthyridin-3-yl)-2,6-dichlorobenzamide (33 mg, 0.06 mmol) in dichloromethane (0.25 mL) and tetrahydrofuran (0.25 mL) was added tetraalkylammonium carbonate resin (2.5-3.5 mmol/g, 40 mg) followed by 2-chloroethylchloroformate (19 μL, 0.18 mmol) and shaken at ambient temperature for 4 hours. Filtered off resin and concentrated. The residue was dissolved in anhydrous tetrahydrofuran (0.5 mL) under nitrogen, cooled to −78° C., then added a 1M solution of potassium tert-butoxide in tetrahydrofuran (0.12 mL, 0.12 mmol). The reaction was warmed to 0° C. After 20 minutes the reaction was quenched by adding 10% citric acid (1 mL). Extracted with ethyl acetate, dried (Na$_2$SO$_4$) and concentrated. The mixture was purified by column chromatography eluting with a gradient of methanol in dichloromethane to yield title compound (8 mg, 21%). $^1$H NMR 400 Hz D$_6$-DMSO δ 11.07 (s, 1H), 8.55 (m, 2H), 8.09 (m, 3H), 7.85 (m, 1H), 7.60 (m, 2H), 7.51 (m, 1H), 4.24-4.18 (m, 3H), 3.80 (m, 2H), 3.47 (m, 2H), 2.94 (m, 2H).

Example 40—Synthesis of (R)-2,6-dichloro-N-(7-(2-oxooxazolidin-3-yl)-5-((3-(trifluoromethyl)phenyl)sulfonyl)-5,6,7,8-tetrahydro-1,5-naphthyridin-3-yl)benzamide (Compound 98)

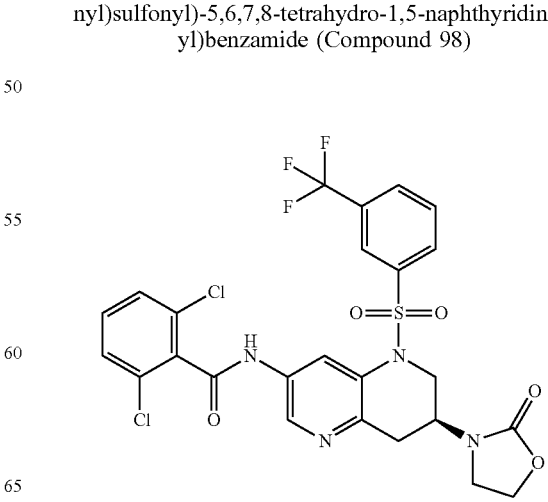

By the method of Example 39, the enantiomer was prepared.

Example 41—Biological Assays for Inhibition of RORγ

Exemplary compounds from the above Examples were tested for ability to inhibit RORγ activity using RORγ-Ligand Binding Domain (LBD) TR-FRET Assay Protocol I or RORγ-Ligand Binding Domain (LBD) TR-FRET Assay Protocol II. Assay procedures and results are described below.

Part I—Procedures for RORγ-Ligand Binding Domain TR-FRET Assay Protocol I

Recombinant, HIS-tagged RORγ-LBD was expressed in SF9 cells using a baculovirus expression system. Cells were lysed and the lysate was used as a source for RORγ-LBD for the assay. A 1:80 dilution of RORγ-LBD lysate in assay buffer (25 mM HEPES pH 7.0, 100 mM NaCl, 0.01% Tween, 0.1% BSA) was prepared and 5 μL was added to each well (RORγ-LBD final concentration ~3 nM). Control wells received lysate from SF9 cells not expressing RORγ-LBD.

Compounds to be tested were diluted to 100× final test concentration in DMSO and further diluted to 4× final test concentration using assay buffer to provide the test compound mixture. An aliquot (5 μL) of the test compound mixture was added to each well.

A 4× stock of biotinylated-LXXLL peptide from SRC1-2 (Biotin-CPSSHSSLTERHKILHRLLQEGSPS) was prepared in assay buffer and a 5 μL aliquot added to each well (450 nM final concentration). A 4× solution of europium tagged anti-HIS antibody (2 nM final concentration) and APC conjugated streptavidin (60 nM final concentration) were prepared and a 5 μL aliquot added to each well.

The final assay mixture was incubated for 4 hours to overnight, and the fluorescence signal was measured on an Envision plate reader: (Excitation filter=340 nm; APC emission=665 nm; Europium emission=615 nm; dichroic mirror=D400/D630; delay time=100 μs, integration time=200 μs).

$EC_{50}$ values for test compounds were calculated from the quotient of the fluorescence signal at 665 nm divided by the fluorescence signal at 615 nm using GraphPad Prism software Part II—Procedures for RORγ-Ligand Binding Domain TR-FRET Assay Protocol II HIS-tagged RORγ-LBD protein was expressed in SF9 cells using a baculovirus expression system. The RORγ-LBD protein was purified by glutathione sepharose chromatography. Separately, SF9 cells not expressing recombinant protein were lysed in TBS buffer (25 mM Tris, pH 8.0, 150 mM NaCl) under sonication. The lysate was added to the purified RORγ-LBD in a volume equivalent of 0.75 μL lysate (from 30,000 SF9 cells) per 75 femtomol of RORγ-LBD protein. The resulting mixture was diluted in assay buffer (50 mM Tris pH 7.0, 50 mM KCl, 1 mM EDTA, 0.1 mM DTT, 0.01% BSA) to obtain RORγ-LBD protein at a final concentration of 3 nM.

Compounds to be tested were injected to the assay plate using Acoustic Droplet Ejection technology by Echo 550 liquid handler (Labcyte, Calif.).

A stock of biotinylated-LXXLL peptide from coactivator SRC1 (Biotin-CPSSHSSLTERHKILHRLLQEGSPS) was prepared in assay buffer and added to each well (100 nM final concentration). A solution of Europium tagged anti-HIS antibody (1.25 nM final concentration) and APC-conjugated streptavidin (8 nM final concentration) were also added to each well.

The final assay mixture was incubated overnight at 4° C., and the fluorescence signal was measured on an Envision plate reader: (Excitation filter=340 nm; APC emission=665 nm; Europium emission=615 nm; dichroic mirror=D400/D630; delay time=100 μs, integration time=200 μs). The $EC_{50}$ value for test compounds was calculated from the quotient of the fluorescence signal at 665 nm divided by the fluorescence signal at 615 nm Part III—Results Compounds 1-43, 45-71, 74-92 and 94-98 from the above Examples were tested in one or both of Protocol I and Protocol II, and each compound was determined to have an $EC_{50}$ less than 7 μM. Compounds 3 and 4 were tested in Protocol I, though compounds 3 and 4 did not provide measurable RORγ inhibition during the assay measuring $EC_{50}$ values less than or equal to 10 μM.

Table 10 below tabulates the biological data disclosed for Compounds 1-43, 45-71, 74-92 and 94-98:

TABLE 10

| Compound | Protocol I Fret $EC_{50}$ (nM) | Protocol II Fret $EC_{50}$ (nM) |
| --- | --- | --- |
| 1 | 1884 | 25 |
| 2 | 2395 | |
| 3 | 48000 | |
| 4 | 50000 | |
| 5 | 2607 | |
| 6 | 2409 | |
| 7 | 6443 | |
| 8 | 1056 | |
| 9 | 3517 | |
| 10 | 3625 | 4327 |
| 11 | 447 | 324 |
| 12 | 250 | 66 |
| 13 | 174 | |
| 14 | 166 | 22 |
| 15 | 31 | 10 |
| 16 | 336 | 123 |
| 17 | 760 | 107 |
| 18 | | 13 |
| 19 | 20 | |
| 20 | 390 | 108 |
| 21 | 200 | |
| 22 | 90 | |
| 23 | 100 | |
| 24 | 132 | 6 |
| 25 | 1034 | 70 |
| 26 | 829 | 63 |
| 27 | 20 | 11 |
| 28 | 810 | 73 |
| 29 | 3047 | 387 |
| 30 | | 111 |
| 31 | | 57 |
| 32 | | 97 |
| 33 | | 152 |
| 34 | | 108 |
| 35 | | 7 |
| 36 | 700 | 202 |
| 37 | 52 | 16 |
| 38 | 414 | 61 |
| 39 | | 25 |
| 40 | | 18 |
| 41 | | 18 |
| 42 | | 25 |

TABLE 10-continued

| Compound | Protocol I Fret EC$_{50}$ (nM) | Protocol II Fret EC$_{50}$ (nM) |
|---|---|---|
| 43 | | 24 |
| 45 | | 6 |
| 46 | | 72 |
| 47 | | 36 |
| 48 | | 10 |
| 49 | | 12 |
| 50 | | 31 |
| 51 | | 852 |
| 52 | | 74 |
| 53 | | 25 |
| 54 | | 17 |
| 55 | | 32 |
| 56 | | 132 |
| 57 | | 24 |
| 58 | | 13 |
| 59 | | 24 |
| 60 | | 23 |
| 61 | | 127 |
| 62 | | 370 |
| 63 | | 26 |
| 64 | | 18 |
| 65 | | 9 |
| 66 | | 204 |
| 67 | | 23 |
| 68 | | 25 |
| 69 | | 13 |
| 70 | | 38 |
| 71 | | 13 |
| 74 | | 174 |
| 75 | | 291 |
| 76 | | 98 |
| 77 | | 553 |
| 78 | | 25 |
| 79 | | 24 |
| 80 | | 26 |
| 81 | | 35 |
| 82 | | 12 |
| 83 | | 1428 |
| 84 | | 60 |
| 85 | | 20 |
| 86 | | 10 |
| 87 | | 52 |
| 88 | | 42 |
| 89 | | 32 |
| 90 | | 30 |
| 91 | | 1327 |
| 92 | | 10000 |
| 94 | | 20 |
| 95 | | 4103 |
| 96 | | 168 |
| 97 | | 42 |
| 98 | | 17 |

INCORPORATION BY REFERENCE

The entire disclosure of each of the patent documents and scientific articles referred to herein is incorporated by reference for all purposes.

EQUIVALENTS

The invention may be embodied in other specific forms without departing from the spirit or essential characteristics thereof. The foregoing embodiments are therefore to be considered in all respects illustrative rather than limiting the invention described herein. Scope of the invention is thus indicated by the appended claims rather than by the foregoing description, and all changes that come within the meaning and range of equivalency of the claims are intended to be embraced therein.

We claim:

1. A compound represented by Formula I:

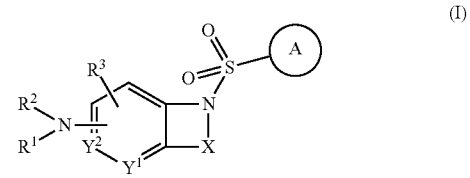

or a pharmaceutically acceptable salt or solvate thereof; wherein:

A is aryl, aralkyl, heteroaryl, cycloalkyl, or heterocycloalkyl; each of which is optionally substituted with 1, 2, or 3 substituents independently selected from the group consisting of halogen, hydroxyl, $C_{1-6}$alkyl, $C_{1-6}$haloalkyl, $C_{1-6}$hydroxyalkyl, $C_{1-6}$alkoxy, $C_{1-6}$haloalkoxy, —N($R^4$)($R^5$), —CO$_2R^6$, —C(O)$R^6$, —CN, —$C_{1-4}$alkylene-$C_{1-4}$alkoxy, —$C_{1-4}$alkylene-N($R^4$)($R^5$), —$C_{1-4}$alkylene-CO$_2R^6$, —O—$C_{1-6}$alkylene-N($R^4$)($R^5$), —N($R^4$)C(O)—$C_{1-6}$alkylene-N($R^4$)($R^5$), —S(O)$_p C_{1-6}$alkyl, —SO$_2$N($R^4$)($R^5$), —N($R^4$)SO$_2$($C_{1-6}$alkyl), —C(O)N($R^4$)($R^5$), and —N($R^4$)C(O)N($R^4$)($R^5$);

X is —O—[C($R^6$)($R^7$)]—[C($R^6$)$_2$]$_m$-ψ, —O—C($R^6$)$_2$—C($R^6$)($R^7$)—C($R^6$)$_2$-ψ, —O—C($R^6$)$_2$—C($R^6$)($R^7$)—ψ, —C($R^6$)$_2$—[C($R^6$)($R^7$)]—[C($R^6$)$_2$]$_m$-ψ, —C(O)—[C($R^6$)($R^7$)]—[C($R^6$)$_2$]$_m$-ψ, —C($R^6$)$_2$—N($R^8$)—[C($R^6$)($R^7$)]—[C($R^6$)$_2$]$_m$-ψ, —C($R^6$)=N-ψ, —C($R^6$)$_2$C($R^6$)=N-ψ, —N=C($R^6$)—ψ, or —N=C($R^6$)C($R^6$)$_2$-ψ; wherein ψ is a bond to the sulfonamide ring nitrogen atom in Formula I;

$Y^1$ is C($R^3$), and $Y^2$ is N;

$R^1$ is hydrogen or $C_{1-6}$alkyl;

$R^2$ is hydrogen, —C(O)-aryl, —C(O)-aralkyl, —C(O)—[C($R^6$)$_2$]$_m$-cycloalkyl, —C(O)—[C($R^6$)$_2$]$_m$-heterocyclyl, —C(O)—$C_{1-8}$alkyl, —C(O)—$C_{1-6}$alkylene-$C_{1-6}$alkoxyl, —C(O)—$C_{1-6}$alkylene-cycloalkyl, or —C(O)—$C_{1-6}$alkylene-heterocycloalkyl; each of which is optionally substituted with 1, 2, or 3 substituents independently selected from the group consisting of halogen, hydroxyl, $C_{1-6}$alkoxy, $C_{1-6}$haloalkoxy, $C_{1-6}$alkyl, $C_{1-6}$haloalkyl, —N($R^4$)($R^5$), —CN, —CO$_2$—$C_{1-6}$alkyl, —C(O)—$C_{1-6}$alkyl, —C(O)N($R^4$)($R^5$), —S(O)$_p C_{1-6}$alkyl, —SO$_2$N($R^4$)($R^5$), and —N($R^4$)SO$_2$($C_{1-6}$alkyl);

$R^3$ represents independently for each occurrence hydrogen, halogen, or $C_{1-6}$alkyl;

$R^4$ and $R^5$ each represent independently for each occurrence hydrogen or $C_{1-6}$alkyl; or $R^4$ and $R^5$ taken together with the nitrogen atom to which they are attached form a 3-7 membered heterocyclic ring;

$R^6$ represents independently for each occurrence hydrogen or $C_{1-6}$alkyl;

$R^7$ is hydrogen, hydroxyl, $C_{1-6}$hydroxyalkyl, $C_{1-6}$alkyl, $C_{1-6}$haloalkyl, —CO$_2R^6$, $C_{1-6}$alkylene-CO$_2R^6$, $C_{1-4}$hydroxyalkylene-CO$_2R^6$, —N($R^4$)($R^5$), $C_{1-6}$alkylene-N($R^4$)($R^5$), $C_{1-6}$hydroxyalkylene-N($R^4$)($R^5$), —N($R^4$)C(O)$R^9$, $C_{1-6}$alkylene-N($R^4$)C(O)$R^9$, $C_{1-6}$alkylene-C(O)N($R^4$)($R^5$), —N($R^4$)CO$_2$—$C_{1-6}$alkyl, or $C_{1-6}$alkylene-N($R^4$)C(O)N($R^4$)($R^5$); or $R^7$ is heterocycloalkyl or $C_{1-4}$alkylene-heterocycloalkyl, wherein the heterocycloalkyl is optionally substituted with 1, 2, or 3 substituents independently selected from the group consisting of oxo, halogen, hydroxyl, $C_{1-6}$alkyl, $C_{1-6}$haloalkyl, $C_{1-6}$hydroxyalkyl, $C_{1-6}$alkoxy, and $C_{1-6}$haloalkoxy;

$R^8$ is hydrogen, $C_{1-6}$alkyl, or —C(O)—$C_{1-6}$alkyl;

$R^9$ is hydrogen, $C_{1-6}$alkyl, $C_{1-6}$hydroxyalkyl, —N($R^4$)($R^5$), $C_{1-6}$alkylene-N($R^4$)($R^5$), or $C_{1-6}$alkylene-N($R^4$)C(O)—$C_{1-6}$alkyl; each of which is optionally substituted with 1, 2, or 3 halogen, hydroxyl or amino, and m and p each represent independently for each occurrence 0, 1, or 2.

2. The compound of claim 1, wherein the compound is represented by Formula I:

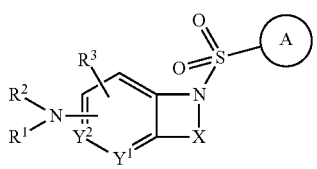

or a pharmaceutically acceptable salt or solvate thereof; wherein:

A is aryl, aralkyl, heteroaryl, cycloalkyl, or heterocycloalkyl; each of which is optionally substituted with 1, 2, or 3 substituents independently selected from the group consisting of halogen, hydroxyl, $C_{1-8}$alkyl, $C_{1-6}$haloalkyl, $C_{1-6}$hydroxyalkyl, $C_{1-6}$alkoxy, $C_{1-6}$haloalkoxy, —N($R^4$)($R^5$), —$CO_2R^6$, —C(O)$R^6$, —CN, —$C_{1-4}$alkylene-$C_{1-4}$alkoxy, —$C_{1-4}$alkylene-N($R^4$)($R^5$), —$C_{1-4}$alkylene-$CO_2R^6$, —O—$C_{1-6}$alkylene-N($R^4$)($R^5$), —N($R^4$)C(O)—$C_{1-6}$alkylene-N($R^4$)($R^5$), —S(O)$_p C_{1-6}$alkyl, —$SO_2$N($R^4$)($R^5$), —N($R^4$)$SO_2$($C_{1-6}$alkyl), —C(O)N($R^4$)($R^5$), and —N($R^4$)C(O)N($R^4$)($R^5$);

X is —O—[C($R^6$)($R^7$)]—[C($R^6$)$_2$]$_m$-ψ, —O—C($R^6$)$_2$—C($R^6$)($R^7$)—C($R^6$)$_2$-ψ, —O—C($R^6$)$_2$—C($R^6$)($R^7$)—ψ, —C($R^6$)$_2$—[C($R^6$)($R^7$)]-[C($R^6$)$_2$]$_m$-ψ, —C(O)—[C($R^6$)($R^7$)]—[C($R^6$)$_2$]$_m$-ψ, —C($R^6$)$_2$—N($R^8$)—[C($R^6$)($R^7$)]—[C($R^6$)$_2$]$_m$-ψ, —C($R^6$)=N-ψ, —C($R^6$)$_2$C($R^6$)=N-ψ, —N=C($R^6$)—ψ, or —N=C($R^6$)C($R^6$)$_2$- ψ; wherein ψ is a bond to the sulfonamide ring nitrogen atom in Formula I;

$Y^1$ is C($R^3$), and $Y^2$ is N;

$R^1$ is hydrogen or $C_{1-6}$alkyl;

$R^2$ is —C(O)-aryl, —C(O)-aralkyl, —C(O)—[C($R^6$)$_2$]$_m$-cycloalkyl, —C(O)—[C($R^6$)$_2$]$_m$-heterocyclyl, —C(O)—$C_{1-8}$alkyl, —C(O)—$C_{1-6}$alkylene-$C_{1-6}$alkoxyl, —C(O)—$C_{1-6}$alkylene-cycloalkyl, or —C(O)—$C_{1-6}$alkylene-heterocycloalkyl; each of which is optionally substituted with 1, 2, or 3 substituents independently selected from the group consisting of halogen, hydroxyl, $C_{1-6}$alkoxy, $C_{1-6}$haloalkoxy, $C_{1-6}$alkyl, $C_{1-6}$haloalkyl, —N($R^4$)($R^5$), —CN, —$CO_2$—$C_{1-6}$alkyl, —C(O)—$C_{1-6}$alkyl, —C(O)N($R^4$)($R^5$), —S(O)$_p C_{1-6}$ alkyl, —$SO_2$N($R^4$)($R^5$), and —N($R^4$)$SO_2$($C_{1-6}$alkyl);

$R^3$ represents independently for each occurrence hydrogen, halogen, or $C_{1-6}$alkyl;

$R^4$ and $R^5$ each represent independently for each occurrence hydrogen or $C_{1-6}$alkyl; or $R^4$ and $R^5$ taken together with the nitrogen atom to which they are attached form a 3-7 membered heterocyclic ring;

$R^6$ represents independently for each occurrence hydrogen or $C_{1-6}$alkyl;

$R^7$ is hydrogen, hydroxyl, $C_{1-6}$hydroxyalkyl, $C_{1-6}$alkyl, $C_{1-6}$haloalkyl, —$CO_2R^6$, $C_{1-6}$alkylene-$CO_2R^6$, $C_{1-4}$hydroxyalkylene-$CO_2R^6$, —N($R^4$)($R^5$), $C_{1-6}$alkylene-N($R^4$)($R^5$), $C_{1-6}$hydroxyalkylene-N($R^4$)($R^5$), —N($R^4$)C(O)$R^9$, $C_{1-6}$alkylene-N($R^4$)C(O)$R^9$, $C_{1-6}$alkylene-C(O)N($R^4$)($R^5$), —N($R^4$)$CO_2$—$C_{1-6}$alkyl, or $C_{1-6}$alkylene-N($R^4$)C(O)N($R^4$)($R^5$); or $R^7$ is heterocycloalkyl or $C_{1-4}$alkylene-heterocycloalkyl, wherein the heterocycloalkyl is optionally substituted with 1, 2, or 3 substituents independently selected from the group consisting of oxo, halogen, hydroxyl, $C_{1-6}$alkyl, $C_{1-6}$haloalkyl, $C_{1-6}$hydroxyalkyl, $C_{1-6}$alkoxy, and $C_{1-6}$haloalkoxy;

$R^8$ is hydrogen, $C_{1-6}$alkyl, or —C(O)—$C_{1-6}$alkyl;

$R^9$ is hydrogen, $C_{1-6}$alkyl, $C_{1-6}$hydroxyalkyl, $C_{1-6}$alkylene-N($R^4$)($R^5$), or $C_{1-6}$alkylene-N($R^4$)C(O)—$C_{1-6}$alkyl; and m and p each represent independently for each occurrence 0, 1, or 2.

3. The compound of claim 1, wherein A is aryl optionally substituted with 1, 2, or 3 substituents independently selected from the group consisting of halogen, $C_{1-6}$alkyl, $C_{1-6}$haloalkyl, $C_{1-6}$alkoxy, and $C_{1-6}$haloalkoxy.

4. The compound of claim 1, wherein A is heteroaryl optionally substituted with 1, 2, or 3 substituents independently selected from the group consisting of halogen, $C_{1-6}$alkyl, $C_{1-6}$haloalkyl, $C_{1-6}$alkoxy, and $C_{1-6}$haloalkoxy.

5. The compound of claim 1, wherein X is —O—[C($R^6$)($R^7$)]—[C($R^6$)$_2$]$_m$-ψ.

6. The compound of claim 1, wherein X is —C($R^6$)$_2$—[C($R^6$)($R^7$)]—[C($R^6$)$_2$]$_m$-ψ.

7. The compound of claim 1, wherein $R^2$ is —C(O)-aryl or —C(O)— aralkyl; each of which is optionally substituted with 1, 2, or 3 substituents independently selected from the group consisting of halogen, hydroxyl, $C_{1-6}$alkoxy, $C_{1-6}$haloalkoxy, $C_{1-6}$alkyl, and $C_{1-6}$haloalkyl.

8. The compound of claim 1, wherein $R^2$ is —C(O)-phenyl or —C(O)-benzyl; each of which is optionally substituted with 1, 2, or 3 substituents independently selected from the group consisting of halogen, $C_{1-6}$alkyl, and $C_{1-6}$haloalkyl.

9. The compound of claim 1, wherein $R^2$ is represented by:

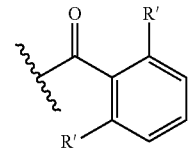

wherein each R' is independently halogen, $C_{1-6}$alkyl, or $C_{1-6}$haloalkyl.

10. The compound of claim 1, wherein $R^2$ is represented by:

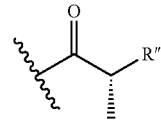

wherein R" is $C_{1-6}$alkyl, aryl, or heterocyclyl, each of which is optionally substituted with 1, 2, or 3 substituents independently selected from the group consisting of halogen, hydroxyl, $C_{1-6}$alkoxy, $C_{1-6}$haloalkoxy, $C_{1-6}$alkyl, $C_{1-6}$haloalkyl, —N(R$^4$)(R$^5$), —CN, —CO$_2$—C$_{1-6}$alkyl, —C(O)—C$_{1-6}$alkyl, —C(O)N(R$^4$)(R$^5$), —S(O)$_p$C$_{1-6}$alkyl, —SO$_2$N(R$^4$)(R$^5$), and —N(R$^4$)SO$_2$(C$_{1-6}$alkyl).

11. The compound of claim 1, wherein R$^7$ is hydroxyl, $C_{1-6}$hydroxyalkyl, $C_{1-6}$alkyl, $C_{1-6}$haloalkyl, —CO$_2$R$^6$, $C_{1-6}$alkylene-CO$_2$R$^6$, $C_{1-4}$hydroxyalkylene-CO$_2$R$^6$, —N(R$^4$)(R$^5$), C$_{1-6}$alkylene-N(R$^4$)(R$^5$), C$_{1-6}$hydroxyalkylene-N(R$^4$)(R$^5$), —N(R$^4$)C(O)R$^9$, C$_{1-6}$alkylene-N(R$^4$)C(O)R$^9$, C$_{1-6}$alkylene-C(O)N(R$^4$)(R$^5$), —N(R$^4$)CO$_2$—C$_{1-6}$alkyl, or —N(R$^4$)C(O)R$^9$.

12. The compound of claim 1, wherein R$^7$ is $C_{1-3}$hydroxyalkyl, methyl, ethyl, or $C_{1-3}$alkylene-N(H)C(O)—C$_{1-4}$alkyl.

13. The compound of claim 1, wherein the compound is represented by Formula II:

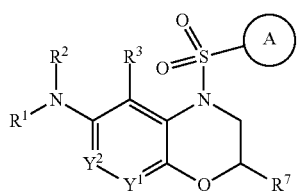

(II)

or a pharmaceutically acceptable salt or solvate thereof; wherein:

A is aryl, aralkyl, heteroaryl, cycloalkyl, or heterocycloalkyl; each of which is optionally substituted with 1, 2, or 3 substituents independently selected from the group consisting of halogen, hydroxyl, $C_{1-6}$alkyl, $C_{1-6}$haloalkyl, $C_{1-6}$hydroxyalkyl, $C_{1-6}$alkoxy, $C_{1-6}$haloalkoxy, —N(R$^4$)(R$^5$), —CO$_2$R$^6$, —C(O)R$^6$, —CN, —C$_{1-4}$alkylene-C$_{1-4}$alkoxy, and —C$_{1-4}$alkylene-N(R$^4$)(R$^5$);

Y$^1$ is C(R$^3$), and Y$^2$ is N;

R$^1$ is hydrogen or $C_{1-6}$alkyl;

R$^2$ is —C(O)-aryl, —C(O)-aralkyl, —C(O)—[C(R$^6$)$_2$]$_m$-cycloalkyl, —C(O)—[C(R$^6$)$_2$]$_m$-heterocyclyl, —C(O)—C$_{1-8}$alkyl, —C(O)—C$_{1-6}$alkylene-C$_{1-6}$alkoxyl, —C(O)—C$_{1-6}$alkylene-cycloalkyl, or —C(O)—C$_{1-6}$alkylene-heterocycloalkyl; each of which is optionally substituted with 1, 2, or 3 substituents independently selected from the group consisting of halogen, hydroxyl, $C_{1-6}$alkoxy, $C_{1-6}$haloalkoxy, $C_{1-6}$alkyl, $C_{1-6}$haloalkyl, —N(R$^4$)(R$^5$), —CN, —CO$_2$—C$_{1-6}$alkyl, —C(O)—C$_{1-6}$alkyl, —C(O)N(R$^4$)(R$^5$), —S(O)$_p$C$_{1-6}$alkyl, —SO$_2$N(R$^4$)(R$^5$), and —N(R$^4$)SO$_2$(C$_{1-6}$alkyl);

R$^3$ represents independently for each occurrence hydrogen, halogen, or $C_{1-6}$alkyl;

R$^4$ and R$^5$ each represent independently for each occurrence hydrogen or $C_{1-6}$alkyl; or R$^4$ and R$^5$ taken together with the nitrogen atom to which they are attached form a 3-7 membered heterocyclic ring;

R$^6$ represents independently for each occurrence hydrogen or $C_{1-6}$alkyl;

R$^7$ is hydrogen, hydroxyl, $C_{1-6}$hydroxyalkyl, $C_{1-6}$alkyl, $C_{1-6}$haloalkyl, —CO$_2$R$^6$, C$_{1-6}$alkylene-CO$_2$R$^6$, C$_{1-4}$hydroxyalkylene-CO$_2$R$^6$, —N(R$^4$)(R$^5$), C$_{1-6}$alkylene-N(R$^4$)(R$^5$), C$_{1-6}$hydroxyalkylene-N(R$^4$)(R$^5$), —N(R$^4$)C(O)R$^9$, C$_{1-6}$alkylene-N(R$^4$)C(O)R$^9$, C$_{1-6}$alkylene-C(O)N(R$^4$)(R$^5$), —N(R$^4$)CO$_2$—C$_{1-6}$alkyl, or C$_{1-6}$alkylene-N(R$^4$)C(O)N(R$^4$)(R$^5$); or R$^7$ is heterocycloalkyl or C$_{1-4}$alkylene-heterocycloalkyl, wherein the heterocycloalkyl is optionally substituted with 1, 2, or 3 substituents independently selected from the group consisting of oxo, halogen, hydroxyl, $C_{1-6}$alkyl, $C_{1-6}$haloalkyl, $C_{1-6}$hydroxyalkyl, $C_{1-6}$alkoxy, and $C_{1-6}$haloalkoxy;

R$^9$ is hydrogen, $C_{1-6}$alkyl, $C_{1-6}$hydroxyalkyl, —N(R$^4$)(R$^5$), C$_{1-6}$alkylene-N(R$^4$)(R$^5$), or C$_{1-6}$alkylene-N(R$^4$)C(O)—C$_{1-6}$alkyl; each of which is optionally substituted with 1, 2, or 3 halogen, hydroxyl or amino; and m and p each represent independently for each occurrence 0, 1, or 2.

14. The compound of claim 13, wherein A is phenyl optionally substituted with 1, 2, or 3 substituents independently selected from the group consisting of halogen, $C_{1-6}$alkyl, $C_{1-6}$haloalkyl, $C_{1-6}$alkoxy, and $C_{1-6}$haloalkoxy.

15. The compound of claim 13, wherein R$^2$ is —C(O)-phenyl or —C(O)-benzyl; each of which is optionally substituted with 1, 2, or 3 substituents independently selected from the group consisting of halogen, $C_{1-6}$alkyl, and $C_{1-6}$haloalkyl.

16. The compound of claim 13, wherein R$^2$ is represented by:

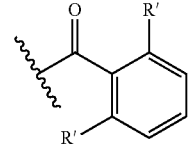

wherein each R' is independently halogen, $C_{1-6}$alkyl, or $C_{1-6}$haloalkyl.

17. The compound of claim 13, wherein R$^7$ is $C_{1-6}$hydroxyalkyl, $C_{1-6}$alkyl, $C_{1-6}$alkylene-CO$_2$R$^6$, C$_{1-6}$alkylene-N(R$^4$)(R$^5$), or C$_{1-6}$alkylene-N(R$^4$)C(O)R$^9$.

18. The compound of claim 1, wherein the compound is represented by Formula III:

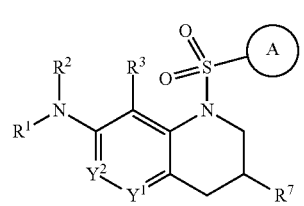

(III)

or a pharmaceutically acceptable salt or solvate thereof; wherein:

A is aryl, aralkyl, heteroaryl, cycloalkyl, or heterocycloalkyl; each of which is optionally substituted with 1, 2, or 3 substituents independently selected from the group consisting of halogen, hydroxyl, $C_{1-6}$alkyl, $C_{1-6}$haloalkyl, $C_{1-6}$hydroxyalkyl, $C_{1-6}$alkoxy, $C_{1-6}$haloalkoxy, —N(R$^4$)(R$^5$), —CO$_2$R$^6$, —C(O)R$^6$, —CN, —C$_{1-4}$alkylene-C$_{1-4}$alkoxy, and —C$_{1-4}$alkylene-N(R$^4$)(R$^5$);

Y$^1$ is C(R$^3$), and Y$^2$ is N;

R$^1$ is hydrogen or $C_{1-6}$alkyl;

R$^2$ is —C(O)-aryl, —C(O)-aralkyl, —C(O)—[C(R$^6$)$_2$]$_m$-cycloalkyl, —C(O)—[C(R$^6$)$_2$]$_m$-heterocyclyl, —C(O)—C$_{1-8}$alkyl, —C(O)—C$_{1-6}$alkylene-C$_{1-}$ ₆alkoxyl, —C(O)—C₁₋₆alkylene-cycloalkyl, or —C(O)—C₁₋₆alkylene-heterocycloalkyl; each of which is optionally substituted with 1, 2, or 3 substituents independently selected from the group consisting of halogen, hydroxyl, $C_{1-6}$alkoxy, $C_{1-6}$haloalkoxy, $C_{1-6}$alkyl, $C_{1-6}$haloalkyl, —N(R⁴)(R⁵), —CN, —CO₂—$C_{1-6}$alkyl, —C(O)—$C_{1-6}$alkyl, —C(O)N(R⁴)(R⁵), —S(O)$_p$C$_{1-6}$ alkyl, —SO₂N(R⁴)(R⁵), and —N(R⁴)SO₂(C$_{1-6}$alkyl);

R³ represents independently for each occurrence hydrogen, halogen, or $C_{1-6}$alkyl;

R⁴ and R⁵ each represent independently for each occurrence hydrogen or $C_{1-6}$alkyl; or R⁴ and R⁵ taken together with the nitrogen atom to which they are attached form a 3-7 membered heterocyclic ring;

R⁶ represents independently for each occurrence hydrogen or $C_{1-6}$alkyl;

R⁷ is hydrogen, hydroxyl, $C_{1-6}$hydroxyalkyl, $C_{1-6}$alkyl, $C_{1-6}$haloalkyl, —CO₂R⁶, $C_{1-6}$alkylene-CO₂R⁶, $C_{1-4}$hydroxyalkylene-CO₂R⁶, —N(R⁴)(R⁵), $C_{1-6}$alkylene-N(R⁴)(R⁵), $C_{1-6}$hydroxyalkylene-N(R⁴)(R⁵), —N(R⁴)C(O)R⁹, $C_{1-6}$alkylene-N(R⁴)C(O)R⁹, $C_{1-6}$alkylene-C(O)N(R⁴)(R⁵), —N(R⁴)CO₂—$C_{1-6}$alkyl, or $C_{1-6}$alkylene-N(R⁴)C(O)N(R⁴)(R⁵); or R⁷ is heterocycloalkyl or $C_{1-4}$alkylene-heterocycloalkyl, wherein the heterocycloalkyl is optionally substituted with 1, 2, or 3 substituents independently selected from the group consisting of oxo, halogen, hydroxyl, $C_{1-6}$alkyl, $C_{1-6}$haloalkyl, $C_{1-6}$hydroxyalkyl, $C_{1-6}$alkoxy, and $C_{1-6}$haloalkoxy;

R⁹ is hydrogen, $C_{1-6}$alkyl, $C_{1-6}$hydroxyalkyl, =N(R⁴)(R⁵), $C_{1-6}$alkylene-N(R⁴)(R⁵), or $C_{1-6}$alkylene-N(R⁴)C(O)—$C_{1-6}$alkyl; each of which is optionally substituted with 1, 2, or 3 halogen, hydroxyl or amino; and m and p each represent independently for each occurrence 0, 1, or 2.

19. The compound of claim 18, wherein A is phenyl optionally substituted with 1, 2, or 3 substituents independently selected from the group consisting of halogen, $C_{1-6}$alkyl, $C_{1-6}$haloalkyl, $C_{1-6}$alkoxy, and $C_{1-6}$haloalkoxy.

20. The compound of claim 18, wherein R² is —C(O)-phenyl or —C(O)-benzyl; each of which is optionally substituted with 1, 2, or 3 substituents independently selected from the group consisting of halogen, $C_{1-6}$alkyl, and $C_{1-6}$haloalkyl.

21. The compound of claim 18, wherein R² is represented by:

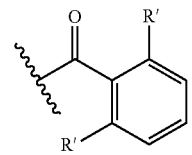

wherein each R' is independently halogen, $C_{1-6}$alkyl, or $C_{1-6}$haloalkyl.

22. The compound of claim 18, wherein R⁷ is $C_{1-6}$hydroxyalkyl, $C_{1-6}$alkyl, $C_{1-6}$alkylene-CO₂R⁶, —N(R⁴)(R⁵), $C_{1-6}$alkylene-N(R⁴)(R⁵), or $C_{1-6}$alkylene-N(R⁴)C(O)R⁹.

23. A compound in any one of Tables 2A, 3A, or 4A or a pharmaceutically acceptable salt thereof:

TABLE 2A

| No. | Y | | Z |
|---|---|---|---|
| II-11 | 2-Cl, 6-CF₃ benzamide | 1,2,3,4-tetrahydro-1,8-naphthyridin-7-yl | piperidinyl |
| II-12 | 2-F, 6-CF₃ benzamide | 1,2,3,4-tetrahydro-1,8-naphthyridin-7-yl | 4-fluorophenyl |

TABLE 2A-continued

| No. | Y | | Z |
|---|---|---|---|
| II-13 | 2,6-difluorobenzamide | 1,2,3,4-tetrahydro-1,6-naphthyridin-7-yl | 3-(trifluoromethyl)phenyl |
| II-14 | 2-chloro-6-fluorobenzamide | 1,2,3,4-tetrahydro-1,6-naphthyridin-7-yl | 3,4-difluorophenyl |
| II-15 | 2,6-dichlorobenzamide | 1,2,3,4-tetrahydro-1,6-naphthyridin-7-yl | 1-methyl-1H-pyrazol-4-yl |
| II-16 | 2-chloro-6-(trifluoromethyl)benzamide | 3,4-dihydro-2H-pyrido[3,4-b][1,4]oxazin-7-yl | piperidin-1-yl |
| II-17 | 2-fluoro-6-(trifluoromethyl)benzamide | 3,4-dihydro-2H-pyrido[3,4-b][1,4]oxazin-7-yl | 4-fluorophenyl |
| II-18 | 2,6-difluorobenzamide | 3,4-dihydro-2H-pyrido[3,4-b][1,4]oxazin-7-yl | 3-(trifluoromethyl)phenyl |
| II-19 | 2-chloro-6-fluorobenzamide | 3,4-dihydro-2H-pyrido[3,4-b][1,4]oxazin-7-yl | 3,4-difluorophenyl |

TABLE 2A-continued

| No. | Y | [A-B core] | Z |
|---|---|---|---|
| II-20 | 2,6-dichloro-benzamide (N-H) | pyrido[3,4-b][1,4]oxazine (linked at 6-position of pyridine and N4) | 1-methyl-1H-pyrazol-4-yl |
| II-21 | 2-chloro-6-(trifluoromethyl)benzamide (N-H) | pyrido[3,4-b][1,4]oxazine (linked at 6-position of pyridine and N4) | 3-chlorophenyl |
| II-22 | 2-fluoro-6-(trifluoromethyl)benzamide (N-H) | 2-(hydroxymethyl)pyrido[3,4-b][1,4]oxazine (linked at 6-position of pyridine and N4) | 4-fluorophenyl |
| II-23 | 2,6-difluorobenzamide (N-H) | 2-(hydroxymethyl)pyrido[3,4-b][1,4]oxazine (linked at 6-position of pyridine and N4) | 3-(trifluoromethyl)phenyl |
| II-24 | 2-chloro-6-fluorobenzamide (N-H) | 2-(hydroxymethyl)pyrido[3,4-b][1,4]oxazine (linked at 6-position of pyridine and N4) | 3,4-difluorophenyl |
| II-25 | 2,6-dichlorobenzamide (N-H) | 2-(acetamidomethyl)pyrido[3,4-b][1,4]oxazine (linked at 6-position of pyridine and N4) | 1-methyl-1H-pyrazol-4-yl |
| II-26 | 2-chloro-6-(trifluoromethyl)benzamide (N-H) | 2-(acetamidomethyl)pyrido[3,4-b][1,4]oxazine (linked at 6-position of pyridine and N4) | piperidin-1-yl |

TABLE 2A-continued
| No. | Y | | Z |
|---|---|---|---|
| II-27 | 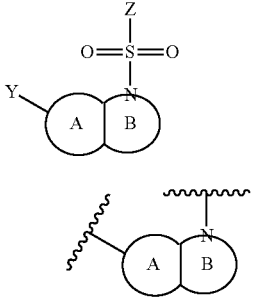 | 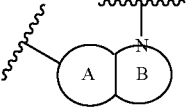 | 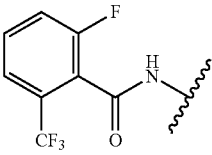 |
| II-28 |  | 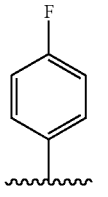 | 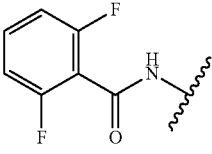 |
| II-29 | 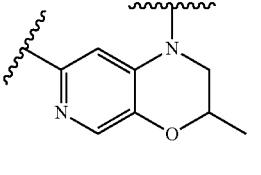 | 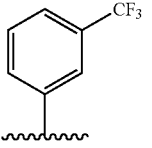 [SMILES: *c1cccc(C(F)(F)F)c1] | 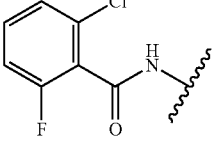 |
| II-30 | 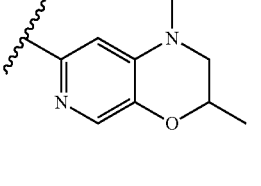 |  | 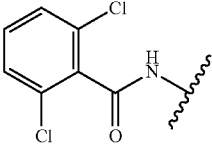 [SMILES: *NC(=O)c1c(Cl)cccc1Cl] |
| II-31 | 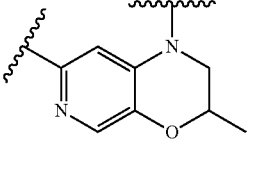 [SMILES: *c1cc2c(cn1)OC(C)CN2*] | 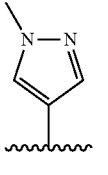 | 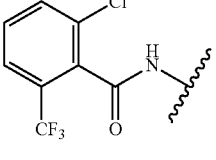 |
| II-32 | 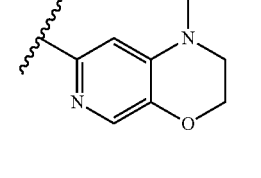 | 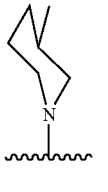 [SMILES: *N1CCCC(C)C1] | 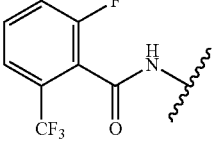 |
| II-33 | 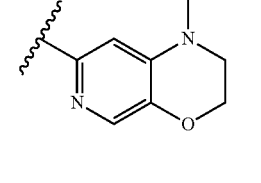 | 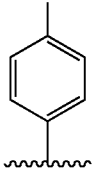 | 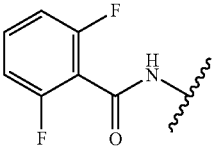 [SMILES: *NC(=O)c1c(F)cccc1F] |

TABLE 2A-continued

| No. | Y | | Z |
|---|---|---|---|
| II-34 | 2-Cl, 6-F benzamide | 7-yl-2,3-dihydro-1H-pyrido[3,4-b][1,4]oxazine (N-linked) | 3,4-difluorophenyl |
| II-35 | 2,6-dichlorobenzamide | 7-yl-2,3-dihydro-1H-pyrido[3,4-b][1,4]oxazine (N-linked) | 1-methyl-1H-pyrazol-4-yl |
| II-36 | 2-Cl, 6-CF$_3$ benzamide | 7-yl-4-oxo-2,3-dihydro-1,5-naphthyridine (N-linked) | piperidin-1-yl |
| II-37 | 2-F, 6-CF$_3$ benzamide | 7-yl-4-oxo-2,3-dihydro-1,5-naphthyridine (N-linked) | 4-fluorophenyl |
| II-38 | 2,6-difluorobenzamide | 7-yl-4-oxo-2,3-dihydro-1,5-naphthyridine (N-linked) | 3-(trifluoromethyl)phenyl |
| II-39 | 2-Cl, 6-F benzamide | 7-yl-4-oxo-2,3-dihydro-1,5-naphthyridine (N-linked) | 3,4-difluorophenyl |

TABLE 2A-continued
| No. | Y | | Z |
|---|---|---|---|
| II-40 | 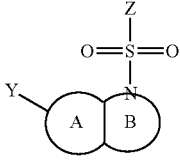 | 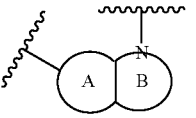 | 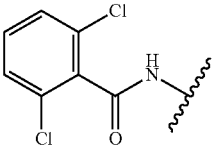 [SMILES: *NC(=O)c1c(Cl)cccc1Cl] |
| II-41 | 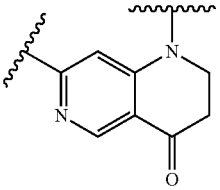 [SMILES: *c1cc2c(cn1)C(=O)CCN2*] | 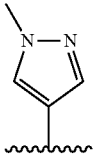 | 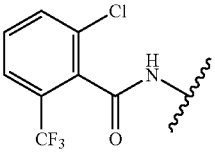 |
| II-42 | 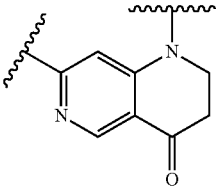 [SMILES: *c1cc2c(cn1)C(=O)CCN2*] |  | 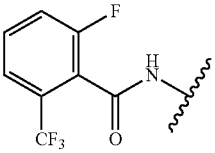 |
| II-43 | 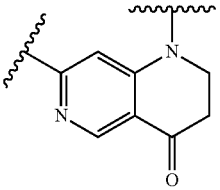 [SMILES: *c1cc2c(cn1)C(=O)CCN2*] | 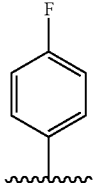 | 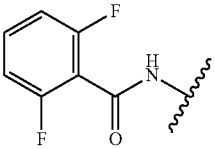 |
| II-44 | 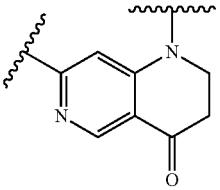 [SMILES: *c1cc2c(cn1)C(=O)CCN2*] | 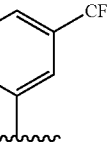 | 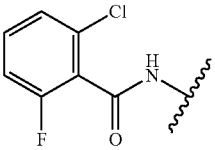 |
| II-47 | 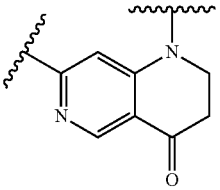 [SMILES: *c1cc2c(cn1)C(=O)CCN2*] | 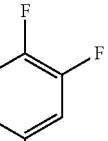 | 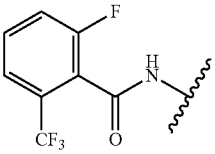 [SMILES: *NC(=O)c1c(F)cccc1C(F)(F)F] |

TABLE 2A-continued
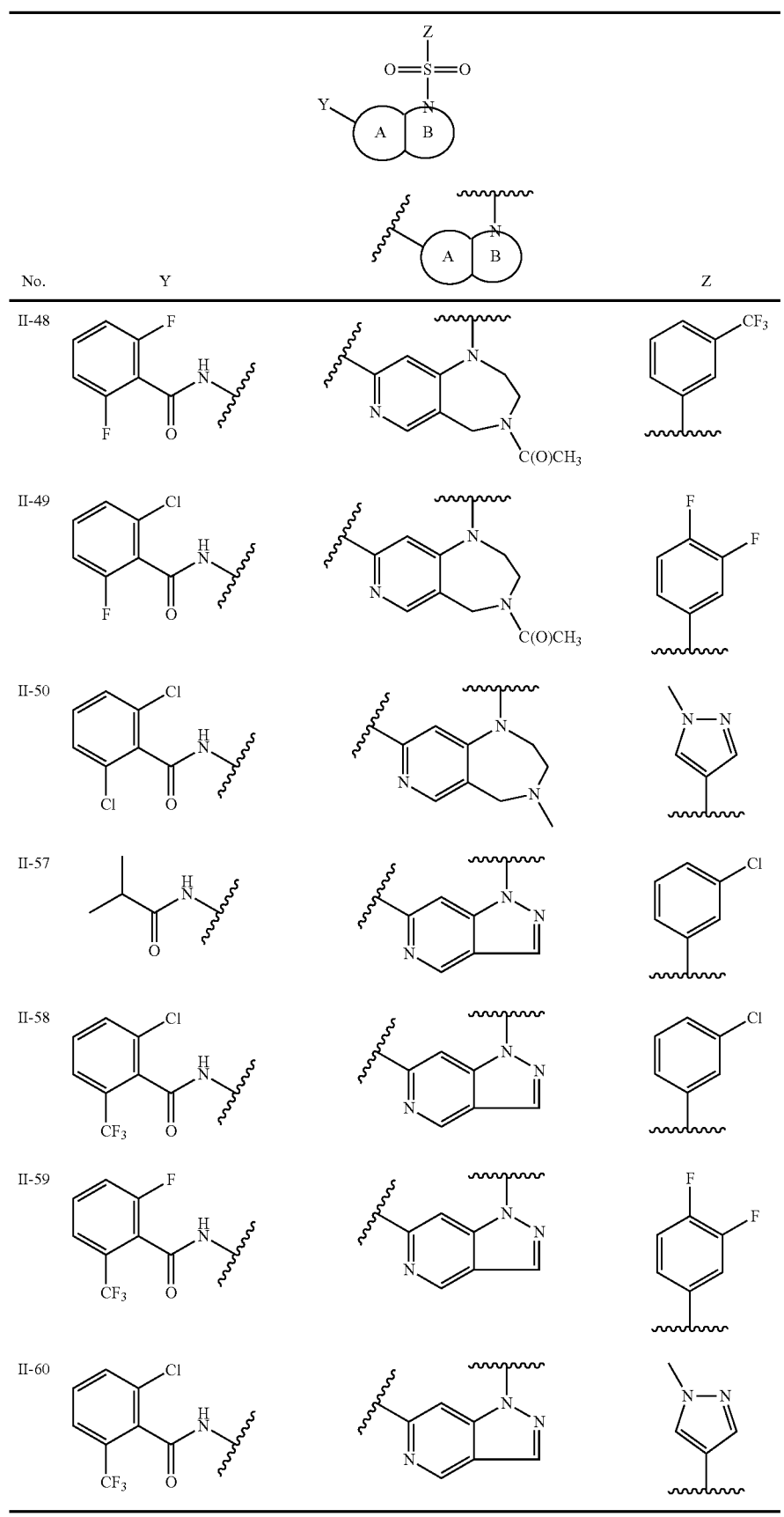

TABLE 3A

| No. | Compound |
|---|---|
| III-59 | (structure) |
| III-60 | (structure) |

TABLE 4A

| Compound No. | Chemical Structure |
|---|---|
| 4 | (structure) |
| 5 | (structure) |

TABLE 4A-continued

| Compound No. | Chemical Structure |
|---|---|
| 6 | (structure) |
| 7 | (structure) |
| 8 | (structure) |
| 9 | (structure) |
| 10 | (structure) |

TABLE 4A-continued

| Compound No. | Chemical Structure |
|---|---|
| 11 | 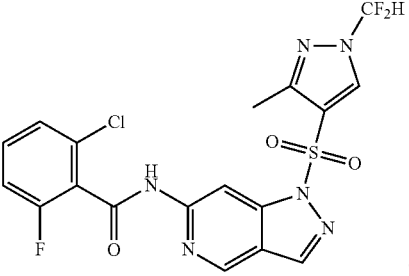 |

24. A pharmaceutical composition comprising a compound of claim 1 and a pharmaceutically acceptable carrier.

25. A method of reducing the amount of interleukin 17 (IL-17) in a subject, comprising administering to a subject an effective amount of a compound of claim 1 to reduce the amount of IL-17 in the subject.

26. A method of inhibiting the activity of RORγ, comprising exposing a retinoid-related orphan receptor γ (RORγ) to an effective amount of a compound of claim 1 to inhibit the activity of said RORγ.

27. The compound of claim 7, wherein X is —C($R^6$)=N-ψ.

28. The compound of claim 27, wherein A is aryl or heteroaryl, each of which is optionally substituted with 1, 2, or 3 substituents independently selected from the group consisting of halogen, $C_{1-6}$alkyl, $C_{1-6}$haloalkyl, $C_{1-6}$alkoxy, and $C_{1-6}$haloalkoxy.

* * * * *